US011058903B2

(12) United States Patent
Thomas et al.

(10) Patent No.: US 11,058,903 B2
(45) Date of Patent: Jul. 13, 2021

(54) METHODS FOR IDENTIFYING AND TREATING CACHEXIA OR PRE-CACHEXIA USING AN INHIBITOR OF RAGE

(71) Applicants: THE BROAD INSTITUTE, INC., Cambridge, MA (US); DANA-FARBER CANCER INSTITUTE, INC., Boston, MA (US)

(72) Inventors: David K. Thomas, Cambridge, MA (US); Todd R. Golub, Cambridge, MA (US)

(73) Assignees: THE BROAD INSTITUTE, INC., Cambridge, MA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/229,176

(22) Filed: Dec. 21, 2018

(65) Prior Publication Data
US 2019/0195862 A1    Jun. 27, 2019

Related U.S. Application Data

(62) Division of application No. 15/101,865, filed as application No. PCT/US2014/068631 on Dec. 4, 2014, now Pat. No. 10,191,033.

(60) Provisional application No. 61/994,677, filed on May 16, 2014, provisional application No. 61/949,139, filed on Mar. 6, 2014, provisional application No. 61/912,338, filed on Dec. 5, 2013.

(51) Int. Cl.
| | | |
|---|---|---|
| *A61P 21/06* | (2006.01) | |
| *A61K 39/395* | (2006.01) | |
| *A61K 38/17* | (2006.01) | |
| *A61K 38/04* | (2006.01) | |
| *C07K 16/28* | (2006.01) | |
| *A61K 31/05* | (2006.01) | |
| *A61K 31/164* | (2006.01) | |
| *A61K 31/454* | (2006.01) | |
| *A61K 31/506* | (2006.01) | |
| *A61K 31/519* | (2006.01) | |
| *A61K 31/7068* | (2006.01) | |
| *A61K 38/00* | (2006.01) | |
| *C07K 14/705* | (2006.01) | |
| *C07K 7/08* | (2006.01) | |
| *G01N 33/53* | (2006.01) | |
| *A61P 3/00* | (2006.01) | |
| *G01N 33/68* | (2006.01) | |
| *G01N 33/50* | (2006.01) | |
| *A61K 45/06* | (2006.01) | |
| *A61K 39/00* | (2006.01) | |

(52) U.S. Cl.
CPC .............. *A61P 21/06* (2018.01); *A61K 31/05* (2013.01); *A61K 31/164* (2013.01); *A61K 31/454* (2013.01); *A61K 31/506* (2013.01); *A61K 31/519* (2013.01); *A61K 31/7068* (2013.01); *A61K 38/00* (2013.01); *A61K 38/04* (2013.01); *A61K 38/1774* (2013.01); *A61K 39/3955* (2013.01); *C07K 16/2803* (2013.01); *A61K 45/06* (2013.01); *A61K 2039/505* (2013.01); *A61P 3/00* (2018.01); *G01N 33/5061* (2013.01); *G01N 33/5067* (2013.01); *G01N 33/53* (2013.01); *G01N 33/5308* (2013.01); *G01N 33/6893* (2013.01); *G01N 2800/04* (2013.01); *G01N 2800/52* (2013.01); *G01N 2800/60* (2013.01)

(58) Field of Classification Search
CPC .............. A61K 38/177; A61K 38/1774; A61K 39/3955; A61K 38/04; A61P 21/06
See application file for complete search history.

(56) References Cited

U.S. PATENT DOCUMENTS

| | | |
|---|---|---|
| 5,385,740 A | 1/1995 | Tisdale et al. |
| 7,485,697 B2 | 2/2009 | Yamamoto et al. |
| 7,981,424 B2 | 7/2011 | Mjalli et al. |
| 8,420,083 B2 | 4/2013 | Strakhova et al. |
| 9,291,621 B2 | 3/2016 | Hahn et al. |
| 2003/0061198 A1 | 3/2003 | Itai et al. |
| 2003/0118592 A1 | 6/2003 | Ledbetter et al. |
| 2003/0133939 A1 | 7/2003 | Ledbetter et al. |
| 2003/0199561 A1 | 10/2003 | Adams et al. |
| 2004/0058445 A1 | 3/2004 | Ledbetter et al. |

(Continued)

FOREIGN PATENT DOCUMENTS

| | | |
|---|---|---|
| WO | 200104354 | 1/2001 |
| WO | 2003064624 | 8/2003 |

(Continued)

OTHER PUBLICATIONS

Das, et al., "The role of triglyceride lipases in cancer associated cachexia," Trends in Molecular Medicine, May 1, 2013 (May 1, 2013), vol. 19, No. 5, p. 292-301.

(Continued)

*Primary Examiner* — Zachary C Howard
(74) *Attorney, Agent, or Firm* — Greenberg Traurig, LLP; Melissa Hunter-Ensor; Leslie Serunian

(57) ABSTRACT

The invention provides markers indicative of pre-cachexia, compositions and methods for identifying patients with a molecular signature indicative of pre-cachexia; a culture system that reproduces the cachetic process in cells in vitro, which facilitates the screening and identification of therapeutic agents useful for disrupting (slowing, reducing, reversing, or preventing) the progression of pre-cachexia to refractory cachexia; as well as therapeutic agents identified using the culture system of the invention.

20 Claims, 91 Drawing Sheets

Specification includes a Sequence Listing.

(56) References Cited

U.S. PATENT DOCUMENTS

| | | |
|---|---|---|
| 2005/0136049 A1 | 6/2005 | Ledbetter et al. |
| 2005/0148536 A1 | 7/2005 | Greenberg |
| 2005/0175614 A1 | 8/2005 | Ledbetter et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2007/0286858 A1 | 12/2007 | Clancy et al. |
| 2009/0270480 A1 | 10/2009 | Amegadzie et al. |
| 2010/0151589 A1 | 6/2010 | Tisdale et al. |
| 2010/0226915 A1 | 9/2010 | Hahn et al. |
| 2012/0196828 A1 | 8/2012 | Marcus |
| 2013/0078728 A1 | 3/2013 | Li et al. |
| 2013/0269046 A1 | 10/2013 | Kinsella et al. |
| 2016/0305934 A1 | 10/2016 | Thomas et al. |
| 2017/0015996 A1 | 1/2017 | Croce et al. |
| 2017/0240632 A1 | 8/2017 | Thomas et al. |
| 2018/0355033 A1 | 12/2018 | Thomas et al. |
| 2018/0362647 A1 | 12/2018 | Thomas et al. |

FOREIGN PATENT DOCUMENTS

| | | |
|---|---|---|
| WO | 2004016229 A2 | 2/2004 |
| WO | 2004/045617 | 6/2004 |
| WO | 2006012415 A2 | 2/2006 |
| WO | 2007089616 A2 | 8/2007 |
| WO | 2007109747 A2 | 9/2007 |
| WO | 2007109749 A2 | 9/2007 |
| WO | 2008137552 A2 | 11/2008 |
| WO | 2009136382 A2 | 11/2009 |
| WO | 2011042548 A1 | 4/2011 |
| WO | 2011053707 A1 | 5/2011 |
| WO | 2016061532 A1 | 4/2016 |
| WO | 2016201319 A1 | 12/2016 |
| WO | 2016201368 A1 | 12/2016 |
| WO | 2017106196 A1 | 6/2017 |

OTHER PUBLICATIONS

Fearon, Kenneth et al., "Understanding the mechanisms and treatment options in cancer cachexia," Nat. Rev. Clin. Oncol., vol. 10, No. 2, pp. 90-99 (2013).

Krepinsky, Joan et al., "Developments in mitogen-induced extracullar kinase 1 inhibitors and their use in the treatment of disease," Expert Opin. Ther. Patents, vol. 12, No. 12, pp. 1795-1811 (2002).

Nerurkar, et al., "Momordica charantia (bitter melon) inhibits primary human adipocyte differentiation by modulating adipogenic genes," Complementary and Alternative Medicine, Jun. 29, 1020 (Jun. 29, 2013), vol. 10, No. 34, pp. 1-10.

Ort, et al. "Recombinant Human FIZZ3/Resistin Stimulates Lipolysis in Cultured Human Adipocytes, Mouse Adipose Explants, and Normal Mice," Endocrinology, Feb. 10, 2005 (Feb. 10, 2005), vol. 146, No. 5, pp. 2200-2209.

Penna, et al., "Muscle Wasting and Impaired Myogenesis in Tumor Bearing Mice Are Prevented by ERK Inhibition," PLoS One, Oct. 27, 2010 (Oct. 27, 2010), vol. 5, No. 10, e13604, pp. 1-11.

Prado, C. et al., "Skeletal muscle anabolism is a side effect of therapy with the MEK inhibitor: selumetinib in patients with cholangiocarcinoma," British Journal of Cancer, vol. 106, pp. 1583-1586 (2012).

Salama, et al., "A review of the S100 proteins in cancer," European Journal of Surgical Oncology, 2008, vol. 34, pp. 357-364.

Scott, et al., "Large-scale isolation of human skeletal muscle satellite cells from post-mortem tissue and development of quantitative assays to evaluate modulators of myogenesis," Journal of Cachexia, Sarcopenia, and Muscle, Jun. 1, 2013 (Jun. 1, 2013), vol. 4, p. 157-169.

Yao et al., "Expression of S100 Protein Family Members in the Pathogenesis of Bladder Tumors", 2007, Anticancer Research, 27: 3051-3058.

International Search Report and Written Opinion for corresponding PCT/US2014/068631, dated Mar. 30, 2015 (19 pages).

Partial Supplemental Search Report for corresponding European patent application No. 14868683.5, dated Apr. 7, 2017, (11 pages).

Extended European Search Report in corresponding to European Patent Application No. 14868683.5, dated Jul. 14, 2017 (17 pages).

Communication pursuant to Rules 70(2) and 70a(2) EPC in corresponding European Patent Application No. 14868683.5, dated Aug. 1, 2017 (1 page).

European Examination Report, dated Apr. 18, 2018, in corresponding to European Patent Application No. 14868683.5 (5 pages).

Acharyya et al., "Cancer cachexia is regulated by selective targeting of skeletal muscle gene products," The Journal of Clinical Investigation, Aug. 2004, vol. 114, No. 3, pp. 370-378 (9 pages).

Arumugam et al., "S100P-Derived RAGE Antagonistic Peptide (RAP) Reduces Tumor Growth and Metastasis," Clinical Cancer Research, Aug. 2012, vol. 18, Iss. 16; DOI: 10.1158/1078-0432.CCR-12-0221 (20 pages).

Azeliragon, PF-04494700, Product Data Sheet, MedChemExpress, downloaded from the Internet on Jun. 10, 2020 (2 pages).

Boehm et al., "Towards systematic functional characterization of cancer genomes," Nature Reviews Genetics, Jul. 2011, vol. 12, Iss. 7, pp. 487-498 (12 pages).

Certificate of Analysis, Product Name: "FPS ZM1," TOCRIS, Sep. 5, 2017 (2 pages).

Neeper et al., "Cloning and Expression of a Cell Surface Receptor for Advanced Glycosylation End Products of Proteins," The Journal of Biological Chemistry, 1992, vol. 267, No. 21, pp. 14998-15004 (7 pages).

Sabbagh et al., "PF-04494700, an Oral Inhibitor of Receptor for Advanced Glycation End Products (RAGE), in Alzheimer's disease," Alzheimer Disease and Associated Disorders, 2011, vol. 25, Iss. 3, pp. 206-212 (14 pages).

Zhou et al., "Reversal of Cancer Cachexia and Muscle Wasting by ActRIIB Antagonism Leads to Prolonged Survival," Cell, Aug. 2010, vol. 142, Iss. 4, pp. 531-543 (13 pages).

Das et al., "Adipose Triglyceride Lipase Contributes to Cancer-Associated Cachexia," Science, 2011, vol. 333, Iss. 6039, pp. 233-238 (8 pages).

Eley et al., "Effect of branched-chain amino acids on muscle atrophy in cancer cachexia," Biochemical Journal, 2007, vol. 407, Iss. 1, pp. 113-120 (8 pages).

Kamphorst et al., "Hypoxic and Ras-transformed cells support growth by scavenging unsaturated fatty acids from lysophospholipids," Proceedings of the National Academy of Sciences, May 28, 2013, vol. 110, No. 22, pp. 8882-8887 (6 pages).

Lieffers et al., "A viscerally driven cachexia syndrome in patients with advanced colorectal cancer: contributions of organ and tumor mass to whole-body energy demands," The American Journal of Clinical Nutrition, 2009, vol. 89, No. 4, pp. 1173-1179 (7 pages).

Nieman et al., "Adipocytes promote ovarian cancer metastasis and provide energy for rapid tumor growth," Nature Medicine, Nov. 2011, vol. 17, No. 11, pp. 1498-1503 (7 pages).

Extended European Search Report dated Jun. 26, 2020 as received in corresponding European Patent Application No. 19189695.0 (12 pages).

Brederson et al., "A Monoclonal Antibody Against the Receptor for Advanced Glycation End Products Attenuates Inflammatory and Neuropathic Pain in the Mouse," European Journal of Pain, Sep. 22, 2015, vol. 20, pp. 607-614, ISSN: 1532-2149, DOI: https://doi.org/10.1002/ejp.775 (8 pages).

Deane et al., "A Multimodal RAGE-Specific Inhibitor Reduces Amyloid [beta]-Mediated Brain Disorder in a Mouse Model of Alzheimer Disease," Journal of Clinical Investigation, Apr. 2, 2012, vol. 122, No. 4, pp. 1377-1392, ISSN: 0021-9738, DOI: 10.1172/JCI58642 (17 pages).

Krishnan et al., "A Molecular Dynamics Study on RAGE-Aβ42 Interaction and the Influence of G82S RAGE Polymorphism on Aβ Interaction," International Journal Bioautomation, 2015, vol. 19, Iss. 4, pp. 433-446 (15 pages).

(56) References Cited

OTHER PUBLICATIONS

Verma et al., "Structural and dynamic insights into S100B protein activity inhibition by melittin for the treatment of epilepsy," International Journal of Computer Applications, NSAAILS, 2013, vol. 1, pp. 55-60 (6 pages).
Yan et al., "Effects of Advanced Glycation End Products on Calcium Handling in Cardiomyocytes," Cardiology, Jan. 1, 2014, vol. 129, No. 2, pp. 75-83, ISSN: 0008-6312, DOI: 10.1159/000364779 (9 pages).
Yatime et al., "Structural Insights Into the Oligomerization Mode of the Human Receptor for Advanced Glycation End-Products," The FEBS Journal, 2013, vol. 280, No. 24, pp. 6556-6568 (13 pages).
Examination Report issued in European Patent Application No. 16876492.6, dated May 28, 2020 (7 pages).
Extended European Search Report issued in European Patent Application No. 16876492.6, dated May 15, 2019 (10 pages).
International Search Report and Written Opinion issued in International Patent Application No. PCT/US2016/066390, dated Mar. 17, 2017 (10 pages).
Ebner et al., "Mechanism and novel therapeutic approaches to wasting in chronic disease," Maturitas, May 9, 2013, vol. 75, No. 3, pp. 199-206 (8 pages).
Murphy et al., "Physiological characterization of a mouse model of cachexia in colorectal liver metastases," American Journal of Physiology: Regulatory, Integrative and Comparative Physiology, May 15, 2013, vol. 304, No. 10, pp. R854-R864 (11 pages).
Partial European Search Report in corresponding European Patent Application No. 19189695.0, dated Feb. 28, 2020 (15 pages).

FIG. 1A

|  | Cachexia | Starvation |
|---|---|---|
| Appetite | decreased | increased |
| Basal Metabolic Rate | increased | decreased |
| Acute Phase Response | yes | no |
| Skeletal Muscle mass | decreased (early) | maintained (early) |
| Adipose Tissue mass | decreased (< LBM) | decreased (> LBM) |
| Hepatomegaly | yes | no (except in Kwashiorkor) |
| Glucose intolerance | yes | no |
| Hyperinsulinemia | yes | no |

*Total Parenteral Nutrition (TPN) has no benefit on weight or LBM in patients with cancer cachexia.

FIG. 1B

| | Case | Age at Diagnosis | Date of Diagnosis | FINDINGS AT INITIAL DIAGNOSIS ||||| RECURRENCE/PROGRESSION IN PANCREAS |||
|---|---|---|---|---|---|---|---|---|---|---|
| | | | | Size of Primary at Dx | Was primarily surgically removed? | Size of Largest Measured Metastasis (cm) | Size Range of Mets (cm) | Recurrence within Remnant Pancreas (if has tumor removed) or documented increase in size of unresectable pancreatic mass before death? | Date that recurrence/progression in pancreas first documented | Size of Mass in Pancreas (cm) |
| Modest (17 months) | 5 | 47 | 12/2/02 | 5 | No | x | x | No | | |
| | 19 | 50 | 4/28/03 | 6 | Yes | x | x | No | | |
| | 25 | 59 | 3/3/03 | 3 | Yes | x | x | Yes | 4/19/04 | 4.4 |
| | 40 | 36 | 12/1/04 | 3 | No | x | x | No | | |
| | 52 | 66 | 3/1/05 | 4 | No | x | x | Yes | 9/28/05 | no data |
| | 53 | 57 | 2/1/05 | 3 | No | x | x | no data | | |
| | 54 | 81 | 10/1/02 | 3 | Yes | x | x | Yes | 12/14/05 | 3.3 |
| | 65 | 72 | 3/28/06 | 3.6 | No | x | x | No | | |
| | 72 | 78 | 6/1/04 | 4 | Yes | x | x | Yes | 1/4/05 | 2 |
| | 77 | 84 | 7/2/07 | 2.6 | No | x | x | No | | |
| | 88 | 64 | 1/4/07 | 3.9 | No | x | x | no data | | |
| | 106 | 71 | 8/1/06 | 3.9 | No | x | x | No | | |
| | 114 | 85 | 5/20/06 | 2.3 | No | x | x | No change in size | 7/3/08 | 2.3 |
| | 128 | 75 | 4/1/10 | 3 | No | x | x | No change in size | 10/26/10 | 3 |
| | 113 | 67 | 7/14/07 | 3 | No | x | x | Yes | 2/24/09 | 4.5 |
| | 1 | 84 | 5/5/95 | 6 | No | x | x | no data | | |
| | 7 | 67 | 11/1/99 | 8 | No | x | x | No | | |
| | 11 | 60 | 4/30/01 | 4 | No | x | x | Yes | 5/2/02 | no data |
| | 12 | 57 | 5/1/03 | 5 | No | x | x | Yes | 9/29/03 | 7 |
| | 13 | 59 | 6/1/03 | 5 | No | 2 | 1-2.0 | no data | | |
| | 15 | 65 | 10/13/03 | 7 | No | x | x | no data | | |
| | 33 | 64 | 10/25/05 | 4 | No | 1.3 | 1.3 | No | | |
| | 34 | 59 | 8/13/03 | 3 | No | x | x | Yes | 10/13/05 | 6.1 |
| | 41 | 82 | 5/30/03 | 1.5 | Yes | x | x | Yes | 11/5/05 | no data |
| | 45 | 66 | 6/1/04 | 2 | Yes | x | x | Yes | 12/22/04 | 2 |
| | 48 | 59 | 2/26/02 | 2 | Yes | x | x | Yes | 6/1/05 | 1.6 |
| | 56 | 54 | 6/1/06 | 4.4 | No | x | x | no data | | |
| | 70 | 78 | 5/1/07 | 2.4 | No | 2.5 | 2.5 | no data | | |
| | 73 | 77 | 12/1/06 | 3.2 | No | x | x | No | | |
| | 76 | 70 | 4/1/05 | 3 | No | x | x | no data | | |
| | 85 | 57 | 7/12/06 | 2.5 | No | 3.4 | 0.5-3.4 | Yes | 4/30/07 | 3.2 |
| | 105 | 64 | 11/12/08 | 4 | No | x | x | No | | |
| | 107 | 72 | 2/6/06 | 3.1 | No | x | x | Yes | 9/10/08 | 4.5 |

FIG. 1B (cont.)

| METASTATIC RECURRENCE | | | METASTATIC PROGRESSION | | |
|---|---|---|---|---|---|
| Metastatic Recurrence (or new metastases) after Initial Diagnosis? | Date that metastases first documented | Size of Largest Measured Metastasis (cm) | Progression of Metastases previously documented (initial diagnosis or afterwards)? | Date of Documented Progression of Metastases after first found? | Size of Largest Measured Metastasis (cm) |
| No | | | x | | |
| No | | | x | | |
| No | | | x | | |
| No | | | x | | |
| No | | | x | | |
| Yes, lung (these regre | 10/28/05 | 0.9 | x | | |
| No | | | No | | |
| No | | | x | | |
| No | | | No | | |
| No | | | x | | |
| No | | | x | | |
| No | | | x | | |
| No | | | No | | |
| No | 10/26/10 | | No | | |
| Yes | 2/24/09 | 0.3 | Yes | 03/03/09 | 0.8 |
| no data | | | no data | | |
| Yes, bladder dome an | 11/01/02 | 3 | Yes, bladder | 1/06/03 | 3.2 |
| Yes, peritoneum | 7/10/02 | no data | no data | | |
| Yes | 9/29/03 | 1.5 | No | | |
| no data | | | no data | | |
| no data | | | no data | | |
| No | | | x | | |
| Yes, lungs | 6/7/05 | 0.47 | Yes, lung met | 10/13/05 | 1.1 |
| Yes, peritoneum | 1/19/05 | 2.1 | No | | |
| Yes, lymph nodes | 12/28/05 | 1 | no data | | |
| Yes, lung and hilar lym | 3/30/04 | 1.1 | Yes, increase in siz | 06/01/05 | 1.5 |
| no data | | | no data | | |
| no data | | | no data | | |
| No | | | x | | |
| no data | | | no data | | |
| Yes, lung | 2/1/07 | 0.8 | Yes | 04/30/07 | 3.7 |
| No | | | No | | |
| Yes, liver | 9/30/08 | 4.9 | Yes, increase in siz | 12/09/08 | 5.7 |

Modest (17 months)

FIG. 1B (cont.)

FINDINGS AT AUTOPSY

| Date of Death | Findings in Pancreas at Autopsy | Size of Recurrent Tumor in Pancreas | Size of Primary at Autopsy (cm) | Metastatic Burden at Autopsy | Mean Size of Metastases (cm) | Range (cm) |
|---|---|---|---|---|---|---|
| 8/15/03 | Present (Not Resected) |  | 5 | 0 |  |  |
| 7/21/04 | Absent (Resected) | 0 | 0 | 0 |  |  |
| 2/10/05 | Recurred after Surgery | 6 | x | 0 |  |  |
| 4/27/06 | Present (Not Resected) |  | 3.7 | 0 |  |  |
| 8/10/06 | Present (Not Resected) |  | 7 | 0 |  |  |
| 8/30/06 | Present (Not Resected) |  | 10 | 0 | x | x |
| 9/24/06 | Absent (Treated) | 0 (only dead) | x | 0 |  |  |
| 3/29/07 | Present (Not Resected) |  | 4 | 0 |  |  |
| 9/12/07 | Recurred after Surgery | 2 | x | 0 |  |  |
| 10/19/07 | Present (Not Resected) |  | 2.5 | 0 | x | x |
| 3/9/08 | Present (Not Resected) |  | 10 | 0 |  |  |
| 2/25/09 | Present (Not resected) |  | 4.5 | 0 |  |  |
| 5/3/09 | Present (Not resected) |  | 3 | 0 | x | x |
| 12/14/10 | Present (Not resected) |  | 3.5 | 0 |  |  |
| 4/28/09 | Present (Not resected) |  | 5 | <10 | 0.5 | 0.3-1.0 |
| 10/26/95 | Present (Not Resected) |  | 6 | 1 to 10 | 1.0 | 0.5-2.8 |
| 10/14/03 | Present (Not Resected) |  | 10 | 1 to 10 | 1.0 | 0.5-3.5 |
| 12/14/03 | Present (Not Resected) |  | 5 | 1 to 10 | no data | no data |
| 12/16/03 | Present (Not Resected) |  | 9 | 1 to 10 | 1.5 | 0.5-2 |
| 1/15/04 | Present (Not Resected) |  | 15 | 1 to 10 | 1.5 | 1.0-3.0 |
| 12/29/03 | Present (Not Resected) |  | 9 | 1 to 10 | 2.0 | 1.0-3.0 |
| 11/17/05 | Present (Not Resected) |  | 4 | 1 to 10 | 0.7 | 0.5-1.3 |
| 11/23/05 | Present (Not Resected) |  | 6 | 1 to 10 | 0.7 | 0.5-1.0 |
| 4/18/06 | Recurred after Surgery | 6 | x | 1 to 10 | 1.0 | 0.2-3.0 |
| 6/12/06 | Recurred after Surgery | 6 | x | 1 to 10 | 1.0 | 0.5-2.0 |
| 7/11/06 | Recurred after Surgery | 7 | x | 1 to 10 | 0.5 | 0.2-1.0 |
| 10/15/06 | Present (Not Resected) |  | 5 | 1 to 10 | 1.0 | 1.0 |
| 6/5/07 | Present (Not Resected) |  | 4 | 1 to 10 | 2.5 | 1.0-2.5 |
| 10/1/07 | Present (Not Resected) |  | 3.5 | 1 to 10 | 0.5 | 0.5 |
| 10/12/07 | Present (Not Resected) |  | 4 | 1 to 10 | no data |  |
| 1/27/08 | Present (Not Resected) |  | 6 | 1 to 10 | 1.5 | 1-4 |
| 2/15/09 | Present (Not resected) |  | 4 | 1 to 10 | 0.5 | 0.3-0.8 |
| 2/26/09 | Present (Not resected) |  | 6 | 1 to 10 | 6 | x |

Modest (17 months)

FIG. 1B (cont.)

| | | | | | | | | | | |
|---|---|---|---|---|---|---|---|---|---|---|
| | 116 | 65 | 4/16/08 | 3 | Yes | x | x | Yes | 1/12/09 | 2 |
| | 118 | 65 | 8/4/08 | 3.3 | No | x | x | No change in size | 12/3/08 | 3.3 |
| | 124 | 74 | 7/26/10 | 2 | No | 13.6 | x | No | 8/11/10 | |
| | 132 | 79 | 4/15/10 | 3 | No | no data | no data | no data | | |
| | 3 | 67 | 7/25/02 | 2 | No | 2 | 1-2 | Yes | 5/12/03 | 4 |
| | 8 | 60 | 7/5/03 | 5 | No | 2.5 | 1-2.5 | No | | |
| | 9 | 56 | 11/1/02 | 3 | No | had mets b | no data | no data | | |
| | 10 | 60 | 11/19/03 | 6 | No | 5 | x | No | | |
| | 14 | 59 | 5/9/03 | 4 | No | 2 | 1-2.0 | Yes | 10/29/03 | 4.6 |
| | 16 | 63 | 8/1/00 | 4 | Yes | x | x | Yes | 10/22/01 | 1.7 |
| | 18 | 67 | 12/26/00 | 4 | No | x | x | Yes | no data | |
| Moderate (10 months) | 20 | 53 | 9/17/02 | 2.4 | Yes | x | x | Yes | 3/9/04 | 3.5 |
| | 21 | 66 | 9/27/02 | 3 | Yes | x | x | Yes | 10/6/04 | 3 |
| | 26 | 48 | 2/1/04 | 3 | No | x | x | No | | |
| | 27 | 54 | 9/1/04 | 4 | No | 4 | 0.5-4 | No | | |
| | 29 | 72 | 9/2/04 | 4 | No | 2 | 1-2 | Yes | 3/1/05 | 6.5 |
| | 30 | 51 | 3/10/03 | 2.2 | Yes | x | x | Yes | 11/3/04 | 5 |
| | 42 | 54 | 5/16/05 | 4 | No | x | x | Yes | 6/14/05 | 4.7 |
| | 58 | 55 | 7/1/03 | 3.1 | No | x | x | Yes | 1/26/04 | 5.1 |
| | 63 | 69 | 5/9/06 | 2.8 | Yes | x | x | No | | |
| | 64 | 74 | 6/17/06 | 3.5 | Yes | x | x | No | | |
| | 69 | 69 | 2/1/07 | 6.5 | No | 3.6 | 1.5-3.6 | No | | |
| | 74 | 76 | 5/1/03 | 3.5 | Yes | x | x | Yes | 12/8/05 | 3 |
| | 78 | 76 | 3/9/07 | 3.8 | No | 1 | x | Yes | 7/3/07 | 5.1 |
| | 80 | 36 | 4/1/07 | 4.2 | No | 2.6 | 1.5-2.6 | No | | |
| | 82 | 60 | 3/1/07 | 4.5 | Yes | 1 | 0.5-1 | No | | |
| | 83 | 55 | 6/1/06 | 6 | Yes | x | x | Yes | 6/8/07 | 3.8 |
| | 86 | 56 | 7/6/07 | 1.9 | No | 0.7 | 0.5-0.7 | no data | | |
| | 112 | 53 | 10/27/08 | 4.2 | No | 1 | 0.5-1.5 | Yes | 3/19/09 | 5.5 |
| | 122 | 70 | 6/24/10 | 2 | No | 0.4 | x | Yes | 9/22/10 | 3.1 |
| | 121 | 51 | 9/1/09 | 2.5 | No | no data | no data | Yes | 12/28/09 | 1.8 |

FIG. 1B (cont.)

| | | | | | |
|---|---|---|---|---|---|
| Yes, liver | 1/12/09 | 0.8 | | | |
| Yes, liver | 4/30/09 | 1 | | | |
| | | | Yes | 8/11/2010 | 14 |
| no data | | | no data | | |
| Yes | 03/19/03 | 2.9 | Yes, lungs and inc | 5/12/03 | 5 |
| No | | | Yes, increase in nu | 09/25/03 | 2.5 |
| no data | | | no data | | |
| No | | | No | | |
| Yes, increase in numb | 10/29/03 | 3.2 | Yes, increase in nu | 1/20/04 | 4.6 |
| Yes, peritoneum | 10/22/01 | 0.3 | Yes, increase in nu | 07/24/03 | no data |
| Yes, lung and spine | 5/12/04 | | no data | | |
| Yes, liver | 2/10/03 | 1.8 | x | | |
| Yes, liver | 4/3/03 | 1 | Yes | 06/03/03 | 2 |
| Yes, multiple in liver, l | 12/22/04 | 9.5 | Yes, increase in siz | 01/19/05 | 14 |
| No | | | No | | |
| No | | | Yes, increase in siz | 03/01/05 | 4 |
| Yes, lung | 11/3/04 | 1.5 | x | | |
| Yes, liver | 6/14/05 | 0.6 | Yes, liver | 08/01/05 | 0.8 |
| no data | | | No | | |
| Yes | 12/22/06 | 0.5 | x | | |
| Yes | 9/25/06 | 0.5 | no data | | |
| no data | | | no data | | |
| Yes | 2/14/06 | 1.4 | Yes | 6/16/06 | 3 |
| No | | | Yes | 04/09/07 | 1.3 |
| No | | | no data | | |
| Yes, liver and bladder | 9/28/07 | 3.3 | no data | | |
| Yes, liver | 6/8/07 | 1 | x | | |
| no data | | | no data | | |
| No | | | Yes | 03/16/09 | 2.5 |
| | | | Yes | 4/21/10 | 4.4 |

Moderate (10 months)

FIG. 1B (cont.)

| Date | Status | | | | |
|---|---|---|---|---|---|
| 6/17/09 | Recurred after surgery 4 | x | 11-100 | 2 | 0.5-4.5 |
| 7/17/09 | Present (Not Resected) | | 11-100 | 1 | 0.5-2.0 |
| 10/23/10 | Present (Not resected) | 3 | 11-100 | 5 | 1.0-14 |
| 2/19/11 | Present (Not Resected) | 4.5 | 11-100 | 2 | 0.5-3 |
| 6/24/03 | Present (Not Resected) | 4 | 11 to 100 | 3.0 | 1.0-5.0 |
| 10/26/03 | Present (Not Resected) | 5 | 11 to 100 | 1.5 | 1.0-2.5 |
| 7/30/03 | Present (Not Resected) | 4 | 11 to 100 | 1.0 | 0.5-2.0 |
| 12/16/03 | Present (Not Resected) | 10 | 11 to 100 | 2.0 | 1.0-4.0 |
| 5/11/04 | Present (Not Resected) | 8 | 11 to 100 | 1.0 | 0.5-5.0 |
| 12/28/03 | Recurred after Surgery 2 | x | 11 to 100 | 0.5 | 0.2-1.0 |
| 6/18/04 | Present (Not Resected) | 6 | 11 to 100 | 1.0 | 0.5-1.5 |
| 8/6/04 | Recurred after Surgery | 8 | 11 to 100 | 1.5 | 1.0-2.8 |
| 10/9/04 | Recurred after Surgery 3 | x | 11 to 100 | 1.5 | 0.5-3.5 |
| 2/16/05 | Present (Not Resected) | 3 | 11 to 100 | 4.0 | 2.0-14.0 |
| 3/6/05 | Present (Not Resected) | 4 | 11 to 100 | 2.0 | 0.5-4.0 |
| 4/16/05 | Present (Not Resected) | 6 | 11 to 100 | 1.5 | 1.0-4.0 |
| 7/9/05 | Recurred after Surgery 4 | x | 11 to 100 | 2.0 | 1-10 |
| 5/10/06 | Present (Not Resected) | 5 | 11 to 100 | 3.0 | 0.5-10 |
| 11/16/06 | Present (Not Resected) | 6 | 11 to 100 | 0.5 | 0.3-1.6 |
| 2/23/07 | Absent (Resected) | | 11 to 100 | 0.2 | 0.1-0.5 |
| 3/2/07 | Absent (Resected) | | 11 to 100 | 0.5 | 0.2-2.0 |
| 6/4/07 | Present (Not Resected) | 6 | 11 to 100 | 2 | 1.5-4 |
| 10/10/07 | Recurred after Surgery 3 | x | 11 to 100 | 2 | 1-5.5 |
| 10/22/07 | Present (Not Resected) | | 11 to 100 | | |
| 12/4/07 | Present (Not Resected) | 6 | 11 to 100 | 2 | 0.5-3 |
| 12/7/07 | Recurred after surgery no data | x | 11 to 100 | 2 | 0.5-3 |
| 12/10/07 | Recurred after surgery 5 | x | 11 to 100 | 1.5 | 1-3 |
| 2/4/08 | Present (Not Resected) | 2.8 | 11 to 100 | 1 | 0.7-1.5 |
| 05/01/09 | Present (Not resected) | 6 | 11 to 100 | 1.5 | 0.2-3 |
| 10/13/10 | Present (Not resected) | 1.7 | 11 to 100 | 1 | 0.5-1.5 |
| 9/5/10 | Present (Not Resected) | 2.5 | 100s | 1.5 | 3.5 |

Moderate (10 months)

FIG. 1B (cont.)

| | | | | | | | | | |
|---|---|---|---|---|---|---|---|---|---|
| | 2 | 62 | 12/16/02 | 3 | No | 2 | 1-2 | Yes | 1/27/03 | 7 |
| | 6 | 57 | 1/15/03 | 4 | No | 1 | 0.3-1 | No | | |
| | 17 | 50 | 2/10/04 | 4 | No | x | x | No | | |
| | 22 | 51 | 5/13/04 | 4 | No | x | x | No | | |
| | 23 | 82 | 8/1/03 | 2.6 | No | 0.6 | 0.5-0.6 | Yes | 6/30/04 | 3.8 |
| | 24 | 61 | 1/22/03 | 1.5 | Yes | x | x | Yes | no data | |
| | 28 | 65 | 6/1/97 | 6 | No | x | x | Yes | 2/6/04 | 11 |
| | 31 | 64 | 9/14/05 | 4 | No | 5 | 0.5-5 | No | | |
| | 32 | 81 | 7/20/05 | 3 | No | x | x | No | | |
| | 36 | 54 | 8/1/05 | 6 | Yes | x | x | Yes | no data | |
| | 38 | 51 | 1/1/05 | 3 | No | 1 | 0.5-1.0 | No | | |
| | 43 | 85 | 3/27/06 | 5 | No | 6 | 0.5-6 | No | | |
| | 44 | 50 | 7/28/05 | 2 | Yes | x | x | Yes | 3/23/06 | 1 |
| | 46 | 51 | 12/26/05 | 5.9 | No | x | x | No | | |
| Extensive (8 months) | 47 | 49 | 2/22/06 | 4.5 | No | 2 | 0.5-2 | No | | |
| | 49 | 68 | 3/1/06 | 5 | No | no data | no data | No | | |
| | 50 | 66 | 2/6/06 | 3.5 | No | x | x | No | | |
| | 55 | 58 | 3/3/06 | 2.5 | No | 1.2 | 1.2 | No | | |
| | 57 | 64 | 8/1/06 | 4.3 | No | 3 | 1.0-3 | yes | 9/6/06 | 5.3 |
| | 60 | 47 | 6/9/06 | 4 | No | x | x | No | | |
| | 61 | 42 | 4/6/06 | 3.8 | No | 3.4 | 1.3-3.4 | No | | |
| | 66 | 74 | 3/1/04 | 2.5 | Yes | x | x | Yes | 9/14/06 | 4.5 |
| | 67 | 90 | 3/1/05 | 6.5 | Yes | x | x | No | | |
| | 68 | 56 | 5/1/06 | 7 | No | 1 | 0.5-1 | no data | | |
| | 81 | 53 | 9/14/05 | 1.8 | Yes | x | x | Yes | 8/30/07 | 1.7 |
| | 87 | 61 | 3/1/06 | 2.5 | No | 0.2 | 0.2 | no data | | |
| | 90 | 88 | 5/1/08 | 3.2 | No | no data | no data | no data | | |
| | 92 | 54 | 1/13/05 | 2 | No | 0.7 | 0.2-0.7 | Yes | 8/22/07 | 2.9 |
| | 93 | 74 | 3/13/08 | 7 | No | 3.5 | 1-3.5 | No | | |
| | 95 | 79 | 3/5/08 | 4.2 | No | 1.8 | 0.5-1.8 | No | | |
| | 98 | 68 | 7/25/07 | 4 | No | 1 | 0.3-1.5 | no data | | |
| | 115 | 57 | 11/30/06 | 2.2 | Yes | x | x | Yes | 10/21/08 | 2.3 |
| | 117 | 50 | 6/6/07 | 5.5 | Yes | x | x | No | | |
| | 119 | 69 | 8/2/07 | 2.5 | Yes | x | x | Yes | 4/14/08 | 2.8 |
| | 120 | 65 | 9/26/08 | 6.5 | No | 2 | 1-2 | No | | |
| | 125 | 69 | 11/11/10 | 3 | No | 2.5 | 0.5-2.5 | No | | |
| | 129 | 55 | 9/1/09 | 1.6 | No | | | Yes | 10/26/09 | 2.6 |

TableS1, Haeno H et al, Cell 2011

FIG. 1B (cont.)

| | | | | | |
|---|---|---|---|---|---|
| | Yes, increase in size a | 01/27/03 | 5 | x | | |
| | No | | | Yes | 6/23/03 | 2 |
| | No | | | No | | |
| | Yes, multiple in liver | 1/4/05 | 1.4 | No | | |
| | No | | | No | | |
| | Yes, multiple in liver | 3/27/03 | 2 | Yes, increase in siz | 05/27/03 | 4.6 |
| | Yes, lungs | 2/6/04 | 0.5 | Yes | 07/06/04 | 1 |
| | no data | | | no data | | |
| | no data | | | no data | | |
| | Yes | no data | no data | x | | |
| | Yes, lungs | 12/1/05 | 0.5 | No | | |
| | no data | | | no data | | |
| | Yes, liver | 3/23/06 | 2.6 | No | | |
| Extensive (8 months) | Yes, liver | 3/23/06 | 1.9 | no data | | |
| | no data | | | no data | | |
| | No | | | No | | |
| | Yes, liver | 5/19/06 | 1 | No | | |
| | no data | | | no data | | |
| | No | | | Yes | 09/06/07 | 4 |
| | Yes, liver | 7/24/06 | 1.2 | No | | |
| | No | | | Yes | 01/04/00 | 4.7 |
| | Yes, lung | 9/14/06 | 1 | no data | | |
| | Yes, peritoneum | 5/1/06 | 1 | no data | | |
| | no data | | | no data | | |
| | Yes, multiple in liver | 8/28/07 | 7.6 | No | | |
| | no data | | | no data | | |
| | no data | | | no data | | |
| | No | | | Yes | 08/22/07 | 2.7 |
| | no data | | | no data | | |
| | no data | | | no data | | |
| | No | | | no data | | |
| | Yes, lung | 10/21/08 | 0.9 | no data | | |
| | Yes, liver | 11/8/07 | 0.8 | Yes, liver | 39450.00 | 1.5 |
| | Yes, liver and lungs | 4/14/08 | 0.9 | | | |
| | Yes, lungs | 4/8/10 | 1.2 | Yes | 3/17/09 | 2.3 |
| | | | | no data | | |
| | Yes | no data | | no data | | |

FIG. 1B (cont.)

| Date | Status | | | Count | | Val1 | Val2 |
|---|---|---|---|---|---|---|---|
| 5/26/03 | Present (Not Resected) | | | 4 | 100s to 1000s | 0.3 | 0.2-2 |
| 9/1/03 | Present (Not Resected) | | | 5 | 100s to 1000s | 0.5 | 0.2-2.0 |
| 7/5/04 | Present (Not Resected) | | | 4 | 100s to 1000s | 1.0 | 0.5-2.5 |
| 1/28/05 | Present (Not Resected) | | | 4 | 100s to 1000s | 0.5 | 0.2-1.5 |
| 2/4/05 | Present (Not Resected) | | | 7 | 100s to 1000s | 0.5 | 0.2-2.0 |
| 2/5/05 | Recurred after Surgery | 1 | | x | 100s to 1000s | 0.5 | 0.2-5.0 |
| 3/12/05 | Present (Not Resected) | | | 11 | 100s to 1000s | 0.5 | 0.2-1.5 |
| 10/20/05 | Present (Not Resected) | | | 4 | 100s to 1000s | 1.0 | 0.5-5.0 |
| 10/20/05 | Present (Not Resected) | | | 3 | 100s to 1000s | 0.3 | 0.1-1.3 |
| 3/15/06 | Recurred after Surgery | 5 | | x | 100s to 1000s | 1.0 | 0.1-4.5 |
| 4/10/06 | Present (Not Resected) | | | 5 | 100s to 1000s | 1.0 | 0.1-2.5 |
| 5/16/06 | Present (Not Resected) | | | 5 | 100s to 1000s | 1.0 | 0.1-6.0 |
| 5/29/06 | Recurred after Surgery | 2.4 | | x | 100s to 1000s | 0.7 | 0.1-3.0 |
| 7/12/06 | Present (Not Resected) | | | 6 | 100s to 1000s | 1.0 | 0.2-2.5 |
| 6/30/06 | Present (Not Resected) | | | 4 | 100s to 1000s | 1.0 | 0.2-2.5 |
| 7/18/06 | Present (Not Resected) | | | 5 | 100s to 1000s | 1.0 | 0.2-3 |
| 7/24/06 | Present (Not Resected) | | | 5 | 100s to 1000s | 1.0 | 0.2-1.5 |
| 10/2/06 | Present (Not Resected) | | | 3 | 100s to 1000s | 0.7 | 1-1.5 |
| 11/4/06 | Present (Not Resected) | | | 6 | 100s to 1000s | 1.0 | 0.1-4.0 |
| 12/5/06 | Present (Not Resected) | | | 4 | 100s to 1000s | 0.5 | 0.3-2.0 |
| 12/28/06 | Present (Not Resected) | | | 4 | 100s to 1000s | 2.0 | 1-6 |
| 4/17/07 | Recurred after Surgery | 4 | | x | 100s to 1000s | 0.8 | 0.5-1.5 |
| 4/18/07 | Absent (Resected) | | | x | 100s to 1000s | 0.5 | 0.5-1.5 |
| 4/18/07 | Present (Not Resected) | | | 9 | 100s to 1000s | 1.0 | 0.3-2.0 |
| 12/4/07 | Recurred after Surgery | 3 | | x | 100s to 1000s | 2 | 1-8 |
| 3/8/08 | Present (Not Resected) | | | 4 | 100s to 1000s | 1 | 0.5-2 |
| 5/21/08 | Present (Not Resected) | | | 4 | 100s to 1000s | 1.5 | 0.5-3 |
| 6/27/08 | Present (Not Resected) | | | 5 | 100s to 1000s | 1 | 0.2-3.0 |
| 7/16/08 | Present (Not Resected) | | | 8 | 100s to 1000s | 1.5 | 0.3-5 |
| 9/19/08 | Present (Not Resected) | | | 4 | 100s to 1000s | 1 | 0.3-3 |
| 10/16/08 | Present (Not Resected) | | | 5.5 | 100s to 1000s | 1.5 | 0.5-2.5 |
| 5/20/09 | Recurred after surgery | 4 | | x | 100s to 1000s | 1.5 | 0.5-2.5 |
| 7/8/09 | Resected (Total Pancreatectomy) | | | x | 100s to 1000s | 1 | 0.2-5.0 |
| 8/4/09 | Recurred after surgery | 3 | | x | 100s to 1000s | 1 | 0.5-2.5 |
| 4/20/10 | Present (Not resected) | x | | 7 | 100s to 1000s | 1 | 0.5-3 |
| 11/28/10 | Present (Not resected) | | | 3 | 100s to 1000s | 2.5 | 0.5-2.5 |
| 12/22/10 | Present (Not resected) | | | 3.5 | 100s to 1000s | 1.5 | 0.5-2.5 |

Extensive (8 months)

n = 101 patients

FIG. 6B

| pr_gene | pr_lmark | Signal to noise | Rank | p-value | FDR(BH) |
|---|---|---|---|---|---|
| FDPS | N | 1.3991 | 1 | 0.0003998 | 0.05364 |
| TUBB2C | N | 1.1667 | 2 | 0.0003998 | 0.05364 |
| SC4MOL | N | 1.1154 | 3 | 0.0003998 | 0.05364 |
| TAGLN2 | N | 1.1131 | 4 | 0.0003998 | 0.05364 |
| C14orf1 | N | 1.0861 | 5 | 0.0003998 | 0.05364 |
| TUBB2C | N | 1.0859 | 6 | 0.0003998 | 0.05364 |
| HMGCS1 | Y | 1.0665 | 7 | 0.0003998 | 0.05364 |
| CSNK2A1 | N | 1.0285 | 8 | 0.0003998 | 0.05364 |
| COPE | N | 1.0116 | 9 | 0.0003998 | 0.05364 |
| ---- | N | 1.0059 | 10 | 0.0003998 | 0.05364 |
| SNRPB | N | 0.9967 | 11 | 0.0003998 | 0.05364 |
| PRPS1 | N | 0.9833 | 12 | 0.0003998 | 0.05364 |
| ISOC2 | N | 0.9706 | 13 | 0.0003998 | 0.05364 |
| SDHC | N | 0.9687 | 14 | 0.0003998 | 0.05364 |
| SFRS2 | N | 0.9667 | 15 | 0.0003998 | 0.05364 |
| SNRPA1 | N | 0.9623 | 16 | 0.0003998 | 0.05364 |
| GLRX3 | N | 0.9583 | 17 | 0.0003998 | 0.05364 |
| DHCR7 | N | 0.956 | 18 | 0.0003998 | 0.05364 |
| TUBA1B | N | 0.9445 | 19 | 0.0003998 | 0.05364 |
| CYC1 | N | 0.944 | 20 | 0.0003998 | 0.05364 |
| HDGF | N | 0.9423 | 21 | 0.0003998 | 0.05364 |
| XRCC6 | N | 0.9395 | 22 | 0.0003998 | 0.05364 |
| LDLR | N | 0.9366 | 23 | 0.0003998 | 0.05364 |
| TUBB | N | 0.9171 | 24 | 0.0003998 | 0.05364 |
| SNRPE | N | 0.9088 | 25 | 0.0003998 | 0.05364 |
| HNRNPR | N | 0.9067 | 26 | 0.0003998 | 0.05364 |
| TNFRSF12A | N | 0.8938 | 27 | 0.0003998 | 0.05364 |
| GRB2 | N | 0.8913 | 28 | 0.0003998 | 0.05364 |
| ARPC4 | N | 0.8909 | 29 | 0.0007997 | 0.06797 |
| ---- | N | 0.8898 | 30 | 0.0003998 | 0.05364 |
| EIF3I | N | 0.8841 | 31 | 0.0003998 | 0.05364 |
| TCP1 | N | 0.8832 | 32 | 0.0007997 | 0.06797 |
| SFRS2 | N | 0.8757 | 33 | 0.0003998 | 0.05364 |
| TUBB3 | N | 0.8754 | 34 | 0.0003998 | 0.05364 |
| TUBA1B | N | 0.8724 | 35 | 0.0003998 | 0.05364 |
| DHCR7 | N | 0.8712 | 36 | 0.0003998 | 0.05364 |
| TUBA1B | N | 0.8611 | 37 | 0.0003998 | 0.05364 |
| TUBB | N | 0.8604 | 38 | 0.0003998 | 0.05364 |
| HPRT1 | Y | 0.8576 | 39 | 0.0003998 | 0.05364 |
| PDIA6 | N | 0.857 | 40 | 0.0003998 | 0.05364 |
| TUBA1B | N | 0.8545 | 41 | 0.0003998 | 0.05364 |
| GPR172A | N | 0.8537 | 42 | 0.0003998 | 0.05364 |
| ENO1 | N | 0.8529 | 43 | 0.0003998 | 0.05364 |
| HDGF | N | 0.8517 | 44 | 0.0003998 | 0.05364 |
| TUBB3 | N | 0.8453 | 45 | 0.0007997 | 0.06797 |
| SFRS2 | N | 0.8337 | 46 | 0.0003998 | 0.05364 |
| HNRNPH1 | N | 0.8289 | 47 | 0.0003998 | 0.05364 |
| FDFT1 | Y | 0.8283 | 48 | 0.0003998 | 0.05364 |
| EIF2S1 | N | 0.8222 | 49 | 0.0007997 | 0.06797 |
| SNRPA1 | N | 0.8206 | 50 | 0.0003998 | 0.05364 |
| RUVBL2 | N | 0.8179 | 51 | 0.0003998 | 0.05364 |
| FDFT1 | N | 0.8178 | 52 | 0.0012 | 0.07318 |
| SEC61G | N | 0.8164 | 53 | 0.0003998 | 0.05364 |
| LSM4 | N | 0.8137 | 54 | 0.0003998 | 0.05364 |
| BFAR | N | 0.8125 | 55 | 0.0003998 | 0.05364 |
| RPL37A | N | 0.81 | 56 | 0.0007997 | 0.06797 |
| ERH | N | 0.8069 | 57 | 0.0003998 | 0.05364 |
| TUBA1B | N | 0.8061 | 58 | 0.0007997 | 0.06797 |
| PFN1 | N | 0.8039 | 59 | 0.0003998 | 0.05364 |
| CCT5 | N | 0.8022 | 60 | 0.0007997 | 0.06797 |
| TMX1 | N | 0.8021 | 61 | 0.0007997 | 0.06797 |
| FKBP1A | N | 0.8018 | 62 | 0.0003998 | 0.05364 |

FIG. 6B (cont.)

| pr_gene | pr_lmark | Signal to noise | Rank | p-value | FDR(BH) |
|---|---|---|---|---|---|
| CNBP | N | 0.7984 | 63 | 0.0003998 | 0.05364 |
| PPID | N | 0.7952 | 64 | 0.0007997 | 0.06797 |
| PITPNB | N | 0.794 | 65 | 0.0003998 | 0.05364 |
| PDIA6 | N | 0.7925 | 66 | 0.0003998 | 0.05364 |
| GNE | N | 0.7921 | 67 | 0.0003998 | 0.05364 |
| FTSJ1 | N | 0.7913 | 68 | 0.0007997 | 0.06797 |
| EIF4G1 | N | 0.7892 | 69 | 0.0003998 | 0.05364 |
| PTGES3 | N | 0.787 | 70 | 0.0003998 | 0.05364 |
| IDI1 | N | 0.7806 | 71 | 0.0007997 | 0.06797 |
| DSTN | N | 0.7778 | 72 | 0.0003998 | 0.05364 |
| SUMO2 | N | 0.7775 | 73 | 0.0003998 | 0.05364 |
| IDI1 | N | 0.7761 | 74 | 0.0012 | 0.07318 |
| MAP2K2 | N | 0.7737 | 75 | 0.0007997 | 0.06797 |
| ACTN4 | N | 0.7722 | 76 | 0.0003998 | 0.05364 |
| UBE2G2 | N | 0.7698 | 77 | 0.0003998 | 0.05364 |
| PRMT5 | N | 0.7671 | 78 | 0.0007997 | 0.06797 |
| PPP4C | N | 0.7659 | 79 | 0.0003998 | 0.05364 |
| RPN2 | N | 0.7644 | 80 | 0.001599 | 0.07879 |
| FKBP1A | N | 0.7639 | 81 | 0.0012 | 0.07318 |
| TIMM17A | N | 0.7638 | 82 | 0.0003998 | 0.05364 |
| PSMD7 | N | 0.7632 | 83 | 0.0007997 | 0.06797 |
| PRPF19 | N | 0.763 | 84 | 0.0003998 | 0.05364 |
| ATP1B1 | Y | 0.7612 | 85 | 0.0003998 | 0.05364 |
| PDIA6 | N | 0.7558 | 86 | 0.0003998 | 0.05364 |
| TUBB | N | 0.7547 | 87 | 0.0003998 | 0.05364 |
| IARS | N | 0.7547 | 88 | 0.0003998 | 0.05364 |
| EBP | N | 0.7532 | 89 | 0.0003998 | 0.05364 |
| OGG1 | N | 0.7512 | 90 | 0.0003998 | 0.05364 |
| PCAM1 | Y | 0.7444 | 91 | 0.0007997 | 0.06797 |
| CACYBP | N | 0.7434 | 92 | 0.0007997 | 0.06797 |
| CRK | Y | 0.7429 | 93 | 0.0003998 | 0.05364 |
| HMGCS1 | N | 0.7418 | 94 | 0.0007997 | 0.06797 |
| HN1 | N | 0.7414 | 95 | 0.0012 | 0.07318 |
| FXR1 | N | 0.7412 | 96 | 0.0003998 | 0.05364 |
| --- | N | 0.7407 | 97 | 0.0003998 | 0.05364 |
| GLRX3 | N | 0.7396 | 98 | 0.0003998 | 0.05364 |
| HNRNPR | N | 0.7378 | 99 | 0.0007997 | 0.06797 |
| TAGLN2 | N | 0.7378 | 100 | 0.0003998 | 0.05364 |
| DST | N | -0.7144 | 22169 | 0.001199 | 0.07318 |
| CD180 | N | -0.7147 | 22170 | 0.001199 | 0.07318 |
| UBXN6 | N | -0.7149 | 22171 | 0.001199 | 0.07318 |
| MYST3 | Y | -0.7156 | 22172 | 0.0003998 | 0.05364 |
| CAMTA2 | N | -0.718 | 22173 | 0.001599 | 0.07879 |
| FAM125B | N | -0.7191 | 22174 | 0.0007997 | 0.06797 |
| ZBTB10 | N | -0.7196 | 22175 | 0.0003998 | 0.05364 |
| KIAA0467 | N | -0.7196 | 22176 | 0.001199 | 0.07318 |
| --- | N | -0.7201 | 22177 | 0.003199 | 0.09227 |
| RPA4 | N | -0.7213 | 22178 | 0.0007997 | 0.06797 |
| TGM3 | N | -0.7226 | 22179 | 0.0007997 | 0.06797 |
| TP53TG1 | N | -0.7235 | 22180 | 0.001199 | 0.07318 |
| FGD1 | N | -0.7237 | 22181 | 0.0007997 | 0.06797 |
| CREBL2 | N | -0.7253 | 22182 | 0.0007997 | 0.06797 |
| EIF3M | N | -0.7259 | 22183 | 0.0007997 | 0.06797 |
| RNF8 | N | -0.7276 | 22184 | 0.0007997 | 0.06797 |
| PAOX | N | -0.7285 | 22185 | 0.001199 | 0.07318 |
| TNFRSF25 | N | -0.7289 | 22186 | 0.0007997 | 0.06797 |
| BIRC3 | N | -0.7294 | 22187 | 0.0003998 | 0.05364 |
| FRAT1 | N | -0.7295 | 22188 | 0.001199 | 0.07318 |
| FAM172A | N | -0.7302 | 22189 | 0.001199 | 0.07318 |
| ANO3 | N | -0.7322 | 22190 | 0.0007997 | 0.06797 |
| CDK19 | N | -0.7323 | 22191 | 0.001599 | 0.07879 |
| --- | N | -0.733 | 22192 | 0.001199 | 0.07318 |
| TBPL1 | Y | -0.733 | 22193 | 0.0007997 | 0.06797 |

FIG. 6B (cont.)

| pr_gene | pr_lmark | Signal to noise | Rank | p-value | FDR(BH) |
|---|---|---|---|---|---|
| SPATA2 | N | -0.7353 | 22194 | 0.0003998 | 0.05364 |
| --- | N | -0.7372 | 22195 | 0.0003998 | 0.05364 |
| WWP1 | N | -0.7391 | 22196 | 0.0007997 | 0.06797 |
| IGK@ /// IGKC /// LOC652493 /// LOC652694 | N | -0.741 | 22197 | 0.001199 | 0.07318 |
| LTBP4 | N | -0.7411 | 22198 | 0.001199 | 0.07318 |
| SMC6 | N | -0.7416 | 22199 | 0.001199 | 0.07318 |
| CCDC91 | N | -0.7443 | 22200 | 0.0007997 | 0.06797 |
| CTF1 | N | -0.7444 | 22201 | 0.0007997 | 0.06797 |
| BAHD1 | N | -0.7458 | 22202 | 0.001199 | 0.07318 |
| HTATIP2 | N | -0.7469 | 22203 | 0.0003998 | 0.05364 |
| ANKRD36B | N | -0.7474 | 22204 | 0.001199 | 0.07318 |
| ZFYVE26 | N | -0.7475 | 22205 | 0.0007997 | 0.06797 |
| MTMR15 | N | -0.7489 | 22206 | 0.0007997 | 0.06797 |
| SGSM2 | N | -0.7492 | 22207 | 0.0007997 | 0.06797 |
| FEM1B | N | -0.7497 | 22208 | 0.0003998 | 0.05364 |
| SEMA4C | N | -0.7503 | 22209 | 0.0007997 | 0.06797 |
| PARP3 | N | -0.7506 | 22210 | 0.0003998 | 0.05364 |
| HDDC2 | N | -0.7515 | 22211 | 0.001599 | 0.07879 |
| HCG26 | N | -0.7521 | 22212 | 0.0007997 | 0.06797 |
| MATN4 | N | -0.7544 | 22213 | 0.001199 | 0.07318 |
| MPPE1 | N | -0.7604 | 22214 | 0.0007997 | 0.06797 |
| KLHL22 | N | -0.7619 | 22215 | 0.0003998 | 0.05364 |
| ACVR1 | N | -0.7624 | 22216 | 0.001199 | 0.07318 |
| FLJ10213 | N | -0.7625 | 22217 | 0.0007997 | 0.06797 |
| PHC1 | N | -0.763 | 22218 | 0.0003998 | 0.05364 |
| SPG11 | N | -0.768 | 22219 | 0.0003998 | 0.05364 |
| NAALADL1 | N | -0.769 | 22220 | 0.0007997 | 0.06797 |
| PTGER1 | N | -0.7691 | 22221 | 0.0007997 | 0.06797 |
| EML3 | N | -0.7721 | 22222 | 0.0003998 | 0.05364 |
| NCRNA00185 | N | -0.7727 | 22223 | 0.0003998 | 0.05364 |
| TBX2 | N | -0.7729 | 22224 | 0.0007997 | 0.06797 |
| TNFRSF14 | N | -0.7794 | 22225 | 0.0003998 | 0.05364 |
| CTNNBL1 | N | -0.7856 | 22226 | 0.0003998 | 0.05364 |
| TBC1D13 | N | -0.7886 | 22227 | 0.0003998 | 0.05364 |
| C6orf26 /// MSH5 | N | -0.7897 | 22228 | 0.0003998 | 0.05364 |
| TBX2 | Y | -0.7898 | 22229 | 0.0007997 | 0.06797 |
| PLCB2 | N | -0.7955 | 22230 | 0.0003998 | 0.05364 |
| ERCC6 | N | -0.7957 | 22231 | 0.0003998 | 0.05364 |
| MAGEA11 | N | -0.7966 | 22232 | 0.0007997 | 0.06797 |
| PLAG1 | N | -0.797 | 22233 | 0.0003998 | 0.05364 |
| VAMP2 | N | -0.797 | 22234 | 0.0007997 | 0.06797 |
| SLC24A1 | N | -0.7992 | 22235 | 0.0007997 | 0.06797 |
| B859 | N | -0.8048 | 22236 | 0.0007997 | 0.06797 |
| KIAA0495 | N | -0.8049 | 22237 | 0.0003998 | 0.05364 |
| SYNJ1 | N | -0.8055 | 22238 | 0.0003998 | 0.05364 |
| FAM193A | N | -0.806 | 22239 | 0.0003998 | 0.05364 |
| C14orf159 | N | -0.8104 | 22240 | 0.0003998 | 0.05364 |
| LTBP1 | N | -0.8127 | 22241 | 0.0003998 | 0.05364 |
| --- | N | -0.8162 | 22242 | 0.0003998 | 0.05364 |
| FES | N | -0.8204 | 22243 | 0.0007997 | 0.06797 |
| ULK1 | N | -0.8236 | 22244 | 0.0003998 | 0.05364 |
| ABCC10 | N | -0.8239 | 22245 | 0.0003998 | 0.05364 |
| NYNRIN | N | -0.8275 | 22246 | 0.0003998 | 0.05364 |
| UST | N | -0.8282 | 22247 | 0.0003998 | 0.05364 |
| TNX8 | N | -0.8323 | 22248 | 0.0003998 | 0.05364 |
| ZNF282 | N | -0.8325 | 22249 | 0.0003998 | 0.05364 |
| MPZL1 | N | -0.836 | 22250 | 0.0003998 | 0.05364 |
| SCN1B | N | -0.8423 | 22251 | 0.0003998 | 0.05364 |
| RAGE | Y | -0.8424 | 22252 | 0.001199 | 0.07318 |
| FLJ38109 | N | -0.8446 | 22253 | 0.0003998 | 0.05364 |
| ZFYVE16 | N | -0.8458 | 22254 | 0.0003998 | 0.05364 |
| MED13L | N | -0.8462 | 22255 | 0.0003998 | 0.05364 |
| CA12 | N | -0.8471 | 22256 | 0.0003998 | 0.05364 |

FIG. 6B (cont.)

| pr_gene | pr_lmark | Signal to noise | Rank | p-value | FDR(BH) |
|---|---|---|---|---|---|
| TRAPPC10 | N | -0.8513 | 22257 | 0.0003998 | 0.05364 |
| LOC644172 /// MAPK8IP1 | N | -0.8527 | 22258 | 0.0003998 | 0.05364 |
| --- | N | -0.8537 | 22259 | 0.0003998 | 0.05364 |
| FTSJD2 | N | -0.8584 | 22260 | 0.0003998 | 0.05364 |
| IGK@ /// IGKC /// LOC652493 | N | -0.8635 | 22261 | 0.0003998 | 0.05364 |
| LOC100287723 /// LOC642424 /// LOC642838 | N | -0.8832 | 22262 | 0.0003998 | 0.05364 |
| EFS | N | -0.8878 | 22263 | 0.0003998 | 0.05364 |
| ZMYND8 | N | -0.9066 | 22264 | 0.0003998 | 0.05364 |
| SLC11A2 | Y | -0.9367 | 22265 | 0.0003998 | 0.05364 |
| PLEKHA5 | N | -0.9577 | 22266 | 0.0003998 | 0.05364 |
| TTC39A | N | -1.0419 | 22267 | 0.0003998 | 0.05364 |
| RALGAPA1 | N | -1.2524 | 22268 | 0.0003998 | 0.05364 |

FIG. 9A
FIG. 9B
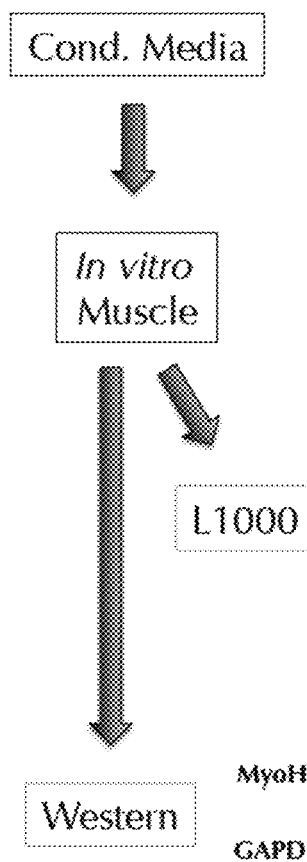
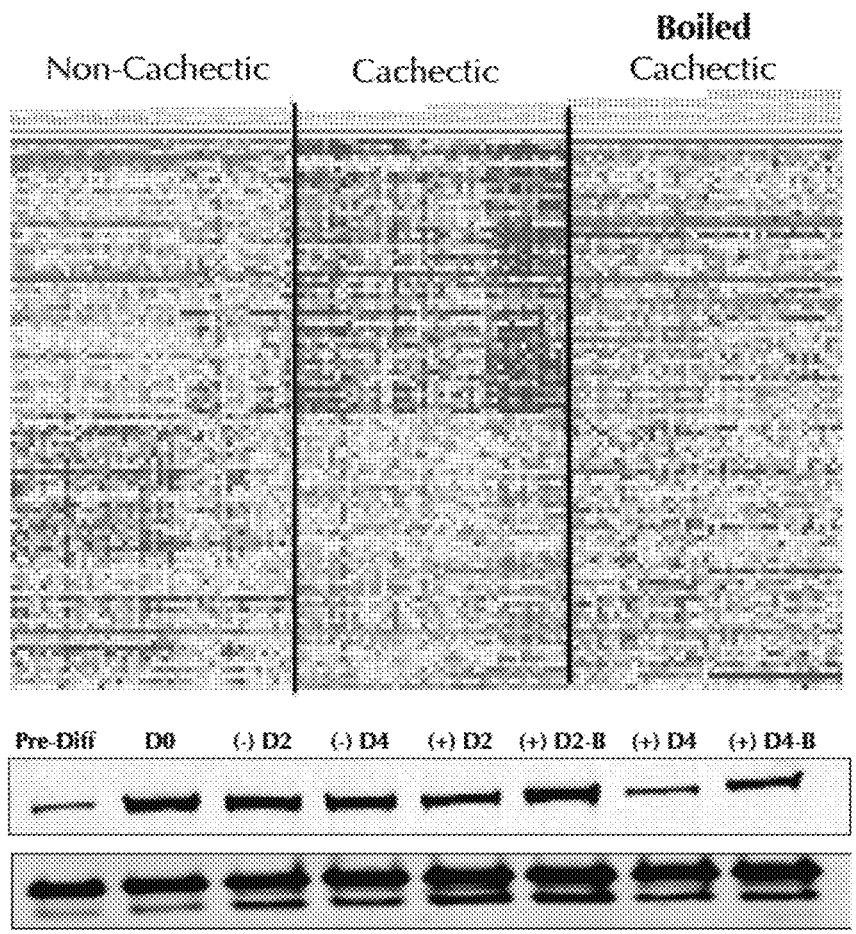
FIG. 9C

FIG. 14A

| group | entry_name | species | protein_mw | 293T numSpectra | 293T totalIntensity |
|---|---|---|---|---|---|
| 71 | Titin | HUMAN | 4014332.4 | 2 | 2.04E+09 |
| 4 | Desmoplakin | HUMAN | 334221.3 | 23 | 2.91E+09 |
| 12 | Hornerin | HUMAN | 283297.9 | 9 | 5.86E+09 |
| 13 | Filaggrin-2 | HUMAN | 249437.6 | 7 | 2.32E+09 |
| 7 | Myosin-1 | HUMAN | 224111.4 | | 0.00E+00 |
| 96 | Probable helicase with zinc finger domain | HUMAN | 220821.6 | | 1.66E+07 |
| 51 | Golgin subfamily A member 3 | HUMAN | 167865.2 | 2 | 3.42E+10 |
| 39 | Collagen alpha-1(I) chain | HUMAN | 139966 | 3 | 5.55E+08 |
| 22 | Collagen alpha-1(III) chain | HUMAN | 139817 | 9 | 1.90E+10 |
| 11 | Desmoglein-1 | HUMAN | 114772.6 | 8 | 7.66E+08 |
| 18 | Desmocollin-1 | HUMAN | 101468.4 | 4 | 5.17E+08 |
| 36 | Plakophilin-1 | HUMAN | 84171.4 | 3 | 2.19E+08 |
| 38 | Polyubiquitin-C | HUMAN | 77037.2 | 2 | 4.54E+08 |
| 16 | Protein-glutamine gamma-glutamyltransferase E | HUMAN | 76972.8 | 6 | 4.42E+08 |
| 33 | Catalase | HUMAN | 59983.3 | 3 | 1.11E+08 |
| 59 | Probable Xaa-Pro aminopeptidase 3 | HUMAN | 57660.2 | 2 | 5.35E+09 |
| 86 | Hyccin (Fragment) | HUMAN | 52835.4 | | 2.83E+09 |
| 68 | Transcriptional adapter 2-beta | HUMAN | 49040 | 2 | 2.18E+10 |
| 21 | Actin, aortic smooth muscle | HUMAN | 42407.6 | 3 | 3.10E+08 |
| 57 | Isoform 2 of Annexin A2 | HUMAN | 40695.7 | 2 | 4.66E+07 |
| 46 | Vesicular integral-membrane protein VIP36 | HUMAN | 40570.3 | 2 | 5.62E+08 |
| 6 | L-lactate dehydrogenase B chain | HUMAN | 36923.1 | 22 | 3.29E+10 |
| 15 | Glyceraldehyde-3-phosphate dehydrogenase | HUMAN | 36223.7 | 6 | 7.14E+08 |
| 27 | Isoform 2 of Heterogeneous nuclear ribonucleoprotein A/B | HUMAN | 36081 | 4 | 1.27E+09 |
| 74 | DNA-(apurinic or apyrimidinic site) lyase | HUMAN | 35953.2 | 2 | 3.64E+08 |
| 45 | Isoform 2 of Arginase-1 | HUMAN | 35834.6 | 3 | 3.55E+08 |
| 65 | Stanniocalcin-2 | HUMAN | 34108.8 | 2 | 6.93E+08 |
| 63 | Inorganic pyrophosphatase | HUMAN | 33115.9 | 2 | 1.23E+08 |
| 37 | Isoform 4 of Tropomyosin alpha-1 chain | HUMAN | 32613.5 | | 0.00E+00 |
| 44 | N(G),N(G)-dimethylarginine dimethylaminohydrolase 1 | HUMAN | 31463.6 | 2 | 6.77E+08 |
| 103 | Cathepsin G | HUMAN | 28179 | 2 | 2.23E+10 |
| 20 | Caspase-14 | HUMAN | 27964.3 | 5 | 1.39E+09 |
| 41 | Insulin-like growth factor-binding protein 6 | HUMAN | 26234.9 | | 0.00E+00 |
| 49 | Peroxiredoxin-1 | HUMAN | 22338.2 | 2 | 1.34E+07 |
| 29 | Myosin light chain 1/3, skeletal muscle isoform | HUMAN | 21201.8 | | 0.00E+00 |
| 35 | Prolactin-inducible protein | HUMAN | 16857.4 | 2 | 5.07E+08 |
| 32 | Calmodulin-like protein 5 | HUMAN | 15892.2 | 2 | 7.14E+08 |
| 47 | Galectin-7 | HUMAN | 15131.8 | 2 | 1.51E+07 |
| 53 | Protein S100-A9 | HUMAN | 13298.8 | 2 | 1.81E+08 |
| 55 | Thioredoxin | HUMAN | 12022.6 | 2 | 1.03E+08 |
| 66 | Protein S100-A7 | HUMAN | 11584.9 | | 0.00E+00 |
| 23 | Dermcidin | HUMAN | 11397.8 | 3 | 4.27E+09 |
| 25 | Cystatin-A | HUMAN | 11006.3 | 2 | 1.11E+08 |
| 64 | Protein S100 A8 | HUMAN | 10831.4 | | 0.00E+00 |

FIG. 14A (cont.)

| G361 numSpectra | G361 totalIntensity | MXN1 numSpectra | MXN1 totalIntensity | accession_number | accession_numbers | percent Coverage | numPeps Unique | score Unique |
|---|---|---|---|---|---|---|---|---|
| | 2.15E+06 | | 0.00E+00 | K7ENY1 | K7ENY1|Q8 | 0 | 2 | 10.37 |
| 23 | 2.18E+09 | 2 | 9.77E+07 | P15924 | P15924|P1! | 13.5 | 34 | 304.27 |
| 6 | 1.28E+09 | 6 | 8.77E+08 | Q86YZ3 | Q86YZ3 | 4.2 | 7 | 103.2 |
| 6 | 7.35E+08 | 2 | 1.65E+08 | Q5D862 | Q5D862 | 3.5 | 6 | 74.73 |
| | 0.00E+00 | 19 | 2.87E+09 | P12882 | P12882|Q8 | 9.9 | 15 | 146.98 |
| 2 | 1.02E+08 | | 2.20E+08 | J3QS41 | J3QS41|P4; | 1 | 1 | 7.16 |
| | 0.00E+00 | | 1.48E+09 | Q08378 | Q08378 | 0.8 | 2 | 15.91 |
| | 0.00E+00 | | 9.78E+06 | P02452 | P02452|Q8 | 2.2 | 3 | 23.34 |
| 6 | 4.01E+09 | 3 | 7.77E+08 | P02461 | P02461|E7! | 2.5 | 3 | 38.54 |
| 6 | 4.11E+08 | 2 | 4.90E+07 | Q02413 | Q02413|87 | 14.1 | 9 | 104.6 |
| 4 | 7.34E+08 | | 1.90E+07 | Q08554 | Q08554|QC | 8 | 5 | 45.14 |
| | 2.60E+06 | | 0.00E+00 | Q13835 | Q13835|Q1 | 4.9 | 3 | 25.33 |
| 2 | 1.89E+08 | 2 | 1.88E+08 | P0CG48 | P0CG48|F5 | 3.6 | 2 | 24.08 |
| 2 | 1.02E+07 | | 5.93E+06 | Q08188 | Q08188 | 10.1 | 6 | 52.53 |
| | 0.00E+00 | | 0.00E+00 | P04040 | P04040 | 7.4 | 3 | 28.98 |
| | 7.13E+09 | | 7.50E+08 | Q9NQH7 | Q9NQH7|Q | 3.1 | 1 | 12.53 |
| | 2.10E+09 | 2 | 3.94E+09 | H7C0W7 | H7C0W7|B! | 3.1 | 1 | 8.01 |
| 2 | 1.07E+10 | 2 | 2.56E+09 | Q86TJ2 | Q86TJ2|Q8 | 1.6 | 1 | 10.94 |
| | 2.42E+07 | 5 | 1.54E+09 | P62736 | P62736|P6! | 20.9 | 5 | 39.05 |
| | 2.70E+07 | | 0.00E+00 | P07355-2 | P07355-2|F | 6.1 | 2 | 13.02 |
| | 0.00E+00 | | 0.00E+00 | Q12907 | Q12907|D6 | 8.7 | 2 | 18.93 |
| 4 | 2.65E+08 | | 0.00E+00 | P07195 | P07195|A8! | 36.5 | 14 | 157.61 |
| 4 | 3.07E+08 | 4 | 8.28E+08 | P04406 | P04406|E7! | 26.2 | 5 | 56.7 |
| | 0.00E+00 | | 0.00E+00 | Q99729-2 | Q99729-2|! | 12.9 | 4 | 33.67 |
| | 0.00E+00 | | 0.00E+00 | P27695 | P27695|G3 | 7.5 | 2 | 9.36 |
| | 0.00E+00 | | 0.00E+00 | P05089-2 | P05089-2|F | 12.4 | 3 | 19.34 |
| | 0.00E+00 | | 0.00E+00 | O76061 | O76061|H0 | 5.6 | 2 | 11.71 |
| | 0.00E+00 | | 0.00E+00 | Q15181 | Q15181|Q5 | 8.6 | 2 | 11.91 |
| | 0.00E+00 | | 1.35E+08 | | | 13.1 | 3 | 35.5 |
| | 0.00E+00 | | 0.00E+00 | O94760 | O94760 | 6.6 | 2 | 19.9 |
| 3 | 5.77E+09 | 2 | 8.16E+09 | P08311 | P08311 | 12.1 | 1 | 6.99 |
| 3 | 3.17E+08 | 2 | 2.01E+08 | P31944 | P31944 | 17.7 | 4 | 42.34 |
| | 4.54E+08 | | 0.00E+00 | P24592 | P24592|P8! | 10.4 | 2 | 22.78 |
| | 3.14E+07 | | 0.00E+00 | Q06830 | Q06830 | 15.5 | 3 | 17.29 |
| | 0.00E+00 | 3 | 3.64E+08 | P05976 | P05976|P9 | 14.4 | 3 | 30.88 |
| | 1.57E+08 | 2 | 2.56E+08 | P12273 | P12273 | 15 | 3 | 26.67 |
| 2 | 5.84E+07 | 2 | 4.49E+07 | Q9NZT1 | Q9NZT1 | 9.5 | 2 | 29.04 |
| | 1.85E+07 | | 1.31E+07 | P47929 | P47929 | 18.3 | 2 | 18.39 |
| | 1.24E+07 | | 0.00E+00 | P06702 | P06702 | 19.2 | 2 | 14.07 |
| | 7.65E+06 | | 0.00E+00 | P10599 | P10599|B1 | 22.8 | 2 | 13.18 |
| 2 | 4.31E+07 | | 3.53E+07 | P31151 | P31151|Q8 | 21.7 | 2 | 11.52 |
| 4 | 3.59E+09 | 4 | 2.25E+09 | P81605 | P81605|P8 | 32.7 | 3 | 38.33 |
| 4 | 1.62E+08 | 3 | 7.85E+07 | P01040 | P01040|CQ; | 38.7 | 3 | 35.12 |
| 2 | 1.88E+08 | | 0.00E+00 | P05109 | P05109 | 13.9 | 2 | 11.84 |

Competition for ligands using soluble RAGE

In-cell Western
MyoHC : Sarc a Actin

*In vitro* cachectic adipocytes up-regulate relevant metabolic gene networks
ABHD5 *activates* Adipocyte Triacyl Glyceride Lipase genetic (L-o-F/ G-o-F) and proteomic (depletion/ repletion) perturbations captured in human target cells and tracked by genome-scale readouts

Fig. 3. Electrostatics properties of the hRAGE VC1 dimer formed through crystal contacts.
Yatime L, Andersen GR, FEBS J, 2013 m*KRAS*$^{G12D}$ / p53$^{-/-}$ Mouse Model of Lung Cancer: Uninduced mice

No tumor burden, therefore normal weight gain m$KRAS^{G12D}$ / p53$^{-/-}$ Mouse Model of Lung Cancer
Majority of induced mice become cachectic m*KRAS* / p53del Mouse Model of Lung Cancer 7 weeks post induction

**m*KRAS* / p53del Mouse Model of Lung Cancer 10 weeks post induction**

Expression levels of RAGE ligands in TCGA data (unsupervised hierarchical clustering)

Melanoma

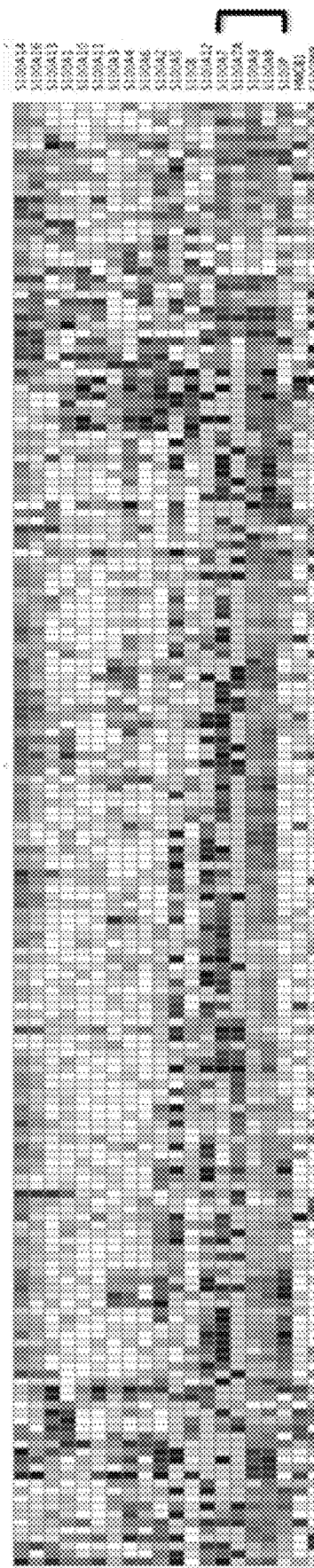
FIG. 41B Breast

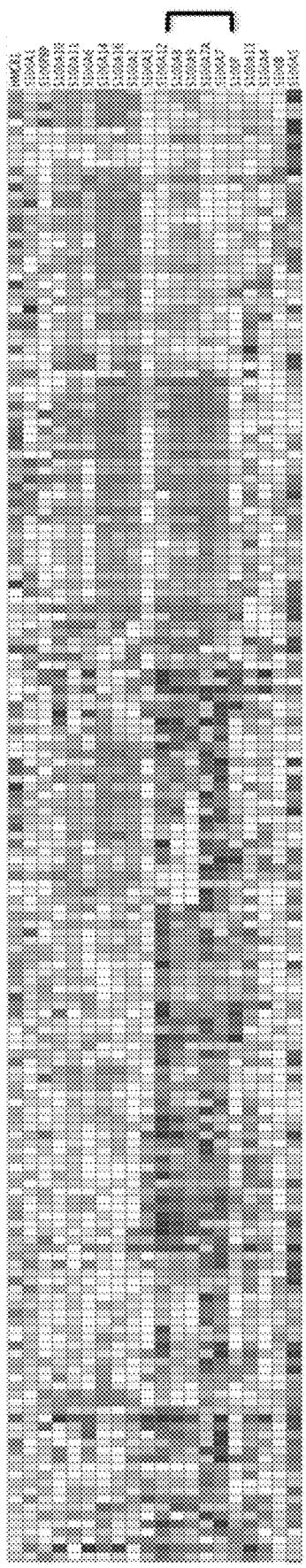
FIG. 41C  *Lung Squam

FIG. 51

Expression of S100 family in the cachexia inducing and non-inducing cancer cell lines Top Scoring Gene Sets with
S100A8 TCGA Pan-Cancer Gene Signature Up Signature

*Table: Snapshot of enrichment results*

Top Scoring Gene Sets with
S100A8 TCGA Pan-Cancer Gene Signature

Down Signature

*Table: Snapshot of enrichment results*

Top Scoring Gene Sets with
S100A8 TCGA Breast Cancer Gene Signature

Up Signature

*Table: Snapshot of enrichment results*

Top Scoring Gene Sets with
S100A8 TCGA Breast Cancer Gene Signature

Down Signature

*Table: Snapshot of enrichment results*

FIG. 53A m*KRAS*$^{G12D}$ / p53-/- Model of Lung Cancer Cachexia: Potential *in vivo* treatment trials 1. anti-mouse RAGE mAB
   e.g. rat anti-mouse RAGE (minimize anti-Ab response)
   not many related species Ab's, epitope, expense, 2. Recombinant soluble RAGE (i.p.)
   human vs mouse rsRAGE
   $T_{1/2}$ issues – dimer/ chimera 3. MEK/ ERK inhibitors (p.o.)
   e.g. Trametinib (*dose sensitive*)

4. Other small molecule candidates

5. Biomarker discovery
   diagnostic, pharmacodynamic, functional

FIG. 53B

Production of recombinant sRAGE for affinity isolation of ligands and *in vivo* treatments

| Summary Information | |
|---|---|
| Expression scale | 1.0 liter |
| Enrichment | mAbSelect |
| Protein Conc. (mg/ml) | 1.00 mg/ml |
| Total Volume (ml) | 8.65 mL |
| Aliquot Size | 8x1.0 mL<br>1x0.65 mL |
| Buffer information | 20 mM MES, pH 6.5 100 mM NaCl 40 mM $CaCl_2$ |
| Storage Temperature (°C) | 4°C |
| Purity (%) | 76% |
| Endotoxin | <0.512 EU/mL |

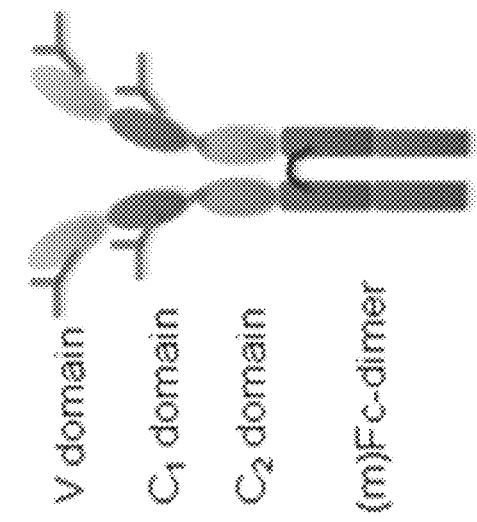

rsRAGE-Fc chimera

V domain
$C_1$ domain
$C_2$ domain
(m)Fc-dimer

```
                        SEQUENCE LISTING

<160> NUMBER OF SEQ ID NOS: 10

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 576
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Ala Gly Thr Ala Val Gly Ala Trp Val Leu Val Leu Ser Leu
1               5                   10                  15

Trp Gly Ala Val Val Gly Ala Gln Asn Ile Thr Ala Arg Ile Gly Glu
            20                  25                  30

Pro Leu Val Leu Lys Cys Lys Gly Ala Pro Lys Lys Pro Pro Gln Arg
        35                  40                  45

Leu Glu Trp Lys Leu Asn Thr Gly Arg Thr Glu Ala Trp Lys Val Leu
    50                  55                  60

Ser Pro Gln Gly Gly Pro Trp Asp Ser Val Ala Arg Val Leu Pro
65                  70                  75                  80

Asn Gly Ser Leu Phe Leu Pro Ala Val Gly Ile Gln Asp Glu Gly Ile
                85                  90                  95

Phe Arg Cys Gln Ala Met Asn Arg Asn Gly Lys Glu Thr Lys Ser Asn
            100                 105                 110

Tyr Arg Val Arg Val Tyr Gln Ile Pro Gly Lys Pro Glu Ile Val Asp
        115                 120                 125

Ser Ala Ser Glu Leu Thr Ala Gly Val Pro Asn Lys Val Gly Thr Cys
    130                 135                 140

Val Ser Glu Gly Ser Tyr Pro Ala Gly Thr Leu Ser Trp His Leu Asp
145                 150                 155                 160

Gly Lys Pro Leu Val Pro Asn Glu Lys Gly Val Ser Val Lys Glu Gln
                165                 170                 175
```

```
Thr Arg Arg His Pro Glu Thr Gly Leu Phe Thr Leu Gln Ser Glu Leu
            180                 185                 190

Met Val Thr Pro Ala Arg Gly Gly Asp Pro Arg Pro Thr Phe Ser Cys
            195                 200                 205

Ser Phe Ser Pro Gly Leu Pro Arg His Arg Ala Leu Arg Thr Ala Pro
            210                 215                 220

Ile Gln Pro Arg Val Trp Glu Pro Val Pro Leu Glu Glu Val Gln Leu
225                 230                 235                 240

Val Val Glu Pro Glu Gly Gly Ala Val Ala Pro Gly Gly Thr Val Thr
            245                 250                 255

Leu Thr Cys Glu Val Pro Ala Gln Pro Ser Pro Gln Ile His Trp Met
            260                 265                 270

Lys Asp Gly Val Pro Leu Pro Leu Pro Pro Ser Pro Val Leu Ile Leu
            275                 280                 285

Pro Glu Ile Gly Pro Gln Asp Gln Gly Thr Tyr Ser Cys Val Ala Thr
            290                 295                 300

His Ser Ser His Gly Pro Gln Glu Ser Arg Ala Val Ser Ile Ser Ile
305                 310                 315                 320

Ile Glu Pro Gly Glu Glu Gly Pro Thr Ala Gly Ser Val Gly Gly Ser
            325                 330                 335

Gly Leu Gly Thr Leu Ala Leu Ala Pro Arg Gly Pro Thr Ile Lys Pro
            340                 345                 350

Cys Pro Pro Cys Lys Cys Pro Ala Pro Asn Leu Leu Gly Gly Pro Ser
            355                 360                 365

Val Phe Ile Phe Pro Pro Lys Ile Lys Asp Val Leu Met Ile Ser Leu
            370                 375                 380

Ser Pro Ile Val Thr Cys Val Val Val Asp Val Ser Glu Asp Asp Pro
385                 390                 395                 400

Asp Val Gln Ile Ser Trp Phe Val Asn Asn Val Glu Val His Thr Ala
            405                 410                 415

Gln Thr Gln Thr His Arg Glu Asp Tyr Asn Ser Thr Leu Arg Val Val
            420                 425                 430

Ser Ala Leu Pro Ile Gln His Gln Asp Trp Met Ser Gly Lys Glu Phe
            435                 440                 445

Lys Cys Lys Val Asn Asn Lys Asp Leu Pro Ala Pro Ile Glu Arg Thr
            450                 455                 460

Ile Ser Lys Pro Lys Gly Ser Val Arg Ala Pro Gln Val Tyr Val Leu
465                 470                 475                 480

Pro Pro Pro Glu Glu Glu Met Thr Lys Lys Gln Val Thr Leu Thr Cys
            485                 490                 495

Met Val Thr Asp Phe Met Pro Glu Asp Ile Tyr Val Glu Trp Thr Asn
            500                 505                 510

Asn Gly Lys Thr Glu Leu Asn Tyr Lys Asn Thr Glu Pro Val Leu Asp
            515                 520                 525

Ser Asp Gly Ser Tyr Phe Met Tyr Ser Lys Leu Arg Val Glu Lys Lys
            530                 535                 540

Asn Trp Val Glu Arg Asn Ser Tyr Ser Cys Ser Val Val His Glu Gly
545                 550                 555                 560

Leu His Asn His His Thr Thr Lys Ser Phe Ser Arg Thr Pro Gly Lys
            565                 570                 575
```

```
<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: K or R
<220> FEATURE:
<221> NAME/KEY: MOD_RES
<222> LOCATION: (9)..(9)
<223> OTHER INFORMATION: P or T
<220> FEATURE:
<221> NAME/KEY: MOD_RES
<222> LOCATION: (11)..(11)
<223> OTHER INFORMATION: Q, R, or K

<400> SEQUENCE: 3

Cys Xaa Gly Ala Pro Lys Lys Pro Xaa Gln Xaa Leu Glu
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Arg Gly Ala Pro Lys Lys Pro Pro Gln Gln Leu Glu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Lys Gly Ala Pro Lys Lys Pro Pro Gln Arg Leu Glu
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Lys Gly Ala Pro Lys Lys Pro Thr Gln Lys Leu Glu
1               5                   10

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 7

Asp Gly Lys Pro Leu Val Pro Asn Glu Lys Gly Val Ser Val Lys Glu
1               5                   10                  15

Gln Thr Arg Arg His Pro Glu Thr Gly Leu Phe Thr Leu Gln
                20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Thr Leu Gln Ser Glu Leu Met Val Thr Pro Ala Arg Gly Gly Asp Pro
1               5                   10                  15

Arg Pro Thr Phe Ser Cys Ser Phe Ser Pro Gly Leu Pro Arg
                20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Pro Arg His Arg Ala Leu Arg Thr Ala Pro Ile Gln Pro Arg Val
1               5                   10                  15

Trp Glu Pro Val Pro Leu Glu Glu Val Gln Leu Val Val Glu
                20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Leu Lys Val Leu Met Glu Lys Glu Leu
1               5                   10
```

METHODS FOR IDENTIFYING AND TREATING CACHEXIA OR PRE-CACHEXIA USING AN INHIBITOR OF RAGE

CROSS REFERENCE TO RELATED APPLICATIONS

This application is a divisional of application of U.S. Ser. No. 15/101,865, filed on Jun. 3, 2016, now U.S. Pat. No. 10,191,033, issued Jan. 29, 2019, which is a national stage entry under 35 U.S.C. § 371 of International PCT Application No. PCT/US14/68631, filed on Dec. 4, 2014, which claims and priority to and benefit of U.S. Provisional Application No. 61/994,677, filed on May 16, 2014; 61/949,139, filed on Mar. 6, 2014; and 61/912,338, filed on Dec. 5, 2013, the contents of all of which are incorporated herein by reference in their entireties.

SEQUENCE LISTING

The application contains a Sequence Listing which has been submitted electronically in ASCII format and is hereby incorporated by reference in its entirety. The ASCII copy, created on Aug. 4, 2020, is named 167741.011610US_SL.txt and is 8,455 bytes in size.

STATEMENT REGARDING FEDERALLY SPONSORED RESEARCH OR DEVELOPMENT

This invention was made with government support under Grant Number CA190101 awarded by the National Institutes of Health. The government has certain rights in the invention.

BACKGROUND OF THE INVENTION

Cachexia is a wasting syndrome associated with chronic diseases. Cachexia is defined as weight loss exceeding 5% within the previous 3-12 months, combined with fatigue, loss of skeletal muscle, and biochemical abnormalities (e.g., anemia or insulin resistance). Cancer-induced cachexia (CIC) is experienced by up to 80% of patients with advanced stage cancer, particularly those with gastrointestinal, pancreatic, thoracic and head and neck malignancies. CIC has been implicated in up to 25% of cancer-related deaths. Despite interventions such as total parenteral nutrition (complete daily intervenous nutrition), anti-inflammatory medications, and anabolic stimulation, a patient with cancer-induced cachexia will continue to lose weight, often becoming so frail that they are unable to receive anti-cancer therapies. This distinguishes CIC from other forms of cachexia, which may respond to nutrition supplementation coupled with anti-inflammatory therapy.

Despite being common in many solid tumour cancers, cachexia remains poorly studied, under-diagnosed and a largely untreated complication that predisposes patients to in increased mortality. Treatment approaches for CIC, including anabolic steroids, anti-catabolic therapies, appetite stimulants, and nutritional interventions, have failed to show significant efficacy. In fact, once established, no therapeutic approach has been able to reverse cancer-induced cachexia. Moreover, no diagnostic for CIC is available; rather clinicians are forced to rely on a description of clinical changes observed in patients with advanced disease.

Accordingly, methods for identifying patients before they meet the clinical criteria for cachexia, i.e., when they are pre-cachectic, are urgently required, as well as therapeutic methods for disrupting the patient's progression from pre-cachexia to cachexia.

SUMMARY OF THE INVENTION

The invention generally provides markers indicative of pre-cachexia and/or cachexia, compositions and methods for identifying patients with a molecular signature indicative of pre-cachexia and/or cachexia; a culture system that reproduces the cachetic process in cells in vitro, which facilitates the screening and identification of therapeutic agents useful for disrupting (slowing, reducing, reversing, or preventing) the progression of pre-cachexia to cachexia; as well as therapeutic agents identified using the culture system of the invention.

In one aspect, the invention generally features a culture system containing a cachexia-inducing factor and a target cell that is any one or more of myocytes, adipocytes, and hepatocytes. In one embodiment, the cachexia-inducing factor is present in plasma obtained from a cachexic subject or a subject with pre-cachexia. In another embodiment, the cachexia-inducing factor is present in conditioned media derived from a human cancer cell or cell line identified as cachexia-inducing. In another embodiment, the cancer cell is any cancer cell or cell line from which conditioned media can be generated. In another embodiment, the cancer is selected from an epithelial-derived cancer or a mesenchymal-derived cancer. In another embodiment, the cancer is that is any one or more of carcinomas and sarcomas and cancers of the skin, pancreas, stomach, colon, thorax, liver, gallbladder, musculoskeletal system, breast, lung, ovary, uterus, endometrium, prostate, colon, skin, mouth, salivary, esophagus, head and neck, plus other tumors of the gastrointestinal tract. In another embodiment, the culture system is present in a multi-well plate suitable for high-throughput screening.

In another aspect, the invention features a composition containing one or more cachexia-inducing factors derived from a cell line identified as cachexia-inducing.

In another aspect, the invention features a composition containing a purified cachexia-inducing factor derived from conditioned media obtained from a cell line identified as cachexia-inducing or derived from human plasma.

In one embodiment of the previous aspects, the cachexia-inducing factor is purified by chromatography, high performance liquid chromatography, size exclusion chromatography, mass spectroscopy, or Multiple Reaction Monitoring (MRM) coupled with mass spectroscopy.

In another aspect, the invention features a method of identifying a cachexia-inducing factor, the method involving contacting a target cell with a cachexia-inducing factor, and detecting an alteration in the target cell indicative of cachexia relative to an uncontacted target cell. In one embodiment, the target cell is a human primary cell that is a myocyte, adipocyte, or hepatocyte. In another embodiment, the cachexia-inducing factor is present in plasma, urine, saliva, or other body fluids from a cachectic subject or in conditioned media. In another embodiment, the conditioned media is obtained from a culture containing a cell line identified as cachexia inducing. In another embodiment, the alteration is in gene expression, metabolism, or level of a protein, metabolite, cytokine, or other macromolecule, or cellular morphology.

In another aspect, the invention features a method of identifying a cachexia-inducing factor, the method involving detecting an alteration in agents present in cachexia-inducing conditioned media relative to non-cachexia-inducing conditioned media, where an alteration in the presence, absence, or level of the agent identifies it as a cachexia-inducing factor. In one embodiment, the agent is a metabolite or marker. In another embodiment, the metabolite is an amino acid or amino acid derivative that is any one or more of histidine, arginine, lysine, valine, leucine, phenylalanine, isoleucine, and tyrosine, and kynurenic acid. In another embodiment, the metabolite is a lipid metabolite that is any one or more of sphingomyelins, lysophospholipids, di-acyl-glycerides, triacyl glycerides, cholesterol esters, and/or phospholipids. In another embodiment, the alteration is lipid loss. In another embodiment, the alteration is a decrease in cell size, morphological change, or the loss or accumulation of myofibrillar proteins in muscle cells or of lipid in fat cells. In another embodiment, where the alteration in metabolism induces lipolysis, proteolysis, autophagy, or apoptosis.

In another aspect, the invention features a method of identifying a cachexia-inducing factor, the method involving biochemically fractionating the cachexia inducing conditioned media; and detecting cachexia-inducing activity in each fraction by evaluating an alteration in a target cell contacted with said fraction. In one embodiment, the alteration is a change in metabolism, in a metabolite, the differential expression of a marker, a morphological change, or the presence of a L1000 cachexia signature in a human primary cell in vitro. In another embodiment, the target cell is a primary myocyte, hepatocyte, or adipocyte. In another embodiment, the fractionation is by size exclusion chromatography, ion exchange chromatography, hydrophobic interaction chromatography, reverse phase chromatography, or similar methods to separate proteins by their biochemical properties.

In another aspect, the invention features a method of inhibiting the loss of myosin heavy chain in a myocyte, the method involving contacting the myocyte with an effective amount of one or more agents that is:
(a) a MEK inhibitor that is any one or more of PD184352 and trametinib;
(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e;
(c) an agent that inhibits RAGE activity, that is any one or more of recombinant soluble RAGE (rsRAGE), an anti-RAGE antibody, a RAGE blocking peptide or small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors.

In another aspect, the invention features a method of inhibiting lipolysis in an adipocyte, the method involving contacting the adipocyte with an effective amount of one or more agents that is:
(a) a MEK inhibitor that is any one or more of PD184352 and trametinib;
(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e;
(c) an agent that inhibits RAGE activity, that is any one or more of recombinant soluble RAGE (rsRAGE), an anti-RAGE antibody, a RAGE blocking peptide or small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors.

In another aspect, the invention features a method of inhibiting atrophy in a cell, the method involving contacting the adipocyte, myocyte, or hepatocyte with an effective amount of one or more agents that is:
(a) a MEK inhibitor that is any one or more of PD184352 and trametinib;
(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e;
(c) an agent that inhibits RAGE activity, that is any one or more of recombinant soluble RAGE (rsRAGE), an anti-RAGE antibody, a RAGE blocking peptide or small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors.

In various embodiments of the above aspects, the myocyte, adipocyte, or hepatocyte cell is in vitro or in vivo. In other embodiments of the above aspects, the myocyte, adipocyte, or hepatocyte cell is present in a subject identified as having at least one cancer. In still other embodiments of the above aspects, the cancer includes but is not limited to one or more carcinomas and sarcomas and cancers of the skin, pancreas, stomach, colon, thorax, liver, gallbladder, musculoskeletal system, breast, lung, ovary, uterus, endometrium, prostrate, colon, skin, mouth, salivary, esophagus, head and neck, plus other tumors of the gastrointestinal tract.

In another aspect, the invention features a method of treating pre-cachexia, the method involving administering to the subject an effective amount of one or more agents that is:
(a) a MEK inhibitor that is any one or more of PD184352 and trametinib;
(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e;
(c) an agent that inhibits RAGE activity, that is any one or more of recombinant soluble RAGE (rsRAGE), an anti-RAGE antibody, a RAGE blocking peptide or small molecule that inhibits binding of RAGE to ligands, a dominant negative RAGE, an inhibitor of RAGE phosphorylation, an inhibitor of RAGE aggregation, FPS1, FPS2, FPS3, FPS-ZM1, PF-04494700, or an inhibitor of RAGE interactions with other heterotypic receptors.

In another aspect, the invention features a method of inhibiting the progression of pre-cachexia to cachexia in a subject, the method involving administering to the subject an effective amount of one or more agents that is:
(a) a MEK inhibitor that is any one or more of PD184352 and trametinib;
(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e;
(c) an agent that inhibits RAGE activity, that is any one or more of recombinant soluble RAGE (rsRAGE), an anti- RAGE antibody, a RAGE blocking peptide or small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors.

In another aspect, the invention features a method of treating or preventing undesirable muscle or fat loss in a cancer patient, the method involving administering to the subject an effective amount of one or more agents that is:

(a) a MEK inhibitor selected that is any one or more of PD184352 and trametinib;

(b) an ERK1/2 inhibitor that is any one or more of SCH772984, ARRY162, AS703026, AZD6244, AZD8330, BIX02188, BIX02189, GSK1120212, honokiol, lenalidomide, PD98059, PD184352, PD325901, PD318088. RDEA119, SCH772984, SL-327, TAK733, trametinib, U0126, and Vx-11e;

(c) an agent that inhibits RAGE activity, that is any one or more of recombinant soluble RAGE (rsRAGE), an anti-RAGE antibody, a RAGE blocking peptide or small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors.

In various embodiments of the above aspects, the subject is pre-selected as having a molecular signature indicative of pre-cachexia or cachexia by detecting an alteration in at least three markers that is any one or more of S100A2 or S100A4; S100A8 or S100A9; and S100A7; detecting an alteration in at least four markers that is any one or more of: S100A2 or S100A4; S100A8 or S100A9; S100A7; and S100A14; or measuring the level of at least five markers that is any one or more of: S100A2 or S100A4; S100A8 or S100A9; S100A7; S100A14; and S100P, thereby pre-selecting the patient as having a molecular signature indicative of pre-cachexia or cachexia.

In another aspect, the invention features a panel of markers for identifying a subject as having pre-cachexia or cachexia, the panel containing three markers containing S100A2 or S100A4; S100A8 or S100A9; and S100A7; four markers that is any one or more of: S100A2 or S100A4; S100A8 or S100A9; S100A7; and S100A14; or five markers that is any one or more of S100A2 or S100A4; S100A8 or S100A9; S100A7; S100A14; and S100P.

In another aspect, the invention features a panel of capture agents for identifying a subject as having pre-cachexia or cachexia, each binding one of three markers that is any one or more of S100A2 or S100A4; S100A8 or S100A9; and S100A7; four markers that is any one or more of: S100A2 or S100A4; S100A8 or S100A9; S100A7; and S100A14; or five markers that is any one or more of: S100A2 or S100A4; S100A8 or S100A9; S100A7; S100A14; and S100P. In one embodiment, the capture agents are antibodies or antigen binding fragments thereof.

In other embodiments of the above aspects, the marker is an S100 family member that is any one or more of HMGB1, S100P, S100A2, S100A3, S100A4, S100A5, S100A7, S100A7A, S100A8, S100A9, S100A11, S100A12, S100A13, S100A14, and S100A15.

In various embodiments of the above aspects, the marker is that is any one or more of Basal cell adhesion molecule (BCAM), Buchang-tang (BCT), Chemokine ligand (CCL)5, CCL28, Dickkopf-related protein 3 (DKK3), Epidermal Growth Factor Receptor (EGFR), Fas Ligand (FASLG), Fibroblast growth factor 4 (FGF4), Follistatin-related peptide 1, intercellular adhesion molecule (ICAM2), High Mobility Group (HMG1), Insulin Growth Factor-2 (IGF-2), Insulin Growth Factor Binding Protein-2 (IGFBP-2), IGFBP-6, interleukin-6 (IL6), Kinase insert domain receptor (KDR), lipolysis-stimulated receptor (LSR), NME/NM23 Nucleoside Diphosphate Kinase 1 (NME1), Nerve Growth Factor (NGF), Platelet Derived Growth Factor-A (PDGFA), PDGFB, PlGF (placenta growth factor), tyrosine-protein kinase receptor (TYRO3), Plasminogen activator inhibitor 1, tissue inhibitor of metalloproteinases (TIMP2), soluble Receptor for Advanced Glycation Endproducts (sRAGE)*, Tumor necrosis factor receptor superfamily member 10C (TNFRSF10C), and tumor necrosis factor superfamily member 18 (TNFSF18). In other embodiments of the above aspects, the alteration is an increase or decrease.

In another aspect, the invention features an addressable array containing the panel of any previous aspect fixed to a substrate. In one embodiment, the substrate is a glass slide, silicon, microwell, nitrocellulose or PVDF membrane, magnetic bead, or microbeads.

In another aspect, the invention features a method for detecting a marker of the invention, the method involving contacting an array comprising a panel of markers fixed to a substrate with a biological sample from a subject and detecting binding. In one embodiment, the biological sample is urine, blood, plasma, serum, or a biopsy sample. In another embodiment, binding is detected in an immunoassay, a radioassay, or mass spectroscopy. In another embodiment, the method detects a molecular signature indicative of pre-cachexia or cachexia.

In another aspect, the invention features a method of identifying a subject as having a pre-cachexia or cachexia signature, the method involving measuring the level of at least three markers that is any one or more of: S100A2 or S100A4; S100A8 or S100A9; and S100A7; measuring the level of at least four markers that is any one or more of: S100A2 or S100A4; S100A8 or S100A9; S100A7; and S100A14; and measuring the level of at least five markers that is any one or more of: S100A2 or S100A4; S100A8 or S100A9; S100A7; S100A14; and S100P, where the levels of markers are measured in a biological sample of the subject, where an increase in the levels of said markers relative to a reference is indicative of pre-cachexia or cachexia signature.

In another aspect, the invention features a method of identifying a subject as having precachexia, the method involving measuring the level of at least three markers that is any one or more of: S100A2 or S100A4; S100A8 or S100A9; and S100A7; measuring the level of at least four markers that is any one or more of: S100A2 or S100A4; S100A8 or S100A9; S100A7; and S100A14; and measuring the level of at least five markers that is any one or more of: S100A2 or S100A4; S100A8 or S100A9; S100A7; S100A14; and S100P, where the levels of markers are measured in a biological sample of the subject, where an increase in the levels of said markers relative to a reference is indicative of pre-cachexia or cachexia.

In another aspect, the invention features a method of selecting a subject for treatment with an agent that inhibits progression of pre-cachexia to cachexia, the method involving measuring the level of at least three markers that is any one or more S100A2 or S100A4, S100A8 or S100A9, and S100A7; measuring the level of at least four markers that is any one or more of S100A2 or S100A4, S100A8 or S100A9, S100A7 and S100A14; and measuring the level of at least five markers that is any one or more S100A2 or S100A4, S100A8 or S100A9, S100A7, S100A14, and S100P, where the levels of markers are measured in a biological sample of the subject, where an increase in the levels of said markers relative to a reference selects the subject for treatment with an agent that inhibits progression of pre-cachexia to cachexia. In one embodiment, the pre-cachexia or cachexia is associated with cancer, disease, age-related weight loss, or age-related sarcopenia.

In another aspect, the invention features a method of identifying an agent that treats pre-cachexia, the method involving contacting a target cell with a candidate agent in the presence of a cachexia inducing factor, and detecting a reduction in a cachexia indicator relative to a reference cell that was not contacted with the candidate agent. In another embodiment, the cachexia inducing factor is present in conditioned media or plasma obtained from a human patient having cachexia. In another embodiment, the target cell is a human primary myocyte, adipocyte, or hepatocyte. In another embodiment, the cachexia indicator is a change in metabolism, in a metabolite, in the expression of a marker, or a morphological change indicative of cachexia. In another embodiment, the method further involves measuring the level of at least three markers that is any one or more of S100A2 or S100A4, S100A8 or S100A9, and S100A7; measuring the level of at least four markers that is any one or more S100A2 or S100A4, S100A8 or S100A9, S100A7 and S100A14; and measuring the level of at least five markers that is any one or more of S100A2 or S100A4, S100A8 or S100A9, S100A7, S100A14, and S100P.

In another aspect, the invention features a method of identifying an agent that inhibits the loss of myosin heavy chain in a myocyte, the method involving contacting the myocyte with an effective amount of a candidate agent in the presence of a cachexia inducing factor, and measuring the level of myosin heavy chain relative to a reference, thereby identifying the agent as inhibiting loss of myosin heavy chain.

In another aspect, the invention features a method an agent that inhibits lipolysis in an adipocyte, the method involving contacting the adipocyte with an effective amount of a candidate agent in the presence of a cachexia inducing factor, and measuring lipolysis in the adipocyte relative to a reference, thereby identifying an agent that reduces lipolysis.

In another aspect, the invention features a method of identifying an agent that inhibits atrophy in a cell, the method involving contacting the cell with an effective amount of a candidate agent in the presence of a cachexia inducing factor, and measuring size in the cell relative to a reference, thereby identifying an agent that reduces atrophy. In one embodiment, the cell is a myocyte, adipocyte, or hepatocyte in vitro.

In another aspect, the invention features a method of monitoring the treatment of pre-cachexia or cachexia involving measuring the level of at least three markers that is any one or more of S100A2 or S100A4, S100A8 or S100A9, and S100A7; measuring the level of at least four markers that is any one or more of S100A2 or S100A4, S100A8 or S100A9, S100A7 and S100A14; and measuring the level of at least five markers that is any one or more of S100A2 or S100A4, S100A8 or S100A9, S100A7, S100A14, and S100P, where the levels of markers are measured in a biological sample of the subject, where an increase in the levels of said markers relative to a reference selects the subject for treatment with an agent that inhibits progression of pre-cachexia to cachexia. In one embodiment, a normalization in said levels is indicative that the treatment is effective.

In another aspect, the invention features a method of enhancing cancer sensitivity to chemotherapy, the method involving administering gemcitabine in combination with an anti-RAGE therapy that is any one or more of recombinant soluble RAGE (rsRAGE), an anti-RAGE antibody, a RAGE blocking peptide, a small molecule that inhibits binding of RAGE to ligands, a dominant negative RAGE, an inhibitor of RAGE phosphorylation, an inhibitor of RAGE aggregation, or an inhibitor of RAGE interactions with other heterotypic receptors, thereby enhancing cancer sensitivity to chemotherapy. In one embodiment, the cancer is that is any one or more of one or more carcinoma or sarcoma, including but not limited to cancers of the skin, pancreas, stomach, colon, thorax, liver, gallbladder, musculoskeletal system, breast, lung, ovary, uterus, endometrium, prostrate, colon, skin, mouth, salivary, esophagus, head and neck, plus other tumors of the gastrointestinal tract.

In another aspect, the invention features a method of identifying a cachexia-inducing factor in a patient sample, the method involving contacting a target cell with a patient sample believed to contain elevated levels of at least one cachexia-inducing factor, and detecting an alteration in the target cell indicative of cachexia relative to an uncontacted target cell. In one embodiment, the target cell is a human primary cell that is a myocyte, adipocyte, or hepatocyte. In another embodiment, the patient sample is selected from plasma, urine, saliva, or other body fluids from a cachectic subject or a subject with pre-cachexia, or is conditioned media from a cultured patient sample. In another embodiment, the conditioned media is obtained from a cultured patient sample containing a cancer or tumor. In another embodiment, the alteration is in gene expression, metabolism, or level of a protein, metabolite, cytokine, or other macromolecule, or in cellular morphology. In another embodiment, the metabolite is an amino acid or amino acid derivative that is any one or more of histidine, arginine, lysine, valine, leucine, phenylalanine, isoleucine, and tyrosine, and kynurenic acid. In another embodiment, the metabolite is a lipid metabolite that is any one or more of sphingomyelins, lysophospholipids, di-acyl-glycerides, triacyl glycerides, cholesterol esters, and/or phospholipids. In another embodiment, the alteration is a decrease in cell size, morphological change, or the loss or accumulation of myofibrillar proteins in muscle cells or of lipid in fat cells. In another embodiment, the alteration in metabolism induces lipolysis, proteolysis, autophagy, or apoptosis. In another embodiment, detecting a change in metabolism, in a metabolite, in the expression of a marker, or a morphological change is indicative of cachexia.

In other embodiments of the above aspects, the marker is an S100 family member that is any one or more of HMGB1, S100P, S100A2, S100A3, S100A4, S100A5, S100A7, S100A7A, S100A8, S100A9, S100A11, S100A12, S100A13, S100A14, and S100A15. In various embodiments of the above aspects, where the marker is that is any one or more of Basal cell adhesion molecule (BCAM), Buchangtang (BCT), Chemokine ligand (CCL)5, CCL28, Dickkopf-related protein 3 (DKK3), Epidermal Growth Factor Receptor (EGFR), Fas Ligand (FASLG), Fibroblast growth factor 4 (FGF4), Follistatin-related peptide 1, intercellular adhesion molecule (ICAM2), High Mobility Group (HMG1), Insulin Growth Factor-2 (IGF-2), Insulin Growth Factor Binding Protein-2 (IGFBP-2), IGFBP-6, interleukin-6 (IL6), Kinase insert domain receptor (KDR), lipolysis-stimulated receptor (LSR), NME/NM23 Nucleoside Diphosphate Kinase 1 (NME1), Nerve Growth Factor (NGF), Platelet Derived Growth Factor-A (PDGFA), PDGFB, PlGF (placenta growth factor), tyrosine-protein kinase receptor (TYRO3), Plasminogen activator inhibitor 1, tissue inhibitor of metalloproteinases (TIMP2), soluble Receptor for Advanced Glycation Endproducts (sRAGE)*, Tumor necrosis factor receptor superfamily member 10C (TNFRSF10C), and tumor necrosis factor superfamily member 18 (TNFSF18). In various embodiments of the above aspects, the alteration is an increase or decrease. In various embodiments of the above aspects, the comparison involves iTRAQ, multi-plex TMT quantitative proteomic analysis, or MMR coupled with mass spectroscopy.

Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "pre-cachexia" is meant a clinical state that fails to meet the criteria for cachexia. For example, a subject may be pre-cachexic when their weight is stable or when their weight loss is about 1%, 2% or 3% of their body mass. As used with respect to the invention described herein, at least a subset of patients with pre-cachexia may be characterized by an increase in one or more S100 RAGE ligands and/or a decrease in soluble RAGE relative to a reference level without unintended weight loss of at least 5% or more of body weight.

By "cachexia" is meant unintended weight loss of at least 5% or more of body weight. In general, cachexia refers to the progressive loss of lean body mass (particularly of muscle mass) that typically is associated with gross body weight loss that is at least 5, 6, 7, 8, 9, 10% or more. Muscle and adipose tissue loss, indicative of cachexia, may be detected by a computed tomography (CT) scan (Martin et al., *J Clin Oncol* 31:1539-1547 (2013)), though this method has not been validated as sufficient to formally diagnose the condition as there are numerous conditions that result in similar findings by imaging studies alone. Currently, there is no molecular biomarker(s) for this condition, as the pathogenesis of cancer-induced cachexia remains to be elucidated.

By "cancer-induced cachexia" is meant cachexia associated with the presence of a cancer or tumor.

By "disease-induced cachexia" is meant cachexia associated with the presence of a disease that is not due to the presence of at least one cancer or tumor. As used herein, at least a subset of patients with disease-induced cachexia may be characterized by an increase in one or more S100 RAGE ligands and/or a decrease in soluble RAGE relative to a reference level.

As used herein, "cellular differentiation" or "differentiation" is the process by which a less specialized cell becomes a more specialized cell type.

"High-throughput screening" (HTS) refers to a process that uses a combination of modem robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

By "PD184352" is meant a small compound MEK inhibitor $C_{17}H_{14}ClF_2IN_2O_2$ (CAS Number 212631-79-3) having the following structure:

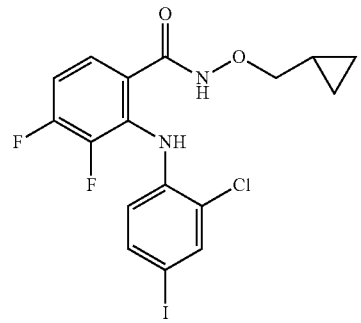 [SMILES: O=C(NOCC1CC1)c1ccc(F)c(F)c1Nc1ccc(I)cc1Cl]

PD184352 is commercially available, for example, from Sigma Aldrich.

By "SCH772984" is meant a small compound selective inhibitor of ERK1/2 $C_{33}H_{33}N_9O_2$ (CAS 942183-80-4) having the following structure:

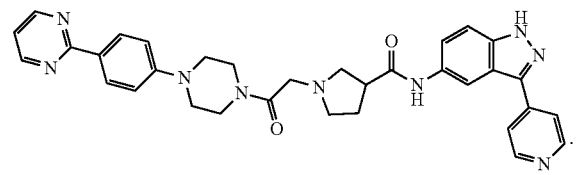 [SMILES: O=C(Nc1ccc2[nH]nc(-c3ccncc3)c2c1)C1CCN(CC(=O)N2CCN(c3ccc(-c4ncccn4)cc3)CC2)C1]

By "trametinib" or "N-[3-[3-Cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]acetamide" is meant a small compound MEK inhibitor $C_{26}H_{23}FIN_5O_4$ (CAS #871700-17-3) having the following structure:

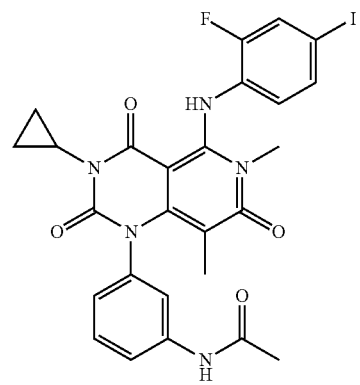

Trametinib is also termed "GSK-1120212."

RAGE inhibitors include, for example, PF-04494700 and FPS1, FPS2, FPS3, or FPS-ZM1.

FPS1

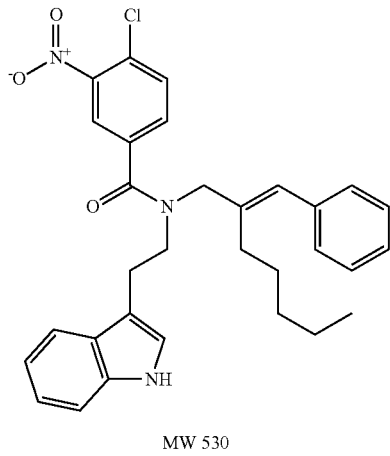

MW 530

FPS2

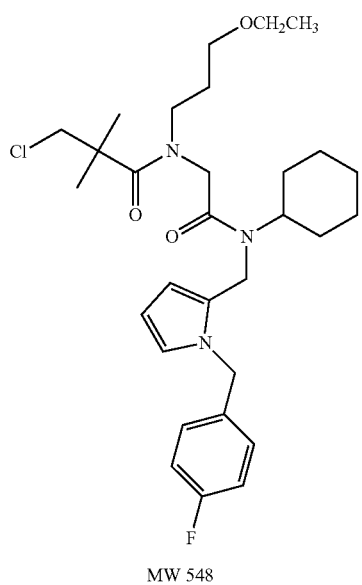

MW 548

FPS3

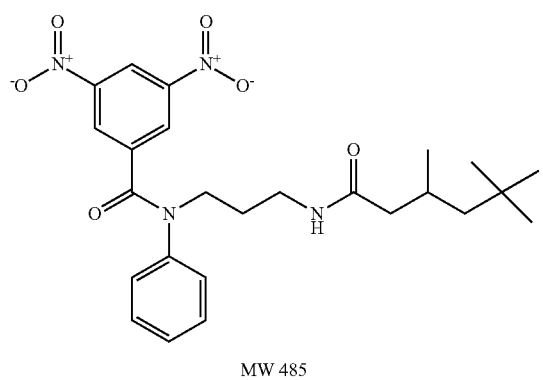

MW 485

FPS-ZM1

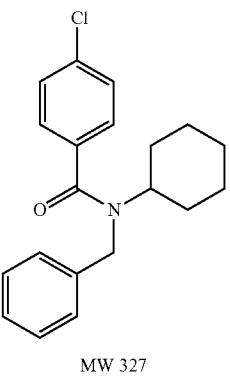

MW 327

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

As used herein, a "subject" means a human or animal (in the case of an animal, more typically a mammal). In one aspect, the subject is a human.

The term "treating" is art-recognized and includes administration to the host of one or more of the subject compositions, e.g., to diminish, ameliorate, or stabilize the existing unwanted condition or side effects thereof.

By "agent" is meant a peptide, nucleic acid molecule, or small compound.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. In one embodiment, the disease is pre-cachexia, cachexia, or refractory cachexia.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any clinical indicator, protein, metabolite, or polynucleotide having an alteration associated with a disease or disorder. In one embodiment, an alteration in body mass, lean body mass, metabolism, or a metabolite is a marker (e.g., clinical indicator) of disease state (e.g., pre-cachexia or cachexia).

By "metabolic profile" is meant alterations in one or more amino acid or lipid metabolites.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a table showing features that distinguish weight loss associated with cachexia from weight loss associated with starvation.

FIG. 1B is a table showing disease burden and median survival. FIG. 1B shows dramatically different disease burden, yet similar clinicopathology. Difference in median survival-9 months.

FIGS. 6A and 6B are images showing a gene expression signature of myocytes exposed to cachectic patient plasma ((+)) or non-cachectic ((−)) patient plasma. The 100 most down- and up-regulated genes in in vitro primary human myocytes were selected based on the signal-to-noise ratio.

FIGS. 9A-9C present a schematic representation, L1000 profiling data and Western blots as described in Example 3 herein. FIG. 9A is a schematic representation of the experimental steps that generated the data shown in FIGS. 9B and 9C.

FIG. 9B is a series of images showing a heatmap of patient plasma-derived gene expression signature of in vitro myocytes treated with non-cachectic (left), cachectic (middle), and heat-denatured cachectic-inducing media (right). Boiling cachexia-inducing media for 10 minutes at 95° C. abolished the gene expression signature of cachexia.

FIG. 9C is images of a Western blot analysis showing the protein content of myosin heavy chain (MyoHC), glyceraldehyde 3-phosphate dehydrogenase (GAPDH), and tropomyosin (Tropomyo) in in vitro myocytes treated with non-cachexia-inducing conditioned media ((−)), cachexia-inducing conditioned media ((+)), and heat-denatured cachexia-inducing conditioned media (B) before differentiation (Pre-Diff) and at Day 0, 2 and 4 post-differentiation (D0, D2, and D4, respectively).

FIG. 14A is a table showing the proteins identified by mass spectrometry within the active fractions of media conditioned with non-cachexia inducing 293T cells and cachexia inducing MkN1 and G361cells.

FIG. 34A is a surface representation of the hRAGE VC1 packing dimer coloured according to its overall electrostatic potential calculated with APBS. Surface areas coloured blue are positively charged and areas in red are negatively charged. FIG. 34B, structure as in FIG. 31A but viewed from the top. Basic residues within the V-shaped platform are indicated for one of the two monomers. FIG. 34C is a surface representation of the hRAGE VC1C2 packing dimer coloured according to the electrostatic potential. The sole C2 domain that could be traced in the VC1C2 structure packs into the V-V dimer formed between two symmetry-related molecules (shown in green) along its electronegative surface. Another C2 domain (light green) from a symmetry-related molecule packs into the V-V basic domain groove.

FIG. 36B depicts RAGE Bivalent Signaling.

FIG. 41B provides a heat map showing RAGE ligands that are differentially regulated in breast cancer. Of particular interest are S100A7, S100A7A, S100A8, S100A9 and S100P.

FIG. 41C provides a heat map showing RAGE ligands that are differentially regulated in squamous lung cancer. Of particular interest are S100A7, S100A7A, S100A8, S100A9 and S100P.

FIG. 51 is a table that quantitates expression of S100 family members are differentially expressed in cachexia inducing and non-inducing cell lines.

FIG. 53A lists potential in vivo treatment of lung cancer with RAGE inhibitors, the MEK/ERK inhibitor trametinib, and other candidates.

DETAILED DESCRIPTION OF THE INVENTION

The invention provides compositions and methods for identifying patients with pre-cachexia and/or cachexia; a culture system that reproduces the tachetic process in cells in vitro; and methods of using this system to identify markers associated with pre-cachexia and/or cachexia, as well as for the discovery of therapeutic agents useful for disrupting (slowing, reducing, reversing, or preventing) the progression of pre-cachexia to cachexia.

The invention is based, at least in part, on the discovery of a molecular signature associated with pre-cachexia and/or cachexia. Accordingly, the invention provides a panel of markers useful for identifying patients that are pre-cachexic. This provides for the identification and treatment of subjects before they develop the progressive weight loss and muscle atrophy that define cachexia, and which has proven refractory to all attempted therapeutic interventions. The invention further provides markers useful for characterizing cachexia.

Cachexia's Effect on Patient Prognosis.

The development of new highly effective oncologic therapies has transformed many cancers into chronically managed diseases. The efficacy of these new treatment regimens does not guarantee an increase in survival. While surgery, radiation or chemotherapy may successfully reduce tumor size, this reduction does not always correlate with an increase in survival. In fact, for many patients, degree of tumor burden does not correlate with prognosis. As shown in FIG. 1B, the difference in survival time for patients with only modest tumor burden is only about eight months more than the survival time of patients with extensive tumor burden. This counter-intuitive result may be attributed, at least in part, to cachexia. The clinical manifestations of cachexia are complex: muscle and fat wasting, multi organ dysfunction (e.g., cardiac, pulmonary, gastrointestinal), and profound metabolic derangement.

Figure 1C:
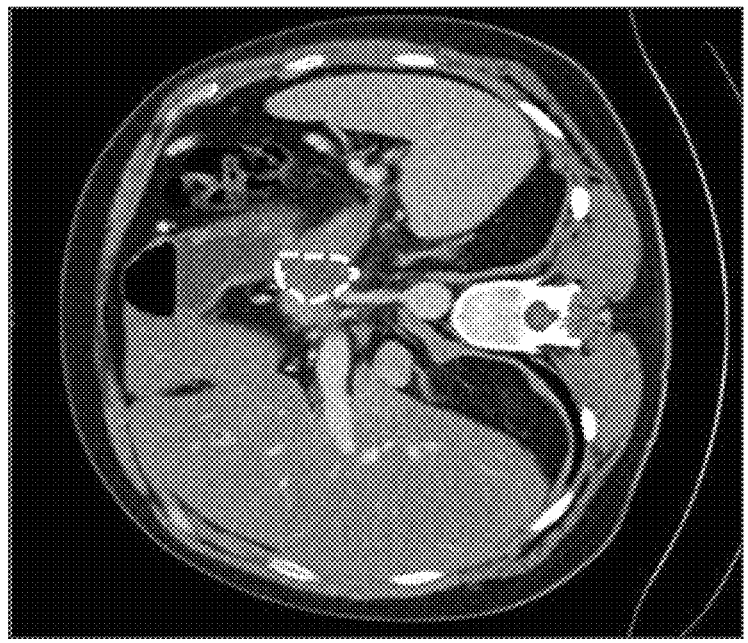
FIG. 1C is a computed tomography angiogram (CTA) image showing a 3×3×2 cm mass in the head of the pancreas.
Figure 1D:
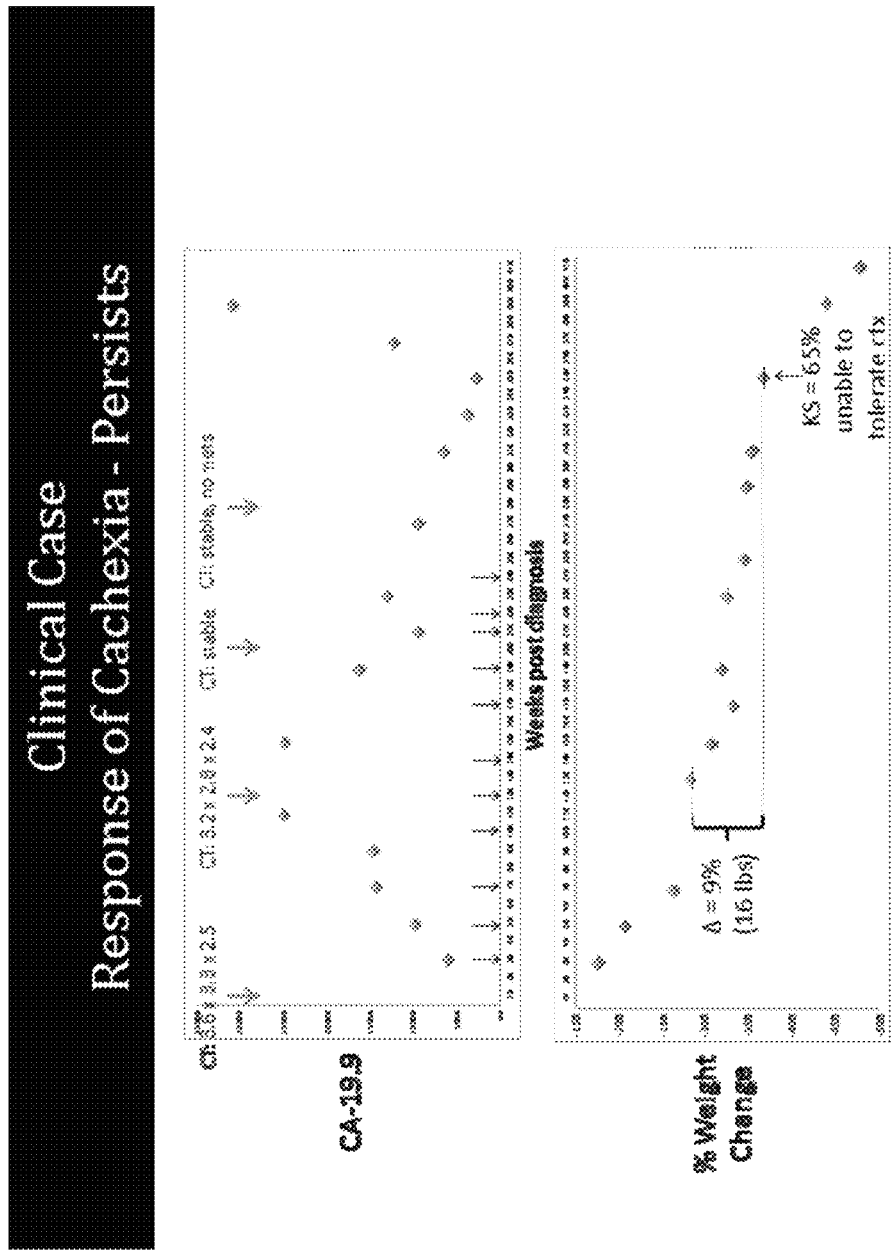
FIG. 1D shows levels of CA-19.9 (top panel), which is a serum biomarker of pancreatic cancer, and percent weight change.

More than twenty-five percent of cancer deaths are caused—not by cancer—but by cachexia. Cachexia associated deaths include death by respiratory failure, cardiac failure, and metabolic derangement. The devastating effects of cachexia are poignantly illustrated in a case study of a sixty-one year old patient with pancreatic cancer. The patient presented with worsening abdominal pain. Upon imaging, a small (3×3×2 cm) tumor was observed in the head of the pancreas (FIG. 1C). The patient was diagnosed with stage III non-resectable pancreatic cancer. She also had cachexia, having lost 35 lbs (17%) of her body weight. The patient was treated with 5'-FU/Leucovorin/Irinotecan/Oxaliplatin. Treatment successfully reduced the size of the patient's tumor, as well as levels of CA-19.9 a serum marker associated with pancreatic cancer. Despite this positive response, the patient continued to lose weight, ultimately becoming so frail that anti-cancer therapy had to be discontinued (FIG. 1D).

While cachexia shares certain phenotypic similarities with food deprivation, in fact cachexia is distinct from starvation (FIG. 1A). Even where patients with cachexia are provided with total parenteral nutrition, weight loss, including loss of lean body mass, continues. These losses have proven refractory to all therapeutic interventions, except for a complete removal of the cancer, which remains elusive for the vast majority of cancer patients.

In Vitro Cachexia/Pre-Cachexia Model System

Figure 1E:
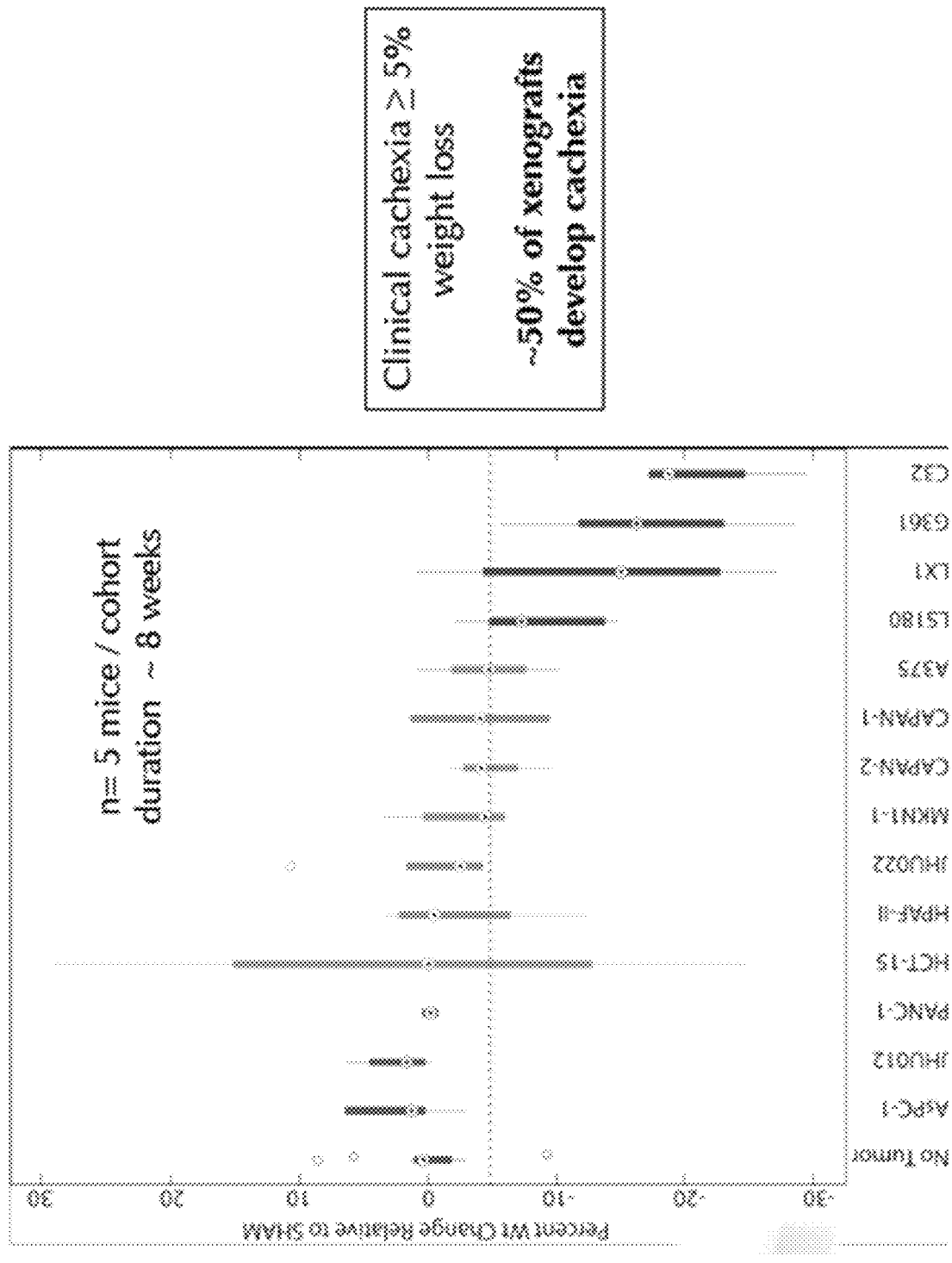
FIG. 1E is a graph showing the mean tumor-free weight change in cohorts of xenograft mice (n=5 mice, per cohort). The most cachexia-inducing cell lines over the 8-week period are shown in red.
Figure 1F:
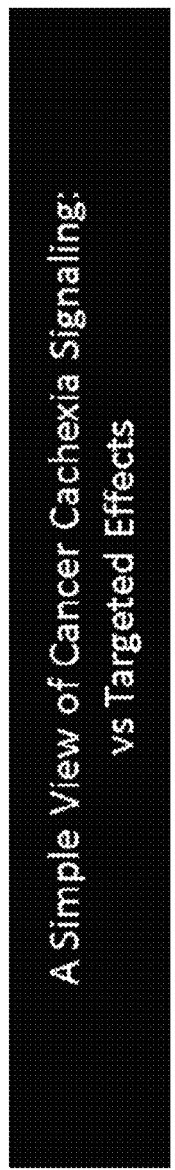
FIG. 1F is a schematic that illustrates cancer cachexia signaling vs. targeted and/or collateral effects on muscle, fat, and liver.
Figure 1F:
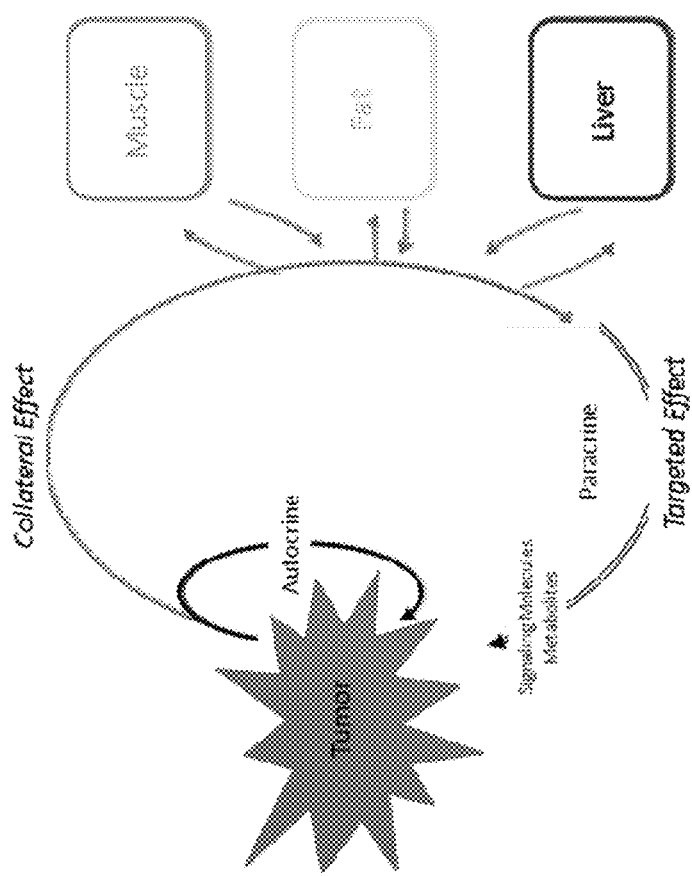

To date, progress in understanding cachexia has been hampered by the lack of an in vitro system that could reproduce the hallmarks of cachexia. The identification of such a system is critical to identifying factors that mediate the tumor-host interaction. In the simplest view of tumor-host interactions, the tumor produces a factor that mediates wasting/dysfunction of target tissues (FIG. 1F). Conventional wisdom has held that mice "do not get cancer cachexia." To the contrary, results provided herein demonstrate that human cancer cell lines induce a cachectic state in murine xenograft models (FIG. 1E). Conventional wisdom also holds to the notion that immune system is required to generate inflammatory cytokines that have been thought to drive cachexia. We have demonstrated that the tumor cells from multiple tumor types grown in isolation produce the mediator(s) that cause target cells (muscle, fat, and liver) to phenocopy clinical cachexia with tremendous specificity, thus the immune is not required. These observations support the premise that tumor cells secrete one or more factors that drive cachexia. The present invention provides an in vitro system that models pre-cachexia and/or cachexia and facilitates the identification of agents that drive cachexia vs. factors that merely contribute to the disease process.

The present invention provides a culture system, comprising a human target cell and a cachexia-inducing factor. In certain embodiments, the target cell is selected from a myocyte, an adipocyte, and a hepatocyte. In one embodiment, the target cell is a myocyte.

In certain embodiments, the cachexia-inducing factor is provided in (i) human plasma from a cachexia patient or (ii) cachexia-inducing conditioned media, such as human cancer cell conditioned media. In certain embodiments, the media is conditioned by a human cancer cell line selected from one or more of the following: AsPC-1, A375, CAPAN-1, CAPAN-2, C32, G361, HCT-15, HPAF-II, JHU012, JHU022, LS180, LX1, MKN1, and PANC-1. In particular embodiments, a cachexia-inducing cell line is the human melanoma cell line A375 (ATCC® CRL1619™); the intestinal human colon adenocarcinoma cell line LS180 (ATCC® CL-187™); the hepatic stellate cell line LX1 (Xu et al., Gut. Jan 2005; 54(1): 142-151); the malignant melanoma human cell line G361 (ATCC® CRL-1424™), or the human malignant melanoma cell line C32 (ATCC® CRL-1585™). In certain embodiments, the media is conditioned by a human cancer cell isolated from a patient.

In certain embodiments, the culture is in a single or a multi-well plate format. In certain embodiments, the invention provides a multi-well plate suitable for use in a high-throughput screening system, the plate having a plurality of wells comprising the culture system described therein. The surface of the multi-well plate may be the surface of a culture well or glass slide, or any other suitable surface. In certain embodiments the multi-well plate contains 384 wells. Cultures can be contained in a multi-well plate having a 96-, 384-, 1536- or more than 1536-well format.

In certain embodiments, the invention further provides a method for producing the model of the present invention, in a single or multi-well plate format.

Uses of the Cachexia/Pre-Cachexia Model System

The present invention provides methods for characterizing an agent for the ability to induce pre-cachexia or cachexia in a target cell. The method generally involves exposing a target cell to a test agent, and characterizing the effect of the agent on the target cell relative to: (i) a control target cell not exposed to the test agent; or (ii) a transcriptional profile of a non-cachectic cell and/or a transcriptional profile of a cachectic cell, wherein the cell type of the target cell and the cachectic and/or non-cachectic cell is the same.

The present invention provides a method for predicting the effect of a test agent on a target cell of a patient in vivo, comprising culturing a target cell obtained from a patient in the system of the invention, exposing it to the test agent, and assaying for a pharmacological effect of the test agent on the target cell relative to: (i) a control target cell not treated with the test agent; or (ii) a transcriptional profile of a non-cachectic cell and/or a transcriptional profile of a cachectic cell, wherein the cell type of the target cell and the cachectic and/or non-cachectic cell is the same.

In certain embodiments, the target cell is isolated from a patient with cancer.

In certain embodiments, the effect is selected from proliferation, viability, and differentiation, or combinations thereof.

In certain embodiments, the effect is detected by assessing a change in gene expression profile between the target cell and the control target cell of step (i); or the cachectic or non-cachectic cell of step (ii).

In certain embodiments, the target cell is selected from a myocyte, an adipocyte, and a hepatocyte. In a preferred embodiment, the target cell is a myocyte.

The cachectic culture system can be used to screen for test agents (such as solvents, small molecule drugs, peptides, and polynucleotides) or environmental conditions (such as culture conditions or manipulation) that affect the characteristics of cells. Two or more agents can be tested in combination (by exposing to the cells either simultaneously or sequentially), to detect possible drug-drug interactions and/or rescue effects (e.g., by testing a toxin and a potential anti-toxin). Agent(s) and environmental condition(s) can be tested in combination (by treating the cells with a drug either simultaneously or sequentially relative to an environmental condition), to detect possible agent-environment interaction effects.

In certain embodiments, the assay to determine the characteristics of cells is selected in a manner appropriate to the cell type and agent and/or environmental factor being studied as disclosed in WO 2002/04113, which is hereby incorporated by reference in its entirety. For example, changes in cell morphology may be assayed by standard light, or electron microscopy. Alternatively, the effects of treatments or compounds potentially affecting the expression of cell surface proteins may be assayed by exposing the cells to either fluorescently labeled ligands of the proteins or antibodies to the proteins and then measuring the fluorescent emissions associated with each cell on the plate. As another example, the effects of treatments or compounds which potentially alter the pH or levels of various ions within cells may be assayed using various dyes which change in color at determined pH values or in the presence of particular ions. The use of such dyes is well known in the art. For cells which have been transformed or transfected with a genetic marker, such as the β-galactosidase, alkaline phosphatase, or luciferase genes, the effects of treatments or compounds may be assessed by assays for expression of that marker. In particular, the marker may be chosen so as to cause spectrophotometrically assayable changes associated with its expression.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015. In certain aspects of this invention, the culture of the invention is used to grow and differentiate a cachectic target cell to play the role of test cells for standard drug screening and toxicity assays.

Assessment of the activity of candidate pharmaceutical compounds generally involves combining the target cell (e.g., a myocyte, an adipocyte or a hepatocyte) with the candidate compound, determining any change in the morphology, marker phenotype, or metabolic activity of the cells that is attributable to the candidate compound (compared with untreated cells or cells treated with an inert compound, such as vehicle), and then correlating the effect of the candidate compound with the observed change. The screening may be done because the candidate compound is designed to have a pharmacological effect on the target cell, or because a candidate compound may have unintended side effects on the target cell. Alternatively, libraries can be screened without any predetermined expectations in hopes of identifying compounds with desired effects.

Cytotoxicity can be determined in the first instance by the effect on cell viability and morphology. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

Additional further uses of the culture of the invention include, but are not limited to, its use in research e.g., to elucidate cachectic mechanisms leading to the identification of novel targets for cachectic therapies, and to generate genotype-specific cells for disease modeling, including the generation of new therapies customized to different genotypes. Such customization can reduce adverse drug effects and help identify therapies appropriate to the patient's genotype.

Methods of Identifying a Patient as Having Pre-Cachexia or Cachexia

As reported herein below, within days of contacting target cells with cachexia-inducing media changes in metabolism, metabolite profiles, the differential expression of markers, and changes in cell morphology are observed. Such changes closely phenocopy overt clinical cachexia as induced by cachectic patient plasma and seen in patient biopsy samples, and likely reproduce the alterations present in pre-cachectic humans and mice. Significantly, many of the changes observed in cells in vitro in response to cachexia inducing factors were reversible (e.g., the cachectic gene expression signature, loss of myosin heavy chain, loss of lipid content, and cell atrophy) with novel treatments identified with this discovery platform Accordingly, the invention provides methods for identifying subjects as pre-cachectic. Such methods are particularly advantageous given that treatment of pre-cachexia could slow or even reverse the progression of pre-cachexia to cachexia. Moreover, early identification of pre-cachectic patients could ensure that subjects are sufficiently strong to benefit from therapies delineated herein.

The invention provides for a transcriptional biomarker profile of a cachectic phenotype (e.g., cachexia, pre-cachexia) suitable for use in diagnosing and/or monitoring a patient with cachexia or pre-cachexia. Accordingly, the present invention provides a method for diagnosing a patient with cachexia or pre-cachexia, comprising (i) obtaining a target cell from the patient; (ii) determining the gene expression profile of that cell; and (iii) comparing the transcriptional profile of that target cell and the transcriptional profile of a cachectic cell, wherein the cell type of the target cell and the cachectic cell is the same.

The invention provides for a transcriptional biomarker profile of a cachectic phenotype suitable for use in diagnosing and/or monitoring a patient with cachexia or pre-cachexia. Accordingly, the present invention provides a method for diagnosing a patient with cachexia or pre-cachexia, comprising (i) obtaining a target cell from the patient; (ii) determining the gene expression profile of that cell; and (iii) comparing the transcriptional profile of that target cell and the transcriptional profile of a cachectic cell, wherein the cell type of the target cell and the cachectic cell is the same.

The present invention further provides a method for monitoring a patient with cachexia or pre-cachexia, comprising (i) obtaining a target cell from the patient; (ii) determining the gene expression profile of that cell; and (iii) comparing the transcriptional profile of that target cell and the transcriptional profile of a cachectic cell, wherein the cell type of the target cell and the cachectic cell is the same. Monitoring the cachectic transcriptional profile of a patient is useful, for example, to determine the patient's pharmacological response to a drug or disease progression.

The invention further provides protein-mediated cachexia-inducing factors, present in media conditioned by certain human cancer cell lines, that induce cellular consequences recapitulated by cachectic-patient-derived plasma samples. For instance, RAGE-based biomarkers were identified herein as associated with the cachexia phenotype. Soluble RAGE (a negative regulator of RAGE signaling that acts as a sink for RAGE ligands) was found to be elevated in non-cachexia-inducing conditioned media in comparison to cachexia-inducing conditioned media. In contrast, levels of certain RAGE ligands, such as S100 proteins and HMG1, were found to be elevated in cachexia-inducing conditioned media in comparison to non-cachexia-inducing conditioned media.

The presence and/or level of the cachexia-inducing proteins, e.g. the factors listed in Table 2, in patient plasma may serve as cachectic biomarker(s) useful for diagnosing and/or monitoring a patient with cachexia. Accordingly, the present invention also provides a method for diagnosing a patient with cachexia, comprising (i) obtaining plasma from the patient; and (ii) detecting the presence or level of a cachexia-inducing factor(s) selected from Table 2. The present invention also provides a method for monitoring a patient with cachexia, comprising (i) obtaining plasma from the patient; and (ii) detecting the presence or level of a cachexia-inducing factor(s) selected from Table 2.

TABLE 2

| Cachexia-Inducing Factors | |
|---|---|
| BCAM | NGF |
| BTC | PDGFA |
| CCL5 | PDGFB |
| CCL28 | Plasminogen activator inhibitor 1 |
| DKK3 | S100A7 |
| EGFR | S100A8 |
| Follistatin-related peptide 1 | S100A9 |
| HMG1 | S100A11 |
| IGF-2 | sRAGE (soluble RAGE)* |
| IGFBP-2 | TNFRSF10C |
| IGFBP-6 | TNFSF18 |
| IL6 | TYRO3 |
| Lipolysis-stimulated lipoprotein receptor | |
| BCAM | |
| BTC | |

(*anti-correlated with cachexia)

In particular embodiments, at least one or more of IGFBP-1, CCL27, AXL, CSF1, ICAM2, PlGF, TMP2, FGF4, KDR and CSF3 are increased in cachexia.

In other embodiments, a marker of cachexia or pre-cachexia is any one or more of three markers selected from S100A2 or S100A4, S100A8 or S100A9, and S100A7; four markers selected from S100A2 or S100A4, S100A8 or S100A9, S100A7 and S100A14; five markers selected from S100A2 or S100A4, S100A8 or S100A9, S100A7, S100A14, and S100P, which are increased in pre-cachexia or cachexia.

In other embodiments, a marker of cachexia or pre-cachexia is Basal cell adhesion molecule (BCAM), Buchang-tang (BCT), Chemokine ligand (CCL)5, CCL28, Dickkopf-related protein 3 (DKK3), Epidermal Growth Factor Receptor (EGFR), FASLG (Fas ligand), Fibroblast growth factor 4 (FGF4), Follistatin-related peptide 1, intercellular adhesion molecule (ICAM2), High Mobility Group (HMG1), Insulin Growth Factor-2 (IGF-2), Insulin Growth Factor Binding Protein-2 (IGFBP-2), IGFBP-6, interleukin-6 (IL6), Kinase insert domain receptor (KDR), lipolysis-stimulated receptor (LSR), NM (NME/NM23 Nucleoside Diphosphate Kinase 1), Nerve Growth Factor (NGF), Platelet Derived Growth Factor-A (PDGFA), PDGFB, PlGF (placenta growth factor), tyrosine-protein kinase receptor (TYRO3), Plasminogen activator inhibitor 1, tissue inhibitor of metalloproteinases (TIMP2), soluble Receptor for Advanced Glycation Endproducts (sRAGE)*, Tumor necrosis factor receptor superfamily member 10C (TNFRSF10C), and tumor necrosis factor superfamily member 18 (TNFSF18). All of the aforementioned markers are increased, with the exception of sRAGE, which is decreased. In other embodiments, the method further involves measuring an increase in an S100 family member selected from HMGB1, S100P, S100A2, S100A3, S100A4, S100A5, S100A7, S100A7A, S100A8, S100A9, S100A11, S100A12, S100A13, S100A14, and S100A15.

In certain embodiments, the patient has cachexia associated with a cancer. In a preferred embodiment, the patient has cachexia associated with a cancer, e.g., an epithelial-derived cancer or a mesenchymal-derived cancer, such as carcinomas and sarcomas and cancers of the skin, pancreas, stomach, colon, thorax, liver, gallbladder, musculoskeletal system, breast, lung, ovary, uterus, endometrium, prostrate, colon, skin, mouth, salivary, esophagus, head and neck, plus other tumors of the gastrointestinal tract.

In other embodiments, the patient has age-related weight loss or has age-related sarcopenia. In the case of age-related sarcopenia, a patient may present with muscle wasting without evidence of unintended weight loss. As used herein, at least a subset of patients with age-related weight loss or has age-related sarcopenia may be characterized by an increase in one or more S100 RAGE ligands and/or a decrease in soluble RAGE relative to a reference level.

In other embodiments, the patient has a disease-related cachexia that is not associated with cancer, but that like cancer-induced cachexia fails to respond to treatment with nutritional support and anti-inflammatory therapy. Such disease-related cachexia may, for example, be associated with AIDS, chronic obstructive lung disease, or congestive heart failure and, like cancer-induced cachexia are characterized by an increase in one or more S100 RAGE ligands and/or a decrease in soluble RAGE relative to a reference level.

In certain embodiments, the target cell is selected from a myocyte, an adipocyte, and a hepatocyte. In a preferred embodiment, the target cell is a myocyte.

The presence or absence of the herein disclosed marker(s) is measured in a tissue (e.g., biopsy) or bodily fluid from a pre-cachectic or cachectic subject. Bodily fluids used to evaluate the presence or absence of the herein disclosed markers include without limitation blood, serum, plasma, urine, and or saliva. For example, levels of biomarker are measured in the blood or biopsy before and after treatment in a subject.

Biopsy refers to the removal of a sample of tissue for purposes of diagnosis. For example, a biopsy is from a muscle, fat, a cancer or tumor, including a sample of tissue from an abnormal area or an entire tumor.

The disclosed methods involve comparing the presence or levels of the disclosed markers in a sample from a subject identified as having cancer or a pre-cancerous condition to the levels of the same markers in a reference (e.g., levels present in a corresponding sample from a healthy control). It is understood a reference includes a concurrently run control, or a standard created by assaying one or more non-cancer cells and collecting the marker data. Thus, the control sample is optionally a standard that is created and used continuously. The standard includes, for example, the average level of a biomarker in a sample from a non-cancer control group.

Also provided is a method of predicting or monitoring the efficacy of an anti-cachectic agent in a subject. The method comprises acquiring a biological sample, such as tissue or bodily fluid, from the subject after administering the agent to the subject. F or example, the tissue or bodily fluid is collected from the subject 1 to 60 minutes, hours, days, or weeks after administering the agent to the subject. The method further comprises detecting levels of one or more biomarkers delineated herein (e.g., S100 family proteins). A decrease in level(s) of one or more biomarkers is evidence of treatment efficacy. Thus, a decline in said increase or time is evidence of decreasing efficacy. Thus, it is preferred that biological samples be systematically acquired over time to monitor changes in marker levels.

Panels and Arrays For Characterizing Pre-Cachexia or Cachexia

The invention provides panels for characterizing cachexia comprising the aforementioned markers. In one embodiment, the panel is present on a protein array. Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software is adapted from that used for DNA arrays, as can much of the hardware and detection systems.

One of the chief formats for characterizing cachexia is the capture array, in which ligand-binding reagents, which are usually antibodies, but can also be alternative protein scaffolds, peptides or nucleic acid aptamers, are used to detect target molecules in mixtures such as plasma or tissue extracts. In diagnostics, capture arrays are used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, optionally in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods are automated for high throughput production. For capture arrays and protein function analysis, it is important that proteins be correctly folded and functional; this is not always the case, e.g., where recombinant proteins are extracted from bacteria under denaturing conditions. Nevertheless, arrays of denatured proteins are useful in screening antibodies for cross-reactivity, and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, N.J.) and specialized chip designs, such as engineered microchannels in a plate (e.g., The Living Chip™, Biotrove, Woburn, Mass.) and tiny 3D posts on a silicon surface (Zyomyx, Hayward Calif.). Particles in suspension are also used as the basis of arrays, providing they are coded for identification; systems include color coding for microbeads (Luminex, Austin, Tex.; Bio-Rad Laboratories), semiconductor nanocrystals (e.g., QDOTS™, Quantum Dot, Hayward, Calif.), barcoding for beads (ULTRAPLEX™ beads, SmartBead Technologies Ltd, Babraham, Cambridge, UK) and multimetal microrods NANOBARCODES™ particles, Nanoplex Technologies, Mountain View, Calif.). Beads are optionally assembled into planar arrays on semiconductor chips (LEAPS™ technology, BioArray Solutions, Warren, N.J.).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control. It may or may not alter the functional properties of the protein, and reproducibility and efficiency are variable. Covalent coupling methods provide a stable linkage, are applied to a range of proteins and have good reproducibility. However, orientation is variable. Furthermore, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately, and the array may require special handling and have variable stability.

Several immobilization chemistries and tags have been described for fabrication of protein arrays. Substrates for covalent attachment include glass slides coated with amino- or aldehyde-containing silane reagents. In the VERSALINX™ system (Prolinx, Bothell, Wash.) reversible covalent coupling is achieved by interaction between the protein derivatized with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HYDROGEL™ (PerkinElmer, Wellesley, Mass.), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions ("hexahistidine" disclosed as SEQ ID NO: 1), having modified the protein appropriately. Biotin may be conjugated to a poly-lysine backbone immobilized on a surface such as titanium dioxide (Zyomyx, Inc., Hayward, Calif.) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences, Affymetrix Inc. and Genetix] as well as manual equipment [e.g., V & P Scientific]. Bacterial colonies are optionally robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Nanosciences Inc. and Nanolink Inc., for example, have developed commercially available nanoarrays.

Fluorescence labeling and detection methods are widely used. The same instrumentation as used for reading DNA microarrays is applicable to protein arrays. For differential display, capture (e.g., antibody) arrays are probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity is amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity is achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, Ariz.), rolling circle DNA amplification (Molecular Staging, New Haven, Conn.), mass spectrometry (Intrinsic Bioprobes; Ciphergen, Fremont, Calif.), resonance light scattering (Genicon Sciences, San Diego, Calif.) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Protein expression and interaction can be interegated with high throughput systems such as Fluidim's PROSEEK™ Multiplex systems, where DNA oligonucleotide labeled antibodies are used as probes that bind in proximity to target proteins, and allow extension and creation of real-time PRC amplicons.

Antibody arrays have the required properties of specificity and acceptable background, and some are available commercially (BD Biosciences, San Jose, Calif.; Clontech, Mountain View, Calif.; BioRad; Sigma, St. Louis, Mo.). Antibodies for capture arrays are made either by conventional immunization (polyclonal sera and hybridomas), or as recombinant fragments, usually expressed in *E. coli*, after selection from phage or ribosome display libraries (Cambridge Antibody Technology, Cambridge, UK; BioInvent, Lund, Sweden; Affitech, Walnut Creek, Calif.; Biosite, San Diego, Calif.). In addition to the conventional antibodies, Fab and scFv fragments, single V-domains from camelids or engineered human equivalents (Domantis, Waltham, Mass.) are optionally useful in arrays.

The term scaffold refers to ligand-binding domains of proteins, which are engineered into multiple variants capable of binding diverse target molecules with antibody-like properties of specificity and affinity. The variants are produced in a genetic library format and selected against individual targets by phage, bacterial or ribosome display. Such ligand-binding scaffolds or frameworks include Affibodies based on *S. aureus* protein A (Affibody, Bromma, Sweden), Trinectins based on fibronectins (Phylos, Lexington, Mass.) and Anticalins based on the lipocalin structure (Pieris Proteolab, Freising-Weihenstephan, Germany). These are used on capture arrays in a similar fashion to antibodies and have advantages of robustness and ease of production.

Nonprotein capture molecules, notably the single-stranded nucleic acid aptamers which bind protein ligands with high specificity and affinity, are also used in arrays (SomaLogic, Boulder, Colo.). Aptamers are selected from libraries of oligonucleotides by the Selex™ procedure (SomaLogic, Boulder, Colo.) and their interaction with protein is enhanced by covalent attachment, through incorporation of brominated deoxyuridine and UV-activated crosslinking (photoaptamers). Photocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains are used to detect binding.

Protein analytes binding to antibody arrays are detected directly or indirectly, for example, via a secondary antibody. Direct labeling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sensitivity and specificity, with low background to give high signal to noise. Since analyte concentrations cover a wide range, sensitivity has to be tailored appropriately. Serial dilution of the sample or use of antibodies of different affinities are solutions to this problem. Proteins of interest are frequently those in low concentration in body fluids and extracts, requiring detection in the picogram (pg) range or lower, such as cytokines or the low expression products in cells.

An alternative to an array of capture molecules is one made through molecular imprinting technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, Calif.). Another methodology which is useful diagnostically and in expression profiling is the ProteinChip™ array (Ciphergen, Fremont, Calif.), in which solid phase chromatographic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and are used to assay a wide range of biochemical functions, such as protein interactions with other proteins, drug-target interactions, enzyme-substrates, etc. Generally they require an expression library, cloned into *E. coli*, yeast or similar from which the expressed proteins are then purified, e.g., via a His tag and immobilized. Cell free protein transcription/translation is a viable alternative for synthesis of proteins which do not express well in bacterial or other in vivo systems.

For detecting protein-protein interactions, protein arrays are in vitro alternatives to the cell-based yeast two-hybrid system and are useful where the latter is deficient, such as interactions involving secreted proteins or proteins with disulphide bridges. High-throughput analysis of biochemical activities on arrays has been described for yeast protein kinases and for various functions (protein-protein and protein-lipid interactions) of the yeast proteome, where a large proportion of all yeast open-reading frames was expressed and immobilized on a microarray. Large-scale proteome chips are also useful in identification of functional interactions, drug screening, etc. (Proteometrix, Branford, Conn.).

As a two-dimensional display of individual elements, a protein array is used to screen phage or ribosome display libraries, in order to select specific binding partners, including antibodies, synthetic scaffolds, peptides and aptamers. In this way, library against library screening is carried out. Screening of drug candidates in combinatorial chemical libraries against an array of protein targets identified from genome projects is another application of the approach.

Multiplexed bead assays use a series of spectrally discrete particles that are used to capture and quantitate soluble analytes. The analyte is then measured by detection of a fluorescence-based emission and flow cytometric analysis. Multiplexed bead assays generate data that is comparable to ELISA based assays, but in a multiplexed or simultaneous fashion. Concentration of unknowns is calculated for the cytometric bead array as with any sandwich format assay, i.e., through the use of known standards and by plotting unknowns against a standard curve. Further, multiplexed bead assays allow quantification of soluble analytes in samples never previously considered due to sample volume limitations. In addition to the quantitative data, powerful visual images are generated revealing unique profiles or signatures that provide the user with additional information at a glance.

In some examples of the disclosed methods, when the level of expression of a biomarker(s) is assessed, the level is compared with the level of expression of the biomarker(s) in a reference standard. By reference standard is meant the level of expression of a particular biomarker(s) from a sample or subject lacking a cancer, at a selected stage of cancer, or in the absence of a particular variable such as a therapeutic agent. Alternatively, the reference standard comprises a known amount of biomarker. Such a known amount correlates with an average level of subjects lacking a cancer, at a selected stage of cancer, or in the absence of a particular variable such as a therapeutic agent. A reference standard also includes the expression level of one or more biomarkers from one or more selected samples or subjects as described herein. For example, a reference standard includes an assessment of the expression level of one or more biomarkers in a sample from a subject that does not have a cancer, is at a selected stage of progression of a cancer, or has not received treatment for a cancer. Another exemplary reference standard includes an assessment of the expression level of one or more biomarkers in samples taken from multiple subjects that do not have a cancer, are at a selected stage of progression of a cancer, or have not received treatment for a cancer.

When the reference standard includes the level of expression of one or more biomarkers in a sample or subject in the absence of a therapeutic agent, the control sample or subject is optionally the same sample or subject to be tested before or after treatment with a therapeutic agent or is a selected sample or subject in the absence of the therapeutic agent. Alternatively, a reference standard is an average expression level calculated from a number of subjects without a particular cancer. A reference standard also includes a known control level or value known in the art. In one aspect of the methods disclosed herein, it is desirable to age-match a reference standard with the subject diagnosed with a cancer.

In one technique to compare protein levels of expression from two different samples (e.g., a sample from a subject diagnosed with a cancer and a reference standard), each sample is separately subjected to 2D gel electrophoresis. Alternatively, each sample is differently labeled and both samples are loaded onto the same 2D gel. See, e.g., Unlu et al. Electrophoresis, 1997; 18:2071-2077, which is incorporated by reference herein for at least its teachings of methods to assess and compare levels of protein expression. The same protein or group of proteins in each sample is identified by the relative position within the pattern of proteins resolved by 2D electrophoresis. The expression levels of one or more proteins in a first sample is then compared to the expression level of the same protein(s) in the second sample, thereby allowing the identification of a protein or group of proteins that is expressed differently between the two samples (e.g., a biomarker). This comparison is made for subjects before and after they are suspected of having a cancer, before and after they begin a therapeutic regimen, and over the course of that regimen.

In another technique, the expression level of one or more proteins is in a single sample as a percentage of total expressed proteins. This assessed level of expression is compared to a preexisting reference standard, thereby allowing for the identification of proteins that are differentially expressed in the sample relative to the reference standard.

There are a variety of sequences related to biomarkers as well as any other protein disclosed herein that are disclosed in GenBank (publicly available via the National Center for Biotechnology Information (NCBI), National Institutes of Health (NIH)), and these sequences and others are herein incorporated by reference in their entireties as well as for individual subsequences contained therein. Those of skill in the art understand how to resolve sequence discrepancies and differences and to adjust the compositions and methods relating to a particular sequence to other related sequences. Primers and/or probes are designed for any sequence given the information disclosed herein and known in the art.

Methods of Treating and/or Preventing Pre-Cachexia and/or Cachexia

In another aspect, the present invention provides a method of treating and/or preventing cachexia or pre-cachexia in a patient, comprising administering to a patient in need thereof an effective dose of a compound that inhibits the MEK/ERK signaling pathway, or a pharmaceutically acceptable salt or prodrug thereof.

The invention provides for treating and/or preventing cachexia or pre-cachexia by modulating MEK/ERK signaling. The prototypical mammalian mitogen-activated protein kinase (MAPK) cascade, the Raf-regulated Raf→MAPK/extracellular signal-regulated kinase (ERK) kinase (MEK) 1/2→ERK 1/2 pathway is a well-defined pathway activated by growth factor stimulation of a receptor tyrosine kinase that ultimately leads to changes in gene expression. Myoblasts/myocytes have a unique biphasic requirement for ERK activity (Knight et al., *Skeletal Muscle* 1: 29 (2011). ERK1/2 is critical for growth factor-induced cellular proliferation, inhibitory to myoblast differentiation, and later required for myocyte fusion, or at least ERK2 appears critical to this last process and may play a role in maintaining satellite cell quiescence (Reed et al., *J Cell Biochem* 101:1394-1408 (2007)).The MEK/ERK pathway is also major target for cancer therapeutics. Constitutive activation of the MEK/MAPK pathway is shown to be associated with the neoplastic phenotypes of a relatively large number of cancer cell types (Hoshino et al., Oncogene 18(3): 813-822 (1999); Kim et al., Blood 93(11): 3893-3899 (1999); Morgan et al., Blood, 97(6): 1823-1834 (2001)).

A plethora of inhibitors that target the MEK/ERK signaling pathway have been developed as cancer therapeutics and are often referred to as 'MEK inhibitors.' The pleiotropic effects of these compounds vary widely among members of this class of compounds, but most strikingly between allosteric inhibitors (which are generally less potent) and active site inhibitors. For example, differential consequences for blocking the activation of MEK versus blocking the enzymatic activity of MEK and ERK1/2 may result due to the myriad of input and output signaling pathways for this major signaling hub. Because the biochemical mechanism of inhibition may differ amongst 'MEK inhibitors', all 'MEK inhibitors' may not affect the pathway in the same way.

Note that inhibitors such as PD98059 and U0126 have effects on the ERK pathway generally, rather than specifically on MEK as they are historically described.

In certain embodiments, the compound inhibits MEK/ERK signaling and is selected from one or more of the following compounds: ARRY162, AS703026, AZD6244, AZD8330, BIX02188, BIX02189, GSK1120212, honokiol, lenalidomide, PD98059, PD184352, PD325901, PD318088, RDEA119, SCH772984, SL-327, TAK733, trametinib, U0126, and Vx-11e.

In certain embodiments, the compound inhibits MEK/ERK signaling. In some embodiments, the compound inhibits MEK. In some embodiments, the compound inhibits ERK.

In one aspect, the present invention provides a method of treating and/or preventing cachexia or pre-cachexia in a patient, comprising administering to a patient in need thereof an effective dose of a compound that inhibits the RAGE signaling pathway, or a pharmaceutically acceptable salt or prodrug thereof. As described herein, activation of RAGE was associated with the cachectic phenotype induced by multiple cancer types.

In certain embodiments, the compound inhibits the Receptor for Advanced Glycation Endproducts (RAGE). RAGE is a member of the immunoglobulin supergene family of molecules and was identified herein to be transcriptionally upregulated in muscle cells exposed to a cachexia-inducing factor(s). The extracellular (N-terminal) domain of RAGE includes three immunoglobulin-type regions: one V (variable) type domain followed by two C-type (constant) domains (see FIG. 34) (Neeper et al., J Biol Chem 267:14998-15004 (1992); and Schmidt et al., Circ (Suppl) 96 #194 (1997)). A single transmembrane-spanning domain and a short, highly charged cytosolic tail follow the extracellular domain. The N-terminal, extracellular domain can be isolated by proteolysis of RAGE or by molecular biological approaches to generate soluble RAGE (sRAGE) comprising the V and C domains. Soluble RAGE (a negative regulator of RAGE signaling that acts as a sink for RAGE ligands) was also identified herein to be elevated in non-cachexia-inducing conditioned media in comparison to cachexia-inducing conditioned media. Additionally, treatment with a blocking peptide or antibody to RAGE has been shown to inhibit and reverse the cachexia-induced loss of myosin heavy chain protein in human muscle cells in vitro. RAGE blocking peptides are known in the art (see, for example, Arumugam et al., Clin Cancer Res. 2012: 18(16): 10.1158/1078-0432.CCR-12-0221), and are commercially available (e.g., RAP; a 10 amino acid sequence from S100P (R&D Systems)).

RAGE binds to multiple functionally and structurally diverse ligands, such as proteins having β-sheet fibrils characteristic of amyloid deposits and pro-inflammatory mediators, and includes amyloid beta (Aβ), serum amyloid A (SAA), Advanced Glycation End products (AGEs), S100 (a proinflammatory member of the Calgranulin 65 family), carboxymethyl lysine (CML), Mac-1, β2-integrin, CD11b/CD18 and high-mobility group protein 1 (HMG1), which is also known as high-mobility group protein box-1 (HMGB1) or amphoterin (see FIG. 35) (Bucciarelli et al., *Cell Mol Life Sci* 59:1117-1128 (2002); Chavakis et al., *Microbes Infect* 6:1219-1225 (2004); Kokkola et al., *Scand J Immunol* 61:1-9 (2005); Schmidt et al., *J Clin Invest* 108:949-955 (2001); Rocken et al., *Am J Pathol* 162:1213-1220 (2003); Donato et al., *Curr Mol Med* 13(1): 24-57 (2013)).

The invention also provides methods for inhibiting RAGE by alternative means, such as with the use of small organic molecules, soluble receptor fragments, fusion proteins, antibodies or peptides (see e.g., FIG. 37), as disclosed in WO2011/042548, WO2007/109747, WO2009/136382, WO2011053707, WO2007/109749, WO2008/137552, WO2004/016229, US2010/0226915A1 and U.S. Pat. Nos. 7,981,424, 7,485,697 and 8,420,083, which are hereby incorporated by reference for the compounds and methods for inhibiting RAGE disclosed therein.

In one embodiment, the soluble receptor is a human soluble RAGE polypeptide (bold) fused to a mouse IgG2A Fc chimera (underline):

(SEQ ID NO: 2)
MAAGTAVGAWVLVLSLWGAVVGAQNITARIGEPLVLKCKGAPKKPPQRLE

WKLNTGRTEAWKVLSPQGGGPWDSVARVLPNGSLFLPAVGIQDEGIFRCQ

AMNRNGKETKSNYRVRVYQIPGKPEIVDSASELTAGVPNKVGTCVSEGSY

PAGTLSWHLDGKPLVPNEKGVSVKEQTRRHPETGLFTLQSELMVTPARGG

DPRPTFSCSFSPGLPRHRALRTAPIQPRVWEPVPLEEVQLVVEPEGGAVA

PGGTVTLTCEVPAQPSPQIHWMKDGVPLPLPPSPVLILPEIGPQDQGTYS

CVATHSSHGPQESRAVSISIIEPGEEGPTAGSVGGSGLGTLALA<u>PRGPTI</u>

<u>KPCPPCKCPAPNLLGGPSVFIFPPKIKDVLMISLSPIVTCVVVDVSEDDP</u>

<u>DVQISWFVNNVEVHTAQTQTHREDYNSTLRVVSALPIQIIQDWMSGKEFK</u>

<u>CKVNNKDLPAPIERTISKPKGSVRAPQVYVLPPPEEEMTKKQVTLTCMVT</u>

<u>DFMPEDIYVEWTNNGKTELNYKNTEPVLDSDGSYFMYSKLRVEKKNWVER</u>

<u>NSYSCSVVHEGLHNHHTTKSFSRTPGK</u>.

Representative RAGE peptides further include peptides derived from the N-terminus of RAGE, e.g., the C-domain and multimerization epitope, as disclosed in US2010/0226915A1. way of example, such RAGE blocking peptides include an amino acid sequence as follows: C(K/R)GAPKKP(P/T)Q(Q/R/K)LE (SEQ ID NO: 3); CRGAPKKPPQQLE (SEQ ID NO: 4); CKGAPKKPPQRLE (SEQ ID NO: 5); CKGAPKKPTQKLE (SEQ ID NO: 6). Other examples of RAGE blocking peptide are as follows: DGKPLVPNEKGVSVKEQTRRHPETGLFTLQ (SEQ ID NO: 7); TLQSELMVTPARGGDPRPTFSCSFSPGLPR (SEQ ID NO: 8); or LPRHRALRTAPIQPRVWEPVPLEEVQLVVE. (SEQ ID NO: 9). Such RAGE blocking peptide sequences are as described in US2010/0226915, which is incorporated herein by reference. In some cases, the RAGE blocking peptide is in the form of a cyclic peptide.

Representative antibodies of the invention include antibodies that specifically bind RAGE and compete for binding to RAGE with an XT-H1, XT-H2, XT-H3, XT-H5, XT-H7, or XT-M4 antibody, or which bind to an epitope of RAGE bound by an XT-H1, XT-H2, XT-H3, XT-H5, XT-H7, or XT-M4 antibody, as disclosed in WO2007/109747.

Representative antibodies further include anti-RAGE antibodies that bind to various domains in RAGE. For example, antibodies that bind to the C1- and C2-domain in RAGE and compete with ligands, e.g., Aβ for binding to RAGE as disclosed in WO 2009/136382; antibodies that bind to the V-domain in RAGE and compete with ligands, e.g., S100b, HMGB1 and amyloid αβ for binding to RAGE, as disclosed in W02007/109749; and antibodies that inhibit the interaction of human RAGE and a complex of HMGB1 and CpG DNA, as disclosed in WO2008/137552.

Antibodies that specifically bind to RAGE suitable for use in the methods of the invention also include variants of any of the antibodies described herein, which may be readily prepared using known molecular biology and cloning techniques. See, e.g., U.S. Published Patent Application Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, all of which are hereby incorporated by reference herein in their entireties.

Suitable antibodies may also comprise a label attached thereto, such as a detectable label (e.g., a radioisotope, fluorescent compound, enzyme or enzyme co-factor). Suitable antibodies include whole antibodies and fragments thereof including chimeric antibodies, humanized antibodies, single chain antibodies, tetrameric antibodies, tetravalent antibodies, heteroconjugate antibodies, bispecific antibodies, multispecific antibodies, domain-specific antibodies, domain-deleted antibodies, diabodies, antibody conjugates (e.g., with an Fc domain (e.g., an antigen binding domain fused to an immunoglobulin constant region), PEG, an immunoglobulin domain, etc.), Fab fragments, Fab' fragments, F(ab')$_2$ fragments, Fv fragments, ScFv fragments, Fd fragments, single domain antibodies, and dAb fragments, and Fc fusion protein.

In certain embodiments, the compound inhibits signals downstream of MEK/ERK.

In certain embodiments, the invention provides methods for the treatment and/or prevention of cachexia or pre-cachexia by administering a low dose(s) of MEK/ERK inhibitors, e.g., as compared to an effective dose of that inhibitor for the treatment of cancer. In certain embodiments, an effective dose of the compound for treating or preventing cachexia or pre-cachexia is at most half the effective therapeutic dose of that compound for the treatment of cancer. In certain embodiments, an effective dose of the compound is half the effective therapeutic dose for the treatment of cancer. In certain embodiments, an effective dose of the compound is less than half the effective therapeutic dose for the treatment of cancer. Accordingly, a dose of a MEK/ERK inhibitor that effectively treats and/or prevents cachexia or pre-cachexia may not be an effective dose for treating cancer. Additionally, because complete inactivation of MEK/ERK in muscle cells can be deleterious, in some embodiments, an effective dose of MEK/ERK inhibitors to treat and/or prevent cachexia results in MEK/ERK pathway activity that is at least 50%, 40%, 30% or 20% of healthy baseline. For example, an effective amount of a MEK/ERK inhibitor to treat and/or prevent cachexia results in MEK/ERK pathway activity that is at least 50%, 40%, 30% or 20% of healthy baseline. In certain embodiments, MEK/ERK and/or RAGE signaling is inhibited in a myocyte. In certain embodiments, the myocyte is a mature or immature myocyte. In certain embodiments, the myocyte is a skeletal myocyte or a cardiac myocyte. In a preferred embodiment, the myocyte is a skeletal myocyte. In certain embodiments, MEK/ERK and/or RAGE signaling is inhibited in an adipocyte. In certain embodiments, the adipocyte is a mature or immature adipocyte. In certain embodiments, MEK/ERK and/or RAGE signaling is inhibited in a hepatocyte. In certain embodiments, the hepatocyte is a mature or immature hepatocyte.

In certain embodiments, an effective dose of the compound increases myofibrillar protein content and does not inhibit cellular proliferation of the myocyte. In certain embodiments, the myofibrillar protein is selected from myosin, actin, tropomyosin, myosin heavy chain, myosin light chain, troponin, titin, and nebulin. In a preferred embodiment, the myofibrillar protein is a myosin heavy chain protein.

In certain embodiments, the patient has cachexia or pre-cachexia associated with a cancer. In a preferred embodiment, the patient has cachexia or pre-cachexia associated with a cancer. In one embodiment, the cancer is an epithelial-derived cancer or a mesenchymal-derived cancer. In one embodiment, the cancer is selected from one or more of a carcinoma, a sarcoma, and cancers of the skin, pancreas, stomach, colon, thorax, liver, gallbladder, musculoskeletal system, breast, lung, ovary, uterus, endometrium, prostrate, colon, skin, mouth, salivary, esophagus, head and neck, plus other tumors of the gastrointestinal tract.

Significantly, no treatment for cancer-induced cachexia was previously available.

In other embodiments, the patient has age-related weight loss or has age-related sarcopenia. In the case of age-related sarcopenia, unintended weight loss is not necessarily present. In at least a subset of this population, such conditions are characterized by an increase in one or more S100 RAGE ligands and/or a decrease in soluble RAGE relative to a reference level.

In other embodiments, the patient has disease-associated or disease-induced cachexia that is not associated with cancer, but that like cancer-induced cachexia fails to respond to treatment with nutritional support and anti-inflammatory therapy. Such disease-associated or disease-induced cachexia may, for example, be associated with AIDS, chronic obstructive lung disease, or congestive heart failure and, like cancer-induced cachexia are characterized by an increase in one or more S100 RAGE ligands and/or a decrease in soluble RAGE relative to a reference level.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLE 1

Identification of Cachexia in Mice

Conventional wisdom held that mice "do not get cancer cachexia." To the contrary, results provided herein demonstrate that human cancer cell lines induce a cachectic state in murine xenograft models. Specifically, 14 cell lines (5 mice each) spanning 6 tumor types were tested, and their ability to induce cachexia based on extensive phenotyping including a) metabolite profiling of plasma, skeletal muscle, adipose tissue and liver, b) gene expression profiling, and c) careful measurement of animal weights was characterized. As in humans, approximately half of the mice developed weight loss that met clinical criteria for cachexia (≥5% of body weight) (FIG. 1C), thus providing a strong basis for future discovery (FIG. 1D).

Figure 2:
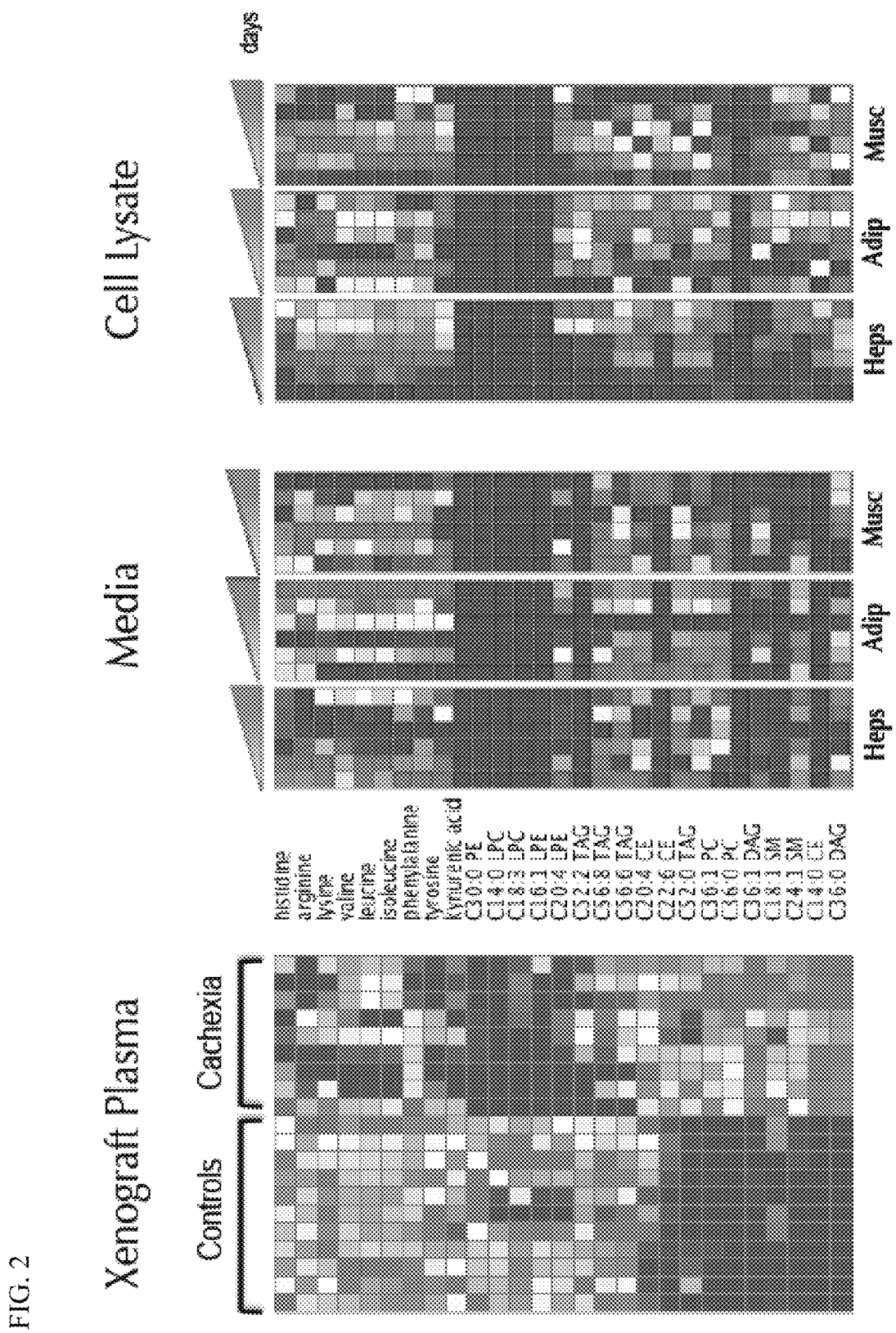
FIG. 2 shows the metabolite signature in mouse xenograft plasma and in in vitro hepatocyte (Heps), adipocyte (Adip), and myocyte (Musc) models. Features of the most differentially abundant metabolites from cachectic xenograft plasma are reflected in specific components and cell types in the in vitro models of cachexia. "PE" refers to phosphatidylethanolamine; "LPC" refers to lysophosphotidylcholine; "LPE" refers to lysophosphatidylethanolamine; "TAG" refers to triacylglycerol; "CE" refers to cholesterol esters; "PC" refers to phosphatidyl choline; "DAG" refers to diacylglycerol; "SM" refers to sphingomyelin. The number in each lipid name is used to describe the fatty acid chains on the lipid, where the number of carbons in fatty acid chain: number of double bonds in fatty acid chain. For example, 16:0 would be 16 carbons in the fatty acid chain with zero double bonds, or the numeric representation of palmitic acid.
Figure 3:
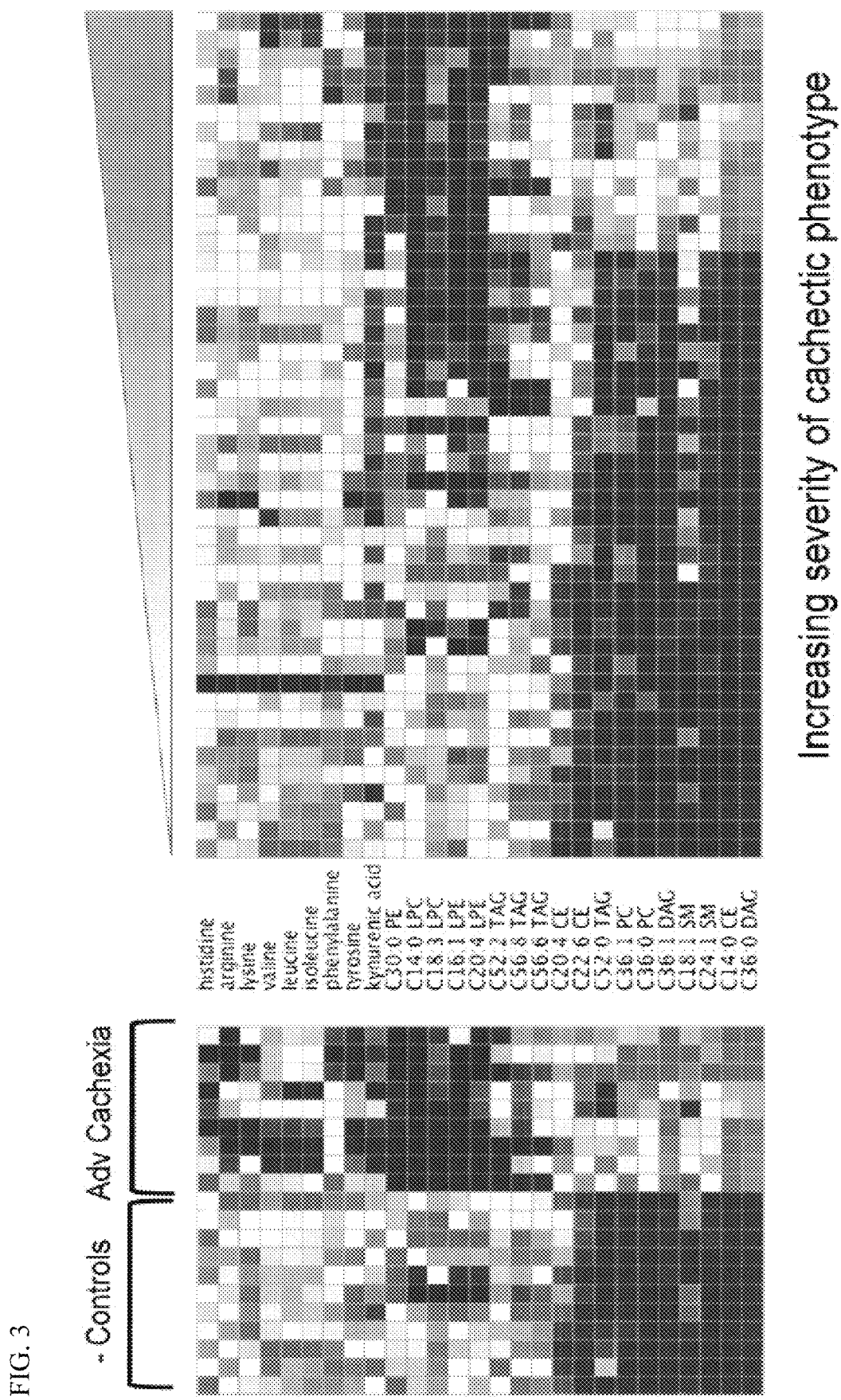
FIG. 3 shows the metabolite signature in mouse plasma across a spectrum of cachectic phenotypes.

Profiling of ≤320 metabolites in relevant tissues showed a consistent pattern in cachectic animals and in vitro models: plasma loss of specific amino acids and lipids with an increase lipid degradation products (e.g., diacylglycerides); myocyte accumulation followed by depletion of these amino acids along with gradual depletion of lipids; adipocyte loss of both; and hepatocyte accumulation of both branched chain amino acids and lipids (FIG. 2). As shown in FIG. 2, metabolites and markers that are altered in cachexia compared to controls include amino acids or amino acid derivatives, such as histidine, arginine, lysine, valine, leucine, phenylalanine, isoleucine, and tyrosine, and kynurenic acid, and include metabolites, such as lipid metabolites, e.g., sphingomyelins, lysophospholipids, di-acyl-glycerides, triacyl glycerides, cholesterol esters, and/or phospholipids. The loss of amino acids and lipids in plasma correlated with increasing severity of the cachectic phenotype (FIG. 3). Basic, branched chain and aromatic amino acids were diminished in the plasma of cachectic animals, a pattern also seen in patients with pancreatic cancer, which is commonly associated with cachexia. Not all amino acid species were elevated, which one might expect if massive myocyte lysis or necrosis had occurred. Many triglycerides were lower.

Sphingomyelins and di-acyl-glycerides were elevated. Pyruvate was slightly elevated, but TCA cycle intermediates were statistically lower. These findings are consistent with recent descriptions of metabolic disturbances in human cachexia, and serve to validate our mouse model of the disease (Das, S. K., et al. *Science* 333(6039): 233-238 (2011); Eley, H. L. et al. *Biochem J* 407(1): 113-120 (2007); Nieman, K. M. et al., *Nat Med* 17(11):1498-1503 (2011); and Lieffers, J. R. et al., *Am J Clin Nutr* 89(4): 1173-1179 (2009)).

EXAMPLE 2

Development of In Vitro Readout of Cachexia in Primary Cells

Figure 4:
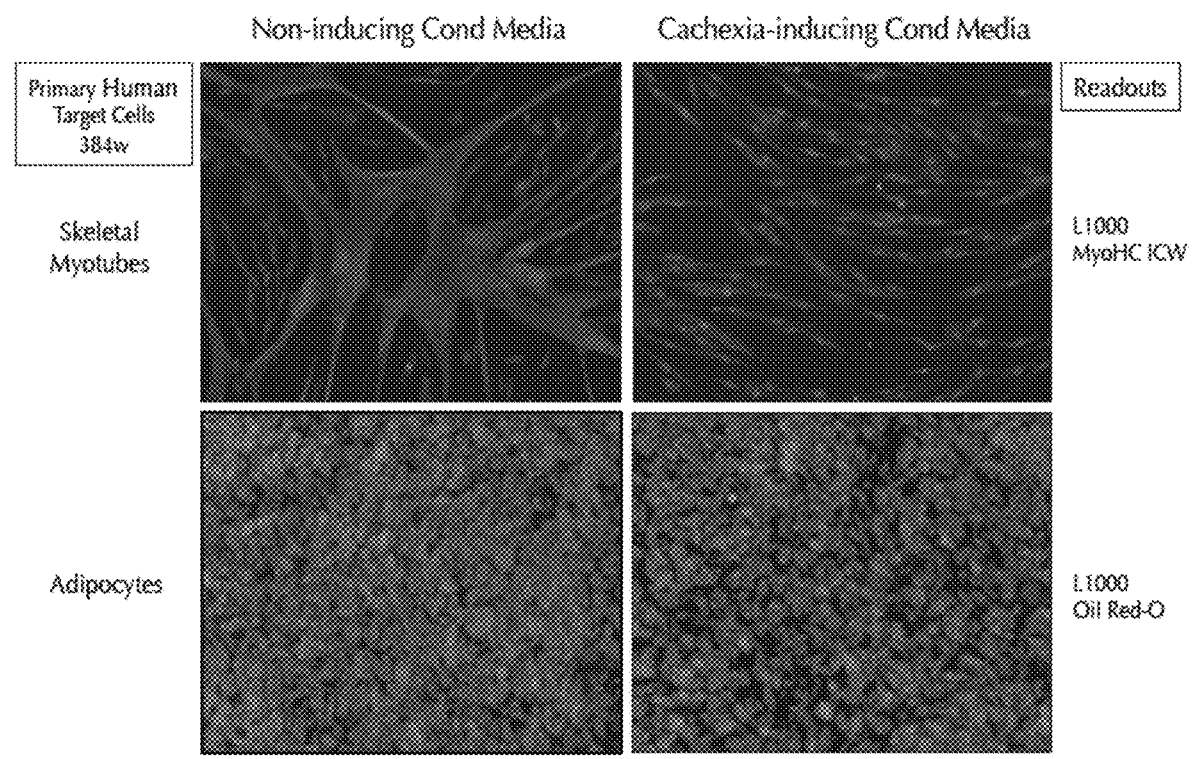
FIG. 4 provides four micrographs showing in vitro fully differentiated human skeletal myocytes (top) and human adipocytes (bottom) treated for 3 days with non-inducing conditioned media (left) or cachexia-inducing conditioned media (right). The fully differentiated human skeletal myocytes and human adipocytes atrophy in response to a cachectic mediator(s) in the conditioned media.

To discover the secreted factors that confer cachexia-inducing ability to cell lines, a tractable in vitro model system was developed. In order to maximize physiological relevance, primary human skeletal muscle (FIG. 4, top). adipocytes (FIG. 4, bottom) and hepatocytes were cultured in vitro. These cell types represent the principal end-organ tissues affected by cachexia. Interestingly, phenotypic alterations were seen in skeletal myotubes and adipocytes within 5-days of treatment with cachexia-inducing conditioned media. This provides for analysis of alterations in gene expression at the earliest stages of disease. By selecting various time points after contact with cachexia inducing media, markers expressed during pre-cachexia, cachexia, and in refractory cachexia can be identified.

Figure 5:
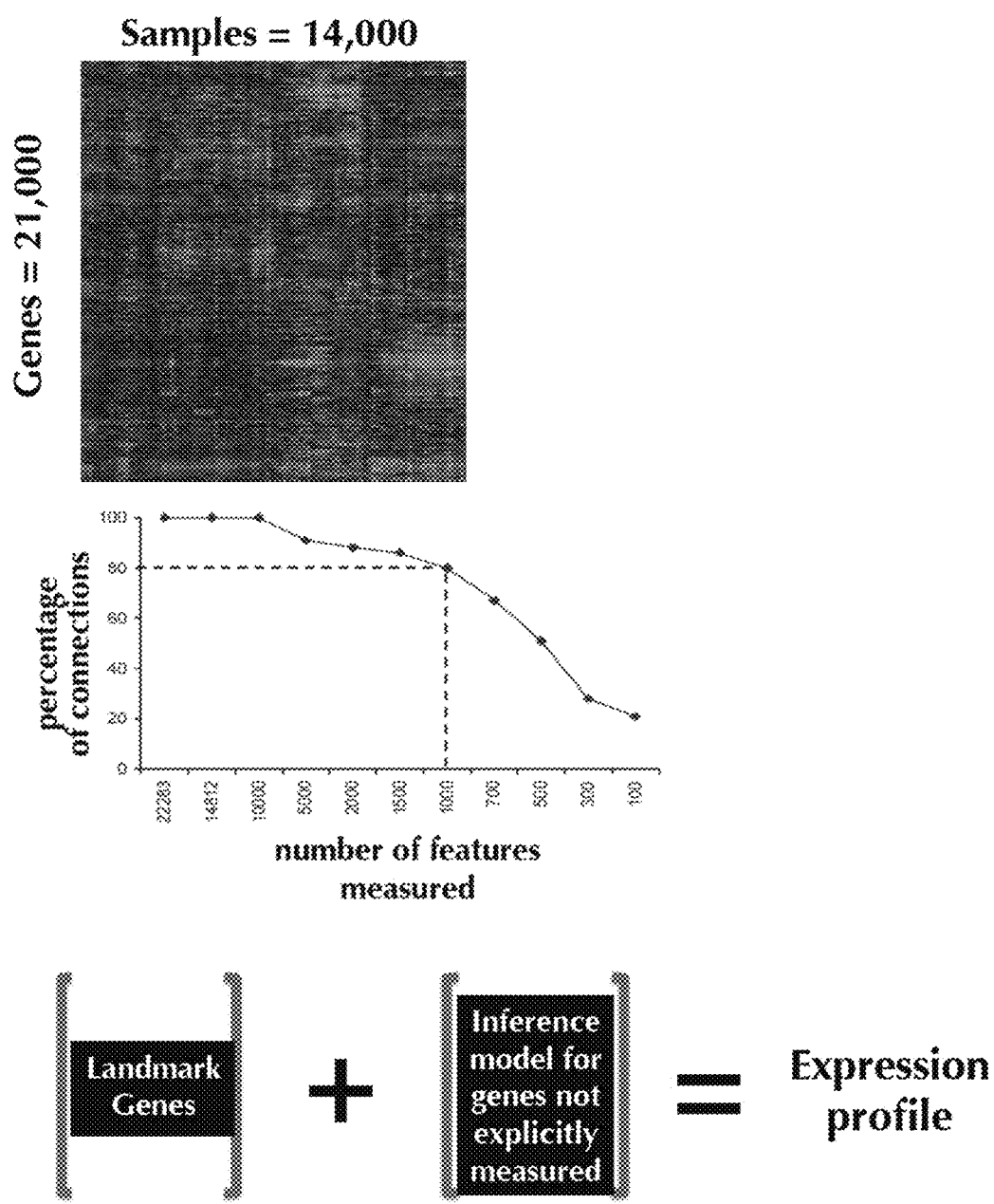
FIG. 5 is a summary of the global high-resolution readout of the L1000 gene expression profile.

A faithful read-out of the cachectic phenotype was also developed using a novel high-throughput, low-cost gene expression profiling method (L1000) (FIG. 5). L1000 involves the profiling of 1000 human transcripts from which the remainder of the transcriptome can be computationally inferred. This method, validated in over 1 million samples, allowed for profiling of small numbers of cells grown in 384-well plates.

The L1000 platform pairs ligation-mediated amplification (LMA) with a Luminex-bead based detection system and is an extension of a previously reported method for expression profiling based on Luminex bead technology (Peck el al., *Genome Biol* 7(7):R61 (2006)) to create a 1,000-plex profiling solution. Briefly, the method involves LMA, using locus-specific probes engineered to contain unique molecular barcodes, universal biotinylated primers, and 5.6-micron optically-addressed polystyrene microspheres coupled to capture probes complementary to the barcode sequences. After hybridizing the LMA products to a mixture of beads and staining with streptavidin-phycoerythrin, the hybridization events are detected using a two-laser flow cytometer, whereby one laser detects the bead color (denoting transcript identity), and the other laser detects the phycoerythrin channel (denoting transcript abundance). The plex limit for this approach (set by the number of available bead colors) is 500, whereby the 500 distinct bead colors is discerned using an instrument with the required capabilities and excellent performance characteristics. Further, a computational strategy was developed that allows for two transcripts to be detected using a single bead color (with subsequent computational deconvolution). The resulting assay is a 1,000-plex assay detectable in a single well of a 384-well plate at very modest cost.

Figure 6A:
Figure 6A:
Figure 6A:
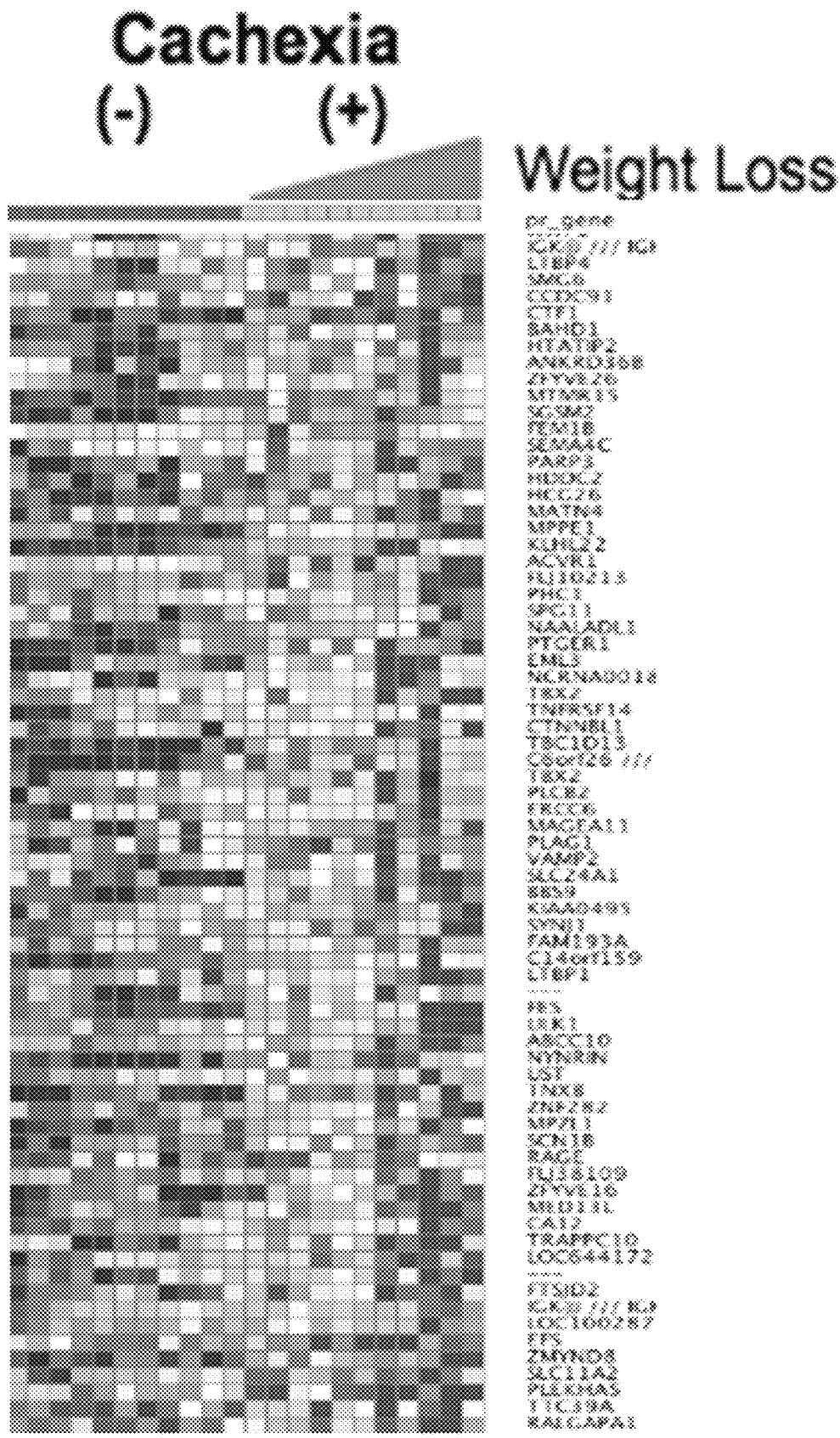
Figure 7:
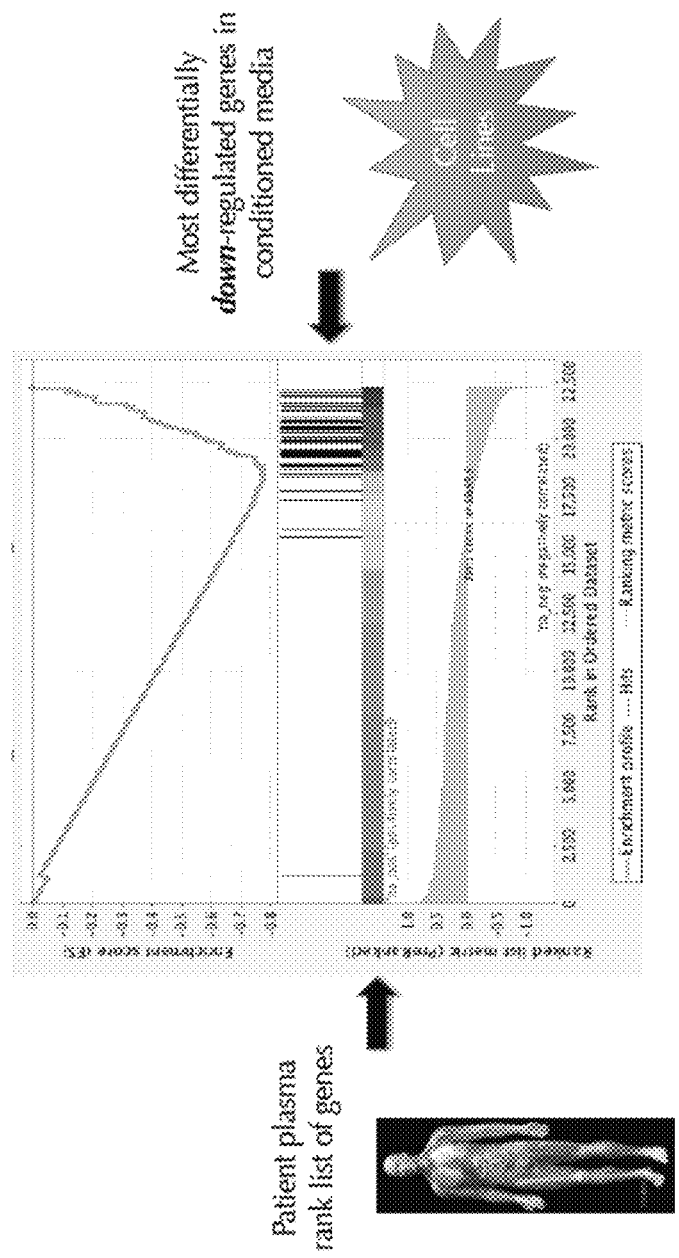
FIG. 7 is a summary of the Gene-Set Enrichment Analysis (GSEA) of genes regulated by cachectic patient plasma and cachexia-inducing conditioned media. GSEA shows that conditioned media and patient plasma induce a common gene expression signature.
Figure 8A:
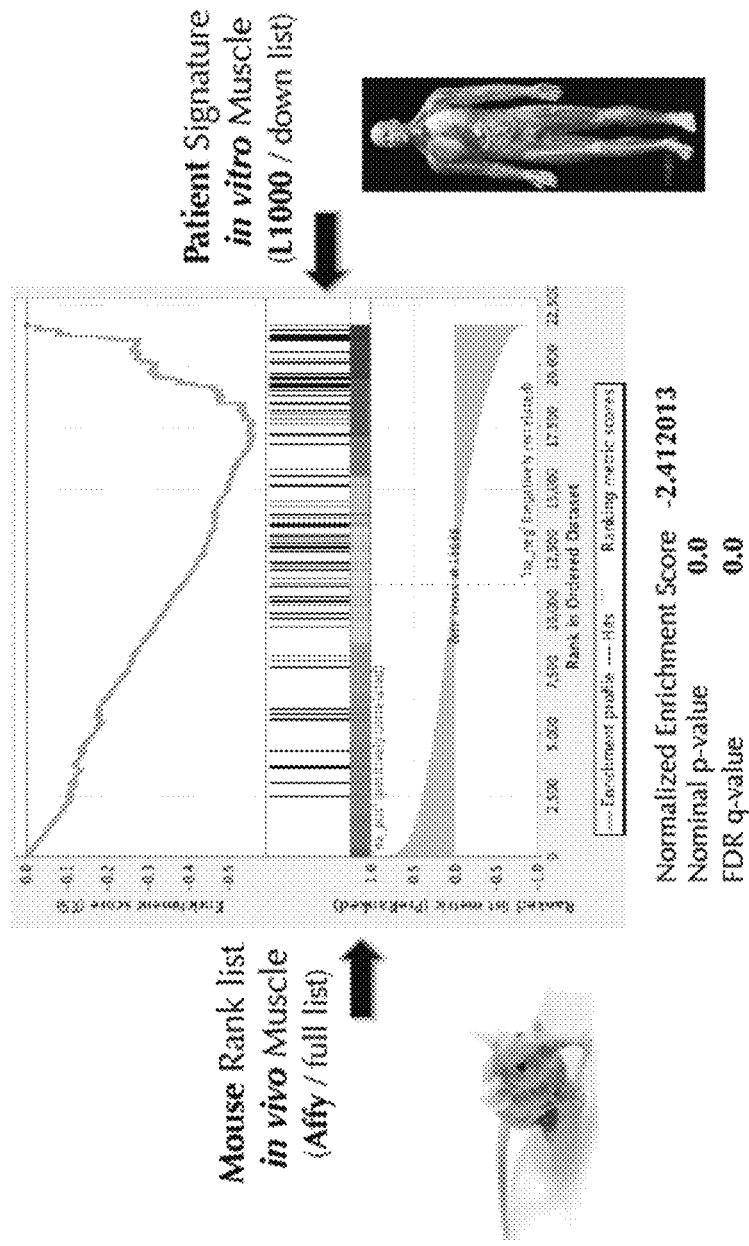
FIG. 8A is a summary of the Gene-Set Enrichment Analysis (GSEA) of genes regulated in in vivo cachectic mouse muscle cells and in vitro cachectic human muscle cells. GSEA shows that the cachectic signature correlates across species and across platforms.
Figure 8B:
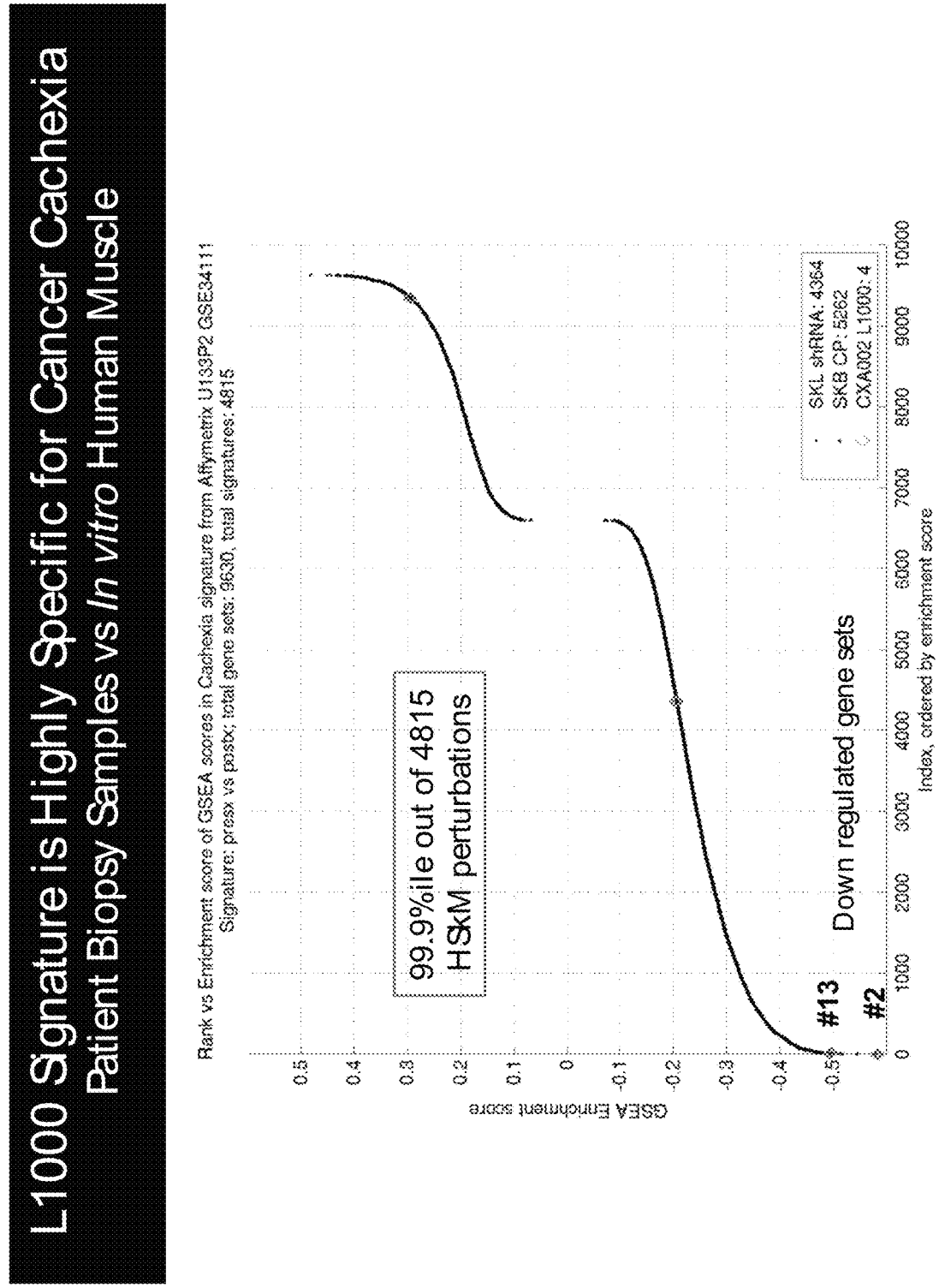
FIG. 8B provides a graph showing the L1000 signature. This demonstrates that the in vitro patient Plasma Cachexia Signatute has tremendous specificity (99.9%-ile out of 4,815 in vitro human skeletal muscle perturbations) for clinical cachexia (determined by serial muscle biopies of a series of patients who fortunately had curative resection of their cancer and reversal of their cachexia).

Using the L1000 method, cachectic patient-derived plasma samples induced a reproducible and characteristic gene expression signature in primary skeletal muscle cells in comparison to non-cachectic patient plasma (FIG. 6). Consistent with this result and with the physiology of cachexia, skeletal myocytes and adipocytes atrophied in size (FIG. 4), and myocytes lost expression of myosin heavy chain protein, as has been previously reported in cancer cachexia (Acharyya, S. et al., *J. Clin Invest* 114(3): 370-378 (2004). Human-cancer-cell-conditioned media recapitulated the L1000 cachexia signature seen in patient plasma in in vitro human muscle cells (FIG. 7). Furthermore, the L1000 cachexia signature was seen in mouse skeletal muscle tissue harvested from cachectic mice and analyzed by Affymetrix gene expression arrays. This analysis showed that the Affymetrix cachexia signature in mouse skeletal muscle tissue correlated with the L1000 cachexia signature of patient human muscles cells (FIG. 8), demonstrating that the cachectic signatures correlated across species and across platforms.

These results showed that (1) L1000 provided a robust read-out of the cachectic state, suitable for large-scale studies, (2) primary skeletal muscle cells grown in vitro was a powerful model system for discovery, and (3) conditioned media from cachexia-inducing cell lines induced an L1000 signature that recapitulated that of cachectic patient samples.

These studies also showed that the immune system was not required to induce cachexia: conditioned media applied directly to primary skeletal muscle in vitro was sufficient to induce the phenotype. And importantly, the conditioned media results proved that the cachexia-inducing factor(s) was a secreted molecule. This is the first-ever experimental system capable of dissecting the biological basis of cancer cachexia.

EXAMPLE 3

Discovery that a Cachexia-Inducing Factor(s) is a Protein

The cachexia-inducing factor(s) could in principle be any secreted biomolecule. To establish whether the factor was a protein, in vitro muscle cells were treated with conditioned media that had either been treated with proteinase K or had been boiled. The cells were analyzed by L1000 profiling and Western blotting (FIG. 9A). Boiling ablated the L1000 cachexia signature (FIG. 9B) and prevented the characteristic loss of myosin heavy chain (MyoHC) protein associated with cachexia. These results indicated that the cachexia-inducing factor is a protein. Similar results were obtained from samples treated with proteinase K (FIG. 9C).

EXAMPLE 4

Testing of Previously Suggested Candidate Cachexia-Inducing Proteins

Prior studies of patient-derived samples or of non-cancer cachexia models had pointed to a number of proteins that showed some relevance to cancer cachexia (Acharyya, S. and Guttridge, D. C., *Clin Cancer Res* 13(5): 1356-61 (2007); and Zhou, X. et al., *Cell* 142(4): 531-543 (2010)). More than 300 such secreted proteins (including IL-1, IL-6, IL-10, TNFα, IFNγ, Myostatin, and Activin) were tested, but none of them strongly induced the cachexia signature in the systems described herein. Therefore, it is likely that the major cachexia-inducing factors were yet to be discovered.

Figure 10:
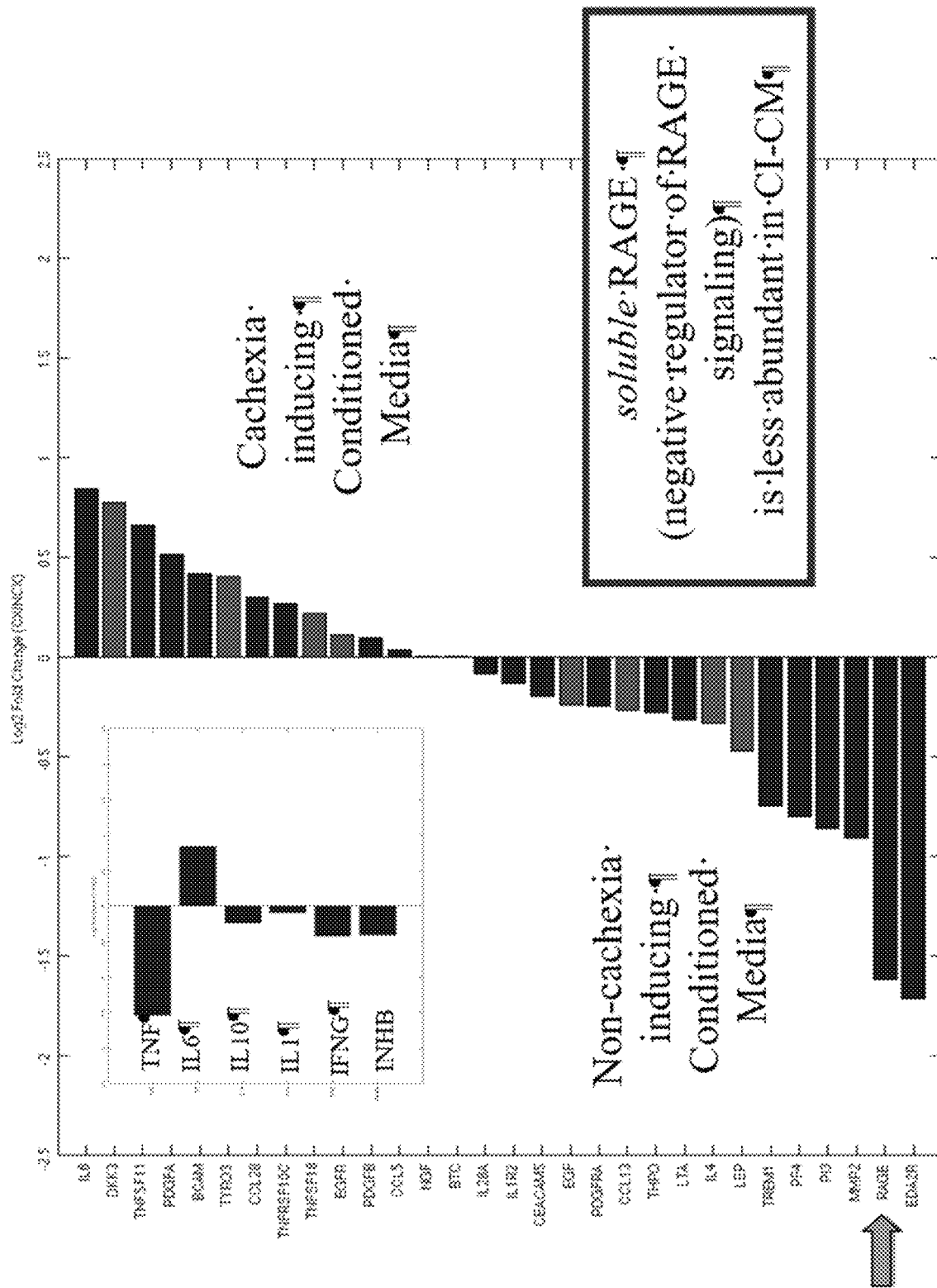
FIG. 10 is a plot showing the relative cytokine array quantification in non-cachexia-inducing conditioned media (NCI-CM) compared to cachexia-inducing conditioned media (CI-CM) (4 each). The plot demonstrates that most of the cytokines purported to have relevance in cachexia (e.g., TNFa, IL-10, IL-1, IFNγ, and INH) are less abundant in CI-CM, as compared to NCI-CM.

The relative abundance of cytokines in cachexia-inducing conditioned media (CI-CM) and non-cachexia-inducing conditioned media (NCI-CM) was determined. In agreement with the above findings, IL-1, IL-10, TNFα, IFNγ, and INHBA were found to be less abundant in CI-CM, as compared to NCI-CM (FIG. 10). Only IL-6 is relatively more abundant in the CI-CM, as compared to NCI-CM. Notably, soluble RAGE (sRAGE), a naturally occurring negative regulator of full length RAGE, was also found to be more abundant in NCI-CM (≥1.5 fold), as compared to CI-CM. RAGE was up-regulated in muscles stimulated by plasma from cachectic patients

EXAMPLE 5

Elucidation of Suitable Protein Separation Methods

To identify cachexia associated factors, conditioned media will be fractionated, and the fractions tested for their cachexia-inducing potential. Typical fractionation methods result in fractions that are eluted in non-physiological buffer conditions, such that they are not suitable for testing in cell culture. The present methods employ ion exchange HPLC with size exclusion ultrafiltration to both reduce the protein complexity of conditioned media fractions and exchange the high salt buffer to one compatible with our in vitro assay. This approach identified 3 consecutive fractions out of 700 that retained cachexia-inducing activity by L1000, thus demonstrating feasibility of the proposed fractionation process.

EXAMPLE 6

Discovery of Candidate Cachexia-Inducing Factors

Having shown that conditioned media from certain cancer cell lines secretes a protein mediator of cachexia, the causal factor could be identified. While in principle a comparative proteomic analysis of conditioned media could be used, the protein complexity of the samples was prohibitively high. Therefore, two parallel approaches were undertaken: (1) biochemical fractionation of conditioned media, tracking the cachexia-inducing activity in each fraction (using L1000), and performing mass spectrometric analysis of fractions that retain the activity; and (2) quantitative proteomic methodology (based on iTRAQ labeling) to compare cachexia-inducing conditioned media to non-cachexia inducing media.

(1) Extensive biochemical fractionation of conditioned media to track/isolate cachexia-inducing activity.

Figure 11:
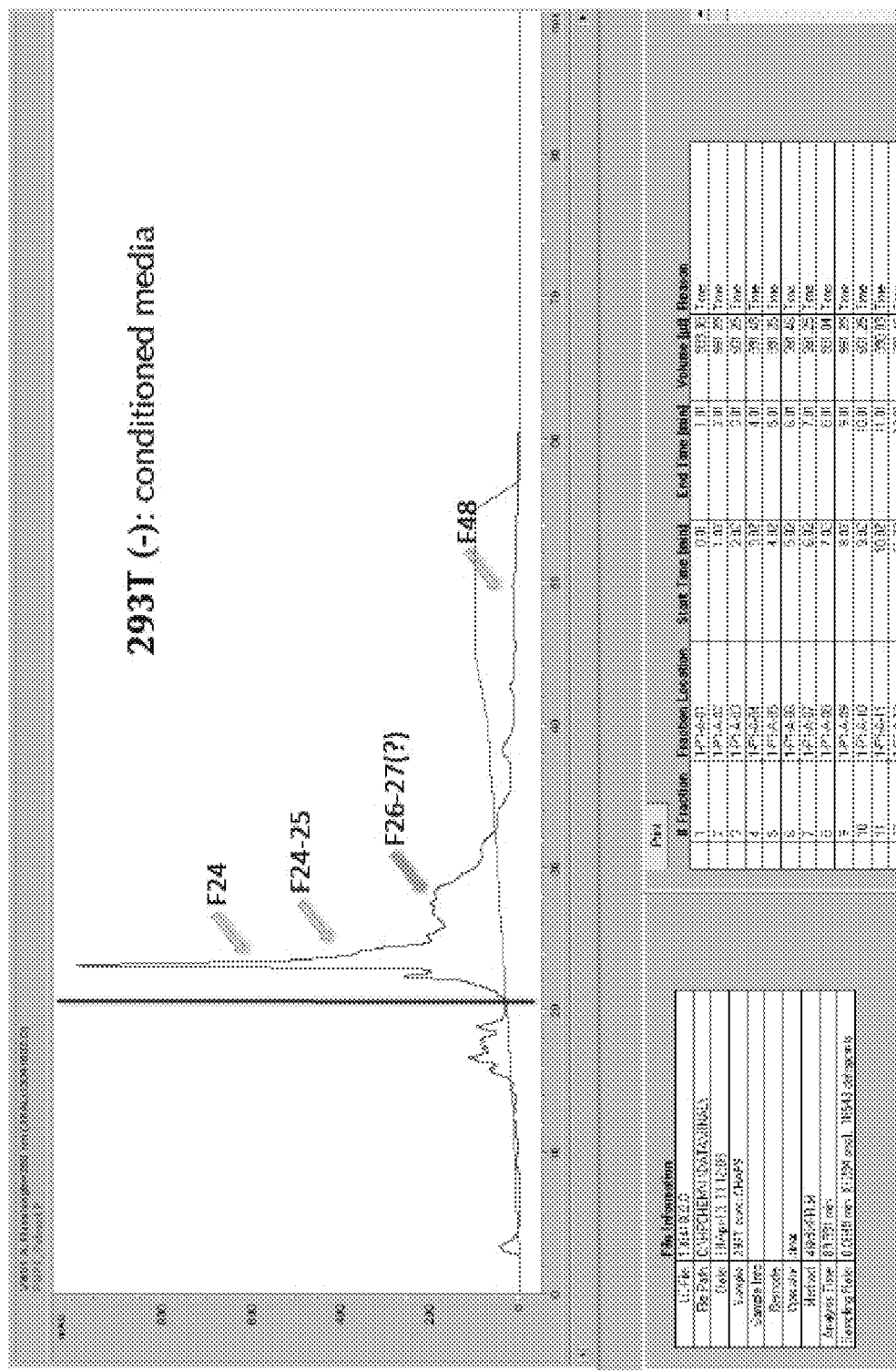
FIG. 11 is a plot showing the UV trace of the IE fractionations of media conditioned with non-cachexia inducing 293T cells.
Figure 12:
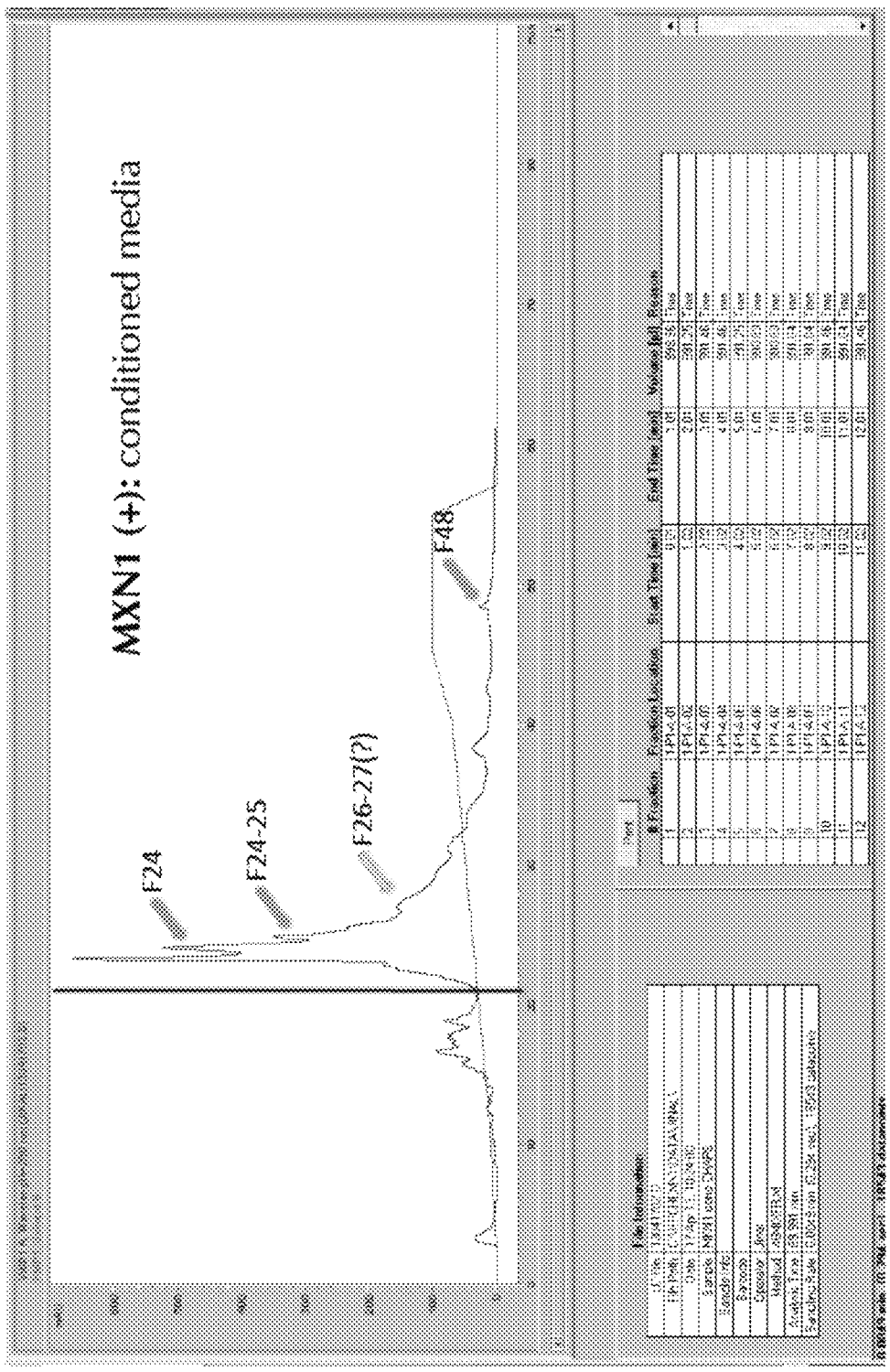
FIG. 12 is a plot showing the UV trace of Ion Exchange fractionations of media conditioned with cachexia-inducing MKN1cells, a human gastric cancer cell line.
Figure 13:
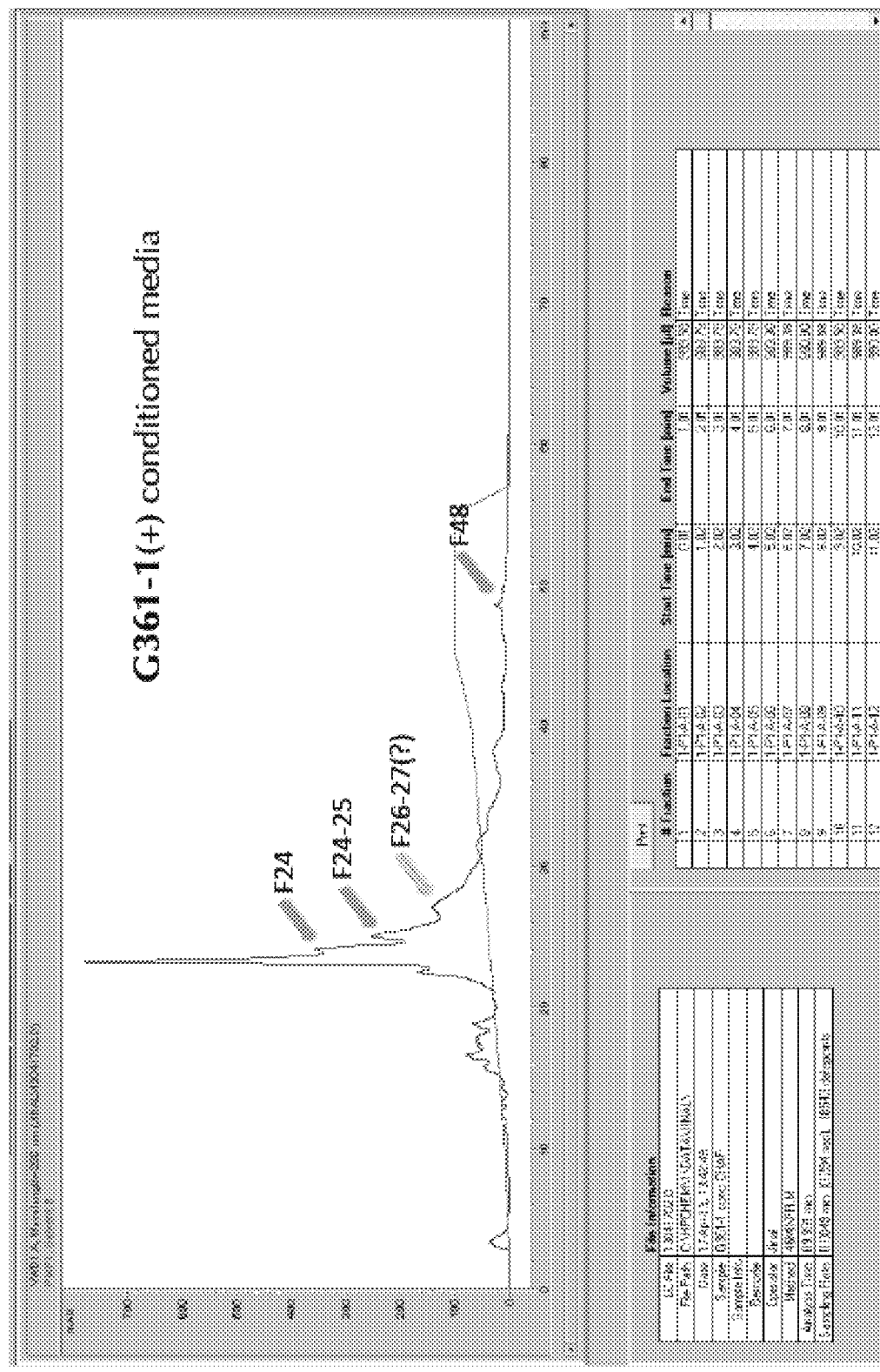
FIG. 13 is a plot showing the UV trace of Ion Exchange fractionations of media conditioned with cachexia inducing G361 cells, which is a human malignant melanoma cell line.

Complementary high performance liquid chromatography techniques were used to identify the cachexia-inducing protein from growth media collected from cachexia-inducing human cancer cell lines. Specifically, conditioned media was subjected to size exclusion chromatography using an Agilent Zorbrax Bio Series GF-250 column (pore diameter of 150 Å), mobile phase of PBS, pH 7.0, at a flow rate of 0.25 ml/min. Each of the ~30 fractions were subjected to L1000 profiling on primary human myocytes, using a custom computational pipeline that calculates an Enrichment Score (Subramanian, A. et al., *Proc Natl Acad Sci USA* 102(43): 15545-15550 (2005)) for each test sample's cachexia signature compared to control. Fractions that induced the signature were subjected to further fractioning using ion exchange chromatography, using a bivalent Poly-CATWAX column with an ammonium acetate gradient (10 mM to 700 mM) (FIGS. 11-13). These fractions were evaluated for cachexia-inducing activity by L1000, and active fractions were further refined through hydrophobic interaction chromatography (HIC) on a TOYOPEARL MD-G Buyl-650S column.

Final fractions that retained the ability to induce the in vitro cachexia phenotype were expected to contain a sufficiently small number of proteins that their identity could be resolved by mass spectrometry. Fractions with identified activity were subjected to tryptic digestion followed by data-dependent nanospray LCMS analysis in order to determine their protein constituents on a Thermo Scientific QExactive high performance mass spectrometer. This analysis yielded a tractable number of candidate cachexia-inducing proteins suitable for subsequent validation.

(2) iTRAQ quantitative proteomic comparison of cachexia-inducing vs. non-inducing conditioned media.

A potential disadvantage of the extensive fractionation approach is the potential for losing activity in the fractionation steps. Therefore, to complement the fractionation approach discussed above, quantitative proteomic analysis was undertaken of conditioned media from cell lines that did or did not induce cachexia. This approach identified seventeen credentialed human cancer cell lines (controlled for lineage along pancreatic, gastric, lung, ovarian, and melanoma cell types) having cachexia-inducing ability in xenograft mice and/or based on L1000 cachexia signature analysis of in vitro human myocytes.

Figure 14B:
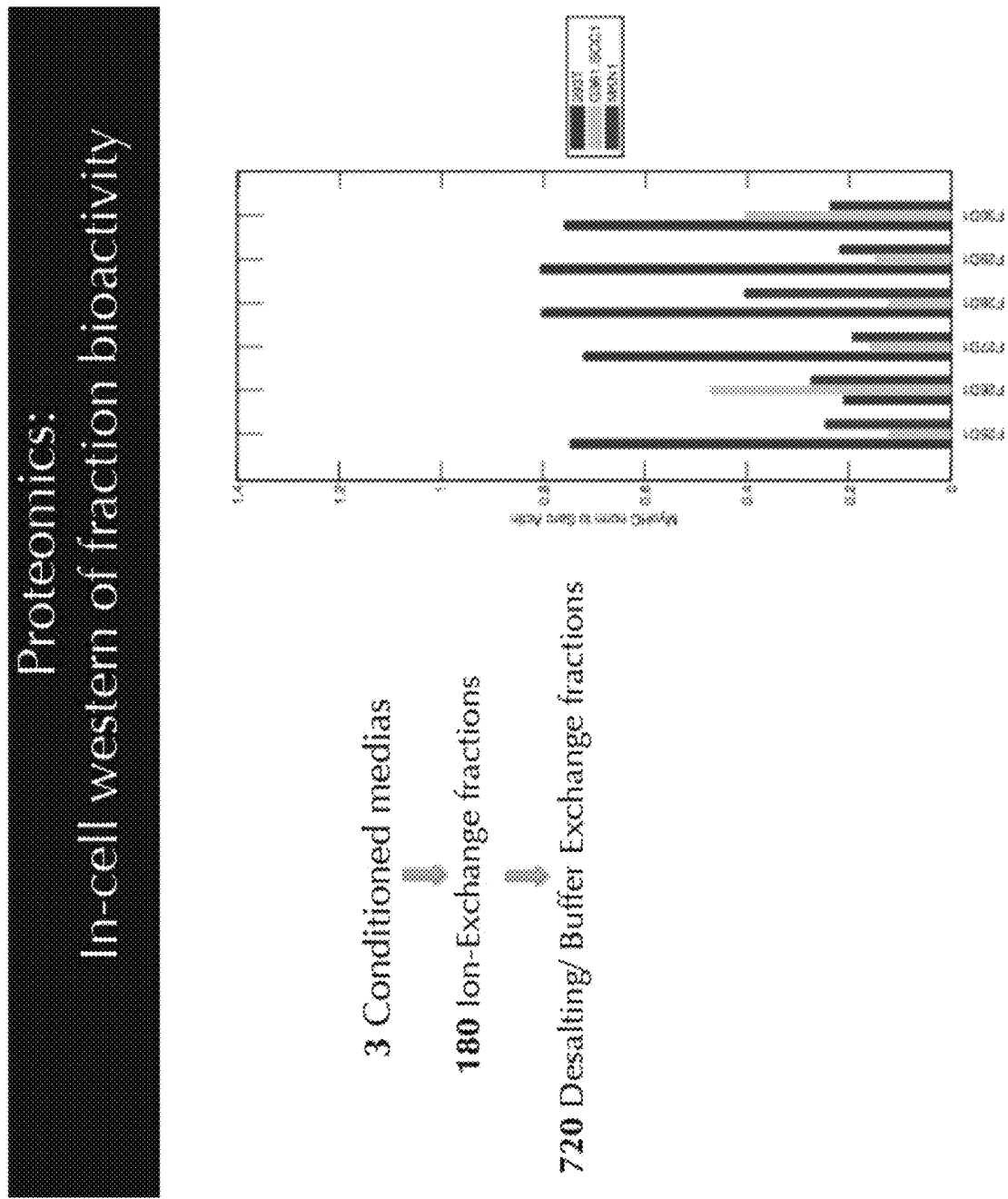
FIG. 14B is a graph comparing the myosin heavy chain protein content determined by In-cell Western (ICW) analysis across fractions 25-30 of non-cachexia-inducing conditioned media (293T) and cachexia-inducing conditioned media (MkN1 and G361).
Figure 14C:
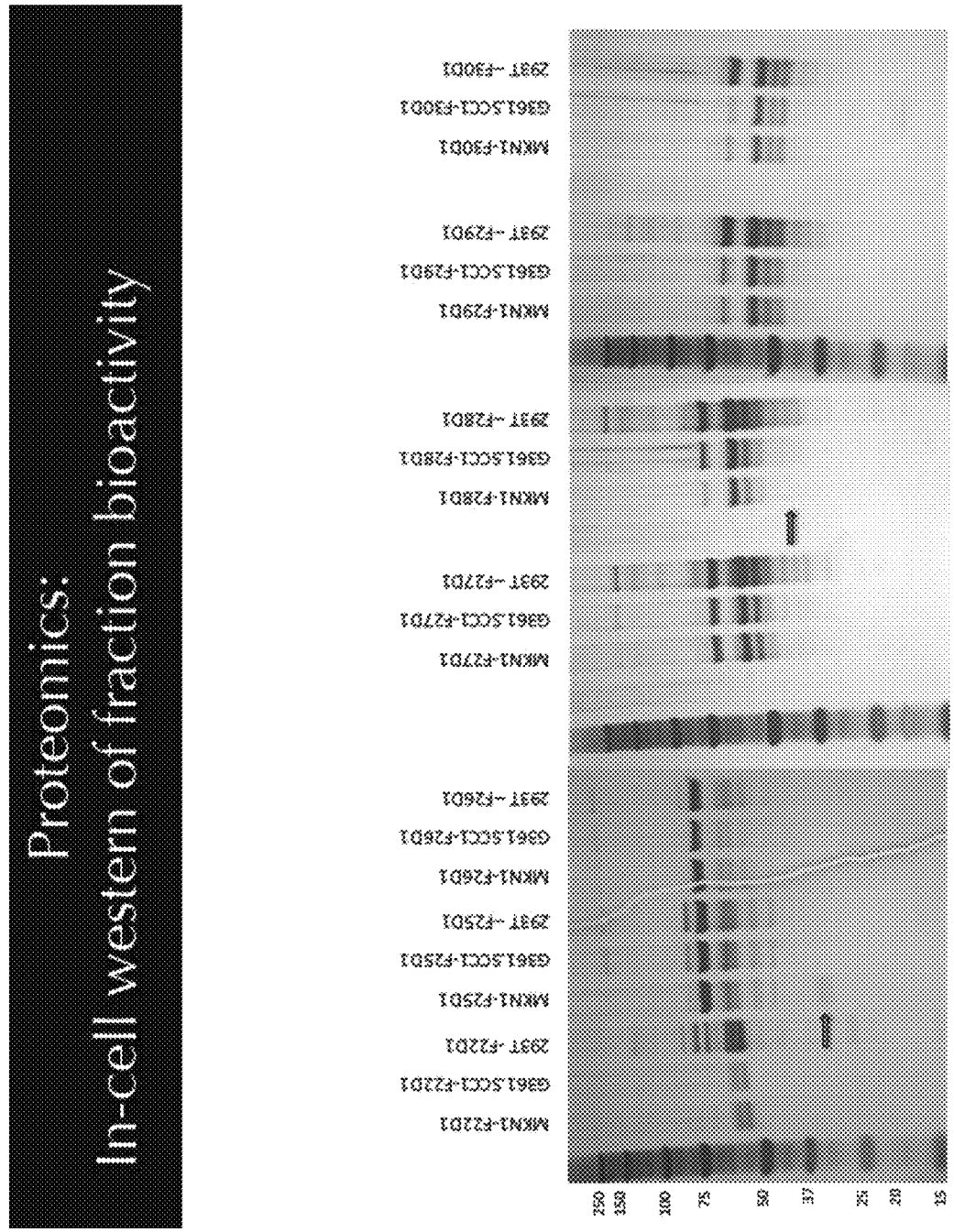
FIG. 14C is a series of images of silver stained SDS-PAGE gels of fractions 22 and 25-30 of non-cachexia-inducing conditioned media (293T) and cachexia-inducing conditioned media (MkN1 and G361).

Candidate cachexia mediators were identified as proteins that were more abundant in cachexia-inducing conditioned media compared to non-cachexia-inducing media. S100A7 and one fragment of DCD were among the candidate mediators differentially abundant in the active fractions in cachexia-inducing conditioned media (CI-CM) compared to the non-cachexia-inducing conditioned media (NCI-CM) (FIG. 14).

Specifically, credentialed conditioned media was subjected to limited ion exchange HPLC fractionation and L1000 profiling, as described above. Active fractions were prepared by reduction of disulfide cysteine bonds, followed by alkylation of the free sulfhydryl group and trypsin digestion. Post digestion peptides were labeled with iTRAQ reagents (SCIEX) for peptide quantitation (Mertins, P. el al., *Mol Cell Proteomics* 11(6): M111014423 (2012)). iTRAQ labeled peptides were directly analyzed or underwent further off-line fractionation using a C18 reverse phase column under basic conditions (Mertins, P. et al., *Nat Methods* 10(7): 634-637 (2013)). Labeled peptides were analyzed using a Q Exactive mass spectrometer and a top 12 Data Dependent Acquisition method. The resulting .RAW file contained peptide spectra along with iTRAQ reporter ions within each spectrum that was searched against a protein database for protein identification and quantitation.

Differentially abundant RAGE ligands were found in conditioned media from cachexia-inducing cell lines (Table 3).

TABLE 3

Differentially Abundant RAGE Ligands in Conditioned Medias from Cachexia-inducing Cell Lines

| Specific Proteins | | Aggregates |
|---|---|---|
| S100A1* (S100P) | S100A12++ | DNA* |
| S100A2 | S100A13 | AGE's |
| S100A4+ | S100A14* (S100A16) | B Amyloid fibrils |
| S100A5 | S100A7A (A15) | Heparin |
| S100A6 | S100B++ | |
| S100A7 | S100P* (S100A1) | |
| S100A8* (S100A9) | HMGB1* (DNA) | |
| S100A9* (S100A8) | | |
| S100A11 | | |

+homodimerizes/
++oligomerizers/
*heterodimerizers

EXAMPLE 7

Prioritization of Candidate Cachexia-Inducing Proteins by Analyzing Patient Samples To refine the list of candidate cachexia-inducing proteins and ensure clinical relevance, the candidates' abundance in plasma samples obtained from cancer patients with and without cachexia are measured. These experiments involve (1) careful collection and curation of patient samples, and (2) targeted mass spectrometry using Multiple Reaction Monitoring (MRM).

blood work performed along with other oncologic care testing (e.g. CT scans to assess tumor progression). 100 new patients per year are expected to meet criteria and enroll in this study along with 100 case-matched negative controls. This study puts a very low burden on patients, as it required no additional invasive studies, leveraging plasma collection along with routinely scheduled blood work. Up to 800 samples are expected to be collected over 2 years. Some patients serve as their own control, given that cachexia will develop in some patients during the course of the study. Details of study inclusion criteria are listed in Table 4.

TABLE 4

Details of study inclusion criteria

| Factor | Criteria | Rationale |
|---|---|---|
| Patients | age 18-70 being seen in MSKCC's PPC clinic | signed informed consent for IRB-approved protocol |
| Diagnosis | any solid tumor | patients with hematologic malignancy rarely have cachexia and are prone to develop chronic infections that may confound analysis |
| Treatment history | no GI surgeries within the last 3 months, no current chemotherapy that results in documented diminished nutritional intake or profound nausea, vomiting, or diarrhea, no radiation therapy within the last month | to avoid confounding issues |
| Co-morbidities | no history of other potentially confounding wasting syndromes | examples: COPD, kidney failure, liver failure, heart failure, advance AIDS, or muscular dystrophies in severe weight loss >20%, plasma |
| Weight change history | 6-month history of weight loss between 5-20% or <2% for negative controls | volume and hematocrit are significantly diminished, confounding analysis |
| Laboratory studies | BUN and creatinine (as a measure of renal function) and routine liver function tests | as a part of the patient's routine clinical care |
| Imaging | when available, abdominal CT Tomovision studies | abdominal muscle attenuation on routine abdominal CT scans is highly associated with future weight loss due to cachexia (Martin, L. et al., J Clin Oncol 31(21): 1539-1547 (2013)) |

(1) Collection and annotation of patient plasma samples.

Candidates from the in vitro system in clinical samples are measured by 1) accessing previously collected serum samples, and 2) prospectively collecting highly annotated samples through the MSKCC Pain and Palliative Care (PPC) clinics.

MSKCC has had a long-established clinical effort to collect patient serum samples across numerous tumor types. 720 serum samples are identified (with appropriate consent obtained through IRB-approved protocol #06-107) through the MSKCC Biomarker Laboratory and Tissue Bank, representing approximately 450 patients across 3 tumor types (pancreatic, colorectal, and ovarian). An advantage of this collection is that it is large and available for immediate analysis. The disadvantages of this collection includes variable access to supporting clinical data, and variable collection and storage protocols over this time period.

To complement the existing retrospective collection, samples are prospectively collected, uniformly processed and clinically annotated. The MSKCC ambulatory PPC clinics see over 700 new patients per year, a substantial proportion of whom have cachexia. Many of these patients are followed longitudinally and have regularly scheduled While the primary purpose of this sample collection is to support the present discovery goals, a secondary benefit is the creation of a resource to facilitate cachexia research in the future—a research direction that is woefully underserved relative to the magnitude of the clinical problem. To estimate the sample numbers required to support the present study, we assume: 1) a fold-change in expression of at least 1.5; 2) biological variation in clinical samples of 0.5; and 3) technical variation in the assay of 0.25. To achieve 90% power to find such proteins using a 100-plex MRM assay at a p-value of 0.05 corrected for multiple hypotheses testing, we require 415 samples. This is well within the number of samples expected during the course of this study, and could also be supplemented by the existing sample bank.

(2) Targeted assessment of candidate cachexia-inducing proteins using MRM. While the high protein complexity of human plasma precludes analysis of the entire proteome, new methods make it possible to perform high throughput, low-cost analysis of a subset of proteins. Multiple Reaction Monitoring (MRM) is used to instruct the mass spectrometer to look for particular peptides of interest based on their mass spectrometric characteristics (defined using synthesized peptide standards). In this manner, the up to 100 candidate cachexia-inducing proteins that were identified could be assayed in a single, 100-plex MRM assay applied to the patient-derived plasma samples. Proteins that are more abundant in plasma samples derived from cachectic patients compared to non-cachectic patients receive highest priority, and proceed to functional validation. Only a handful of proteins are expected to pass this filter.

Specifically, MRM coupled with stable isotope dilution mass spectrometry (SID/MRM-MS) employs two stages of mass filtering on a triple quadrupole mass spectrometer. In the first stage, ions of interest are preselected in Q1 and fragmented by collisional excitation with a neutral gas in a pressurized collision cell (Q2). In the second stage, only a small number of sequence-specific fragment ions are mass analyzed in Q3, instead of obtaining all the possible fragment ions derived from the precursors. MRM assay development starts with the synthesis of reference peptides with heavy labeled Arginine or Lysine. The MS parameters are optimized for maximum transmission and sensitivity of each MRM transition, defining lower limits of detection and quantification by generating calibration curves for each peptide. Abundant protein depletion is performed and limited fractionation at the peptide level prior to SID/MRM-MS to achieve low nanogram/mL sensitivity. Data is acquired using an Agilent 6490 triple quadrupole mass spectrometer fitted with an integrated nanospray ChipCube system and analyzed using Skyline software. Given the high reproducibility and quantitative performance of the MRM assay, the levels of the desired protein analytes are measured across all patient samples, thus powering statistical analysis to correlate levels of the candidate cachexia-inducing proteins with degree of cachexia (Addona, T. A. et al., *Nat Biotech* 27(7): 633-641 (2009); and Hasmik Keshishian, T. A. et al., *Mol & Cell Proteomics* pp. 2212-2229 (2012).

EXAMPLE 8

In Vivo Validation of High Priority Candidate Cachexia-Inducing Proteins

These studies demonstrate that cachexia-associated proteins are causal of the cachexia phenotype by two approaches: (1) overexpressing candidate cDNAs in non-cachexia-inducing cell lines, and determining whether xenografted mice harboring the transduced cell lines develop cachexia; and (2) ablating expression of candidate genes in cachexia-inducing cell lines, and determining whether xenografted mice now fail to develop cachexia (Boehm, J. S. and Hahn, W. C., *Nat Rev Genet* 12(7): 487-98 (2011)). Proteins that passed both these tests are likely to be those that explain, at least in large part, cachexia in humans, and should thus be fast-tracked for future therapeutic antibody production aimed at blocking protein activity as a treatment for cachexia.

(1) Gain-of-function testing of candidate cachexia-inducing proteins.

In parallel experiments, sequence-validated open reading frame (ORF) constructs for each of up to 10 candidate genes are transduced into two non-cachexia-inducing cell lines (AsPC-1 and JHU012) and incorporated into the pLX_TRC206 vector with an in-frame V5 epitope tag and the blasticidin selection marker. Western blot analysis of the V5 epitope tag confirms expression in blasticidin-resistant cells. Five Balb/c nude mice are injected for each transduced cell line and its parental control. Mouse tumor volumes and measures of the cachexia phenotype are collected as described above, in order to determine which ORFs were sufficient to induce cachexia.

(2) Loss-of-function targeting of candidate cachexia-inducing proteins.

Figure 15A:
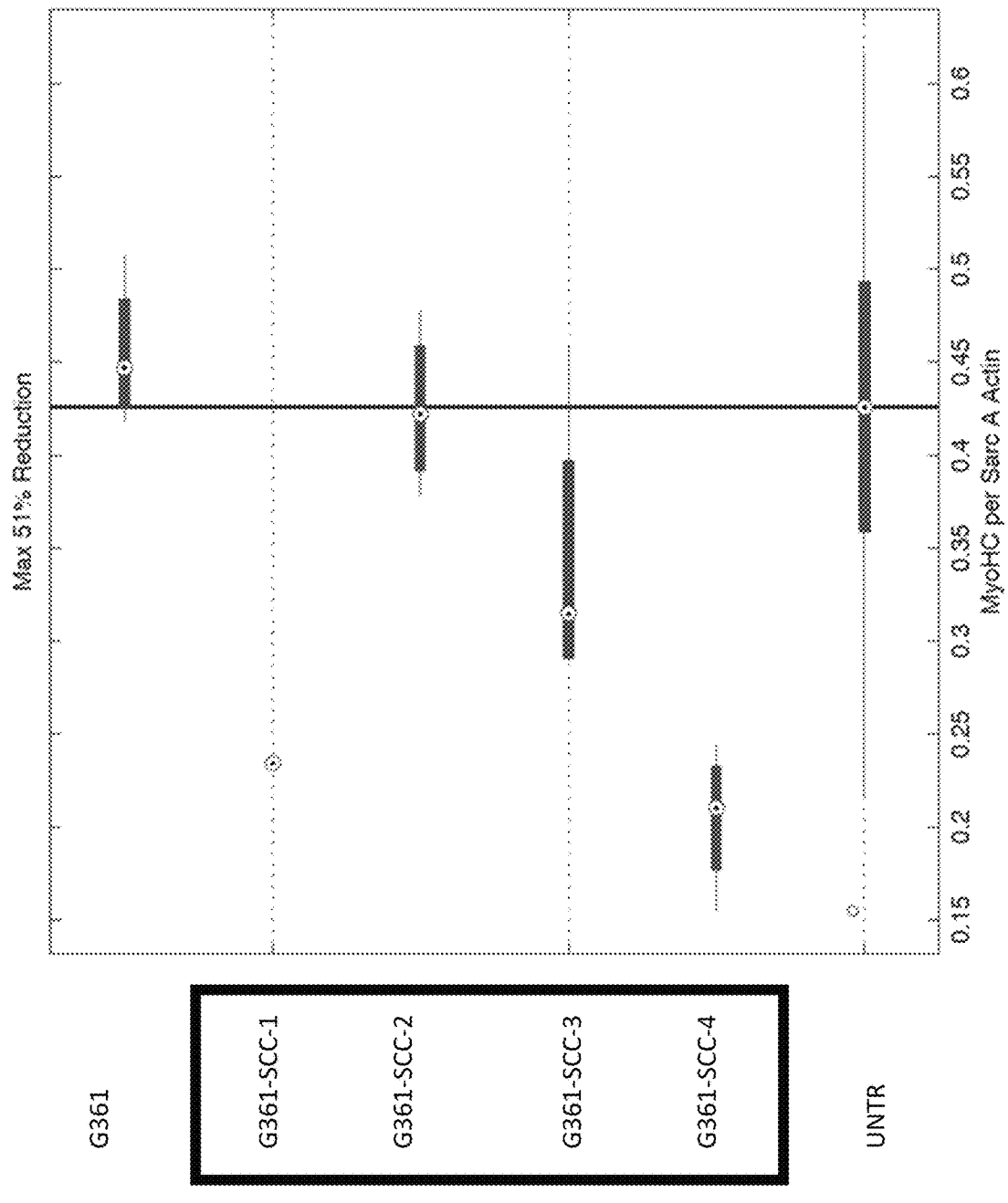
FIGS. 15A and 15B are a series of plots showing the cachexia-inducing ability of isogenic unselected (FIG. 15A) and drug-resistant (FIG. 15B) single cell clones of a cachexia-inducing cell line. The plots show that drug resistance increases the frequency of cachexia-inducing single cell clones.
Figure 15B:
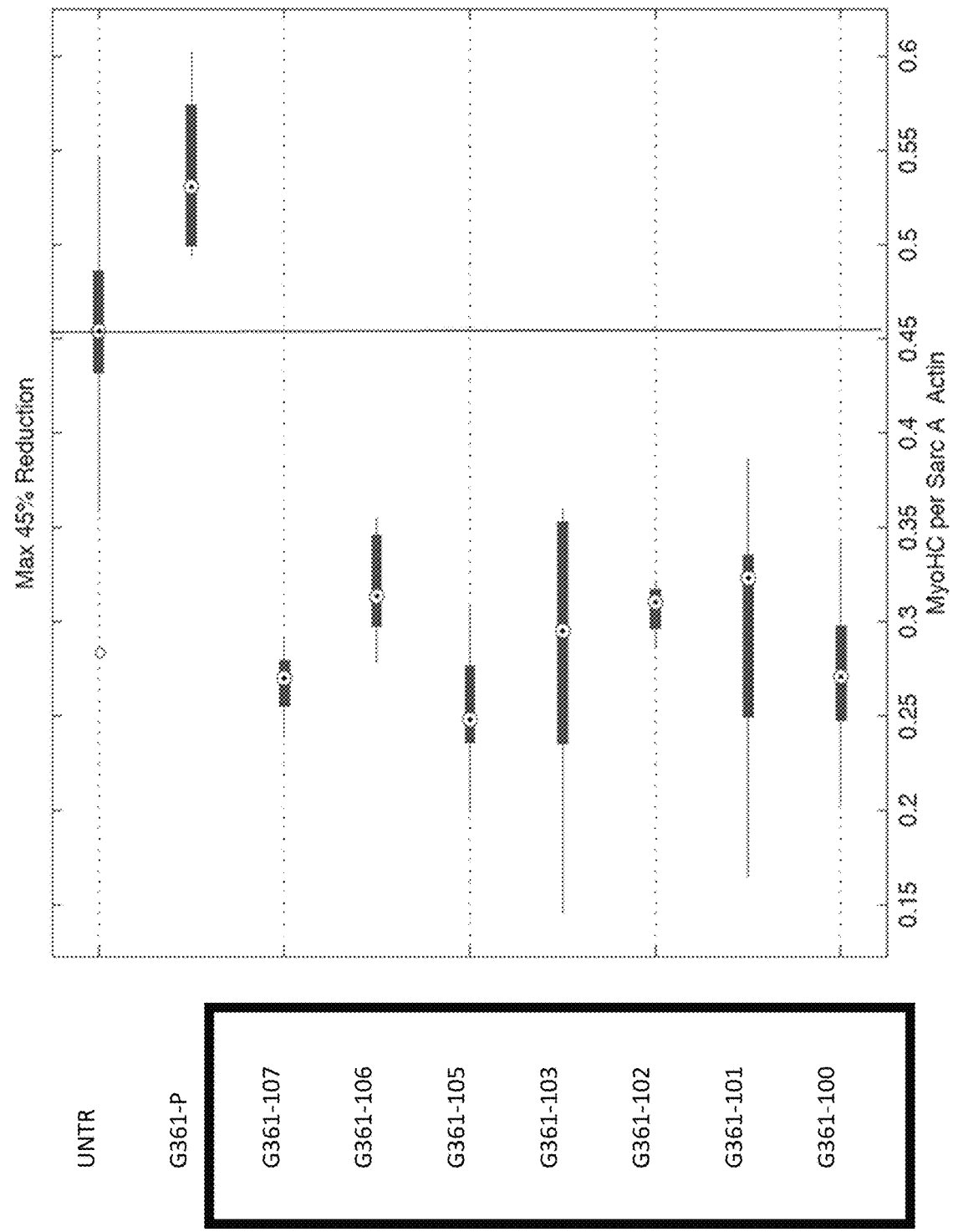
Figure 16:
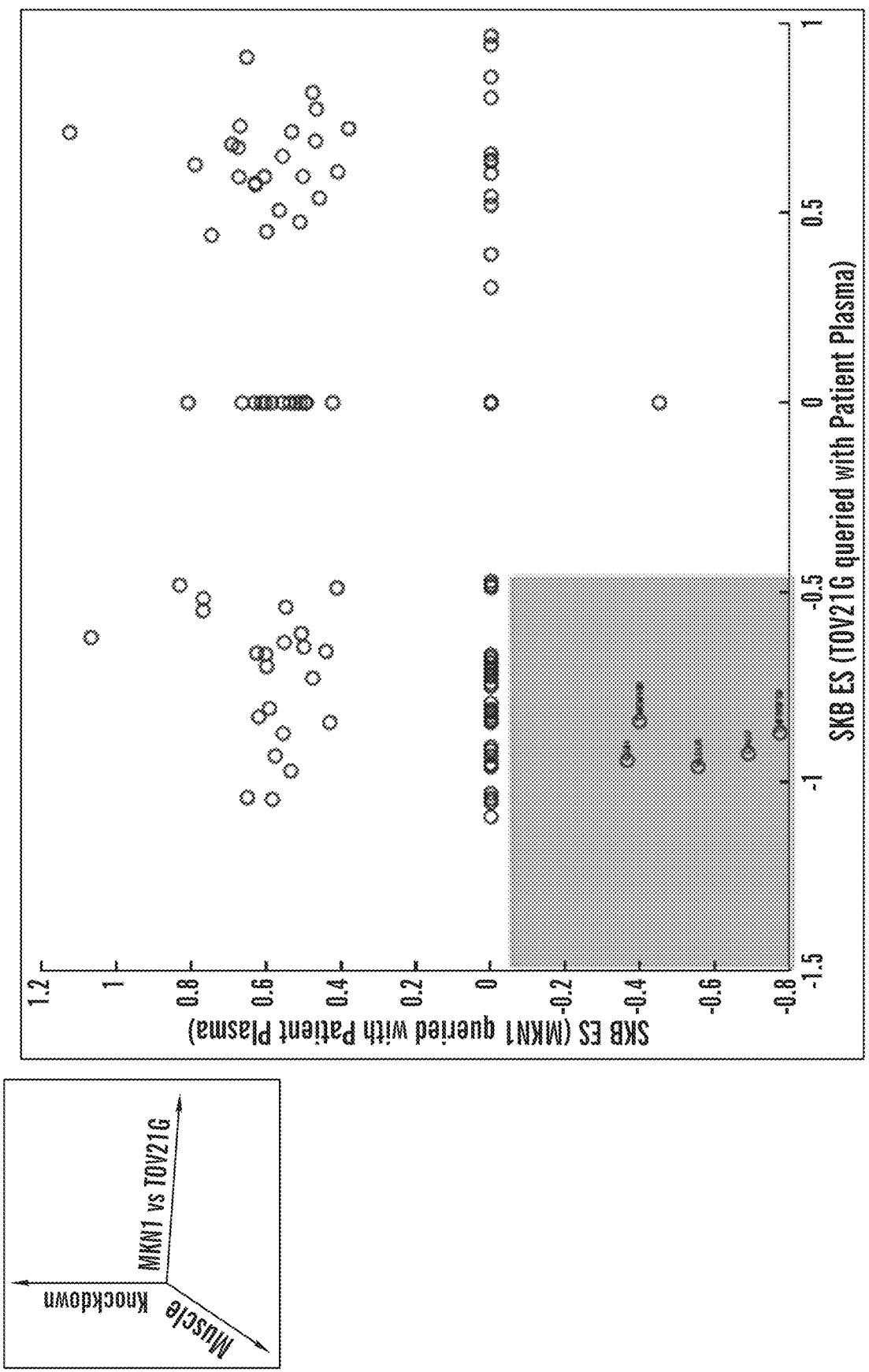
FIG. 16 is a scatter plot of dnEnrichment Score analysis of MkN1 and Tov21G gene knock-downs in HSkM cells.

For each of up to 10 candidates, expression is knocked down using at least two validated and shRNA constructs, each internally controlled by preserving the 7 nucleotide seed sequence of each shRNA, while mutating the remaining sequence. The vast majority of off-target effects of shRNAs are mediated by their seed sequence. Such off-target effects could be ruled out by using shRNA-specific seed controls. Stably transduced clones from cachexia-inducing cell lines (MKN1, G361 and TOV21G) are generated and assessed by qPCR, Western blots of targeted protein, and assessment of resulting conditioned media on in vitro myocytes (FIG. 15 and data not shown). The transduced cells are then injected subcutaneously into the hind limb of 5 female Balb/c nude mice ($5e^6$ cells per clone per animal). Tumor size, animal weight, and plasma, muscle, fat, and liver tissues are harvested under standard approved protocols over 8 weeks or a maximal tumor size of 1 $cm^3$. Assessment of weight change is calculated by tumor-free carcass weight/median weight of sham-injected negative controls. Cachexia is defined as weight loss of ≥−5%. As an alternative strategy, CRISPR/Cas9-mediated somatic cell knock-out of candidate cachexia-inducing genes could be used rather than RNAi (Martin, L. et al., *J Clin Oncol* 31(12): 1539-1547 (2013)).

EXAMPLE 9

Discovery of Candidate Cachexia-Inducing Proteins by Chemical Perturbation

Figure 17:
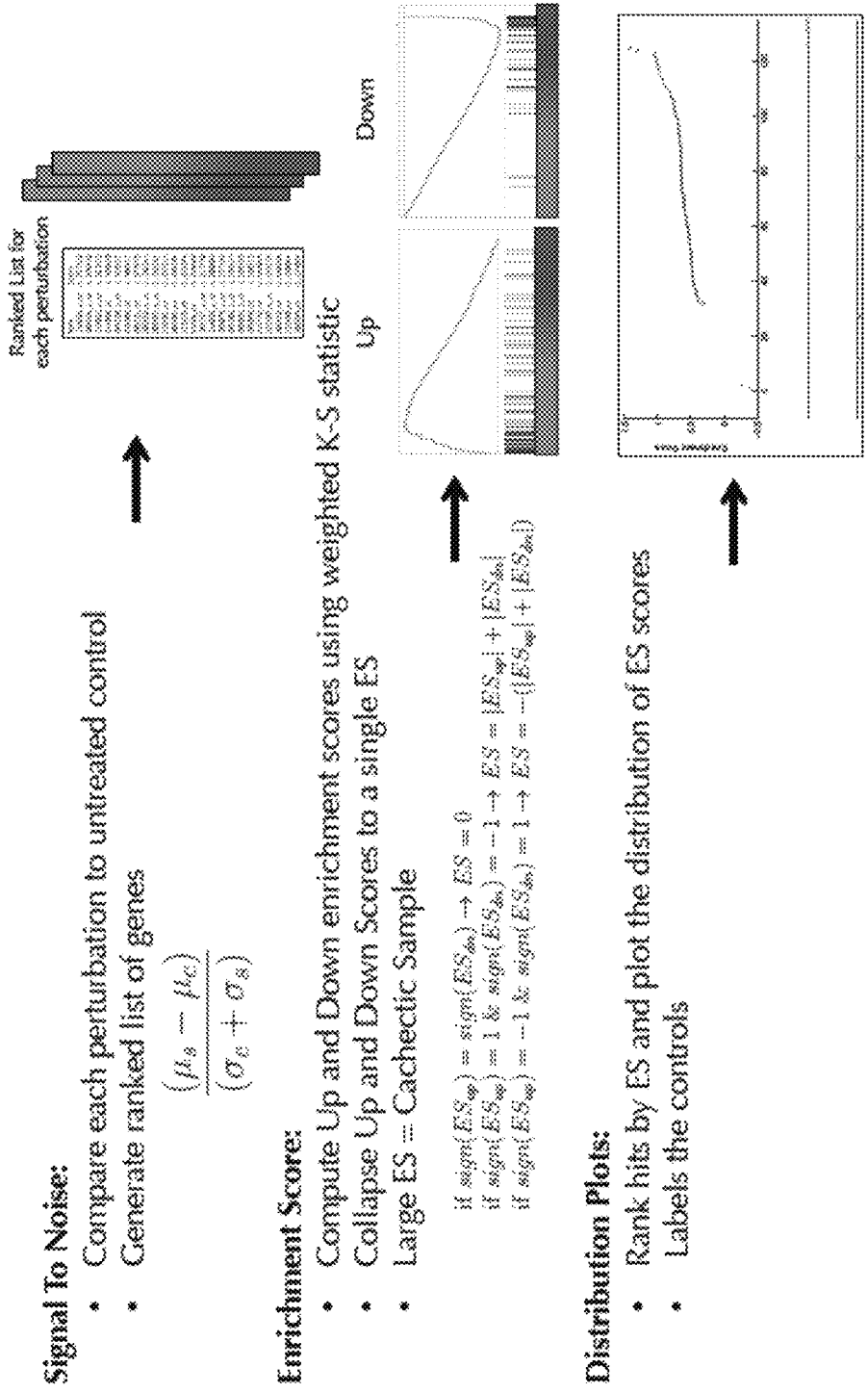
FIG. 17 is an example calculation of a gene signature Enrichment Score.
Figure 18:
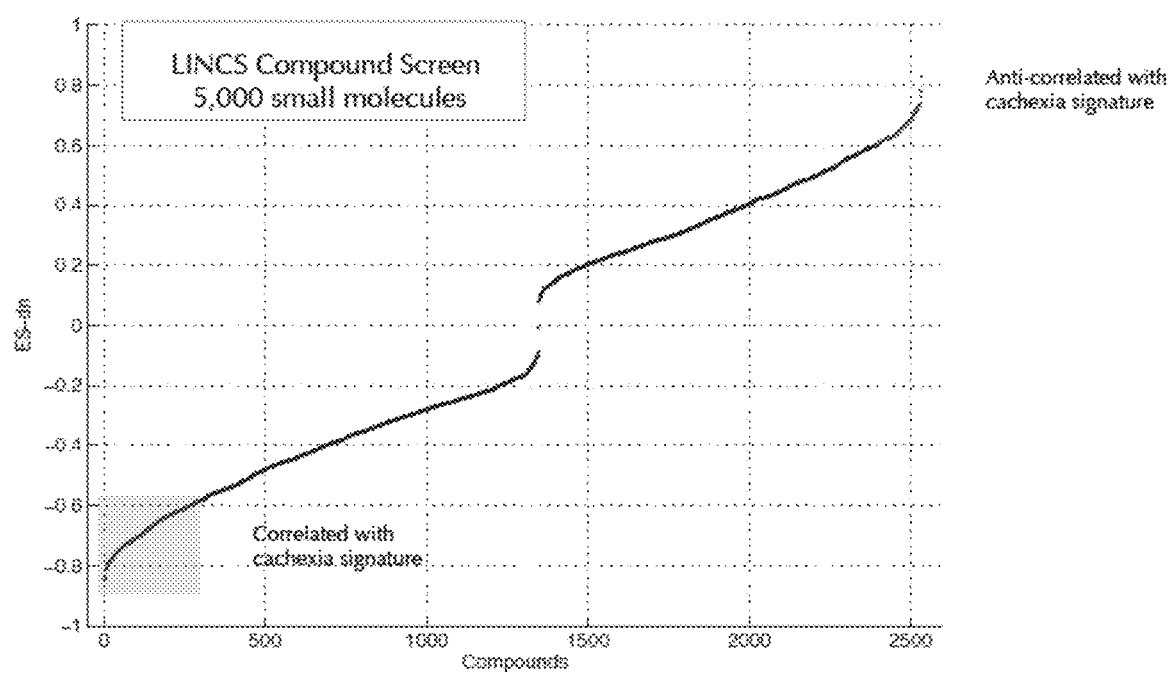
FIG. 18 is a distribution plot showing the dnEnrichment Scores of a small compound screen in HSkM cells. The top score hits (upper right corner) are anti-correlated to the patient plasma cachexia signature in HSkM cells.
Figure 19:
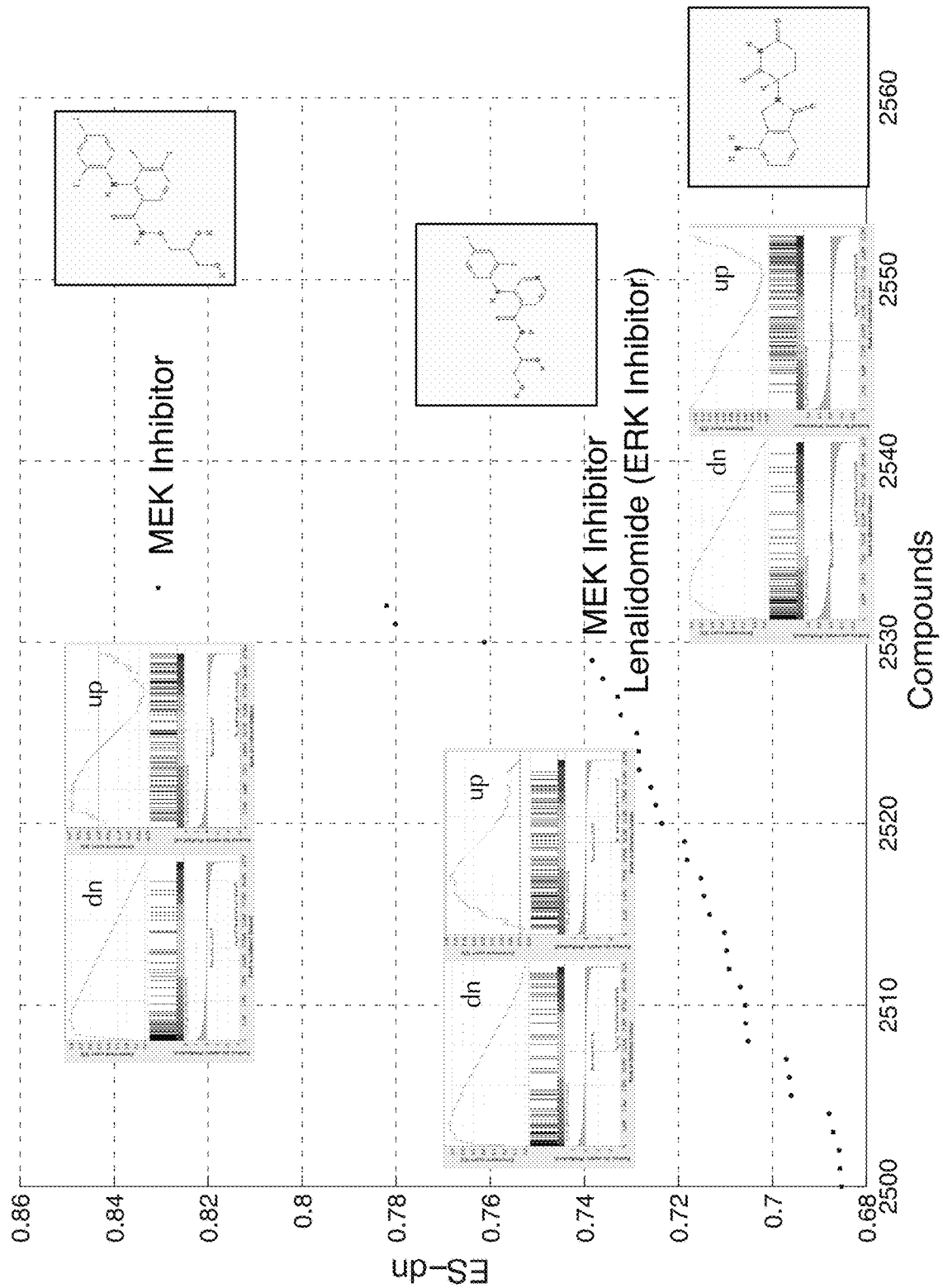
FIG. 19 is a magnified image of the upper right corner of the plot in FIG. 18 showing that MEK/ERK inhibitors comprise 3 of the top 10 hits.

A compound screen was performed on in vitro human muscle cells exposed to cachectic patient plasma to identify cachectic mediators. The compound library consisted of 5,000 small molecules. Compound mediated effects on the muscle cells were assessed using a cachectic gene expression signature-based screening method (FIG. 17). Muscle cells treated with compounds that enhanced the cachectic phenotype exhibited a gene expression signature that correlated with the cachexia signature (FIG. 18). Cells treated with compounds that inhibited the cachectic phenotype exhibited a gene expression signature that anti-correlated with the cachexia signature. Strikingly, the distribution of compounds that anti-correlated with the cachectic signature correlated with MEK/ERK inhibition (FIG. 19).

Figure 20:
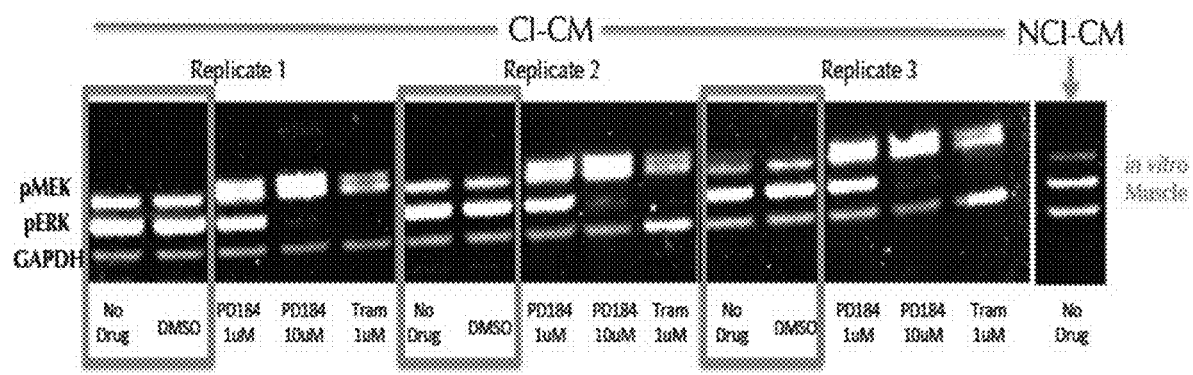
FIG. 20 is an image of a Western blot showing phosphorylated MEK (pMEK) and phosphorylated ERK (pERK) in muscle cells exposed to cachexia-inducing conditioned media (CI-CM), either in the absence or presence of the MEK/ERK inhibitors, PD184352 (PD184) and trametinib (Tram). Also shown are pMEK and pERK levels in muscle cells exposed to non-cachexia-inducing conditioned media (NCI-CM). The results demonstrate that MEK/ERK is activated by cachexia-stimuli contained in the CI-CM, relative to control NCI-CM, and that this activation is inhibited by treatment with PD184352 and trametinib.
Figure 21:
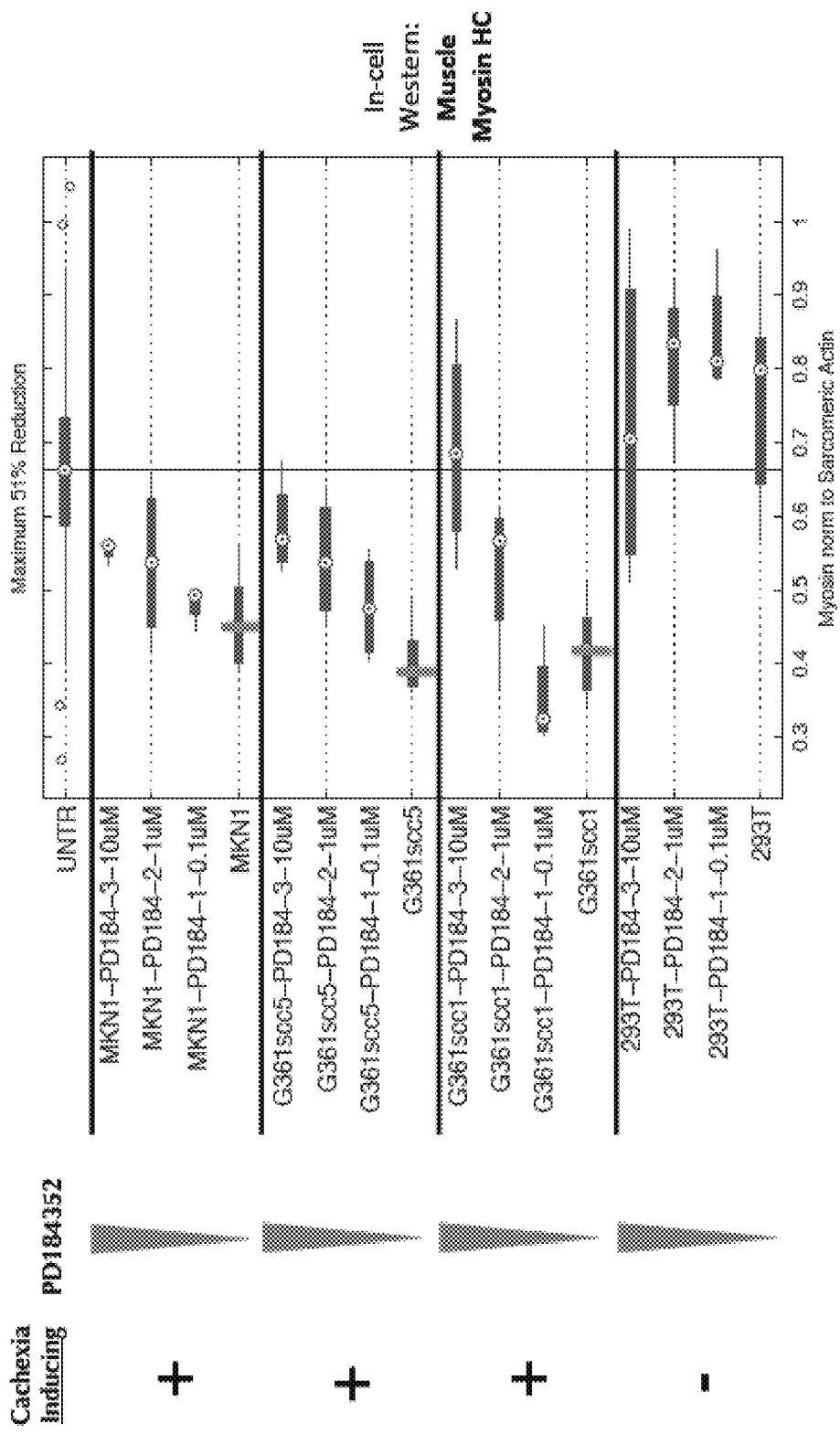
FIG. 21 is a chart showing the quantification of myosin heavy chain (MyoHC) content determined by In-Cell Western analysis of in vitro HSkM cells treated with media conditioned by cachexia-inducing MkN1 and G361 cells and in vitro HSkM cells treated with media conditioned by non-cachexia-inducing 293 cells, either in the presence or absence of a MEK/ERK inhibitor PD184352 (PD184). The dose curve shows that MEK/ERK inhibition blocks loss of MyoHC in muscle cells exposed to cachexia-inducing conditioned media.
Figure 22:
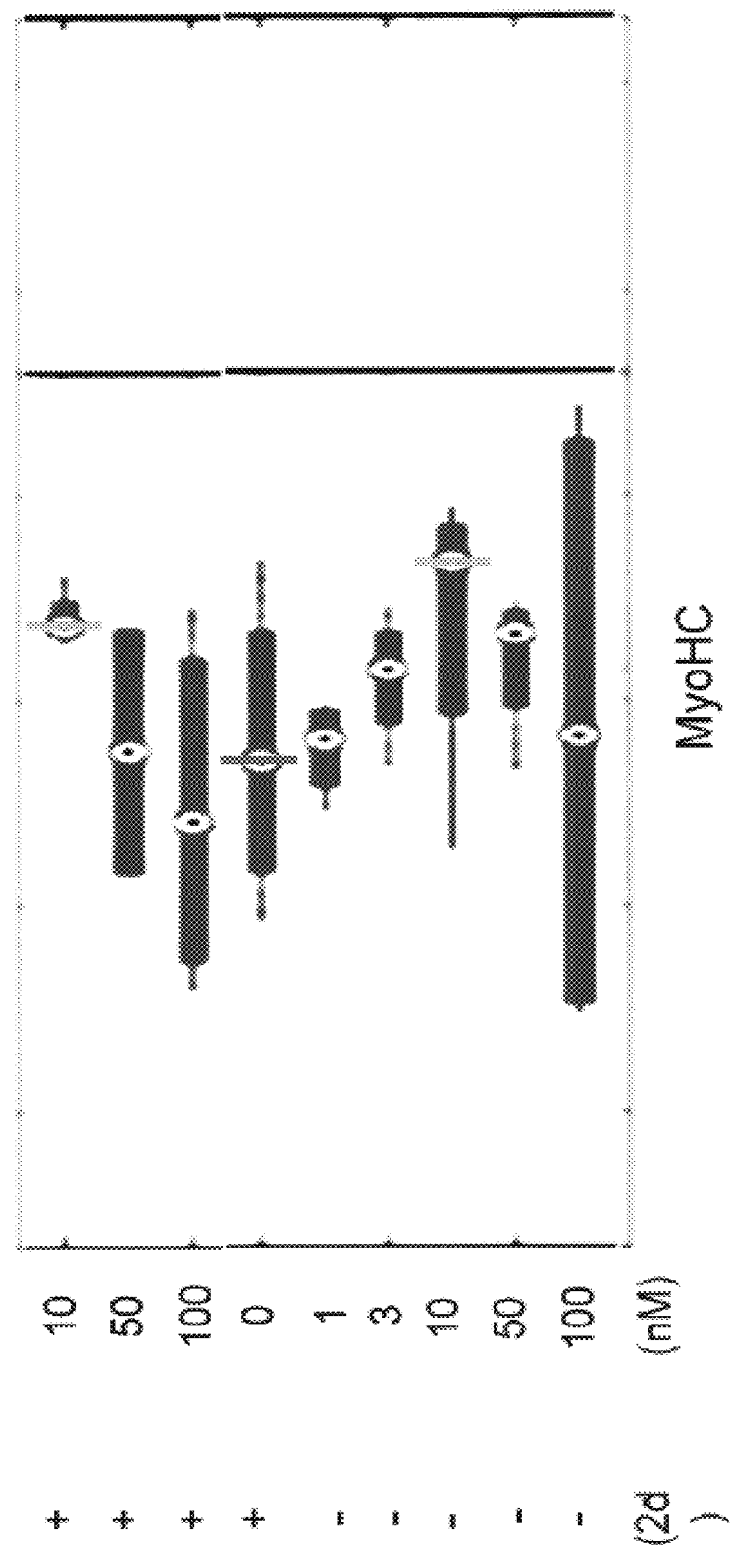
FIG. 22 is a chart showing the myosin heavy chain (MyoHC) content determined by In-Cell Western analysis of in vitro HSkM cells pre-treated (for 2 days) or not pre-treated with cachexia-inducing conditioned media ("CI-CM"), either in the presence or absence of an ERK1/2 inhibitor, SCH772984 (SCH2984). The dose response curve shows that SCH772984 can reverse the MyoHC loss at a certain dose, beyond which the benefit is lost.

Examination of MEK/ERK activation in human muscle cells stimulated by cachexia-inducing conditioned media (CI-CM) revealed an upregulation of MEK/ERK activation compared to muscle cells exposed to non-cachexia-inducing conditioned media (NCI-CM) (FIG. 20). Inhibition of MEK by exposure to PD184352 or trametinib blocked CI-CM stimulated phosphorylation of ERK (FIG. 20). Additional data demonstrated that low-dose treatment of cachectic cell lines with PD184352 or SCH772984 was sufficient to block or (partially) reverse, respectively the cachectic induced loss of myosin heavy chain protein (FIGS. 21 and 22, respectively). Similar results for trametinib, both in MKN1 and Panc1 conditioned media, were also observed.

Figure 23A:
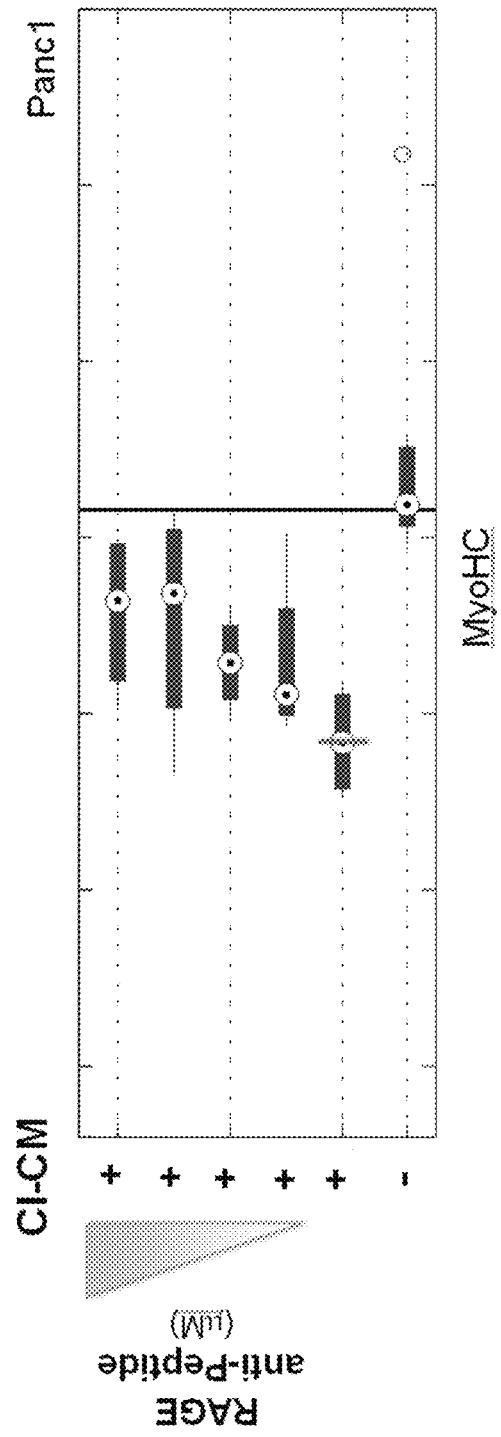
FIGS. 23A and 23B are a series of charts showing the dose response of myosin heavy chain (MyoHC) content determined by In-Cell Western analysis of muscle cells treated with a RAGE Anti-Peptide (FIG. 23A) or an anti-RAGE mAb (FIG. 23B), either in the absence or presence of cachexia-inducing conditioned media (CI-CM). The results demonstrate that blockade of RAGE blocks loss of MyoHC in response to CI-CM.
Figure 23B:
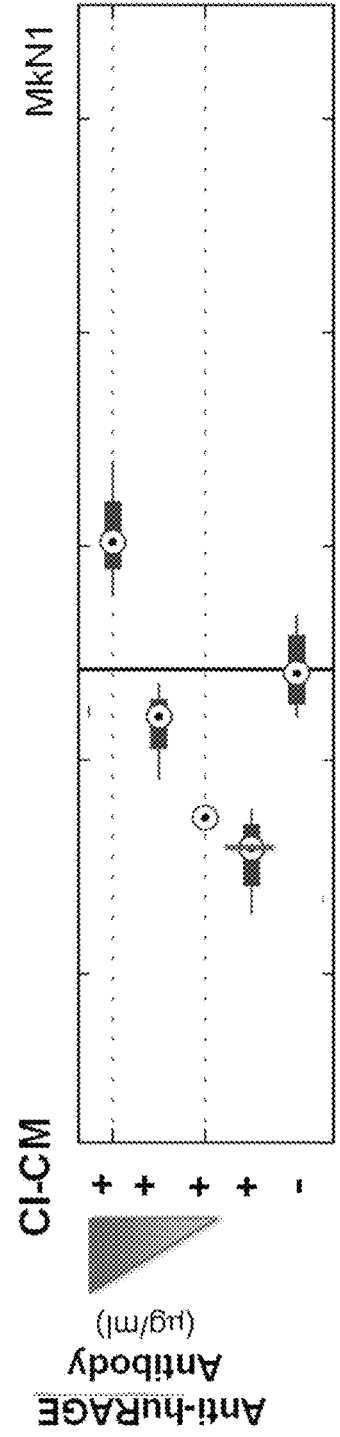

Finally, treatment with a blocking peptide or antibody to RAGE was also shown to inhibit and reverse the cachectic induced loss of myosin heavy chain (MyoHC) protein in human muscle cells in vitro (FIG. 23). Muscle cells were treated with 0, 1, 10, 50, or 100 µM of the RAGE anti- Peptide (RAP; a 10 amino acid sequence from S100P (R&D Systems)) (FIG. 23A) or with 0, 1, 10, or 30 µg/ml of the anti-RAGE monoclonal antibody (mAb) (R&D Systems) (FIG. 23B). Treatment with the RAGE anti-peptide did not completely block MyoHC loss, but did block receptor oligomerization and full signal strength. Treatment with the anti-RAGE mAb not only protected against MyoHC loss, but also promoted higher baseline levels, possibly by blocking normal baseline RAGE activity.

Together, these results demonstrated that MEK/ERK dysfunction is associated with cachexia and that MEK/ERK and/or RAGE inhibition, is a therapeutic strategy to clinically block or reverse the cachexia phenotype.

EXAMPLE 10

Figure 24:
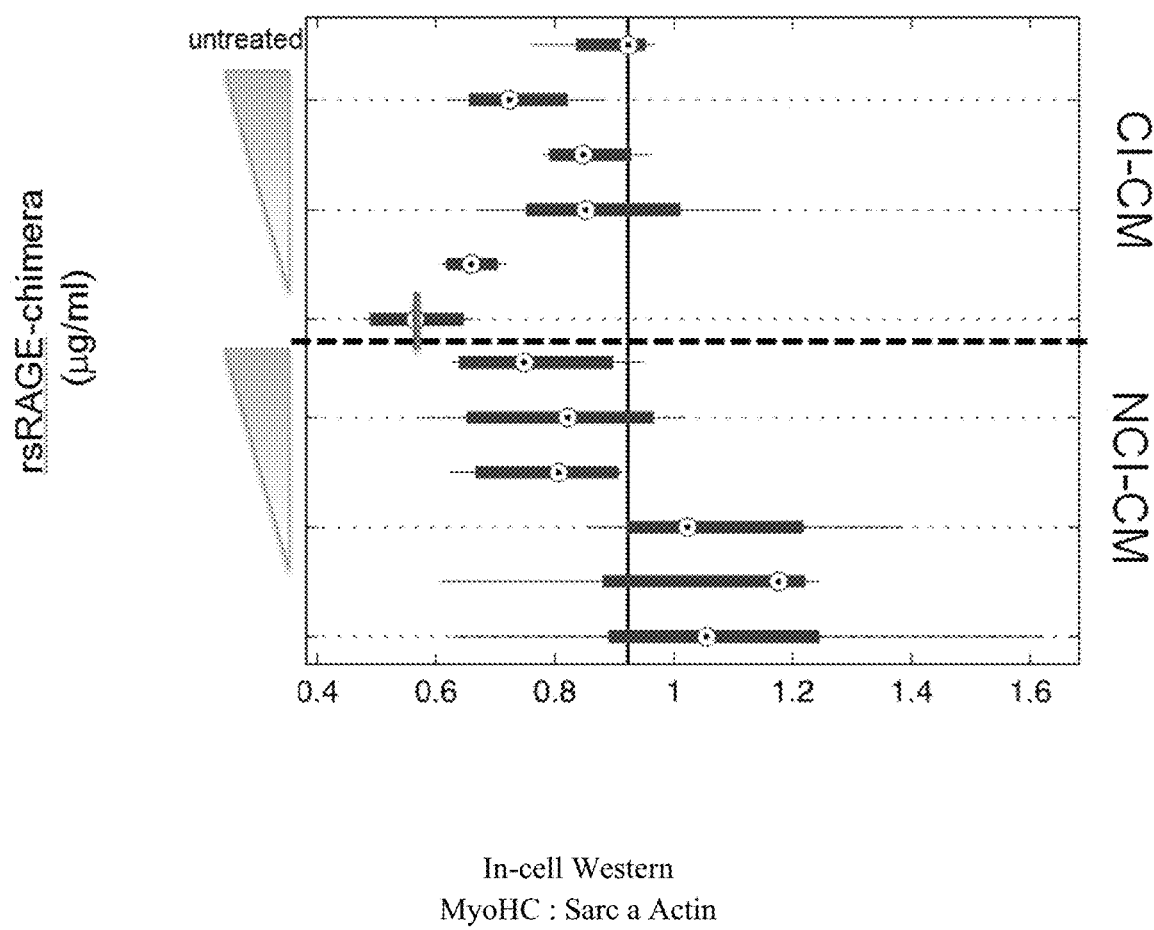
FIG. 24 is a chart showing the dose response of myosin heavy chain (MyoHC) content determined by In-Cell Western analysis of muscle cells treated with a recombinant soluble RAGE, either in the presence of cachexia-inducing conditioned media (CI-CM) or non-cachexia-inducing conditioned media (NCI-CM).
Figure 25:
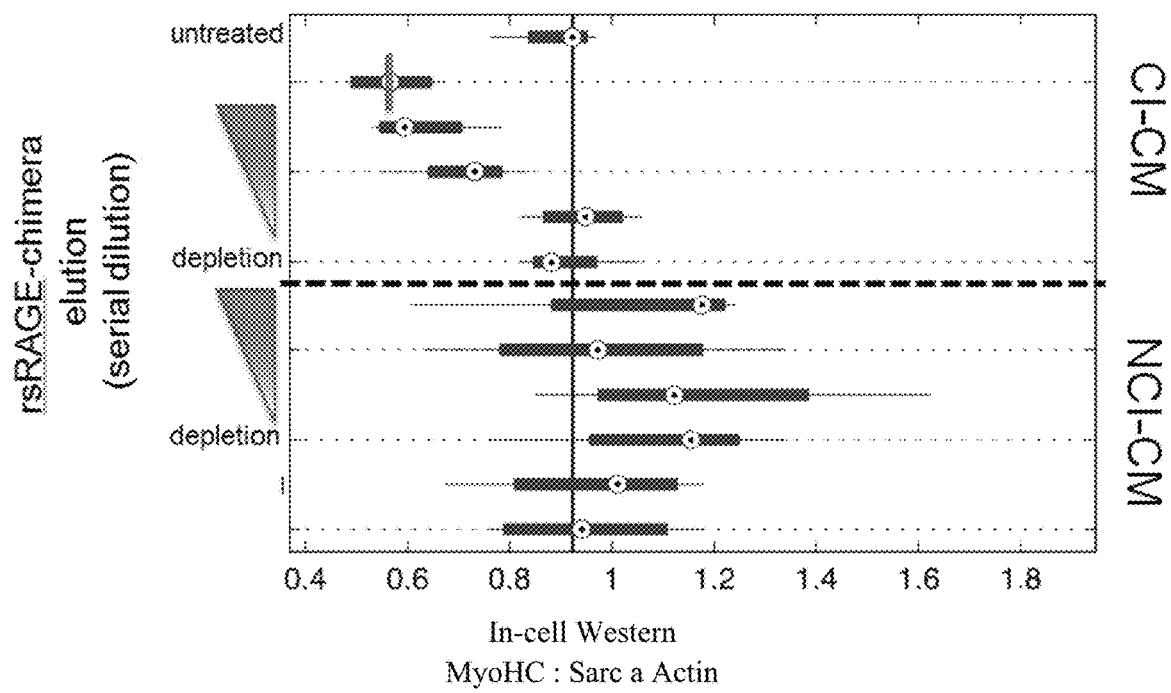
FIG. 25 is a chart showing the dose response of myosin heavy chain (MyoHC) content determined by In-Cell Western analysis of muscle cells under RAGE ligand depletion/repletion experimental conditions, either in the presence of cachexia-inducing conditioned media (CI-CM) or non-cachexia-inducing conditioned media (NCI-CM).

Competition, Depletion and Reconstitution of RAGE Ligands Using a Recombinant Soluble RAGE Inhibition of RAGE signaling by treatment with recombinant soluble RAGE (rsRAGE) that competes with membrane-bound RAGE for binding RAGE ligands was also shown to inhibit the cachectic induced loss of MyoHC protein in human muscle cells in vitro (FIG. 24). Muscle cells were treated with 1, 2, 10, 30 µg/ml rsRAGE in the presence of either cachexia-inducing conditioned media (CI-CM) or non-cachexia-inducing conditioned media (NCI-CM). Furthermore, depletion followed by reconstitution of RAGE ligands was shown to promote the cachectic induced loss of MyoHC protein in human muscle cells in vitro (FIG. 25). RAGE ligands were depleted by treatment with 10 µg/ml rsRAGE and reconstituted by treatment with 1×, 0.5×, 0.25× of eluent (PBS).

Together these results further indicate that RAGE is a suitable therapeutic target for the treatment of cachexia.

EXAMPLE 11

Cachexic Signature in Xenograft Mouse Target Tissues

Figures 26A, 26B:
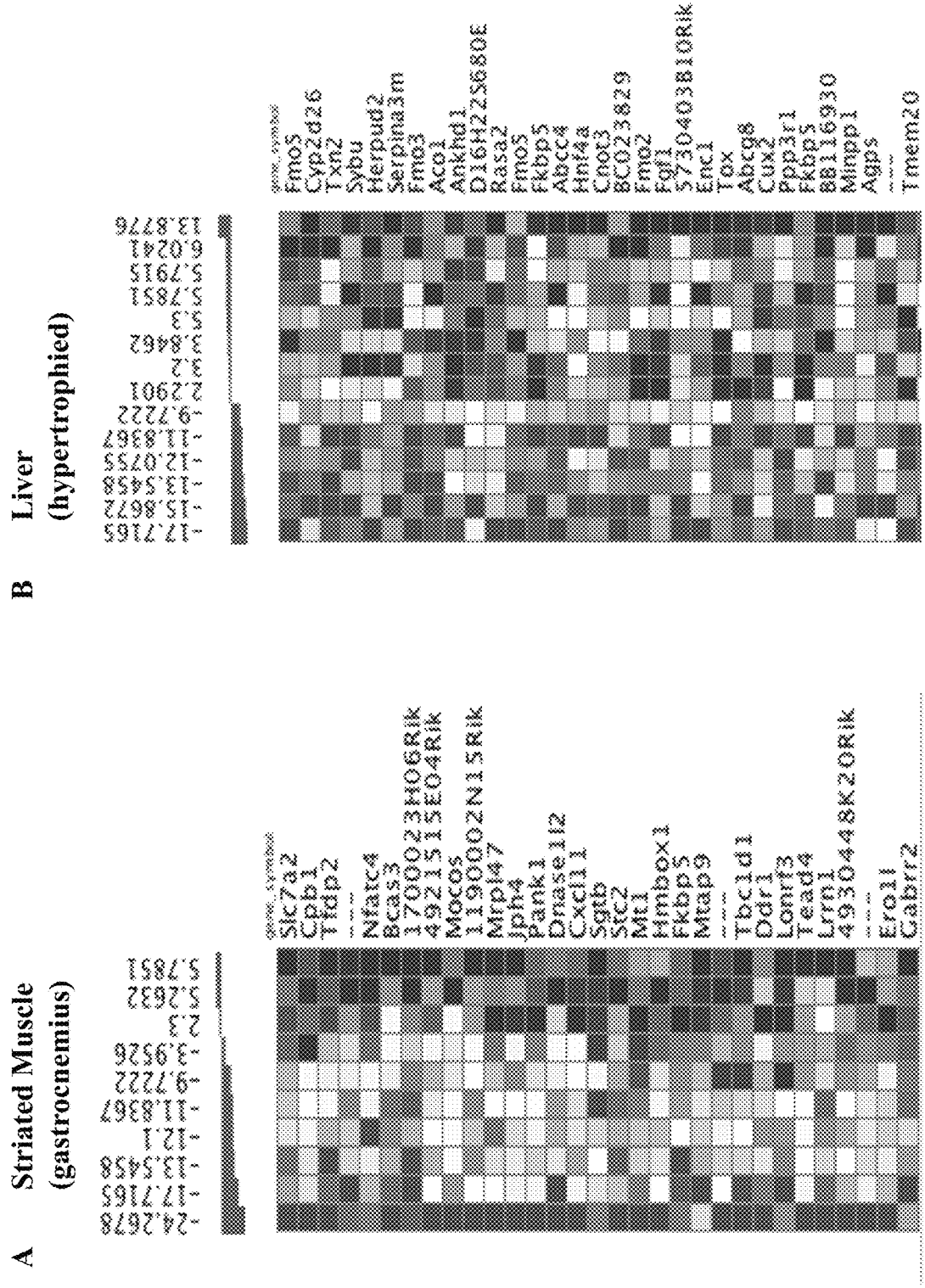
FIGS. 26A and 26B are a series of images showing the gene expression signatures of skeletal muscle (FIG. 26A) and liver (FIG. 26B) from cachectic and non-cachectic xenograft mice.
Figures 26A, 26B:
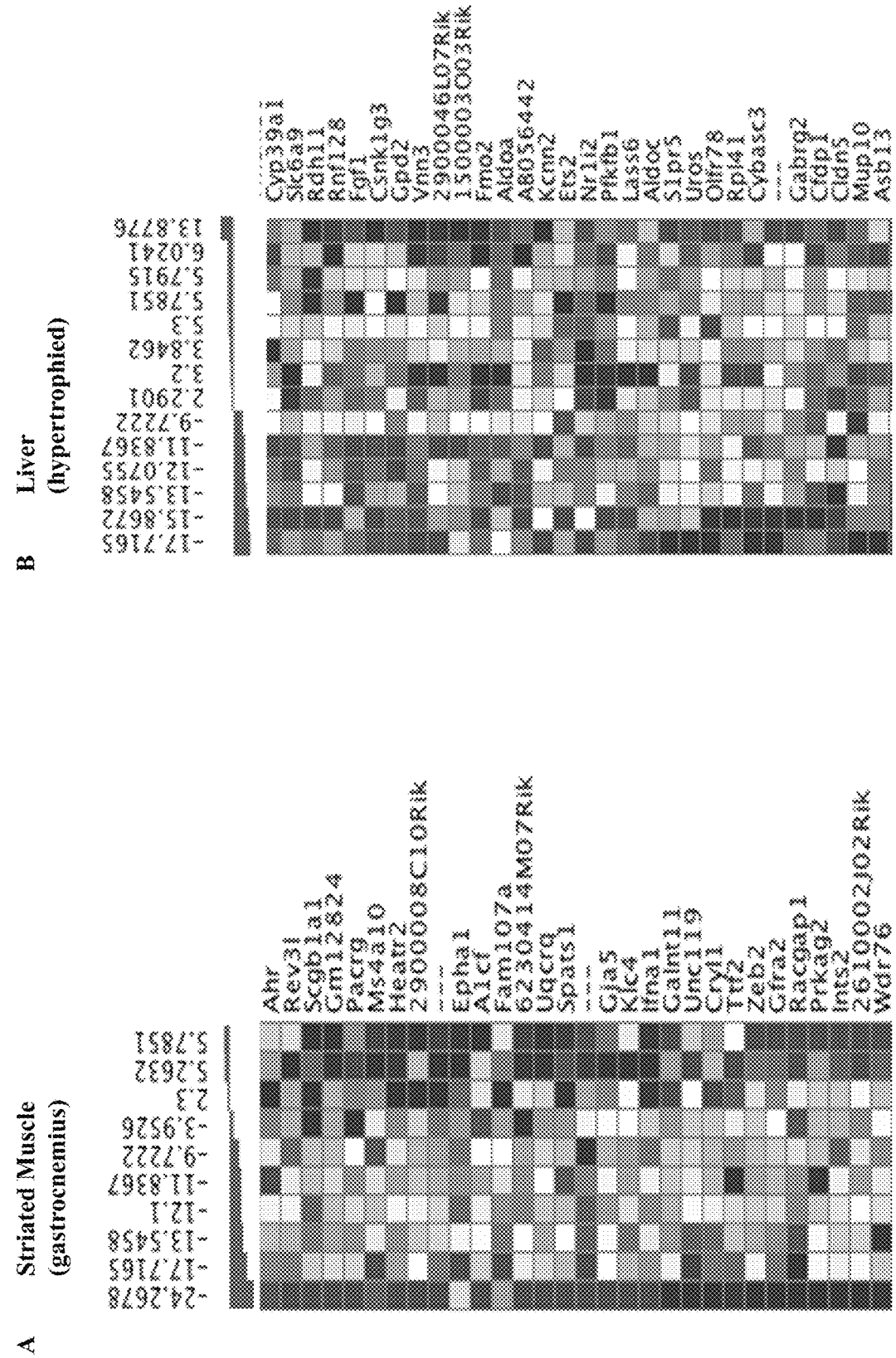
Figures 26A, 26B:
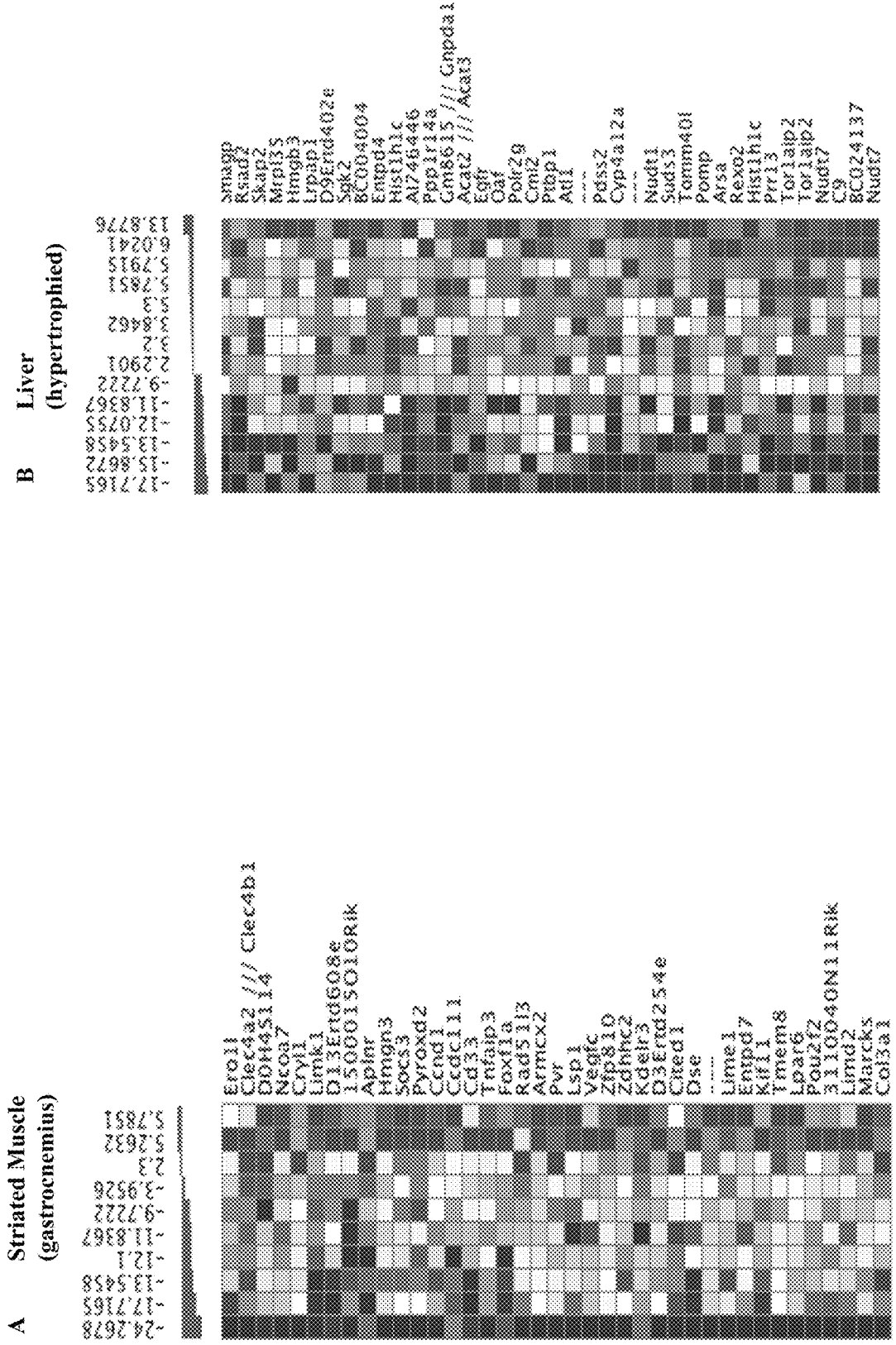

Using the Affymetrics gene expression arrays, the in vivo signatures of cancer cachexia in muscle (FIG. 26A) and liver (FIG. 26B) was determined in xenograft mouse target tissues.

EXAMPLE 12

In Vito Adipocyte Model of Cachexia

Figure 27A:
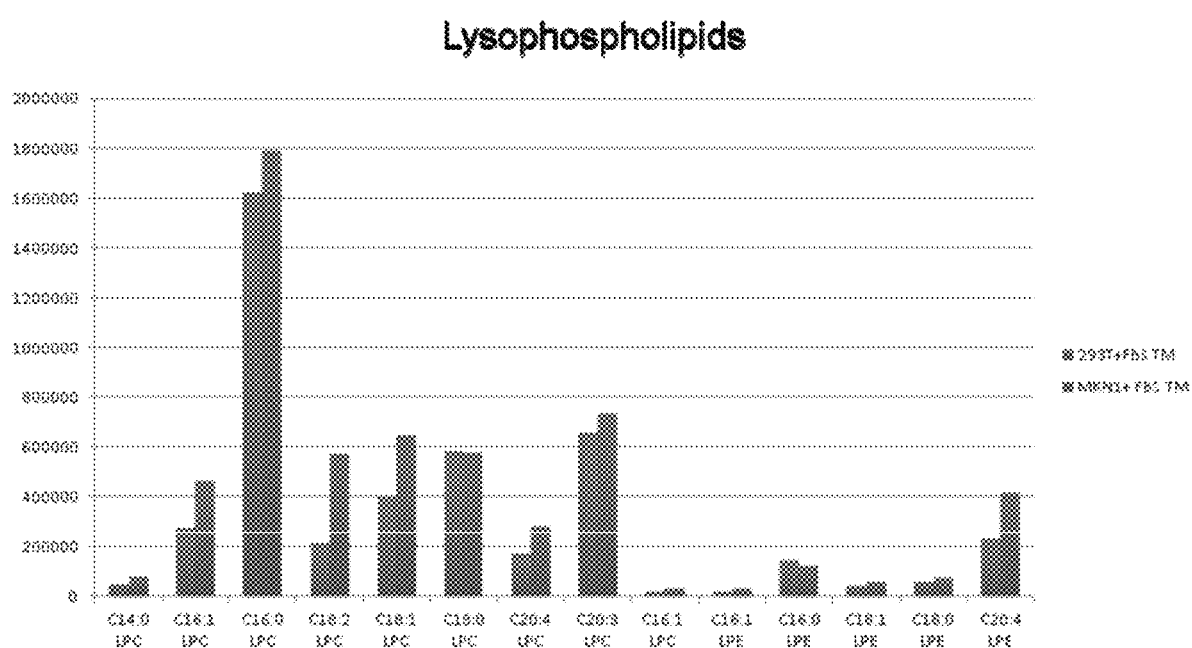
FIGS. 27A and 27B show the metabolite profile and quantification of diacylglycerides and lysophospholipids, respectively, in in vitro primary human adipocytes treated with media conditioned by non-cachexia-inducing 293T cells or by cachexia-inducing MkN1 cells. The charts demonstrate a relative increase in lipolysis intermediates stimulated by cachexia-inducing conditioned media.
Figure 27B:
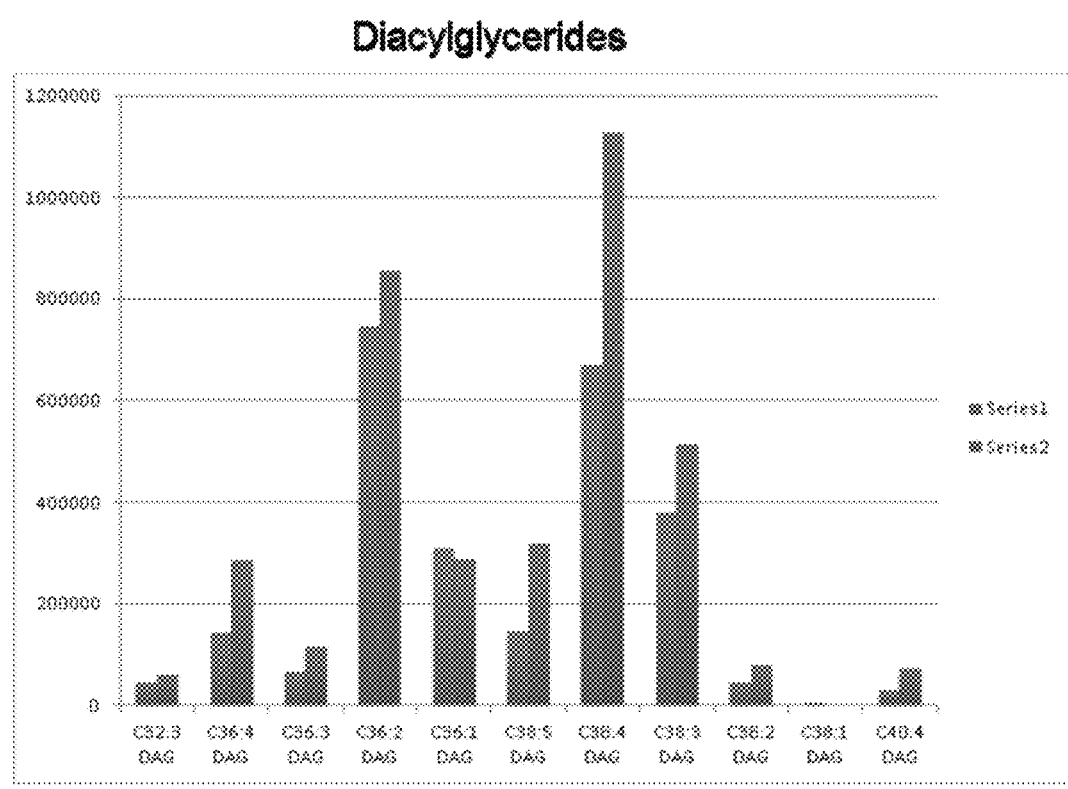

FIG. 27A is a graph showing the upregulation of lysophospholipids in adipocytes exposed to cachexia-inducing media derived from MKN1 cells relative to adipocytes treated with non-cachexia inducing media derived from 293T cells. FIG. 27B is a graph showing the upregulation of diacylglycerols in adipocytes exposed to cachexia-inducing media derived from MKN1 cells relative to adipocytes treated with non-cachexia inducing media derived from 293T cells.

Figure 28:
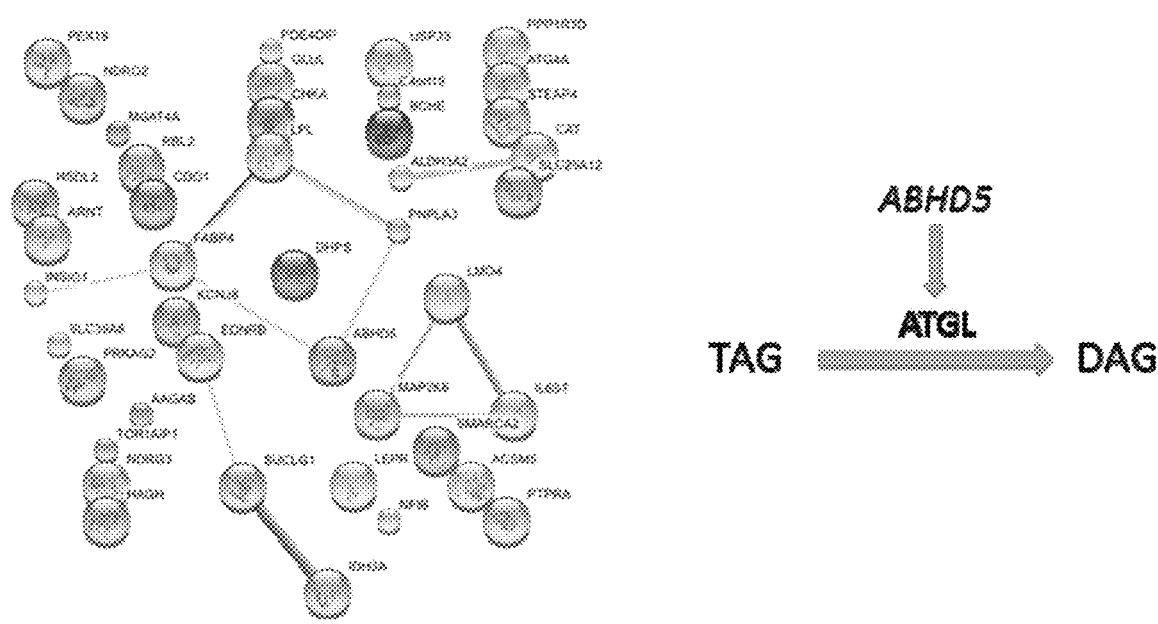
FIG. 28 is an image showing the string DB Network Analysis of genes up-regulated in in vitro primary human adipocytes co-cultured with cachexia-inducing or non-cachexia-inducing cancer cell lines. The model shows that a core network of genes involved in lipolysis is up-regulated, a finding confirmed by the lipid metabolite profile in FIG. 27.

The lipid profiles determined in in vitro human adipocytes exposed to cachexia-inducing conditioned media (FIGS. 27A and 27B) indicate the up-regulation of relevant metabolic gene networks, as shown in FIG. 28.

Figure 27C:
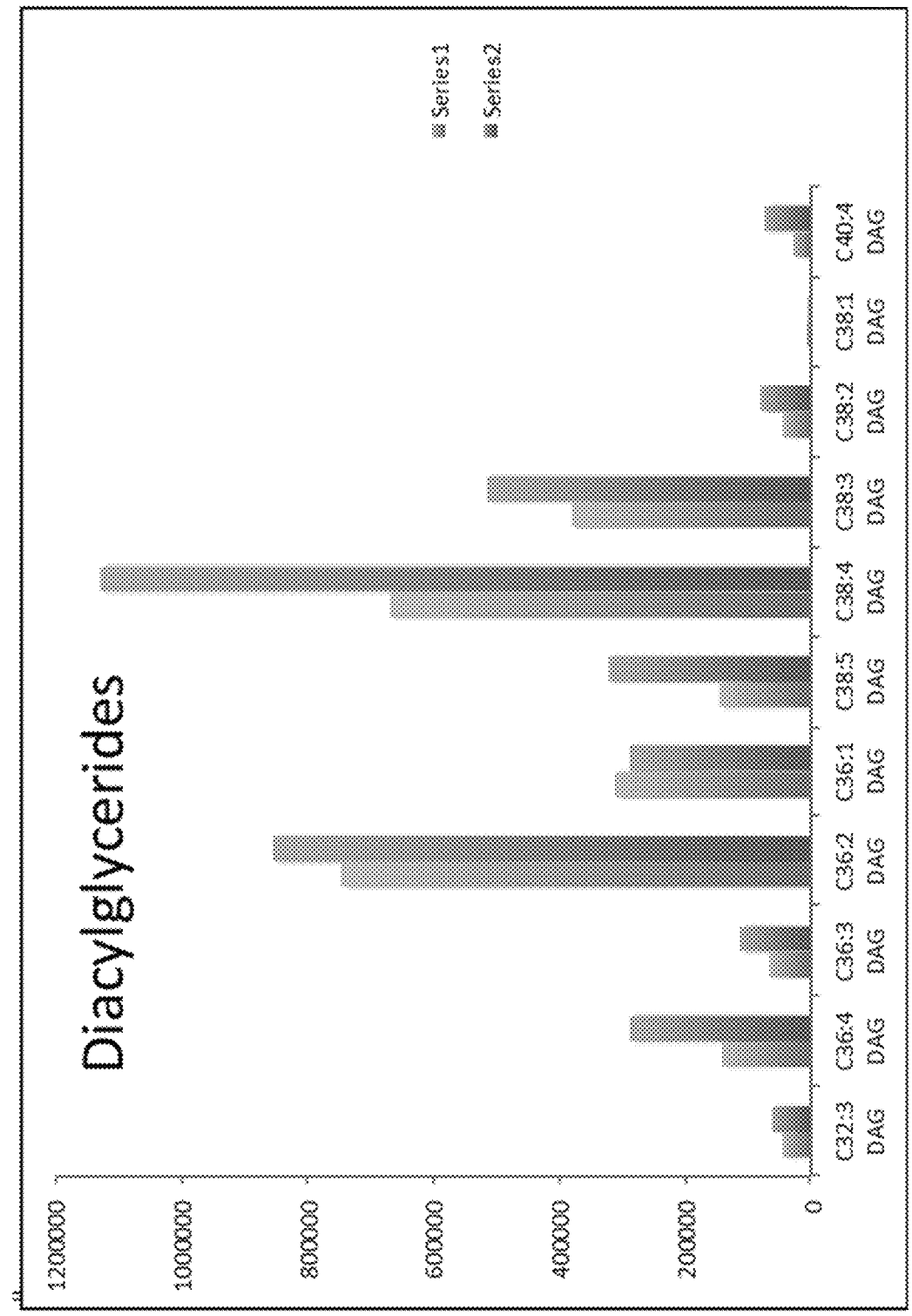
FIG. 27C shows that adipocytes generate relevant lipid metabolites in response to cachexia-inducing media.
Figure 27C:
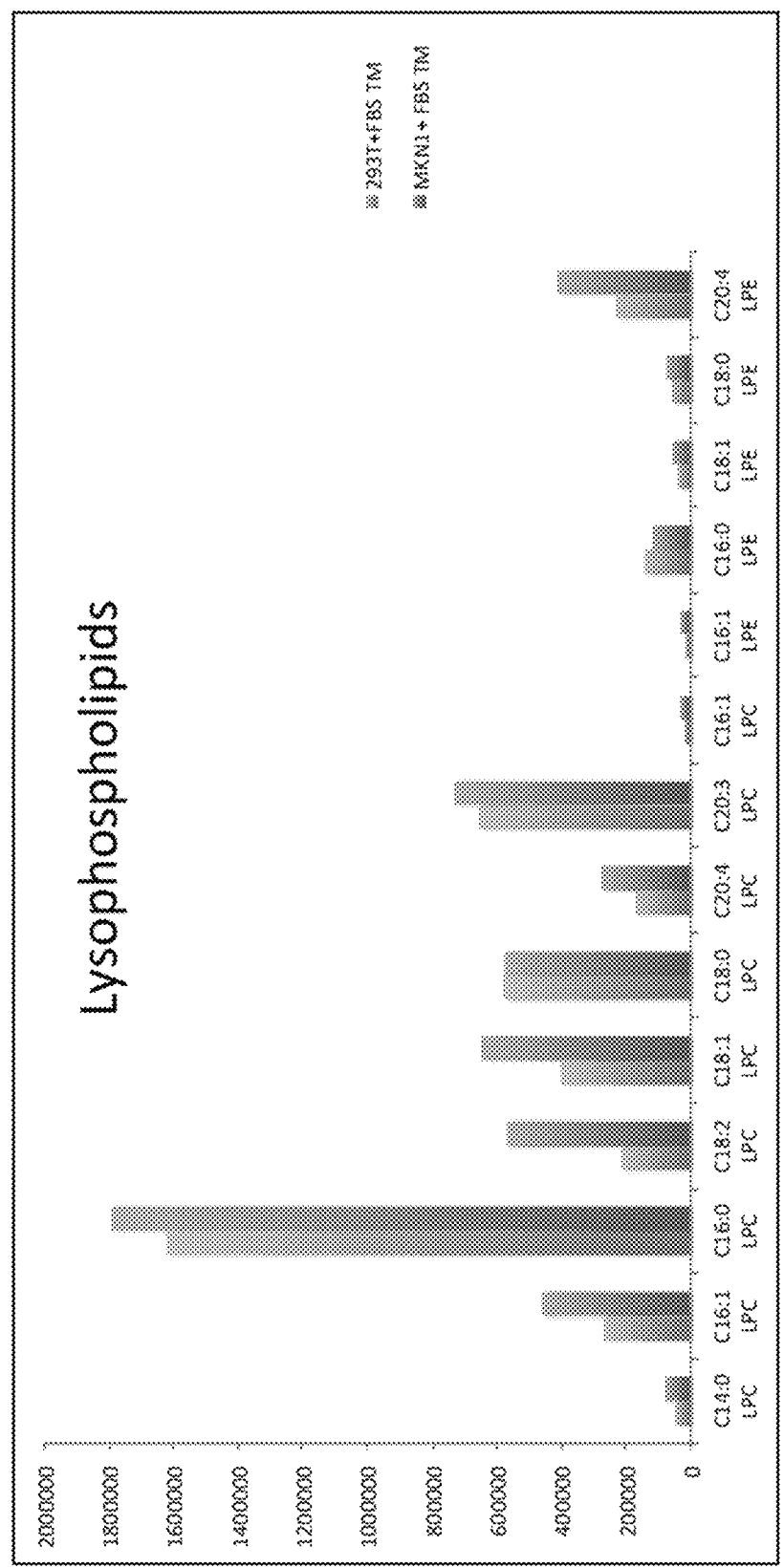

FIG. 27C includes two graphs showing lipid metabolite profiling of adipocytes treated with NI-CM or CI-CM (5 days), then maintenance media (1 day). Interestingly, adipocytes generate relevant lipid metabolites in response to cachexia inducing conditioned media (red bars) compared to non-inducing conditioned media (blue bars). The specific profile of lysophosphilipid changes stimulated by cachexia-inducing conditioned media (MKN1) compared to non-inducing conditioned media (293T) match exactly those lysopholipids that are actively taken up by RAS driven cancer cells (Kamphorst J J. et al., PNAS, 110(22): 8882-8887 2013). Both profiles of lysophospholipid and di-acyl glyercide changes are indicative of cachexia-induced lipolysis and are commensurate with the diminished quantities of specific tri-acyl glycerides (FIG. 3 and additional data not shown). These changes in lipid metabolites are also consistent with the specific lipolysis gene expression networks upregulated in cachexia-induced apidocytes (FIG. 28).

EXAMPLE 13

Discovery Approaches

Figure 29:
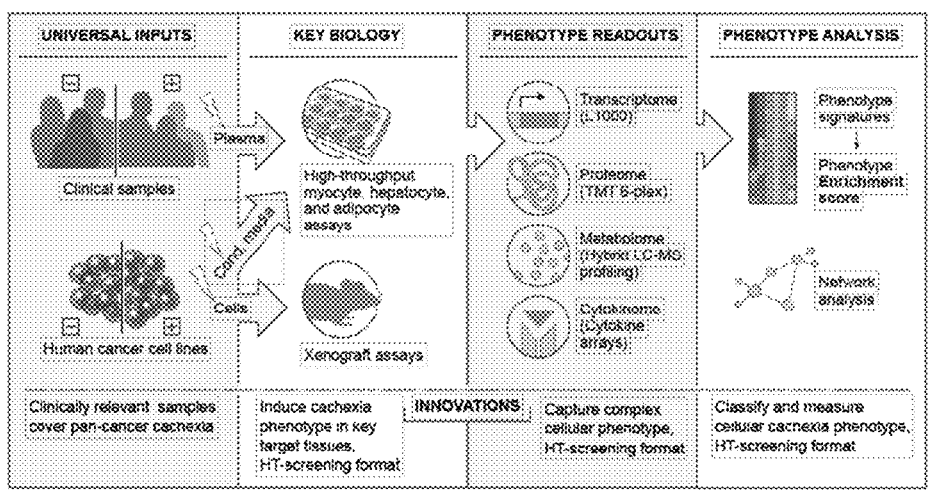
FIG. 29 is a schematic of a clinical sample derived phenotypic screening platform for cancer cachexia mediator discovery.
Figure 30:
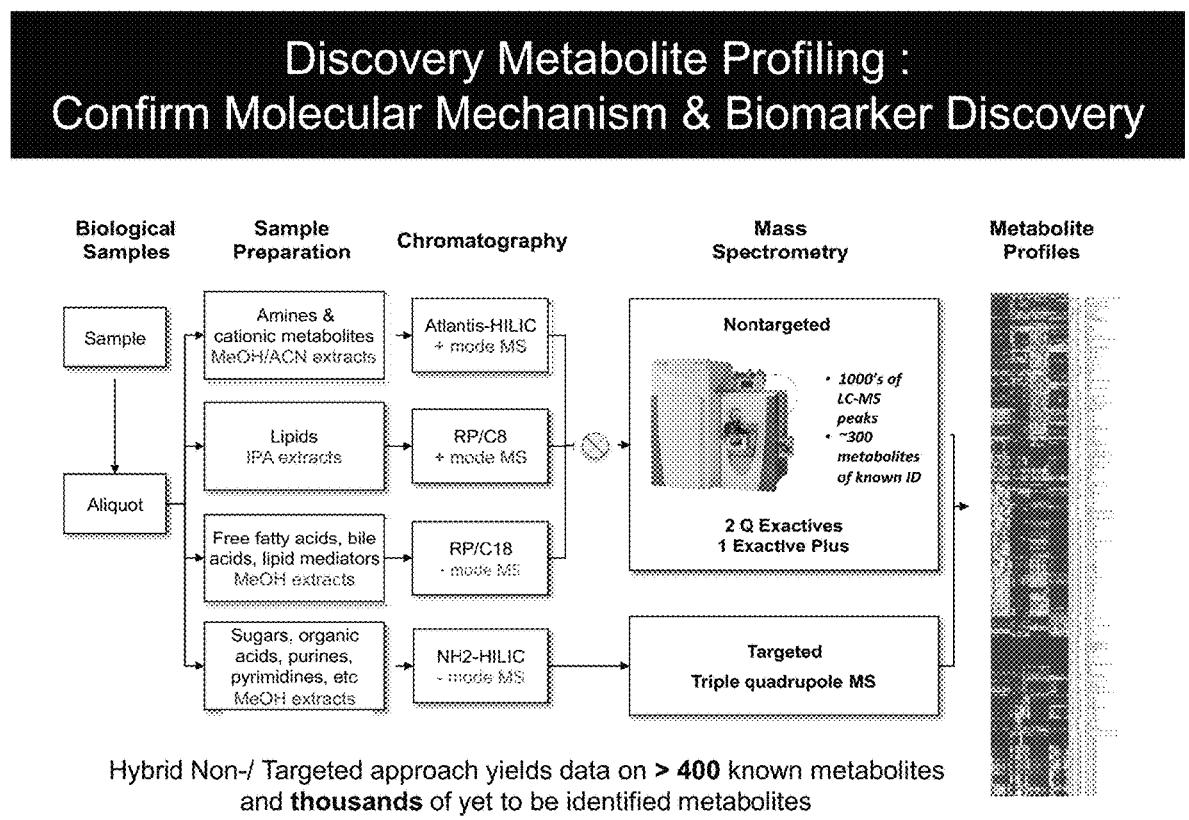
FIG. 30 is a schematic of a process for discovery metabolite profiling for confirming molecular mechanism and biomarker discovery.

FIG. 29 shows an approach to cancer cachexia mediator discovery. FIG. 30 shows an approach to metabolite profiling.

Figure 31:
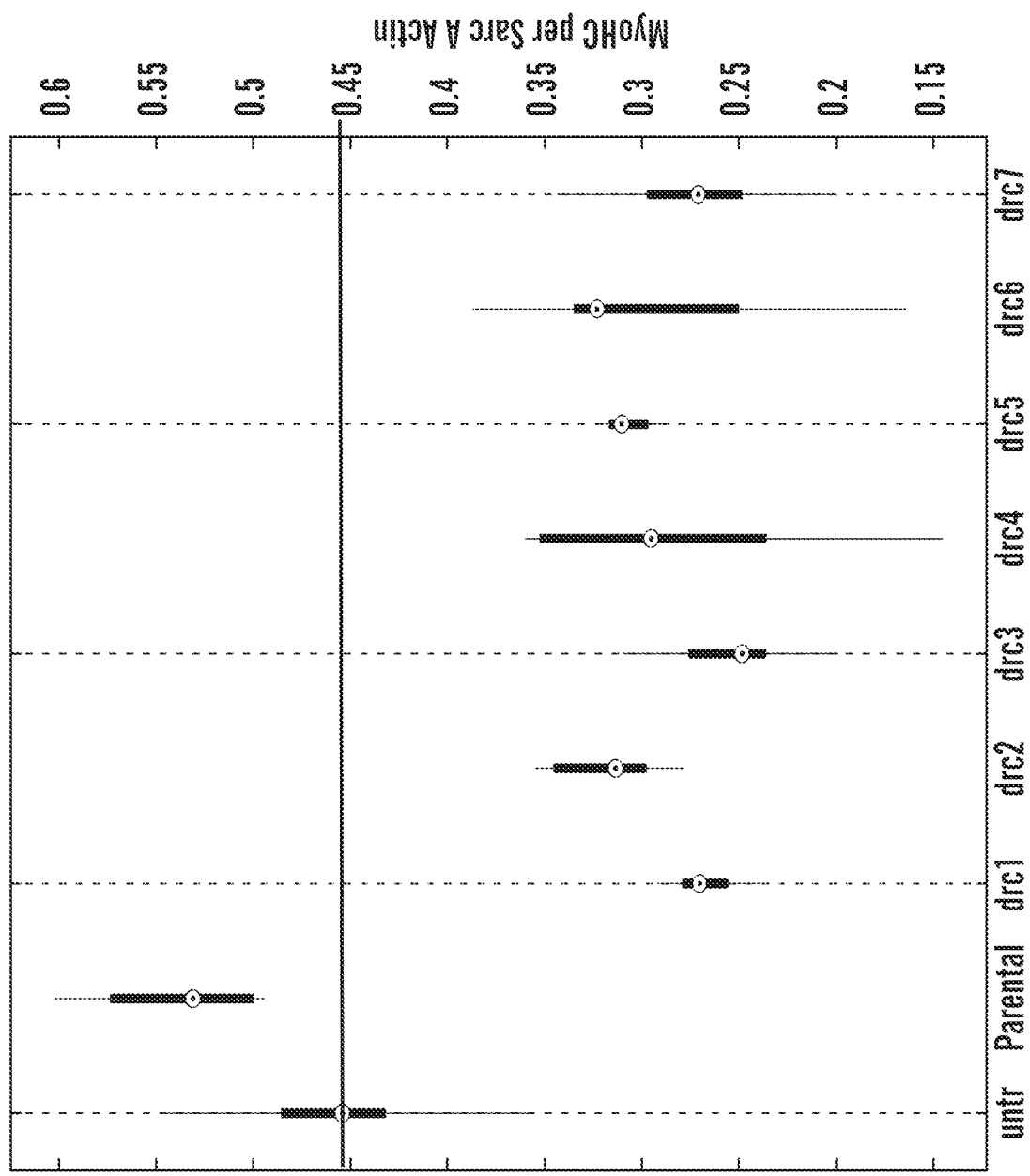
FIG. 31 includes a graph showing that isogenic single cell clones had differential cachexia inducing activity. Isogenic single cell clones with differential cachexia inducing phenotype are important tools for both Proteomic and Genetic discovery efforts by minimizing the background noise to signal for these assays. Drug resistance increased the frequency of cachexia-inducing clones.

FIG. 31 shows that selecting for drug resistance increases the frequency of cachexia inducing clones.

Figure 32:
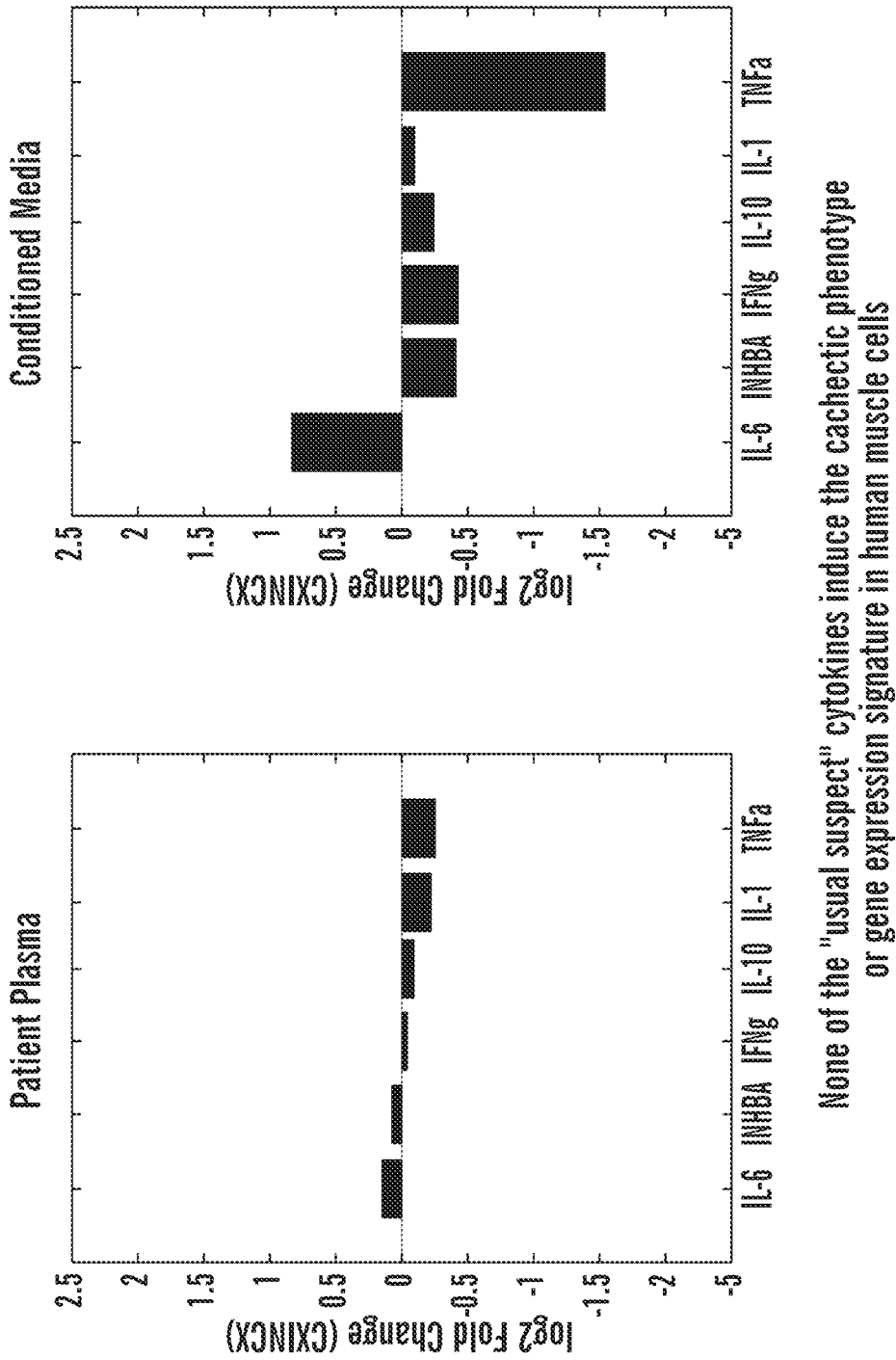
FIG. 32 are graphs showing cytokine abundance relative to cachexia in patient plasma and conditioned media. Human cytokines (300 on cytokine array) in muscle were tested. None of the expected "usual suspect" cytokines induced the cachectic phenotype or gene expression signature in human muscle cells. IL6, INHBA, IFNG, IL10, IL1, TNFa was assayed in patient plasma and conditioned media. Similar results were obtained in mouse.

FIG. 32 shows the abundance of cytokines IL-6, inhibin beta A, interferon gamma, IL-10, IL-1, and TNFalpha.

Figure 33:
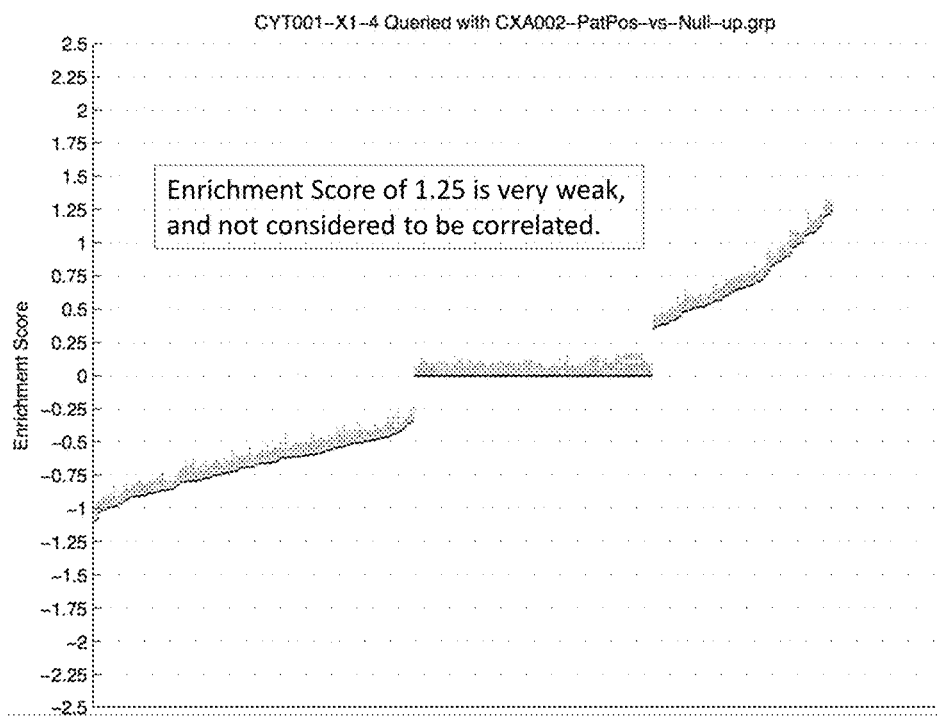
FIG. 33 is a graph showing testing of human cytokines for induction of cancer cachexia signature. For some the enrichment score was weak (e.g., 1.25).

FIG. 33 shows the testing of human cytokines to determine whether they could induce a cachexia signature.

Figures 34A, 34B, 34C:
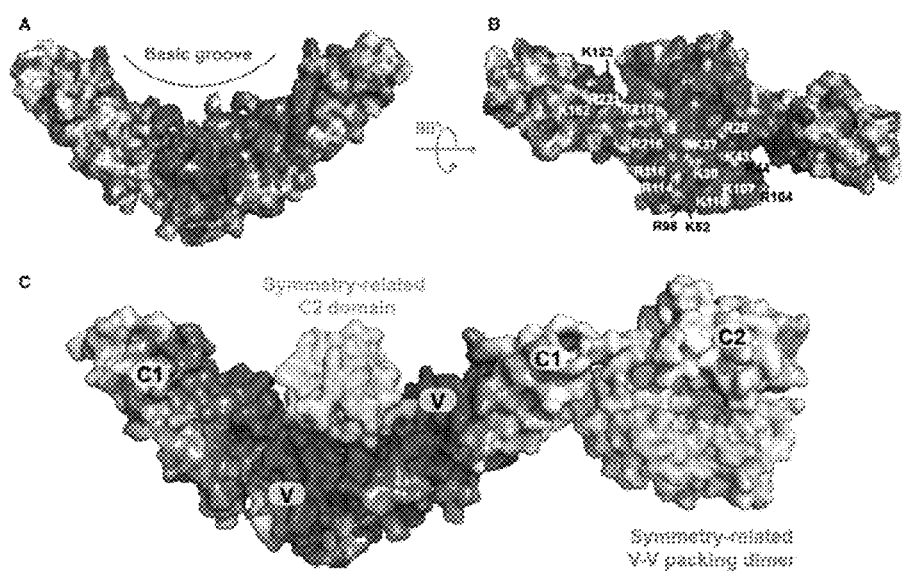
FIGS. 34A-C show electrostatics properties of the hRAGE VC1 dimer formed through crystal contacts.

FIG. 34 shows the RAGE crystal structure.

Figure 35:
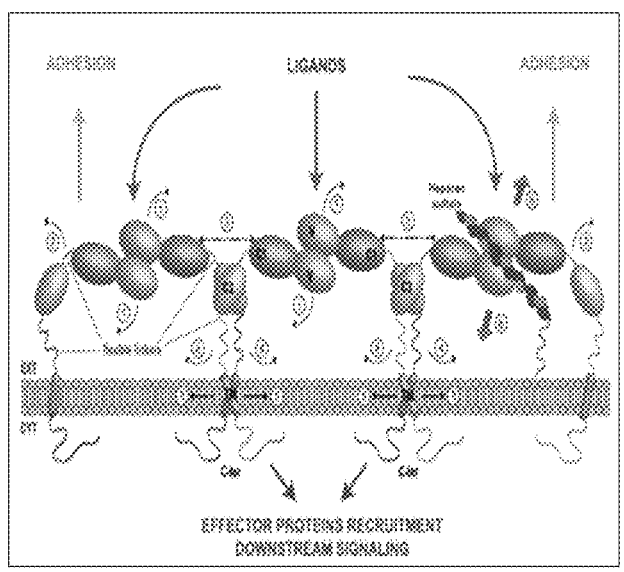
FIG. 35 is a schematic diagram depicting models of RAGE ligand binding and extracellular signaling. Without being bound to a particular theory. RAGE activity is non-catalytic, and may act as a docking platform for other effector molecules. The strength of signaling may be dependent on degree of oligomerization (octomers) and persistence of oligomerization (e.g., Hetero-dimerization: FGF's).
Figure 36A:
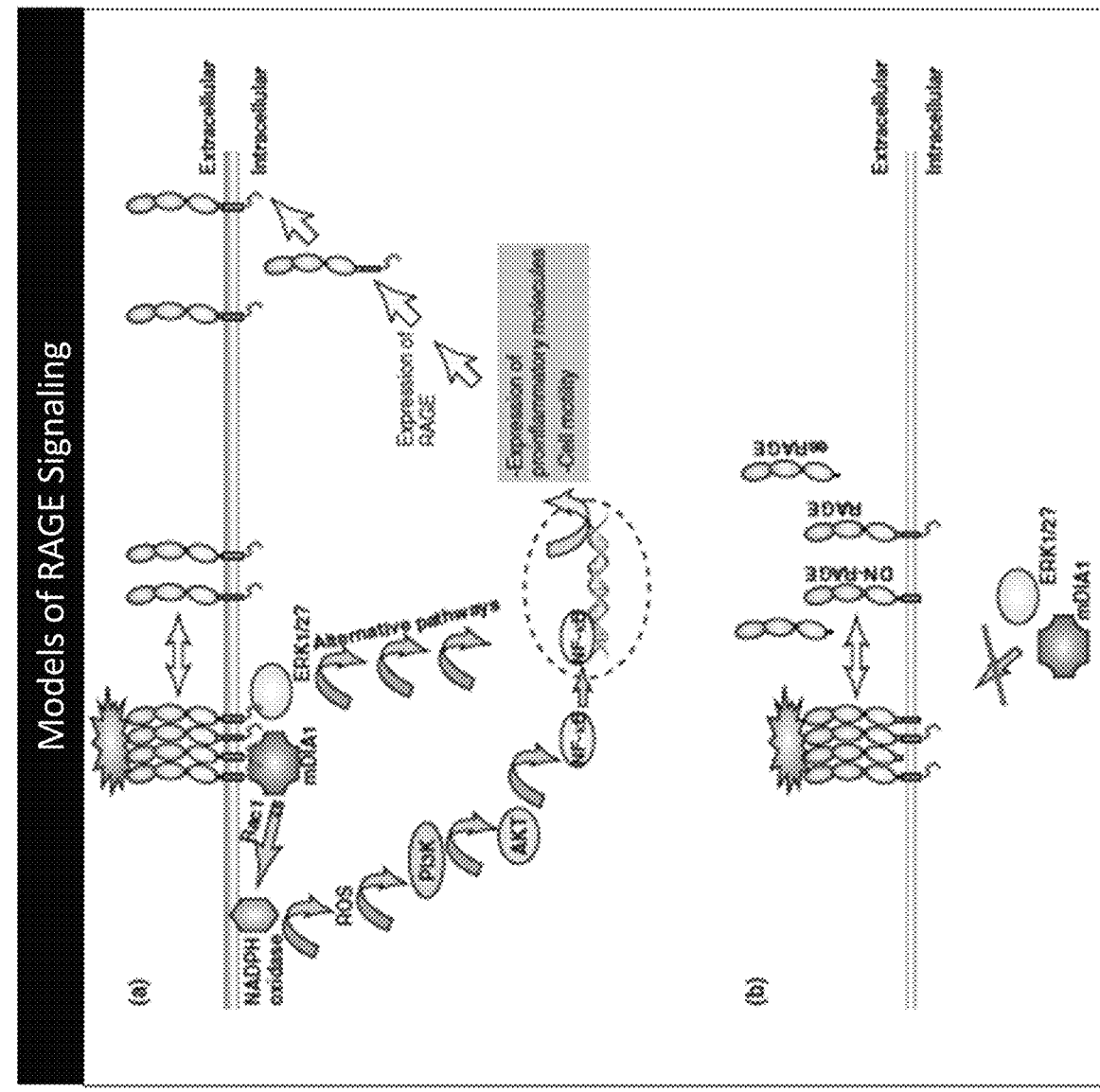
FIGS. 36A and 36B are schematic diagrams depicting models of RAGE signaling.
Figure 36B:
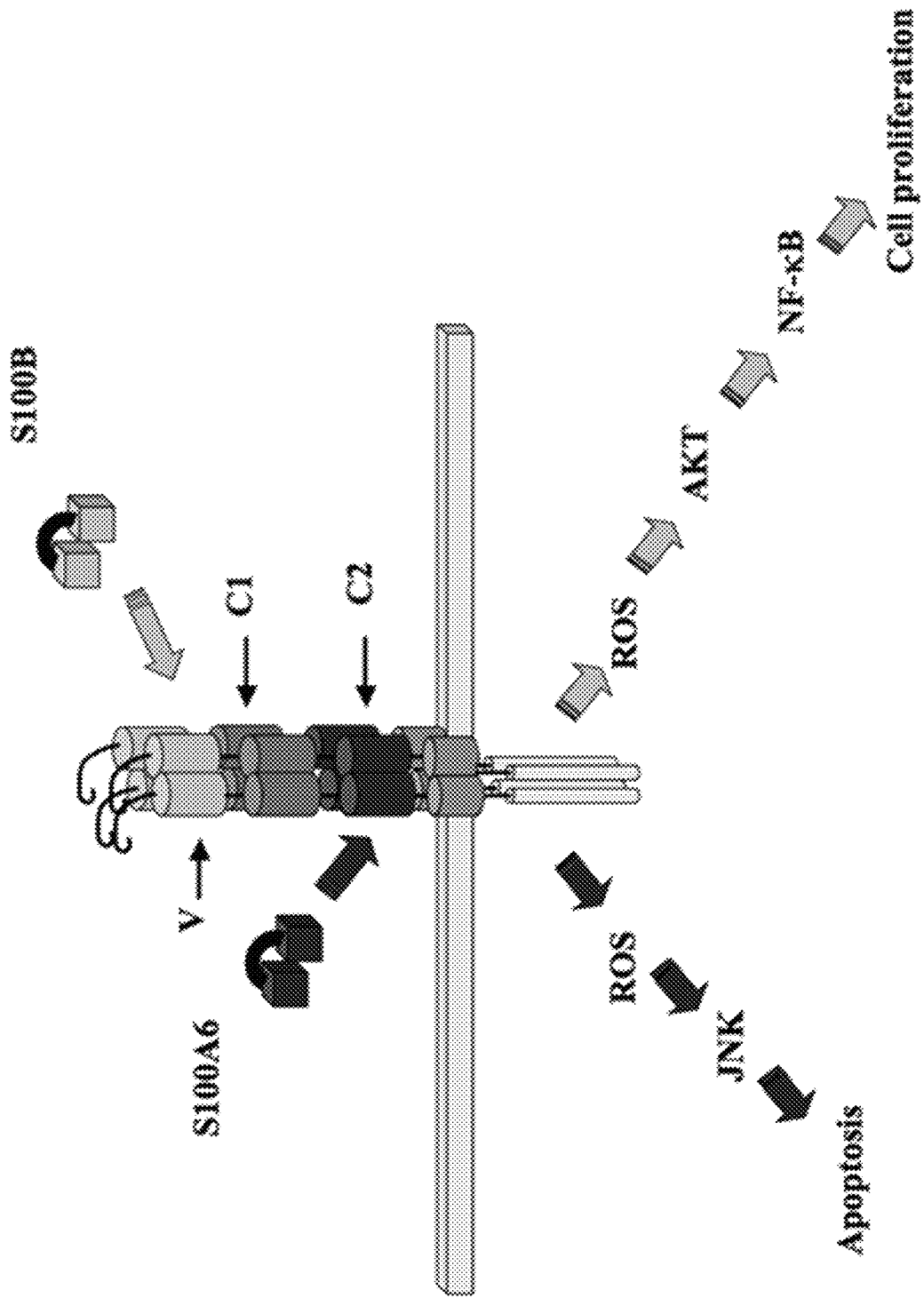

FIGS. 35 and 36 show models for RAGE signaling.

Figure 37:
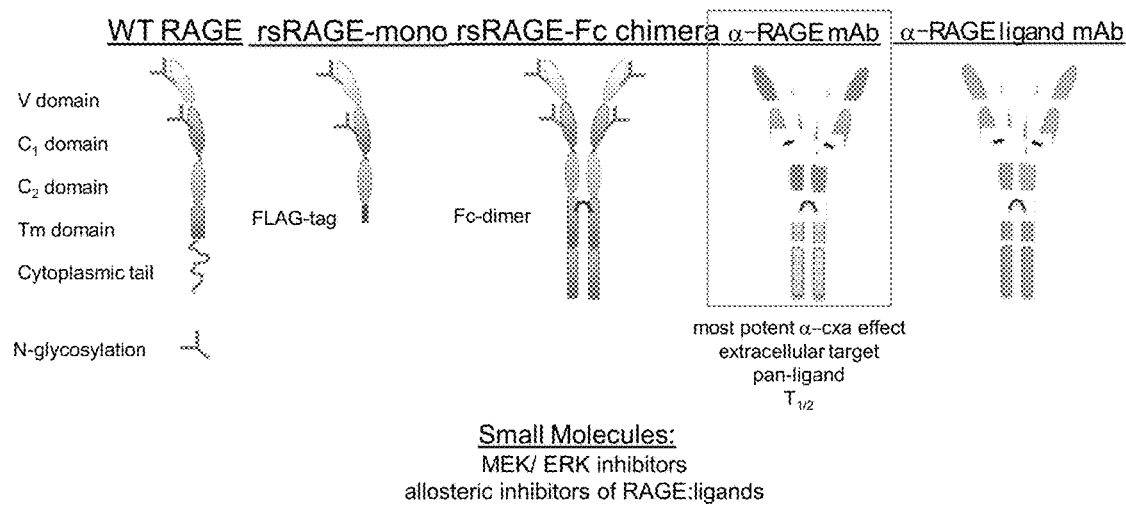
FIG. 37 is a schematic diagram depicting therapeutic modalities targeting RAGE.

FIG. 37 indicates therapeutics that could be used to target RAGE.

EXAMPLE 14

Figure 38A:
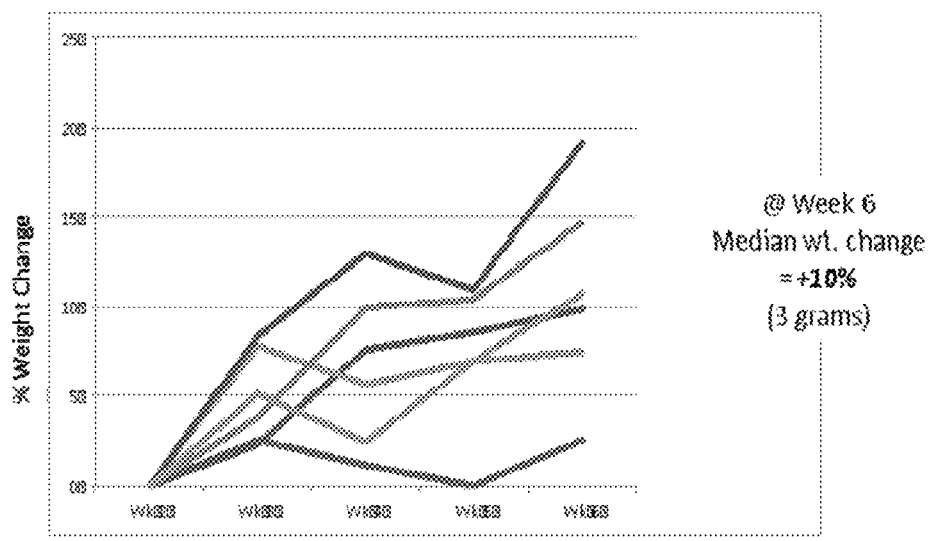
FIGS. 38A and 38B are graphs showing changes in weight in a conditional murine model of lung cancer. The growth of control (uninduced) 6 week old mKRASG12D/p53$^{-/-}$ mice is shown at FIG. 38A. Weight loss following induction of lung cancer is shown at FIG. 38B.
Figure 38B:
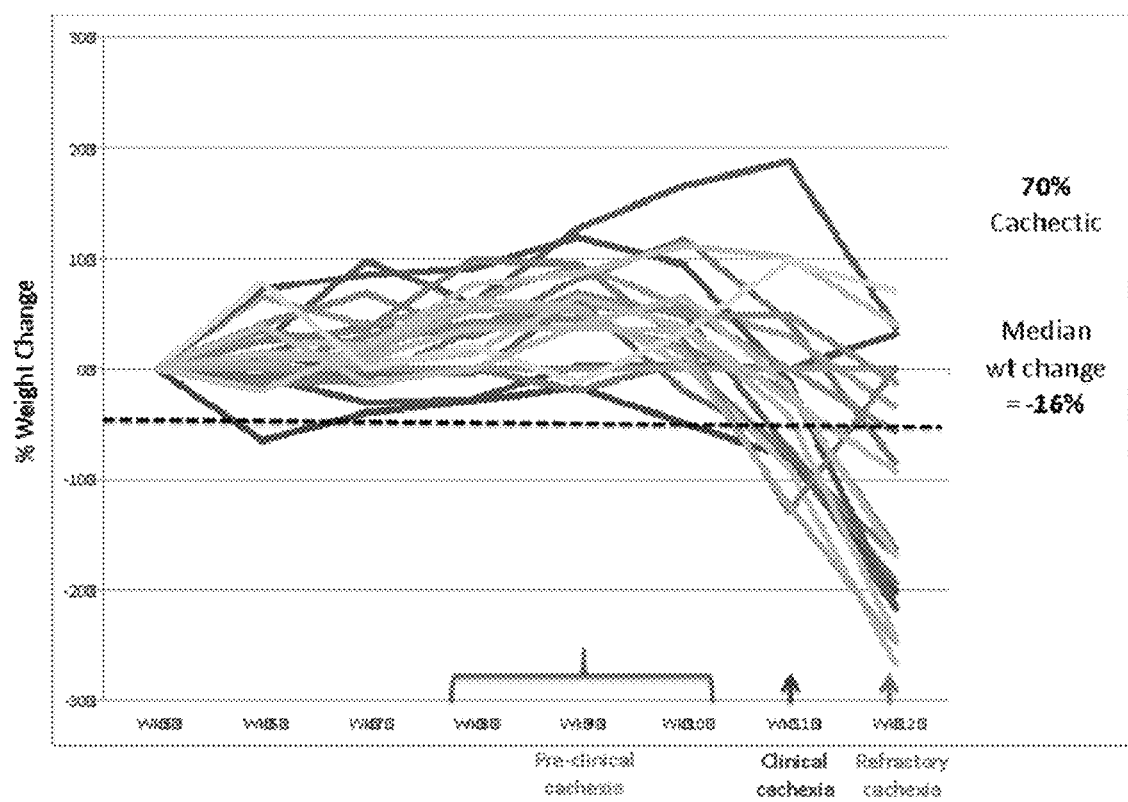

Development of Pre-Cachexia, Cachexia, and Refractory Cachexia in a Murine Model Conventionally, cachexia was strictly defined as weight loss greater than 5 percent. While a number of therapeutic approaches have been tried, to date there is no effective method for treating cachexia. Even when a patient is supplied with all the necessary nutrients and calories, weight loss continues unabated. It may be that once a patient has progressed to full-blown cachexia, the metabolism has become so dysregulated that it is difficult, if not impossible, to disrupt the disease process. To that end, the invention provides methods for identifying the factors that drive changes occurring at the earliest stages of the disease process when the subject is pre-cachexic, markers that identify subjects as pre-cachexic, and that provides compositions and methods for identifying agents that can effectively disrupt the transition from pre-cachexia to cachexia or refractory cachexia (FIGS. 38A and 38B).

The invention provides in vitro and in vivo models that facilitate the identification of factors that drive the induction of cachexia at it's earliest stages to elucidate changes occurring in precachexia, a stage of disease that precedes cachexia. FIGS. 38A and 38B provide an analysis of cachexia progression in a conditional murine model of lung cancer, where delivery of Cre recombinase initiates tumor development. As illustrated in FIG. 38A, at 6 weeks uninduced mice are actively growing and putting on weight. As shown in FIG. 38B, cancer induction results in the development of cachexia in 70% of the induced mice. The graph delineates 3 distinct phases of disease progression: pre-cachexia, clinical cachexia, and refractory cachexia.

Figure 39:
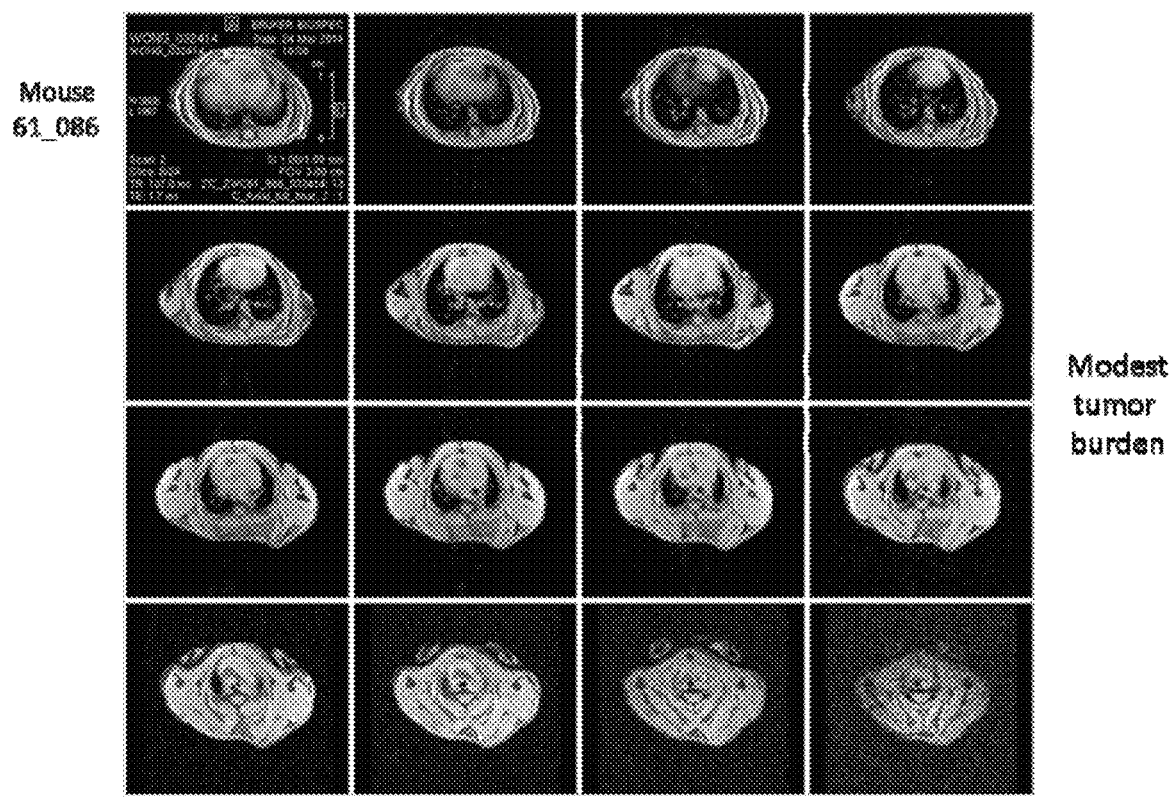
FIG. 39 provides imaging studies of a mouse 7 weeks post induction. At this time point, the mouse has a modest tumor burden.
Figure 40:
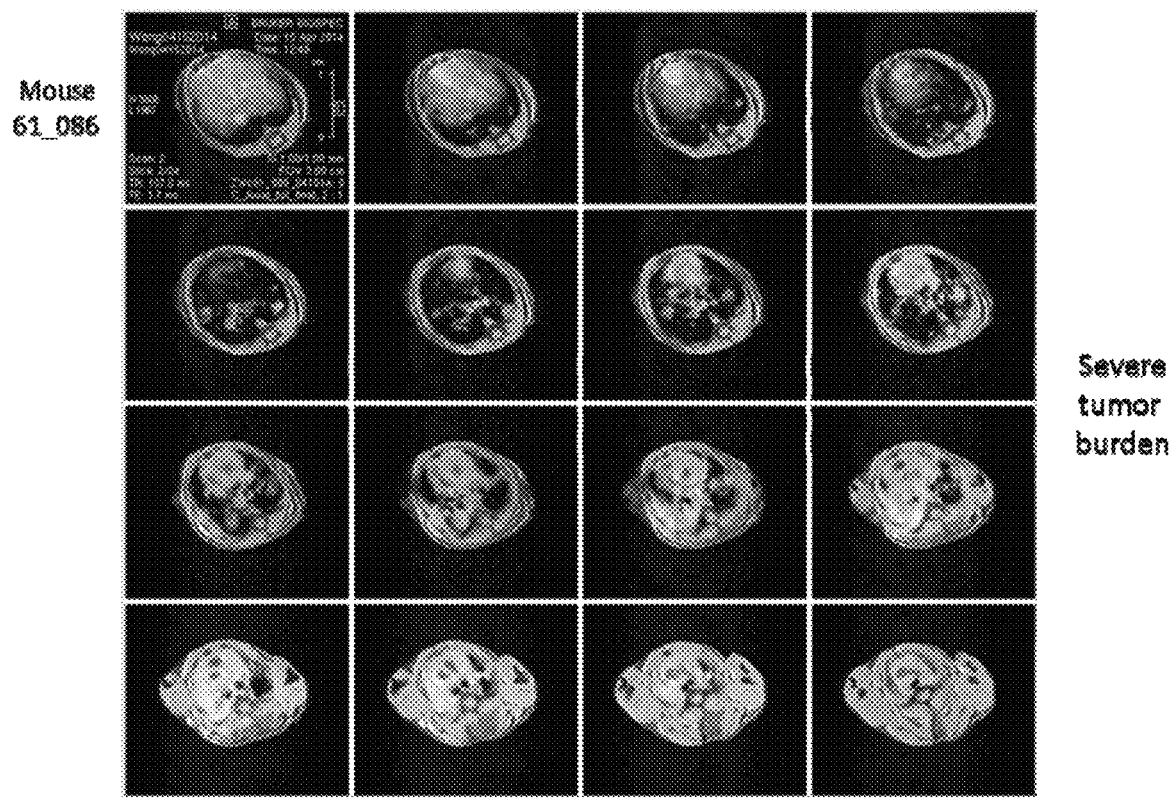
FIG. 40 provides imaging studies of a mouse 10 weeks post induction. At this time point, the mouse has a severe tumor burden.

Tumor growth at 7 and 10 weeks post-induction is shown at FIGS. 39 and 40. Interestingly, the cachexic disease process is initiated prior to the accumulation of extensive tumor burden.

EXAMPLE 15

Cachexia-Induced Lipid Loss is Reduced by RAGE Inhibition

Figure 41A:
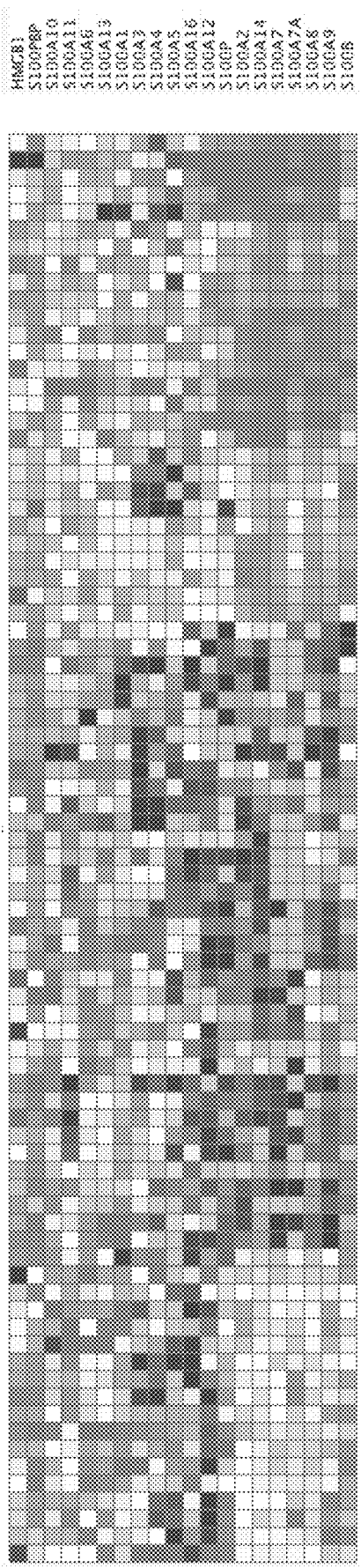
FIG. 41A provides a heat map showing RAGE ligands that are differentially regulated in melanoma. Of particular interest are S100A7, S100A7A, S100A8, and S100A9 RAGE ligands that were found to be more abundant by proteomic analysis in the conditioned medias of a set of human cancer cell lines that induce cachexia in both in vitro and in vivo assays.

Shown are differential Expression levels of RAGE ligands in TCGA data. In Melanoma, Breast, and Lung Cancer, levels of S100A7, S100A7A, S100A9, and S100A9 are reduced (FIGS. 41A, 41B, 41C). Each of the TCGA gene expression heat maps (FIGS. 41-45) demonstrates that there are a subset of clinical tumors with high expression of RAGE ligands. Of particular interest are S100A7, S100A7A, S100A8, and S100A9.

Lipid loss from differentiated primary adipocytes occurs within 5 days of contact with cachexia-inducing conditioned media (FIG. 42A). This loss is inhibited in adipocytes treated with Rage inhibitors, anti-RAGE monoclonal antibody AF1145 or Tramatenib. This phenotypic response is also seen in melanoma cells.

FIG. 41A provides a heat map showing RAGE ligands that are differentially regulated in melanoma. Of particular interest are S100A7, S100A7A, S100A8, and S100A9.

FIG. 41B provides a heat map showing RAGE ligands that are differentially regulated in breast cancer. Of particular interest are S100A7, S100A7A, S100A8, S100A9 and S100P.

FIG. 41C provides a heat map showing RAGE ligands that are differentially regulated in squamous lung cancer. Of particular interest are S100A7, S100A7A, S100A8, S100A9 and S100P.

Figure 42:
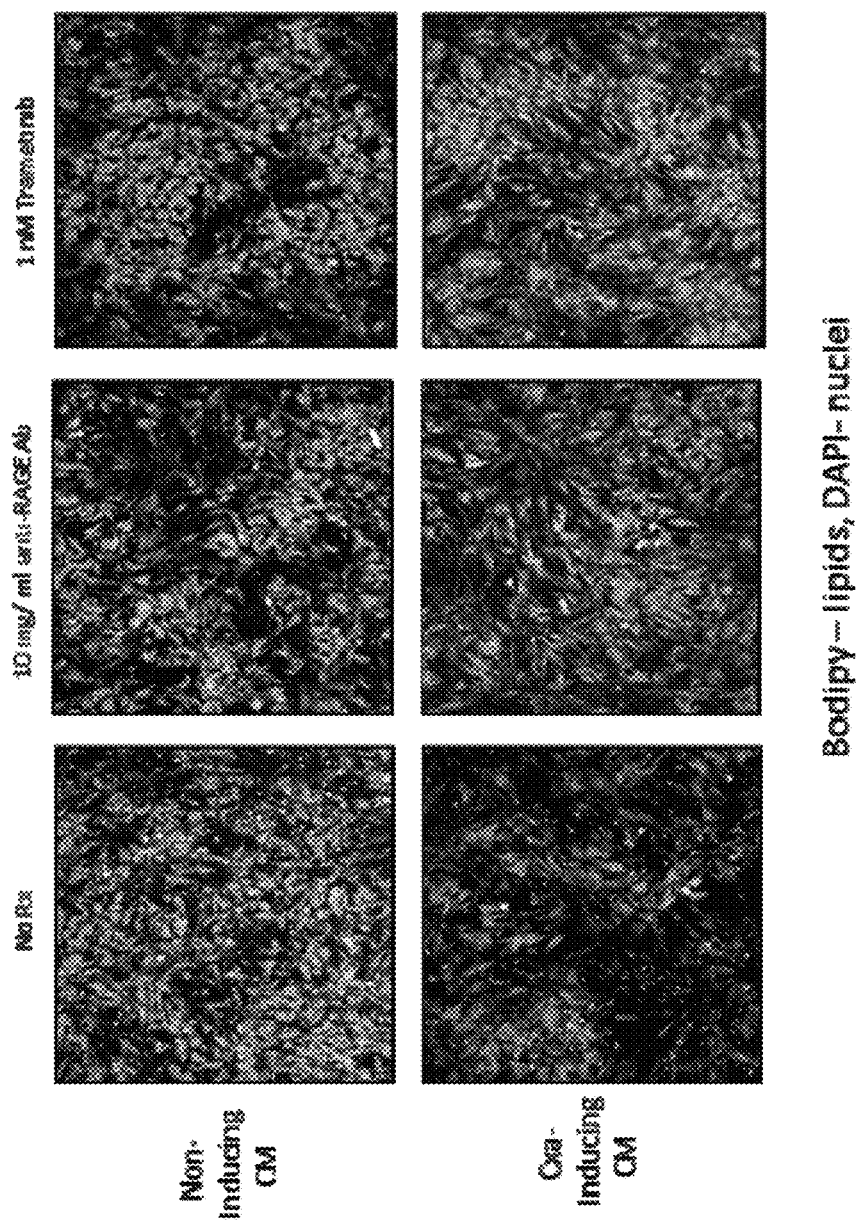
FIG. 42 includes six panels showing adipocytes in cultured stained with bodipy to highlight lipids and DAPI to stain nuclei. Lipids are lost in cells treated for 5 days with cachexia (CXA) inducing conditioned media (CM). Lipid loss is inhibited by inhibiting RAGE signaling.

FIG. 42 includes six panels showing adipocytes in cultured stained with bodipy to highlight lipids and DAPI to stain nuclei. Lipids are lost in cells treated for 5 days with cachexia (CXA) inducing conditioned media (CM). Lipid loss is inhibited by inhibiting RAGE signaling.

Figure 43:
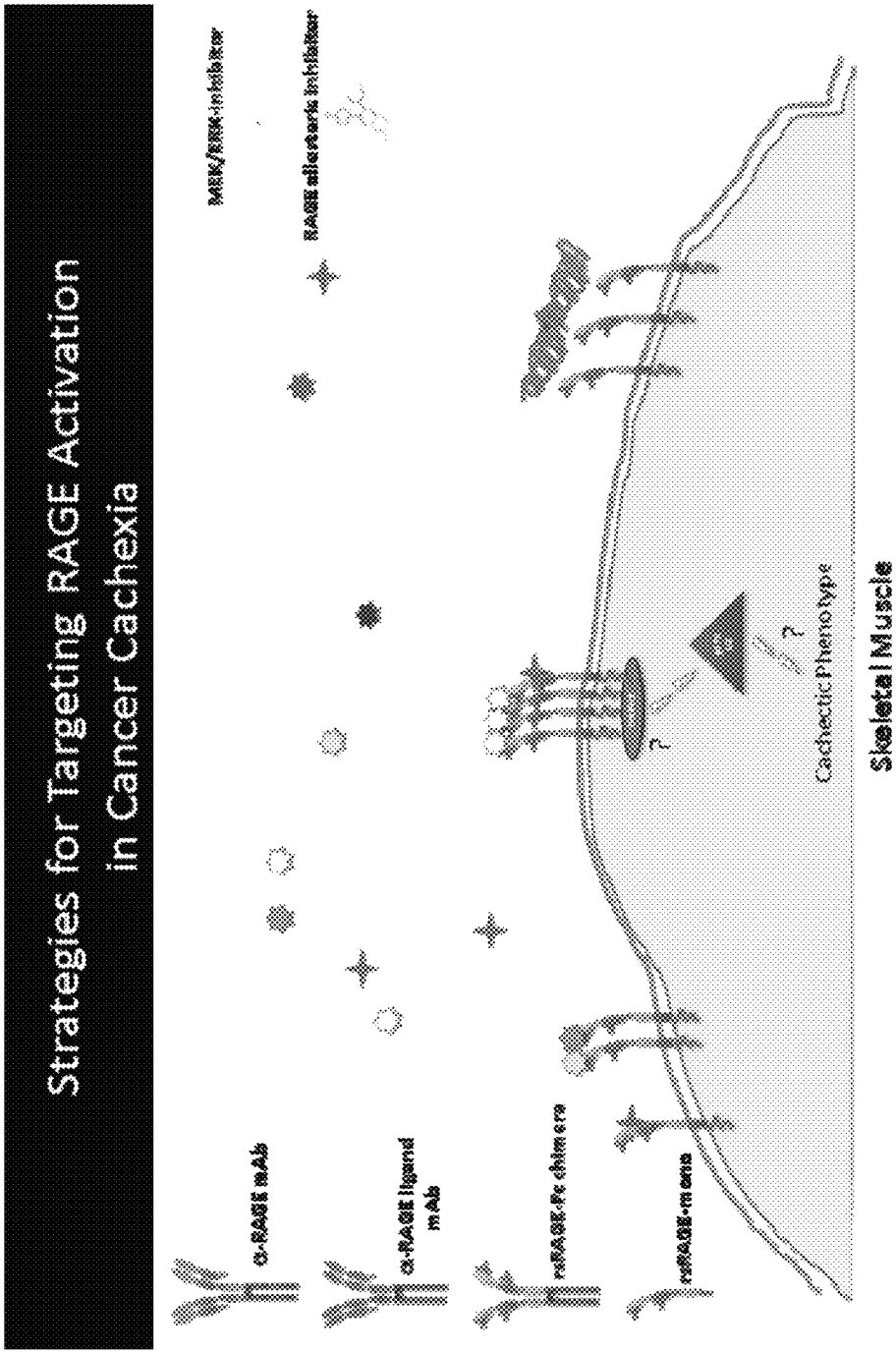
FIG. 43 is a schematic illustrating the treatment of cachexia by inhibiting RAGE.

FIG. 43 us a schematic illustrating the treatment of cachexia by inhibiting RAGE.

Figure 44:
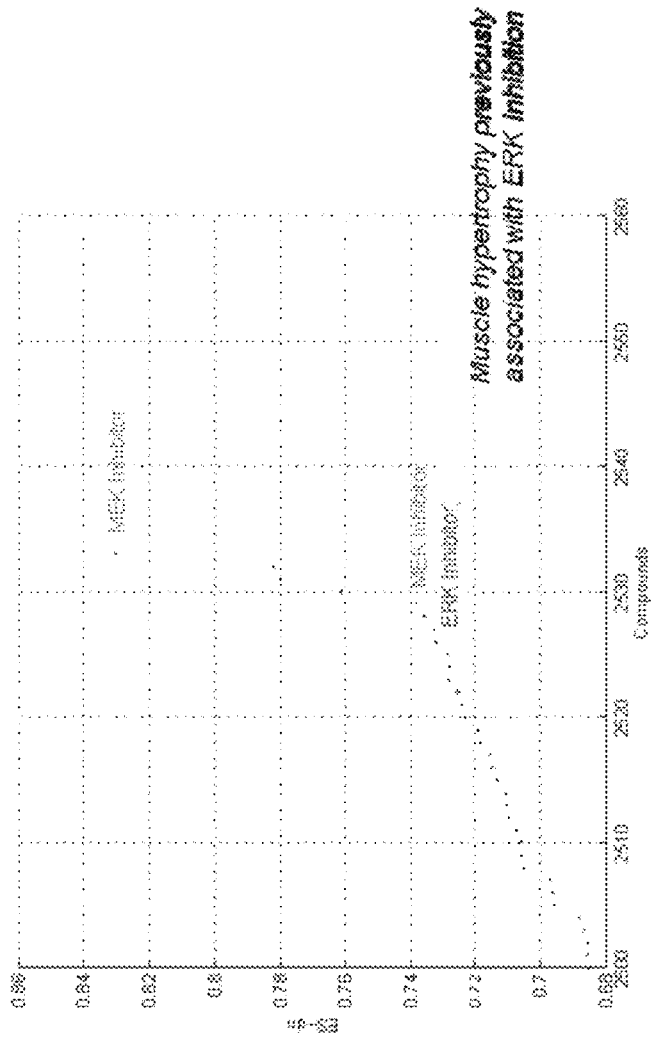
FIG. 44 is a graph that shows the distribution of compounds negatively correlated with the patient plasma cachexia signature.

FIG. 44 shows a query of a connectivity map with cachexia signature, which yields MAPK pathway.

Figure 45:
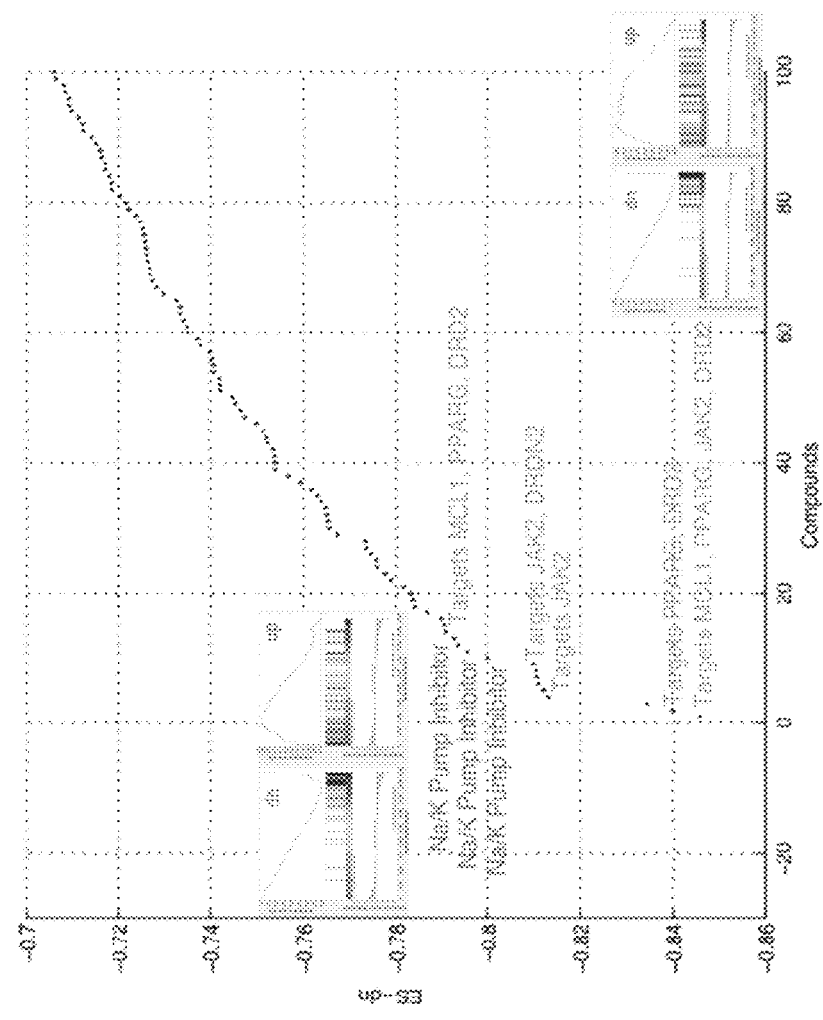
FIG. 45 is a graph that shows the distribution of compounds positively correlated with the patient plasma cachexia signature.

FIG. 45 is a graph that shows the distribution of compounds correlated with patient plasma cachexia signature in muscle.

EXAMPLE 17

Cachexia-Induced Conditioned Media Stimulates MEK/ERK Activation in Adipocytes

As reported herein above, cachexia-inducing conditioned media stimulates MEK/ERK activation in muscle (FIGS. 20, 21). As shown in FIG. 22, myocytes treated with conditioned media derived from a cachexia-inducing cell line showed a dramatic decrease in myosin heavy chain. The effect of treatment with cachexia inducing media was reduced in a dose-dependent manner by administration of SCH772984, which is an ERK1/2 inhibitor.

Figure 47:
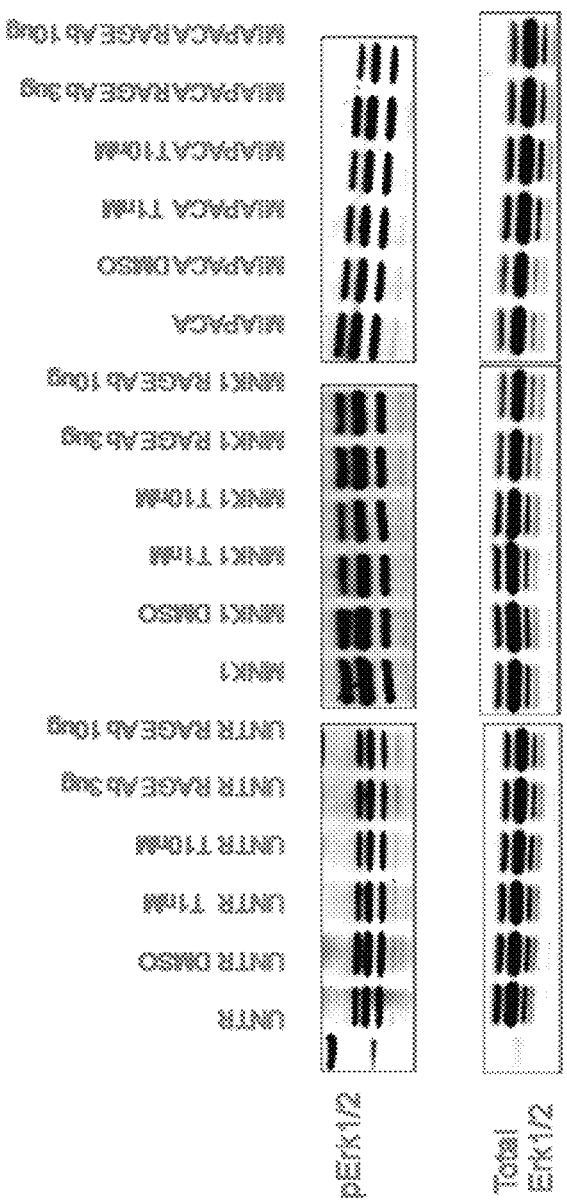
FIG. 47 is a Western blot showing the effects of conditioned media on adipocytes treated with conditioned media from a Cachexia-inducing cell line (CI) MnK1 or a Non-Cachexia-Inducing Cell Line MIAPACA cells. Results of treatment with tremetinib and a RAGE-blocking antibody are also shown.
Figure 48:
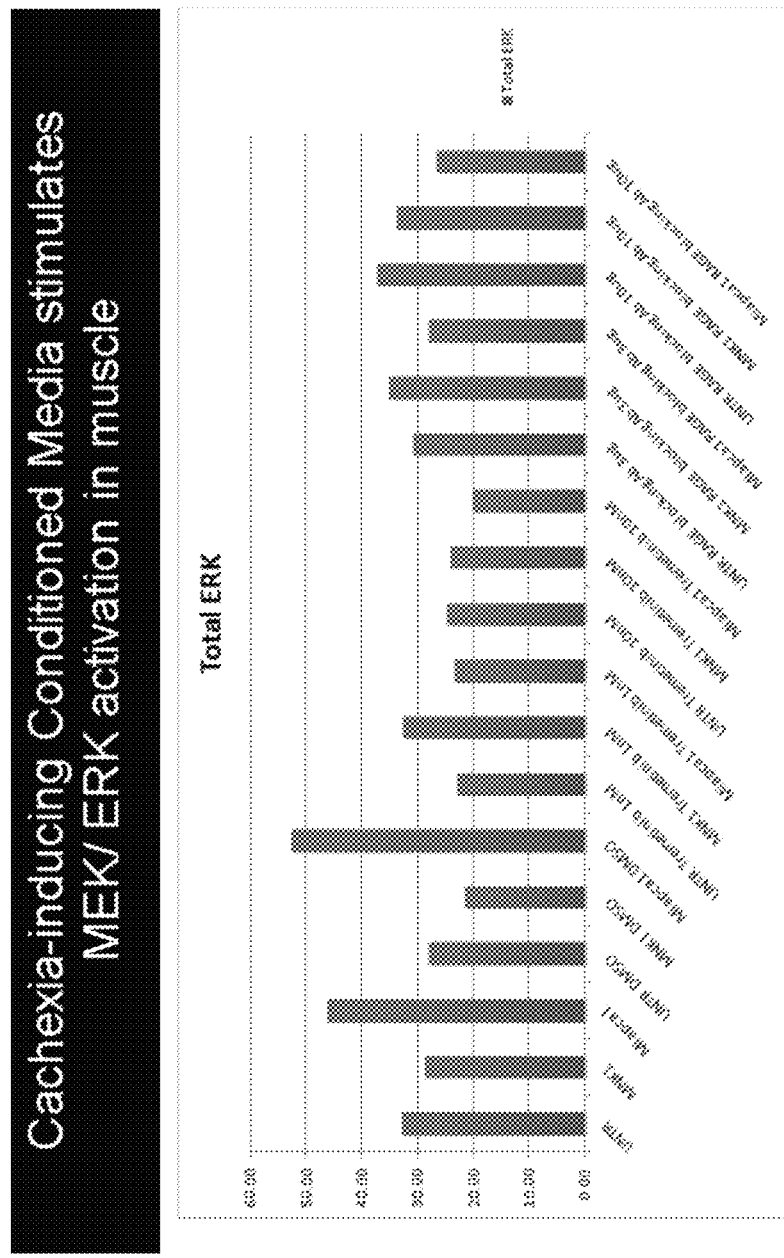
FIG. 48 is a graph that quantitates the effect of the experiment shown at FIG. 50.
Figure 49:
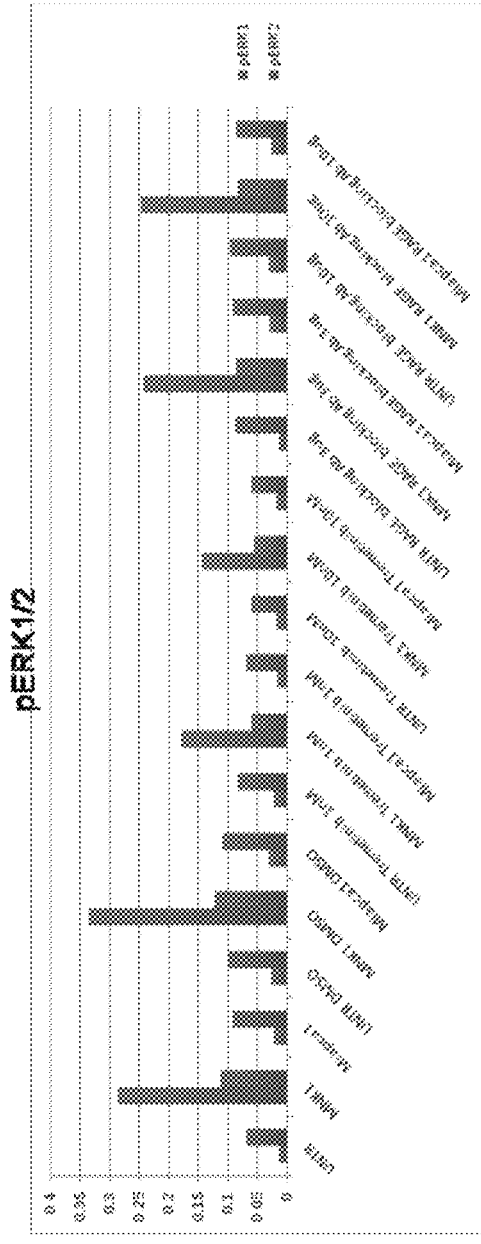
FIG. 49 is a graph that quantitates the effect of the experiment shown at FIG. 50. These results show that cachexia-inducing conditioned media stimulates MEK/ERK activation in muscle. 51 Total ERK is used to demonstrate that the increases in phosphorylated ERK (particularly ERK1) seen in cachexia-inducing MkN1 compared to the 2 negative controls (untreated and MiaPaca) is not attributable to an increase in total ERK—rather this is a result of the true activating phosphylation seen in FIG. 49.

Similar results were seen in adipocytes. Conditioned media was derived from Cachexia-inducing cell line MNK1 or non-cachexia-inducing cell line MIAPACA cells (FIGS. 47, 48, 49).

The effects of treatment with RAGE blocking antibodies and Tremetinib are shown (FIG. 42). Both treatements block the loss of lipid caused by the cachexia-inducing conditioned media compared to the non-inducing control.

EXAMPLE 18

Figure 50:
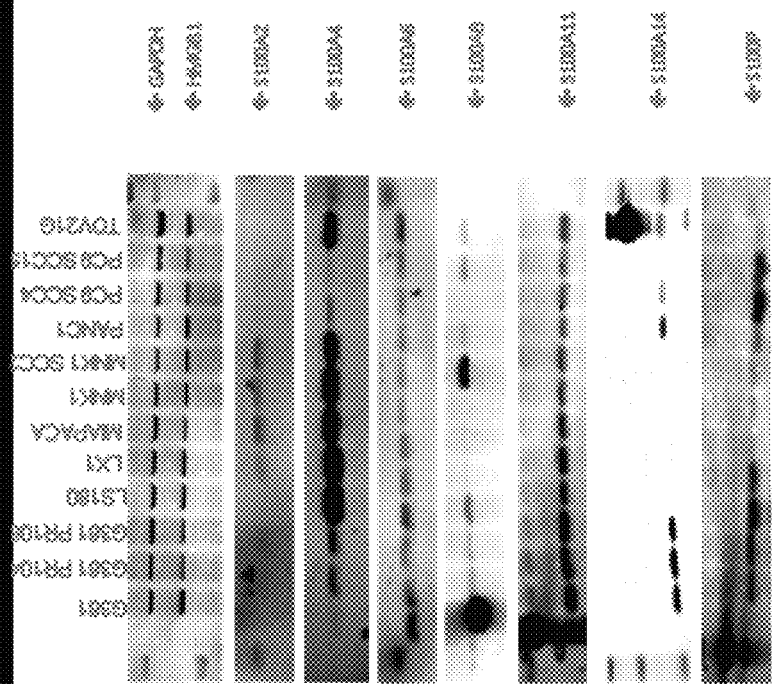
FIG. 50 shows a series of Western blots showing that S100 family members are differentially expressed in cachexia inducing and non-inducing cell lines.

S100 Family Proteins are Differentially Expressed in Cachexia-Inducing vs. Non-Cachexia-Inducing Cell Lines Non-Cachexia-Inducing Cell Lines (NCI), including G361 and MIAPACA express different levels of RAGE ligands than do Cachexia-inducing cell lines, including G361 PR106, G361 PR104, MNK1, and PANC1 (FIGS. 50A, 50B and 51).

PANC1 (ATCC® CRL-1469) is a human cell line derived from an epithelioid carcinoma of the pancreas/duct. MKN1 cells are derived from a human gastric cancer.

Importantly, levels of S100A2, S100A4, S100A8, S100A9, S100A7, S100A14, and S100P were differentially regulated in the cachexia inducing vs. non-inducing cell lines.

Figure 52A:
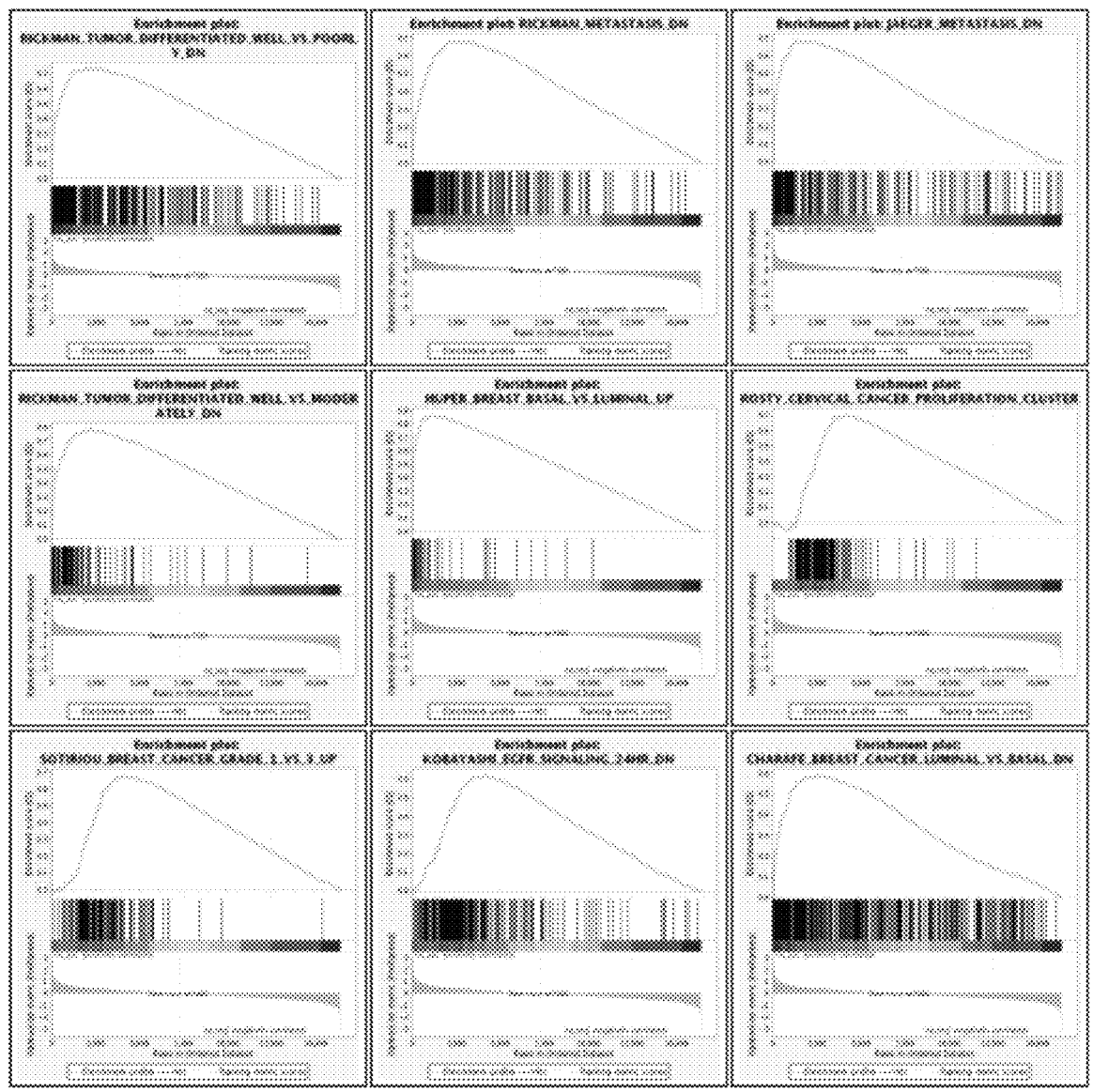
FIGS. 52A and 52B show the top scoring gene sets for S100A8 TCGA Pan-Cancer gene signature.
Figure 52A:
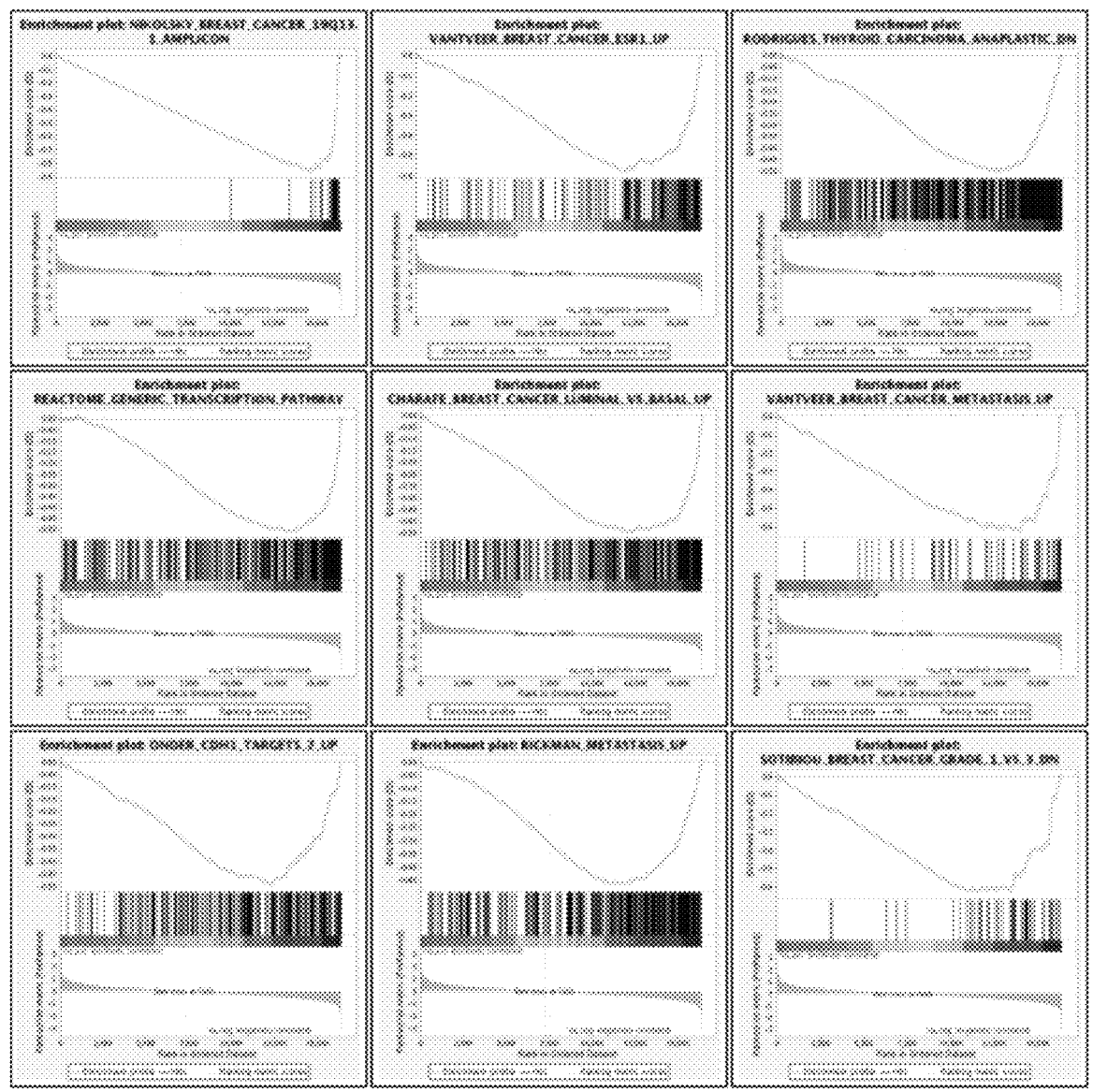
Figure 52B:
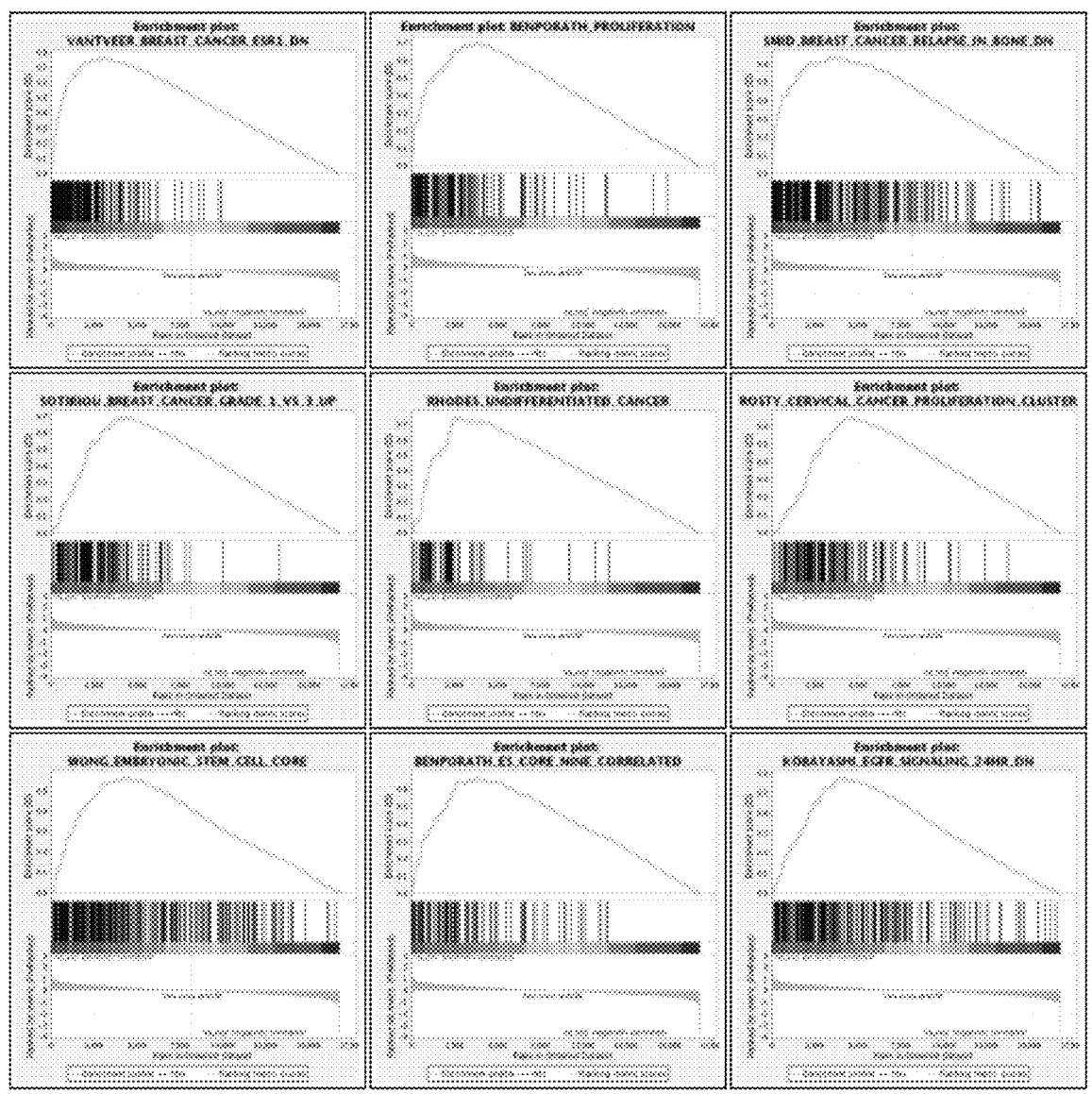
Figure 52B:
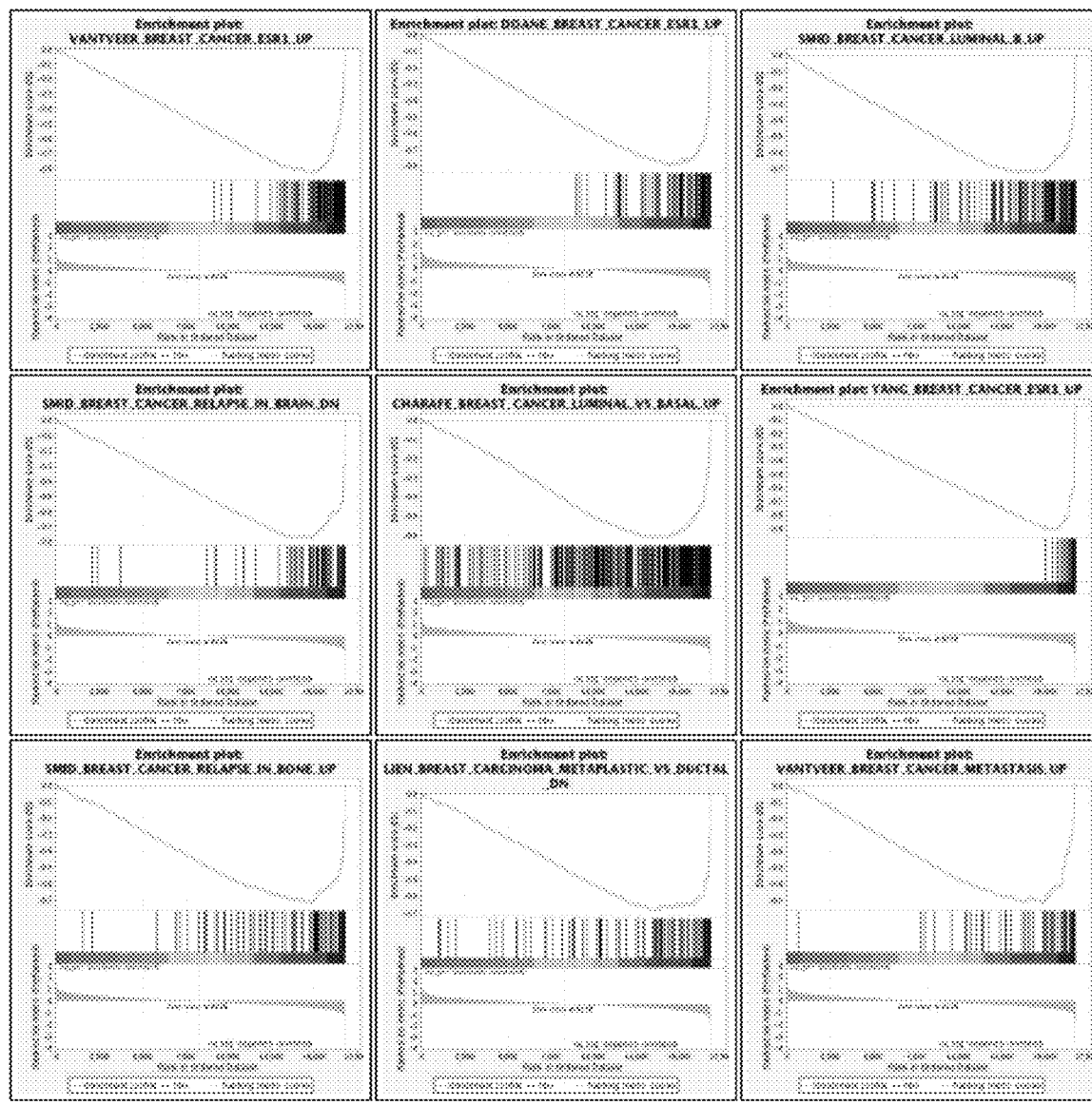

FIGS. 52A and 52B show the top scoring gene sets for S100A8 TCCA Pan-Cancer gene signature.

Figure 53B:
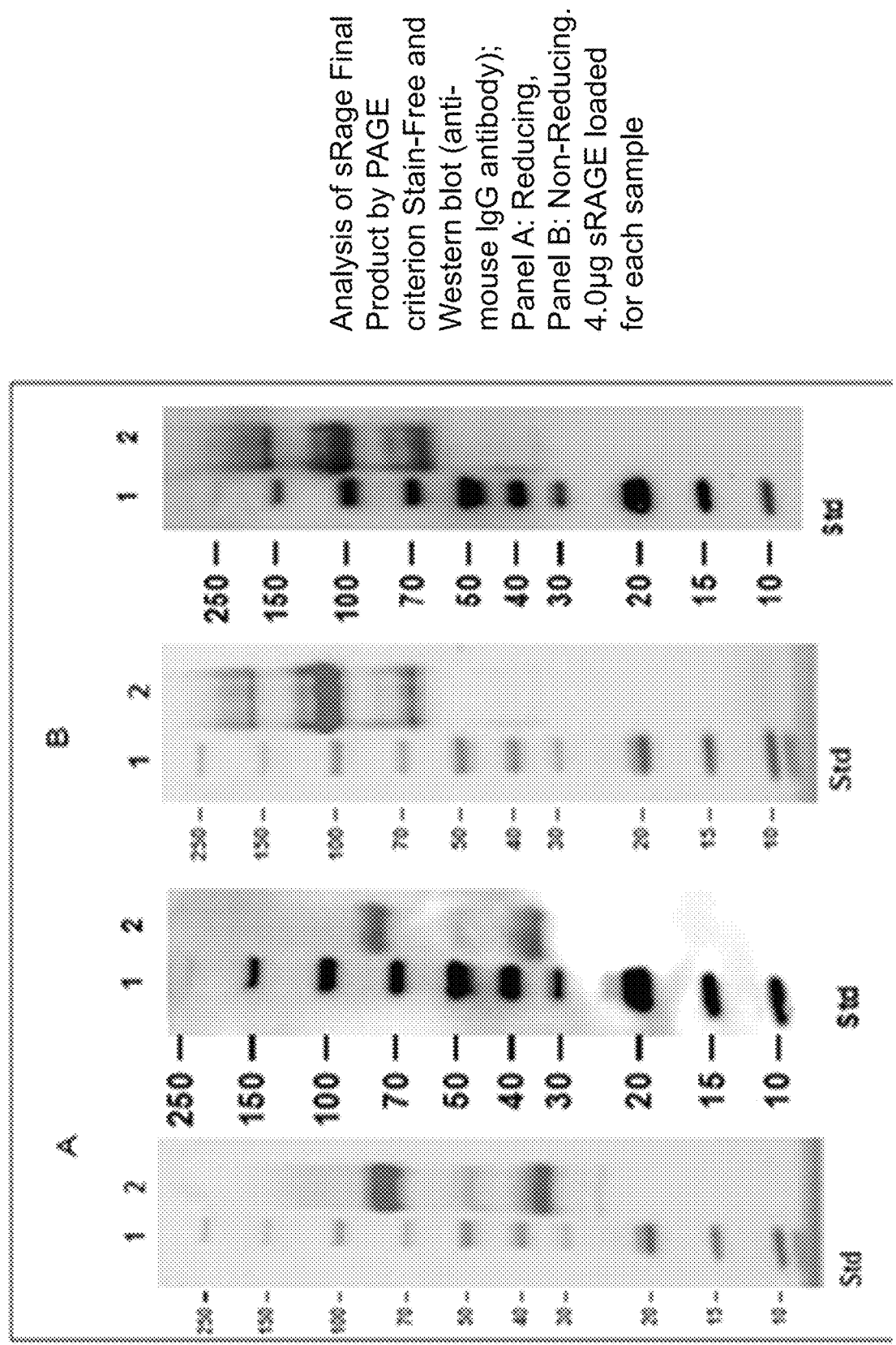
FIG. 53B is a schematic diagram showing an rsRAGE FC chimera and a Western blot, and Coomassie staining of a gel showing analysis of soluble Rage.

FIG. 53A lists potential in vivo treatment of lung cancer with RAGE inhibitors, the MEK/ERK inhibitor trametinib, and other candidates. FIG. 53B is a schematic diagram showing an rsRAGE FC chimera and a Western blot, and Coomassie staining of a gel showing analysis of soluble Rage. Other RAGE inhibitors include PF-04494700 (Sabbagh et al., Alzheimer Dis Assoc Disord. 2011; 25(3): 206-212) and a high-affinity RAGE-specific inhibitor (FPS-ZM1) (Deane et al., J. Clin Invest. 122:1377-1392, 2012).

FIG. 45 is a graph showing the distribution of JAK2 inhibitor compounds correlated with cachexia signature at the relatively high doses (10 µM) used in small molecule screens.

EXAMPLE 19

Combination Therapy Enhances Cancer Sensitivity to Chemotherapy

Figure 46:
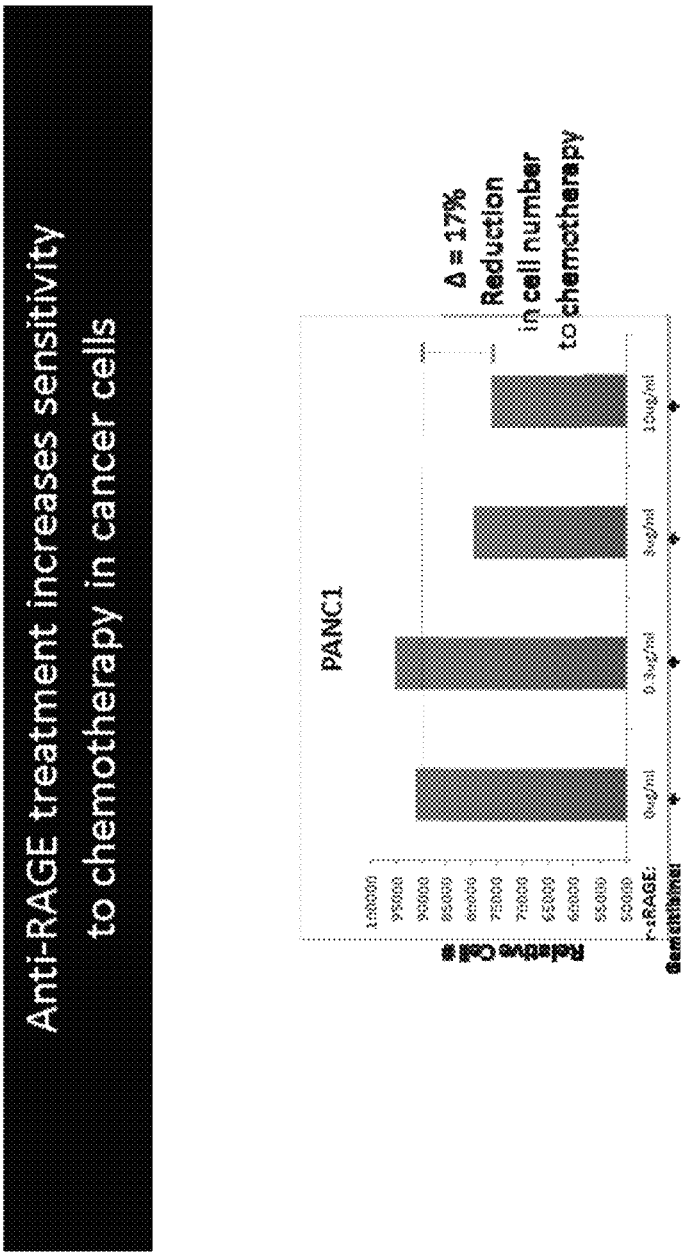
FIG. 46 is a graph showing a large Gene Set Enrichment Analysis of TCGA RAGE ligand gene expression profiles across multiple tumor types.

Anti-RAGE treatment increases sensitivity to chemotherapy in cancer cells. FIG. 46 is a graph demonstrating a reduction in pancreatic cancer cell numbers (by CellTiter Glo assay, Promega Inc.), when cells were treated for 5 days with Gemcitibine alone or in combination with increasing doses of recombinant human soluble RAGE. Similar increases in chemosensitivity were seen in Vemurafinib-resistent melanoma cells (G361) and Gefitinib-resistent lung cancer cells (PC9), when treated with these respective chemotherapies. The diversity of tumor types and chemotherapies that demonstrate increased chemosensitivity indicate that this finding is generalizable to other chemotherapy-resistent or nominally responding cancers.

EXAMPLE 20

Gene Set Enrichment Analysis of TCGA RAGE Ligand Gene Expression Profiles Across Multiple Tumor Types Gene expression profiles of different tumors with high vs low expression of individual RAGE ligands (based on z-score) were generated using TCGA clinical data. These genome-wide gene expression profiles were then queried with Molecular Signature Data Base (MSigDB) using Gene Set Enrichment Analysis (GSEA) computational algorithms to generate statistically significant lists of published functional gene sets. Given their extraordinary consistency and overlap, these lists of correlated and anti-correlated gene sets provide insight into the functionality of the queried gene expression profiles of these RAGE ligands in a wide variety of cancer cell types.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of inhibiting the loss of myosin heavy chain in a myocyte, inhibiting lipolysis in an adipocyte, or inhibiting atrophy in a myocyte, adipocyte, or hepatocyte, the method comprising:

contacting the myocyte, adipocyte, or hepatocyte with an effective amount of an agent that inhibits Receptor for Advanced Glycation Endproducts (RAGE) activity, wherein the RAGE inhibitor agent is soluble RAGE (sRAGE) comprising amino acid residues 1-344 of SEQ ID NO: 2, or a RAGE ligand-binding portion thereof; an anti-RAGE antibody; a RAGE blocking peptide that inhibits binding of RAGE to ligands, wherein said RAGE blocking peptide comprises one or more of C(K/R)GAPKKP(P/T)Q(Q/R/K)LE (SEQ ID NO: 3); CRGAPKKPPQQLE (SEQ ID NO: 4); CKGAPKKPPQRLE (SEQ ID NO: 5); CKGAPKKPTQKLE (SEQ ID NO: 6); DGKPLVPNEKGVSVKEQTRRHPETGLFTLQ (SEQ ID NO: 7); TLQSELMVTPARGGDPRPTFSCSFSPGLPR (SEQ ID NO: 8); LPRHRALRTAPIQPRVWEPVPLEEVQLVVE (SEQ ID NO: 9); or ELKVLMEKEL (SEQ ID NO: 10); or a small molecule selected from PF-04494700, FPS1, FPS2, FPS3, FPS-ZM1, or a combination thereof, that inhibits binding of RAGE to ligands.

2. The method of claim 1, wherein the myocyte, adipocyte, or hepatocyte is in vitro or in vivo.

3. The method of claim 2, wherein the myocyte, adipocyte, or hepatocyte is present in a subject identified as having at least one cancer selected from the group consisting of carcinomas, sarcomas, cancers of the skin, pancreas, stomach, colon, thorax, liver, gallbladder, musculoskeletal system, breast, lung, ovary, uterus, endometrium, prostrate, mouth, salivary, esophagus, head and neck, and tumors of the gastrointestinal tract.

4. The method of claim 1, wherein loss of lipid in the adipocyte is inhibited by contacting the adipocyte with an anti-RAGE antibody and trametinib.

5. A method of treating pre-cachexia or preventing undesirable muscle or fat loss in a cancer patient, the method comprising
administering to the subject an effective amount of an agent that inhibits Receptor for Advanced Glycation Endproducts (RAGE) activity, wherein the RAGE inhibitor agent is soluble RAGE (sRAGE) comprising amino acid residues 1-344 of SEQ ID NO: 2, or a RAGE ligand-binding portion thereof; an anti-RAGE antibody; a RAGE blocking peptide that inhibits binding of RAGE to ligands, wherein said RAGE blocking peptide comprises one or more of C(K/R)GAPKKP(P/T)Q(Q/R/K)LE (SEQ ID NO: 3); CRGAPKKPPQQLE (SEQ ID NO: 4); CKGAPKKPPQRLE (SEQ ID NO: 5); CKGAPKKPTQKLE (SEQ ID NO: 6); DGKPLVPNEKGVSVKEQTRRHPETGLFTLQ (SEQ ID NO: 7); TLQSELMVTPARGGDPRPTFSCSFSPGLPR (SEQ ID NO: 8); LPRHRALRTAPIQPRVWEPVPLEEVQLVVE (SEQ ID NO: 9); or ELKVLMEKEL (SEQ ID NO: 10); or a small molecule selected from PF-04494700, FPS1, FPS2, FPS3, FPS-ZM1, or a combination thereof, that inhibits binding of RAGE to ligands.

6. The method of claim 5, wherein, prior to treatment, a protein marker signature is detected in a biological sample obtained from the subject by
detecting in the sample an alteration in at least three markers selected from the group consisting of S100A2 or S100A4; S100A8 or S100A9; and S100A7 relative to a reference;
detecting in the sample an alteration in at least four markers selected from the group consisting of: S100A2 or S100A4; S100A8 or S100A9; S100A7 and S100A14 relative to a reference; or
measuring the levels of at least five markers selected from the group consisting of S100A2 or S100A4; S100A8 or S100A9; S100A7; S100A14 and S100P in the sample.

7. The method of claim 5, comprising administering to the patient an anti-RAGE antibody in combination with trametinib to inhibit the loss of lipid or fat in the patient.

8. A method of inhibiting the progression of pre-cachexia to cachexia, the method comprising
administering to the subject an effective amount of an agent that inhibits Receptor for Advanced Glycation Endproducts (RAGE) activity, wherein the RAGE inhibitor agent is soluble RAGE (sRAGE) comprising amino acid residues 1-344 of SEQ ID NO: 2, or a RAGE ligand-binding portion thereof; an anti-RAGE antibody; a RAGE blocking peptide that inhibits binding of RAGE to ligands, wherein said RAGE blocking peptide comprises one or more of C(K/R)GAPKKP(P/T)Q(Q/R/K)LE (SEQ ID NO: 3); CRGAPKKPPQQLE (SEQ ID NO: 4); CKGAPKKPPQRLE (SEQ ID NO: 5); CKGAPKKPTQKLE (SEQ ID NO: 6); DGKPLVPNEKGVSVKEQTRRHPETGLFTLQ (SEQ ID NO: 7); TLQSELMVTPARGGDPRPTFSCSFSPGLPR (SEQ ID NO: 8); LPRHRALRTAPIQPRVWEPVPLEEVQLVVE (SEQ ID NO: 9); or ELKVLMEKEL (SEQ ID NO: 10); or a small molecule selected from PF-04494700, FPS1, FPS2, FPS3, FPS-ZM1, or a combination thereof, that inhibits binding of RAGE to ligands.

9. The method of claim 8, wherein, prior to treatment, a protein marker signature is detected in a biological sample obtained from the subject by
detecting in the sample an alteration in at least three markers selected from the group consisting of S100A2 or S100A4; S100A8 or S100A9; and S100A7 relative to a reference;
detecting in the sample an alteration in at least four markers selected from the group consisting of: S100A2 or S100A4; S100A8 or S100A9; S100A7 and S100A14 relative to a reference; or
measuring the levels of at least five markers selected from the group consisting of S100A2 or S100A4; S100A8 or S100A9; S100A7; S100A14 and S100P in the sample.

10. The method of claim 8, wherein the pre-cachexia or cachexia is associated with cancer, disease, age-related weight loss, or age-related sarcopenia.

11. A method of enhancing cancer sensitivity to chemotherapy, the method comprising:
administering gemcitabine in combination with an anti-RAGE therapy; wherein the anti-RAGE therapy comprises soluble RAGE (sRAGE) comprising amino acid residues 1-344 of SEQ ID NO: 2, or a RAGE ligand-binding portion thereof; an anti-RAGE antibody, a RAGE blocking peptide that inhibits binding of RAGE to ligands, wherein said RAGE blocking peptide comprises one or more of C(K/R)GAPKKP(P/T)Q(Q/R/K)LE (SEQ ID NO: 3); CRGAPKKPPQQLE (SEQ ID NO: 4); CKGAPKKPPQRLE (SEQ ID NO: 5); CKGAPKKPTQKLE (SEQ ID NO: 6); DGKPLVPNEKGVSVKEQTRRHPETGLFTLQ (SEQ ID NO: 7); TLQSELMVTPARGGDPRPTFSCSFSPGLPR (SEQ ID NO: 8); LPRHRALRTAPIQPRVWEPVPLEEVQLVVE (SEQ ID NO: 9); or ELKVLMEKEL (SEQ ID NO: 10); or a small molecule selected from PF-04494700, FPS1, FPS2, FPS3, FPS-ZM1, or a combination thereof, that inhibits binding of RAGE to ligands.

12. The method of claim 11, wherein the cancer is selected from the group consisting of one or more carcinoma or sarcoma, skin, pancreas, stomach, colon, thorax, liver, gallbladder, musculoskeletal system, breast, lung, ovary, uterus, endometrium, prostrate, mouth, salivary, esophagus, head and neck, plus other tumors of the gastrointestinal tract.

13. The method of claim 1, wherein soluble RAGE is derived from the amino (N) terminal extracellular domain comprising the V, C1 and/or C2 domains of the RAGE protein comprising amino acid residues 1-344 of SEQ ID NO: 2.

14. The method of claim 5, wherein soluble RAGE is derived from the amino (N) terminal extracellular domain comprising the V, C1 and/or C2 domains of the RAGE protein comprising amino acid residues 1-344 of SEQ ID NO: 2.

15. The method of claim 8, wherein soluble RAGE is derived from the amino (N) terminal extracellular domain comprising the V, C1 and/or C2 domains of the RAGE protein comprising amino acid residues 1-344 of SEQ ID NO: 2.

16. The method of claim 11, wherein soluble RAGE is derived from the amino (N) terminal extracellular domain comprising the V, C1 and/or C2 domains of the RAGE protein comprising amino acid residues 1-344 of SEQ ID NO: 2.

17. The method of claim 1, wherein the RAGE inhibitor agent is a recombinant soluble RAGE (rsRAGE).

18. The method of claim 5, wherein the RAGE inhibitor agent is a recombinant soluble RAGE (rsRAGE).

19. The method of claim 8, wherein the RAGE inhibitor agent is a recombinant soluble RAGE (rsRAGE).

20. The method of claim 11, wherein the RAGE inhibitor agent is a recombinant soluble RAGE (rsRAGE).

\* \* \* \* \*